(12) United States Patent
Frincke et al.

(10) Patent No.: US 7,723,532 B2
(45) Date of Patent: May 25, 2010

(54) PHARMACEUTICAL COMPOSITIONS 3

(75) Inventors: James M. Frincke, San Diego, CA (US); Christopher L. Reading, San Diego, CA (US); Clarence N. Ahlem, San Diego, CA (US)

(73) Assignee: Harbor BioSciences, Inc., San Diego, CA (US)

( * ) Notice: Subject to any disclaimer, the term of this patent is extended or adjusted under 35 U.S.C. 154(b) by 477 days.

(21) Appl. No.: 11/552,095

(22) Filed: Oct. 23, 2006

(65) Prior Publication Data

US 2008/0176824 A1 Jul. 24, 2008

Related U.S. Application Data

(63) Continuation of application No. 10/319,356, filed on Dec. 13, 2002, now Pat. No. 7,396,827, which is a continuation of application No. 09/535,675, filed on Mar. 23, 2000, now Pat. No. 6,667,299, which is a continuation-in-part of application No. 09/414,905, filed on Oct. 8, 1999, now abandoned.

(60) Provisional application No. 60/190,140, filed on Mar. 16, 2000, provisional application No. 60/164,048, filed on Nov. 8, 1999, provisional application No. 60/140,028, filed on Jun. 16, 1999, provisional application No. 60/126,056, filed on Mar. 23, 1999.

(51) Int. Cl.
*C07D 311/78* (2006.01)
*A01N 43/16* (2006.01)
*A61K 31/35* (2006.01)

(52) U.S. Cl. ........................ 549/383; 514/453
(58) Field of Classification Search ................. 549/383; 514/453
See application file for complete search history.

(56) References Cited

U.S. PATENT DOCUMENTS

| | | | |
|---|---|---|---|
| 3,101,350 A | 8/1963 | Pappo | |
| 3,128,283 A | 4/1964 | Pappo | |
| 3,246,014 A | 4/1966 | Jung et al. | |
| 3,280,149 A | 10/1966 | Jung et al. | |
| 4,898,694 A | 2/1990 | Schwartz et al. | |
| 5,292,730 A | 3/1994 | Lardy | |
| 5,387,583 A | 2/1995 | Loria | |
| 5,424,463 A | 6/1995 | Lardy et al. | |
| 5,461,042 A | 10/1995 | Loria | |
| 5,478,566 A | 12/1995 | Loria | |
| 5,635,496 A | 6/1997 | Daynes et al. | |
| 5,837,269 A | 11/1998 | Daynes et al. | |
| 5,859,000 A | 1/1999 | Dowell et al. | |
| 6,667,299 B1 | 12/2003 | Ahlem et al. | |
| 7,396,827 B2 | 7/2008 | Ahlem et al. | |
| 7,462,610 B2 | 12/2008 | Lardy et al. | |
| 2004/0220114 A1 | 11/2004 | Ahlem et al. | |
| 2006/0073099 A1 | 4/2006 | Frincke et al. | |
| 2006/0079492 A1 | 4/2006 | Ahlem et al. | |
| 2007/0014719 A1* | 1/2007 | Reading et al. | 424/1.11 |
| 2007/0077203 A1* | 4/2007 | Garsd et al. | 424/9.2 |
| 2007/0129282 A1 | 6/2007 | Ahlem et al. | |
| 2007/0275936 A1 | 11/2007 | Ahlem et al. | |
| 2007/0275937 A1 | 11/2007 | Reading et al. | |
| 2008/0004250 A1 | 1/2008 | Lardy et al. | |
| 2008/0015174 A1 | 1/2008 | Reading et al. | |
| 2008/0021006 A1 | 1/2008 | Lardy et al. | |
| 2008/0045490 A1 | 2/2008 | Frincke et al. | |
| 2008/0058301 A1 | 3/2008 | Lardy et al. | |
| 2008/0146532 A1* | 6/2008 | Flores-Riveros et al. | 514/182 |
| 2008/0153792 A1* | 6/2008 | Frincke et al. | 514/178 |
| 2008/0153797 A1* | 6/2008 | Frincke et al. | 514/182 |
| 2008/0176823 A1 | 7/2008 | Lardy et al. | |
| 2008/0221074 A1* | 9/2008 | Flores-Riveros et al. | 514/182 |

FOREIGN PATENT DOCUMENTS

| | | |
|---|---|---|
| DE | 3812595 | 7/1997 |
| EP | 0289327 | 11/1988 |
| EP | 0133995 | 3/1995 |
| WO | WO 00/32176 | 6/2000 |
| WO | WO 00/32177 | 6/2000 |

(Continued)

OTHER PUBLICATIONS

Araghi-Niknam et al, Cytokine dysregulation and increased oxidation is prevented by dehydroepiandrosterone in mice infected with murine leukemia retrovirus, *Proc. Soc. Exp. Biol. Med.*, 216(3):386-391 (1997).

(Continued)

*Primary Examiner*—Alton N Pryor
(74) *Attorney, Agent, or Firm*—Daryl D Muenchau

(57) ABSTRACT

The invention provides compositions comprising formula 1 steroids, e.g., 16α-bromo-3β-hydroxy-5α-androstan-17-one hemihydrate and one or more excipients, typically wherein the composition comprises less than about 3% water. The compositions are useful to make improved pharmaceutical formulations. The invention also provides methods of intermittent dosing of steroid compounds such as analogs of 16α-bromo-3β-hydroxy-5α-androstan-17-one and compositions useful in such dosing regimens. The invention further provides compositions and methods to inhibit pathogen (viral) replication, ameliorate symptoms associated with immune dysregulation and to modulate immune responses in a subject using certain steroids and steroid analogs. The invention also provides methods to make and use these immunomodulatory compositions and formulations.

15 Claims, 6 Drawing Sheets

FOREIGN PATENT DOCUMENTS

| | | |
|---|---|---|
| WO | WO 00/32201 | 6/2000 |
| WO | WO 01/23405 | 4/2001 |
| WO | WO 01/30802 | 5/2001 |

OTHER PUBLICATIONS

Araghi-Niknam et al, Modulation of immune dysfunction during murine leukaemia retrovirus infection of old mice by dehyroepiandrosterone sulphate (DHEAS), *Immunology* 90(3):344-349 (1997).

Bebo et al, Androgens alter the cytokine profile and reduce encephalitogenicity of myelin-reactive T cells, *J. Immunol*, 162(1): 35-40 (1999).

Henderson et al, Dehydroepiandrosterone and 16α-bromoepiandrosterone: inhibitors of Epstein-Barr virus induced transformation of human lymphocytes, *Carcinogenesis*, 2(7):683-686 (1981).

Hernandez-Pando et al, The effects of androstenediol and dehydroepiandrosterone on the course and cytokine profile of tuberculosis in BALB/c mice, *Immunology*, 95(2):234-241 (1998).

Horn, Y., The effect of androgenic hormones on bone marrow of rats receiving chemotherapy, *Oncology* 25:512-519 (1971).

Inserra et al, Modulation of cytokine production by dehydroepiandrosterone (DHEA) plus melatonin (MLT) supplementation of old mice, *Proc. Soc. Exp. Biol. Med.*, 218(1):76-82 (1998).

Kang et al, Dehydroepiandrosterone and β-endorphin enhance IL-12 gene expression, *Taehan Misaengmulhak Hoechi (J. Korean Soc. Microbiology)* 31(4):399-404 (1996) (translation from Korean).

Kang et al, Dehydroepiandrosterone and β-endorphin enhance IL-12 gene expression, *Chemical Abstracts* 126(9):99 (1997).

Manz et al, Methyl 17β-Carboxyester Derivatives of Natural and Synthetic Glucocorticoids: Correlation Between Receptor Binding and Inhibition of in vitro Phytohaemagglutinin-Induced Lymphocyte Blastogenesis, *J. Clin. Chem. Clin. Biochem.* 21(2):69-75 (1983).

Pappo et al, 2-Oxasteroids: A new class of biologically active compounds, *Tetrahedron Letters*, 9:365-371 (1962).

Sigg et al, 3α-Acetoxyätien-(8:9 oder 8:14)-säure-methylester, *Helvetica Chimica Acta*, 39(6):1507-1525 (1956) (translation from German).

Das et al, 18-Substituted Steroids. Part 11. Synthesis of 3β,16α,18-trihydroxyandrost-5-en-17-one, a neonatal urinary metabolite, and the 3,16,18-triacetate of its 16β-epimer, J. Chem. Soc. Perkin Trans. I pp. 1821-1831, 1984.

Waskiewicz et al, Induction of "male-specific" cytochrome P450 isozymes in female rast by oxandrolone, *Drug Metab. Dispo.* 23(11):1291-1296 (1995).

Xia et al, Anti-AIDS agents. Part 36:1 17-carboxylated steroids as potential anti-HIV agents, *Bioorganic & Medicinal Chem.* 7(9):1907-1911 (1999).

Fennessey et al, Anabolic steroids in body builders: use, metabolic disposition and physiological effects, *J. Pharmaceutical and Biomed. Analysis*, 6(6-8):999-1002 (1988).

Yang et al, Inhibition of HIV-1 Latency Reactivation by Dehydroepiandrosterone (DHEA) and an Analog of DHEA, *Aids Research and Human Retroviruses* 9(8):747-754 (1993).

Zhang et al, Prevention of immune dysfunction and vitamin E loss by dehydroepiandrosterone and melatonin supplementation during murine retrovirus infection, *Immunology*, 96(2):291-297 (1999).

\* cited by examiner

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Peptide sequence from fibronectin gamma chain

<400> SEQUENCE: 1

Lys Gln Ala Gly Asp Val
1               5
```

PHARMACEUTICAL COMPOSITIONS 3

CROSS-REFERENCE TO RELATED APPLICATIONS

This application is a continuation application under 37 C.F.R. §1.53(b) of U.S. patent application Ser. No. 10/319,356, filed Dec. 13, 2002, now U.S. Pat. No. 7,396,827, which is a continuation of patent application Ser. No. 09/535,675, filed Mar. 23, 2000, now U.S. Pat. No. 6,667,299, which (1) is a continuation-in-part of U.S. patent application Ser. No. 09/414,905, filed Oct. 8, 1999, and (2) claims priority from U.S. Provisional Application Ser. No. 60/190,140, filed Mar. 16, 2000, U.S. Provisional Application Ser. No. 60/164,048, filed Nov. 8, 1999, abandoned U.S. Provisional Application Ser. No. 60/140,028, filed Jun. 16, 1999, and U.S. Provisional Application Ser. No. 60/126,056, filed Mar. 23, 1999, all of which are incorporated herein by reference.

BACKGROUND OF THE INVENTION

The invention relates to methods to make and use steroids, such as 16α-bromo-3β-hydroxy-5α-androstane-17-one (16α-bromoepiandrosterone or hereafter "BrEA") and new analogs thereof. The steroids are useful for a number of therapeutic and non-therapeutic applications, including their use as immune modulators. The present invention also relates to methods to make the compounds, compositions and formulations.

BrEA and its preparation from the steroid compound 3β-hydroxyandrost-5-en-17-one (dehydroepiandrosterone or "DHEA") have been described (see, e.g., J. Org. Chem. 1962 27:2937-2938). Methods to prepare DHEA and other steroids and their biological properties have been described, see, e.g., U.S. Pat. Nos. 2,833,793, 2,911,418, 3,148,198, 3,471,480, 3,976,691, 4,268,441, 4,427,649, 4,542,129, 4,666,898, 4,956,355, 5,001,119, 5,043,165, 5,077,284, 5,028,631, 5,110,810, 5,157,031, 5,162,198, 5,175,154, 5,277,907, 5,292,730, 5,296,481, 5,372,996, 5,387,583, 5,407,684, 5,424,463, 5,461,042, 5,478,566, 5,506,223, 5,518,725, 5,527,788, 5,527,789, 5,532,230, 5,559,107, 5,562,910, 5,583,126, 5,585,371, 5,587,369, 5,591,736, 5,593,981, 5,610,150, 5,635,496, 5,641,766, 5,641,768, 5,656,621, 5,660,835, 5,686,438, 5,696,106, 5,700,793, 5,707,983, 5,709,878, 5,710,143, 5,714,481, 5,728,688, 5,736,537, 5,744,462, 5,753,237, 5,756,482, 5,776,921, 5,776,923, 5,780,460, 5,795,880, 5,798,347, 5,798,348, 5,804,576, 5,807,848, 5,807,849, 5,811,418, 5,824,313, 5,824,668, 5,824,671, 5,827,841, 5,837,269, 5,837,700, 5,843,932, 5,846,963, 5,859,000, 5,872,114 and 5,872,147; German patent numbers 2035738 and 2705917; PCT publication numbers WO 95/21617, WO 97/48367, WO 98/05338, WO 98/50040, WO 98/50041, WO 98/58650; European publication number 0020029; Ben-David, et al., Proc. Soc. Expt. Biol. Med. 1967 125:1136-1140, Coleman et al., Diabetes 1982 31:830, Oertel, et al., J. Steroid Biochem. 1972 3:493-496, Pashko, et al., Carcinogenesis 1981 2:717-721, Schwartz et al., Nutr. Cancer 1981 3:46-53; Dyner et al., J. Acquired Immune Deficiency Syndromes 1993 6:459-465; A. A. Afanasii and Y. A. Titov, Total Steroid Synthesis, Plenum Press, New York, 1970, see, e.g., p 1-304.

The use DHEA and other steroids in various applications, e.g., modulating immune responses have been described, e.g., U.S. Pat. Nos. 5,869,090, 5,863,910, 5,856,340, 5,824,668, 5,804,576, 5,753,237, 5,714,481, 5,709,878, 5,407,684, 5,206,008, 5,077,284, 4,978,532, 4,898,694, 4,542,129, 3,711,606 and 3,710,795. U.S. Pat. No. 4,956,355 and PCT publication number WO 97/48367, have described the use of BrEA and certain steroid compounds to treat certain virus or bacterial infections, such as human immunodeficiency virus ("HIV") infection.

Various biological effects and/or metabolic conversions of steroid compounds have been described, e.g., Batta et al., J. Biol. Chem. 1986 25:127-133, Belli et al., Liver 1991 11:162-169, Bhattacharjee et al., Anal. Biochem. 1992 201:233-236, Blake et al., Int. J. Peptide Protein Res. 1982 20:97-101, 1986 25:127-133, Bonaventura, Am. J. Obstet. Gynecol. 1978 131:403-409, Bucala et al., J. Steroid Biochem. 1986 25:127-133, Carey et al., Biochem. 1981 20:3637-3648, Chen et al., Carcinogenesis 1999 20:249-254, Chen et al., Carcinogenesis 1998 19:2187-2193, Chow et al., Antisense Res. Dev. 1994 4:81-86, Citro et al., Dis. Colon Rectum 1994 37(2 Suppl):S127-S132, Cleary, Proc. Soc. Exp. Biol. Med. 1991 196:8-16, Cleary, Int. J. Biochem. 1990 22:205-210, Crawford et al., Lab. Invest. 1994 71:42-51, Danenberg et al., Antimicrob. Agents Chemother. 1992 36:2275-2279, Dotzlaw et al., Cancer Res. 1999 59:529-532, Falany et al., J. Steroid Biochem. Mol. Biol. 1994 48:369-375, Faredin et al., J. Investigative Dermatol. 1969 52:357-361, Galigniana et al., Mol. Pharmacol. 1999 55:317-323, Goto et al., J. Chromatogr. 1983 276:289-300, Grenot Biochem. 1992 31:7609-7621, Hofbauer et al., Life Sci. 1999 64:671-679, Huijghebaert et al., J. Lipid Res. 1986 27:742-752, Hurd et al., Oncogene 1999 18:1067-1072, Iida et al., J. Lipid Res. 1995 36:628-638, Jellinck et al., Steroids 1967 10:329-346, Jonsson et al., J. Pediatr. Gastroenterol. Nutr. 1995 20:394-402, Kalimi et al, Mol. Cell. Biochem. 1994 131:99-108, Kramer et al., J. Biol. Chem. 1994 269:10621-10627, LaRochelle et al., Steroids 1984 43: 209-217, Liao et al., Carcinogenesis 1998 19:2173-2180, Lillienau et al., J. Clin. Invest. 1992 89:420-431, Loria, Psychoneuroendocrinology 1997 22:S103-S108, Luscher et al Mol. Immunol. 1983 20:1099-1105, Manna et al., J. Biol. Chem. 1999 274:5909-5918, Marschall et al., J. Biol. Chem. 1989 264:12989-12993, Medh et al., Cancer Res. 1998 15:3684-3693, Mohan et al., Steroids 1992 57:244-247, Munoz de Toro et al., J. Steroid Biochem. Mol. Biol. 1998 67:333-339, Padgett et al., J. Neuroimmunol. 1998 84:61, Padgett et al., Ann. N.Y. Acad. Sci. 1995 774:323, Padgett et al., J. Immunol. 1994 153:1544-1552, Pashko et al., Carcinogenesis 1984 5:463-466, Pashko et al., Carcinogenesis 1981 2:717, Petrylak et al., J. Clin. Oncology 1999 17:958-967, Podesta et al., Steroids 1996 61:622-626, Regelson et al., Ann. N.Y. Acad. Sci. 1994 719:564, Schmassmann et al., Gastroenterology 1993 104:1171-1181, Schmassmann et al., Hepatology 1990 11:989-996, Schreiber et al., Lancet 353: 459-461, Schreiber, Neth. J. Med. 1998 53:S24-31, Schwartz et al., Cancer Res. 1988 48:4817, Shahidi et al., Biochem. Biophys. Res. Commun. 1999 254:559-565, Steer et al., Ann. Rheum. Dis. 1998 57:732-737, Suzuki et al., Steroids 1998 63:672-677, Suzuki et al., Steroids 1996 61:296-301, Swaan et al., Bioconjugate Chem. 1997 8:520-525, Tang et al, Anti-cancer Drug Res. 1998 13:815-824, Thomas et al., J. Steroid Biochem. 1986 25:103-108, Utsumi et al., Cancer Res. 1999 59:377-381, Vanden Heuvel, J. Nutr. 1999 129(2S Suppl.):575S-580S, Wang et al., Endocrinology 1998 139:3903-3912, Wong et al., J. Biol. Chem. 1999 274:5443-5453, Xie et al., Endocrinology 1999 140:219-227, Yen et al., Lipids 1977 12:409-413, Zackheim et al., Arch. Dermatology 1998 134:949-954, Zhang et al., Biochim. Biophys. Acta 1991 1096:179-186, Zhu et al., Carcinogenesis 1988 19:2101-2106.

Compositions containing BrEA that were used to deliver the compound to cells or cell extracts usually included a significant amount of water. Such compositions contained solvents such as dioxane or dimethylsulfoxide ("DMSO"), which contained water, or an aqueous cyclodextrin solutions to facilitate compound delivery to cells, see, e.g., *J. Pharmacol Exp. Ther.* 1998, 285:876-83, *Cancer Res.* 1986 46:3389-95, *Carcinogenesis* 1985 6:333-35, *Carcinogenesis* 1981 2:717-721, *Carcinogenesis* 1981 2:683-86. Such compositions are typically delivered to animals by injection or to cells in tissue culture by addition to cell culture medium. European publication number EP 429 187 describes formulations that contain DHEA or BrEA and polyvinylpyrrolidone and crosslinked polyvinylpyrrolidone. Some of these compositions may have undesired or suboptimal properties. For example, solvents such as dioxane, DMSO or chloroform are generally not preferred or suitable parenteral excipients, particularly for human use. Formulations that contain BrEA or related steroids and that have improved properties, e.g., lower toxicity, improved chemical stability or desirable characteristics for large-scale synthesis are needed.

Mammalian immune responses to infections or other conditions are often characterized by responses mediated by different effector cell populations. In some situations, helper T cells designated Th1 in the murine system, facilitate immune effector functions that are typically dominated by cell-mediated responses. In other cases, helper T cells designated Th2 cells facilitate immune effector functions that are typically dominated by humoral responses. A vigorous Th1 response is usually needed to clear infections or to slow the progression of an infection. When a subject's immune response is biased to, or dominated by, a Th2-type response, the cytokines associated with the Th2 response tend to suppress the immune system's capacity to mount a vigorous Th1 response at the same time. The converse is also generally true. When mammalian immune responses begin to result in an increasing Th2 response, the Th1 response to the same condition tends to weaken. Weak Th1 responses may be associated with progression of some infections or other conditions, see, e.g., M. Clerici and G. M. Shearer, *Immunol. Today* 14:107-111, 1993; M. Clerici and G. M. Shearer, *Immunol. Today* 15:575-581, 1994. The invention provides compounds and compositions useful to enhance Th1 immune responses.

OBJECTS OF THE INVENTION

The invention compositions, formulations or methods accomplish one or more of the following objects.

One object of the invention is to provide new steroid compounds or analogs that are suitable for therapeutic and other applications, such as immune modulators. Invention objects further include providing BrEA hemihydrate (BrEA$_2$H$_2$O), compositions that comprise BrEA hemihydrate and methods to make and use it. Another object of the invention is to provide liquid compositions and formulations that comprise a formula 1 compound(s), and that comprise about 3% (v/v) or less of water. Another object is to provide compositions one can use as intermediates to prepare human pharmaceutical and veterinary formulations containing a formula 1 compound(s). Another object is to provide intermittent dosing methods to deliver a formula 1 compound to a subject to enhance Th1 immune responses. Further objects are to provide methods to modulate innate immunity or to enhance Th1 immune responses in a subject by administering to the subject a formula 1 compound(s) such as BrEA. Other objects are to provide methods to inhibit pathogen, e.g., viral, replication in a subject by administering to the subject a formula 1 compound(s) such as BrEA. Invention objects include providing formula 1 compounds or formulations useful to ameliorate one or more symptoms of a pathological condition associated with immune suppression or with deficient Th1 immune responses. Other objects are to provide methods to make and use compositions and formulations comprising a formula 1 compound(s).

SUMMARY OF THE INVENTION

Figure 1:
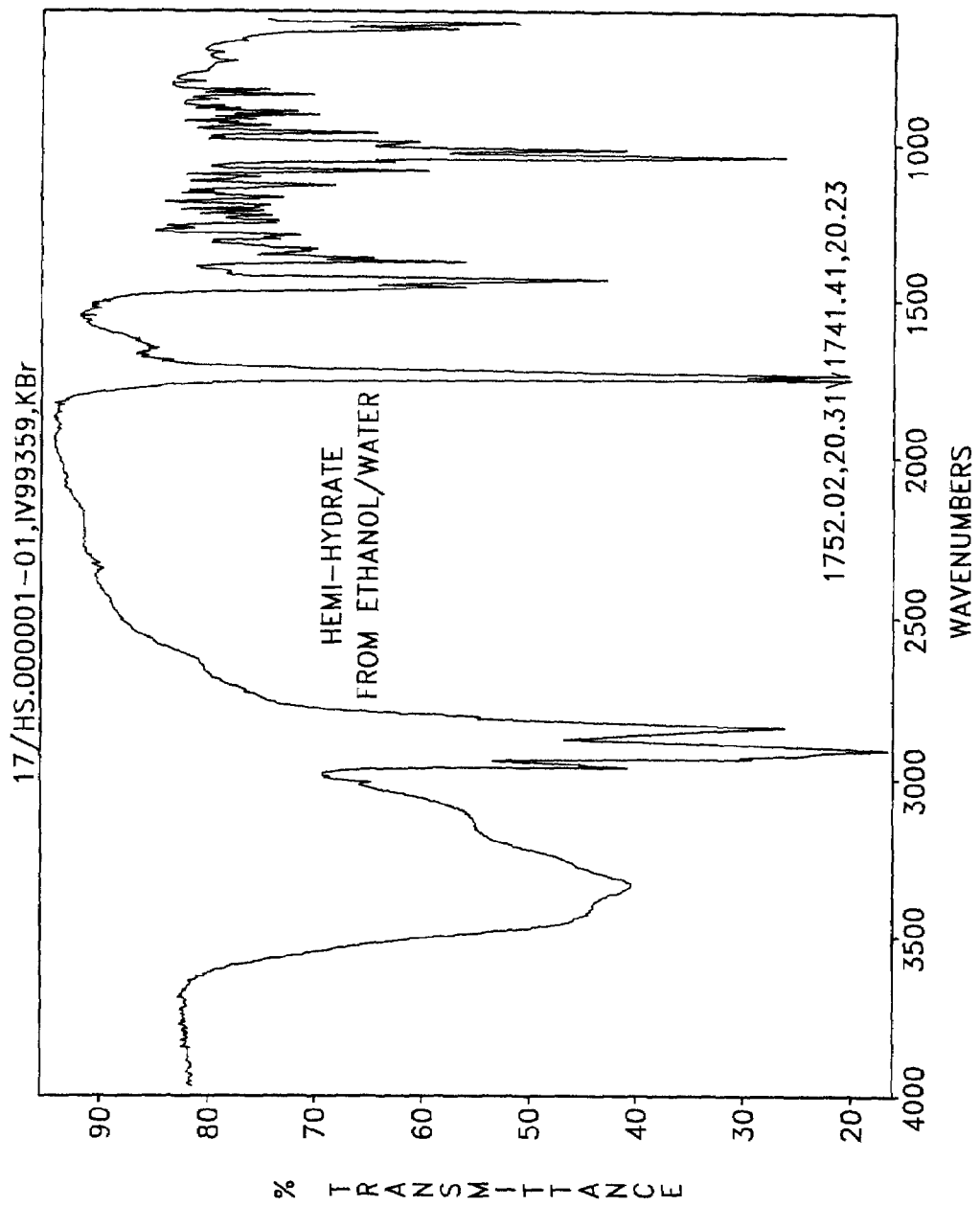
FIG. 1 is an FTIR (Fourier transform infrared) spectrum obtained by USP method <197> of BrEA hemihydrate that was prepared by precipitation of BrEA from ethanol and water.
Figure 2:
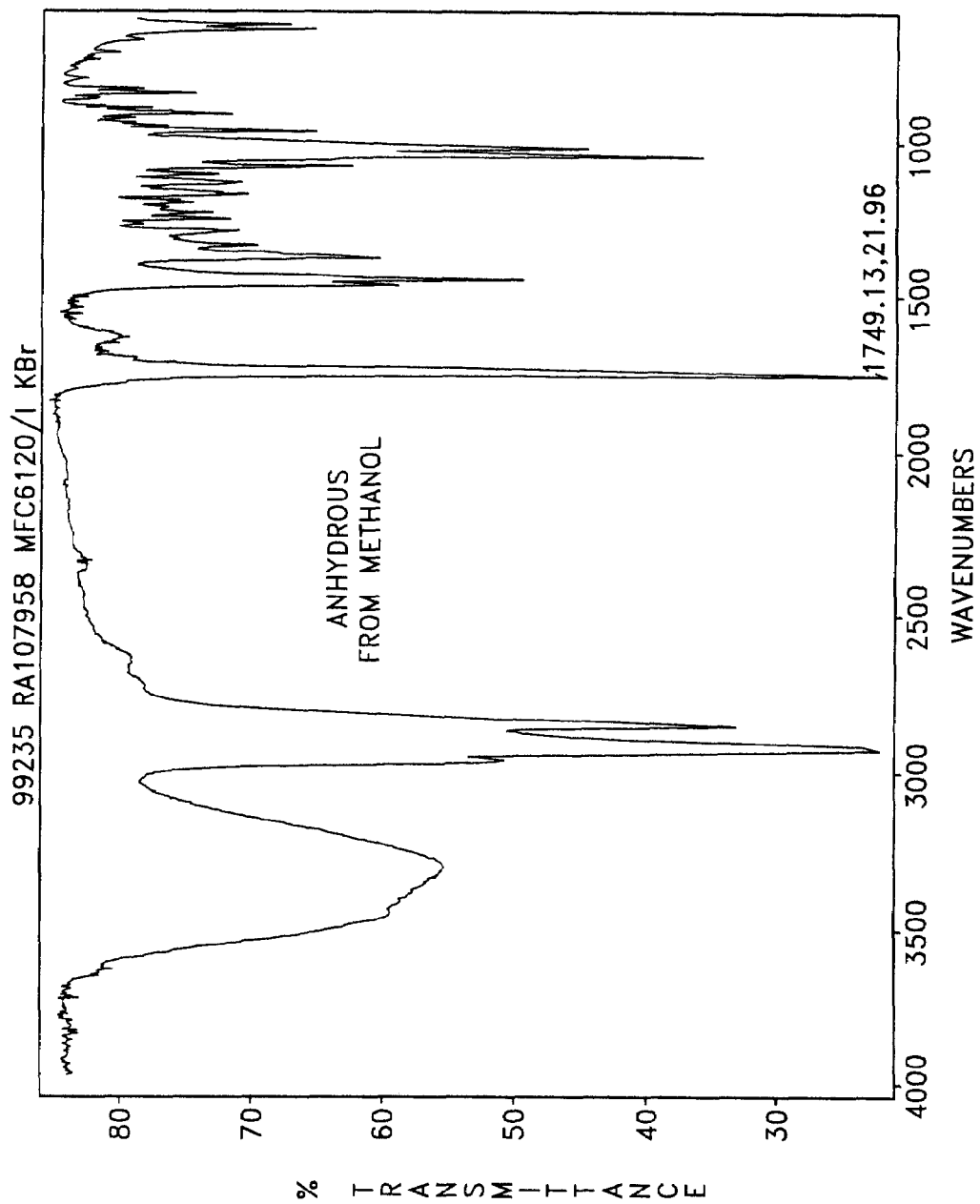
FIG. 2 is a FTIR spectrum obtained by USP method <197> of anhydrous BrEA that was prepared by precipitation of BrEA from anhydrous methanol.
Figure 3:
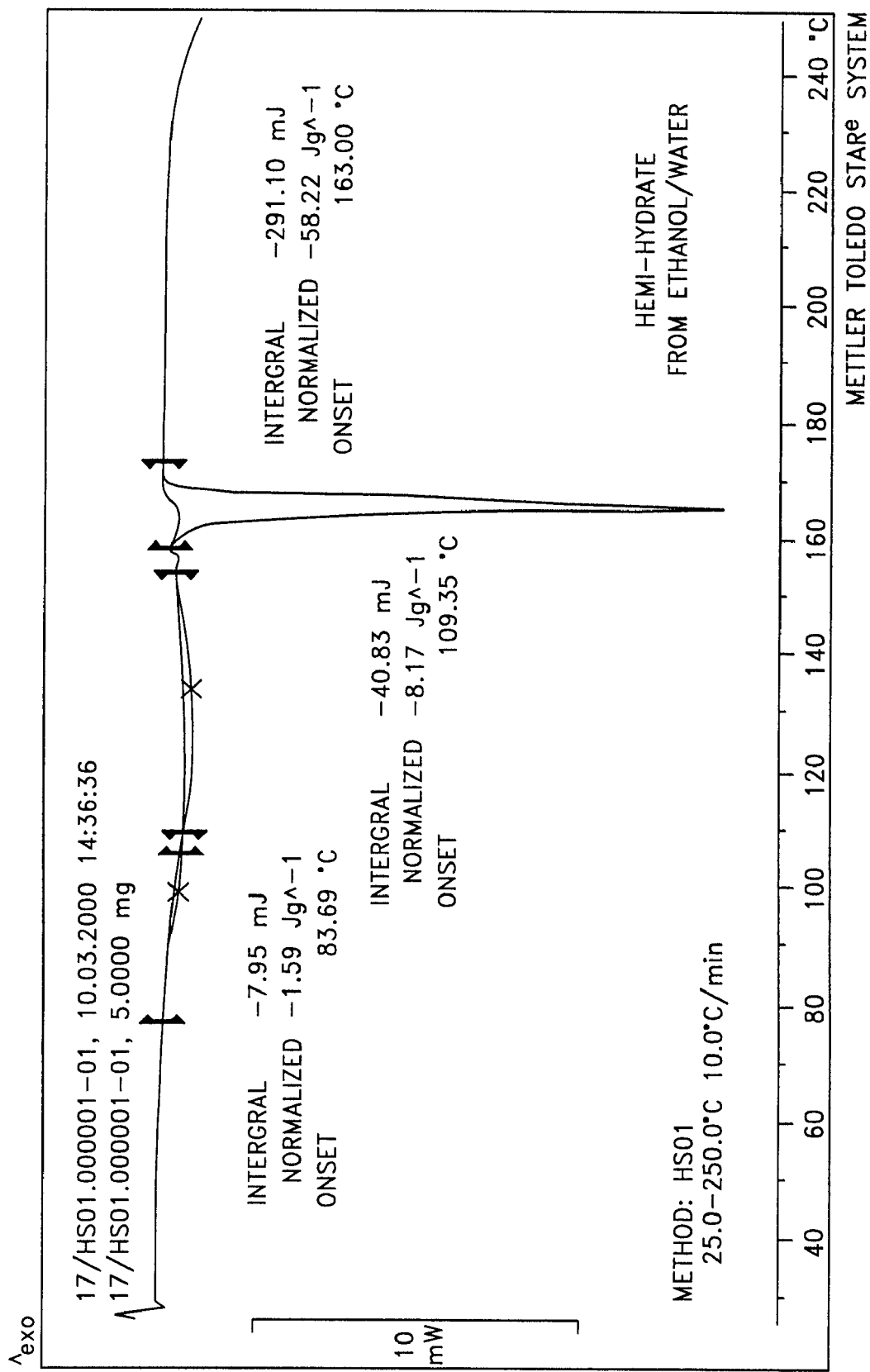
FIG. 3 shows a DSC endotherm of BrEA hemihydrate that was prepared by precipitation of BrEA from ethanol and water.
Figure 4:
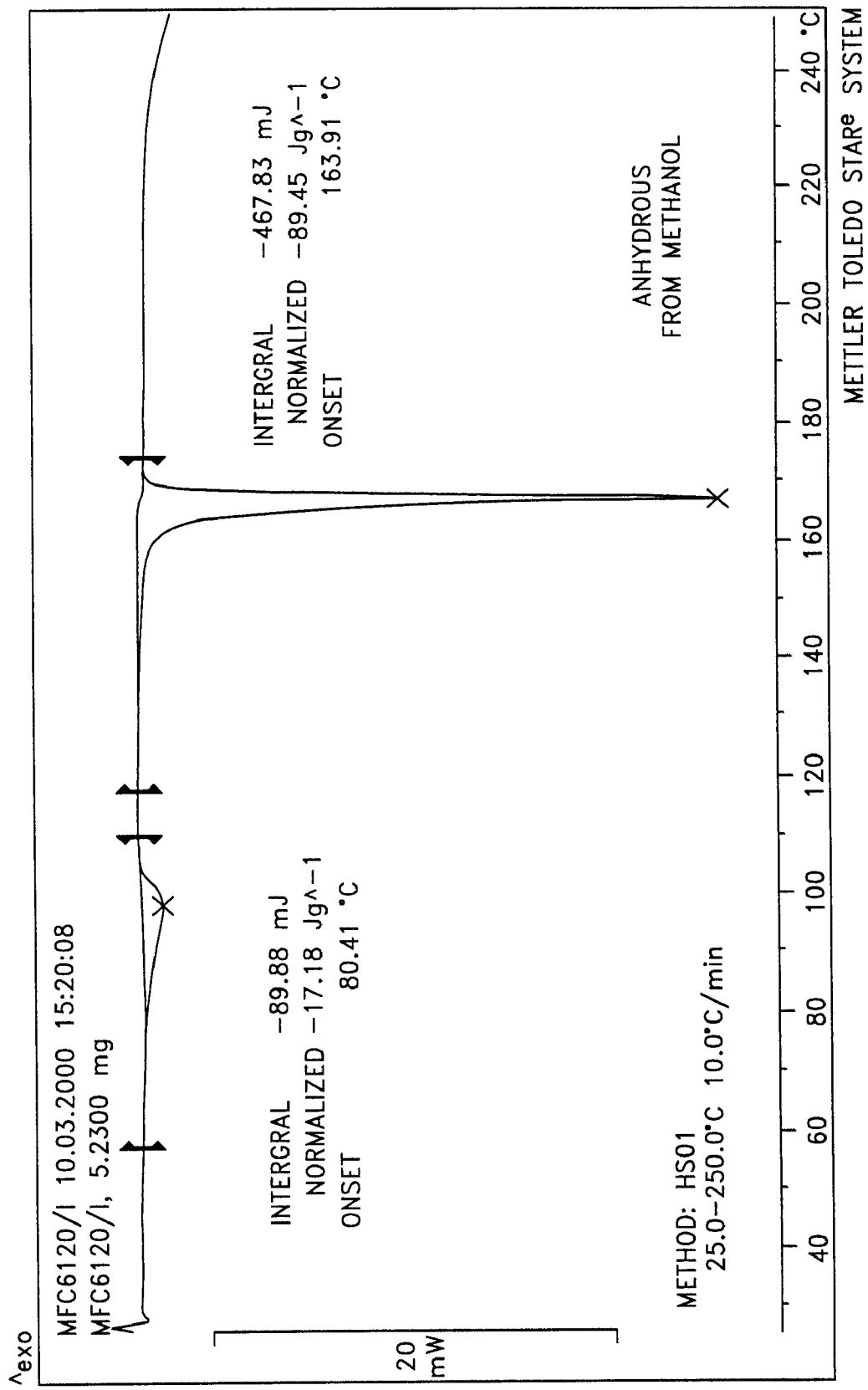
FIG. 4 shows a DSC endotherm of anhydrous BrEA that was prepared by precipitation of BrEA from anhydrous methanol.
Figure 5:
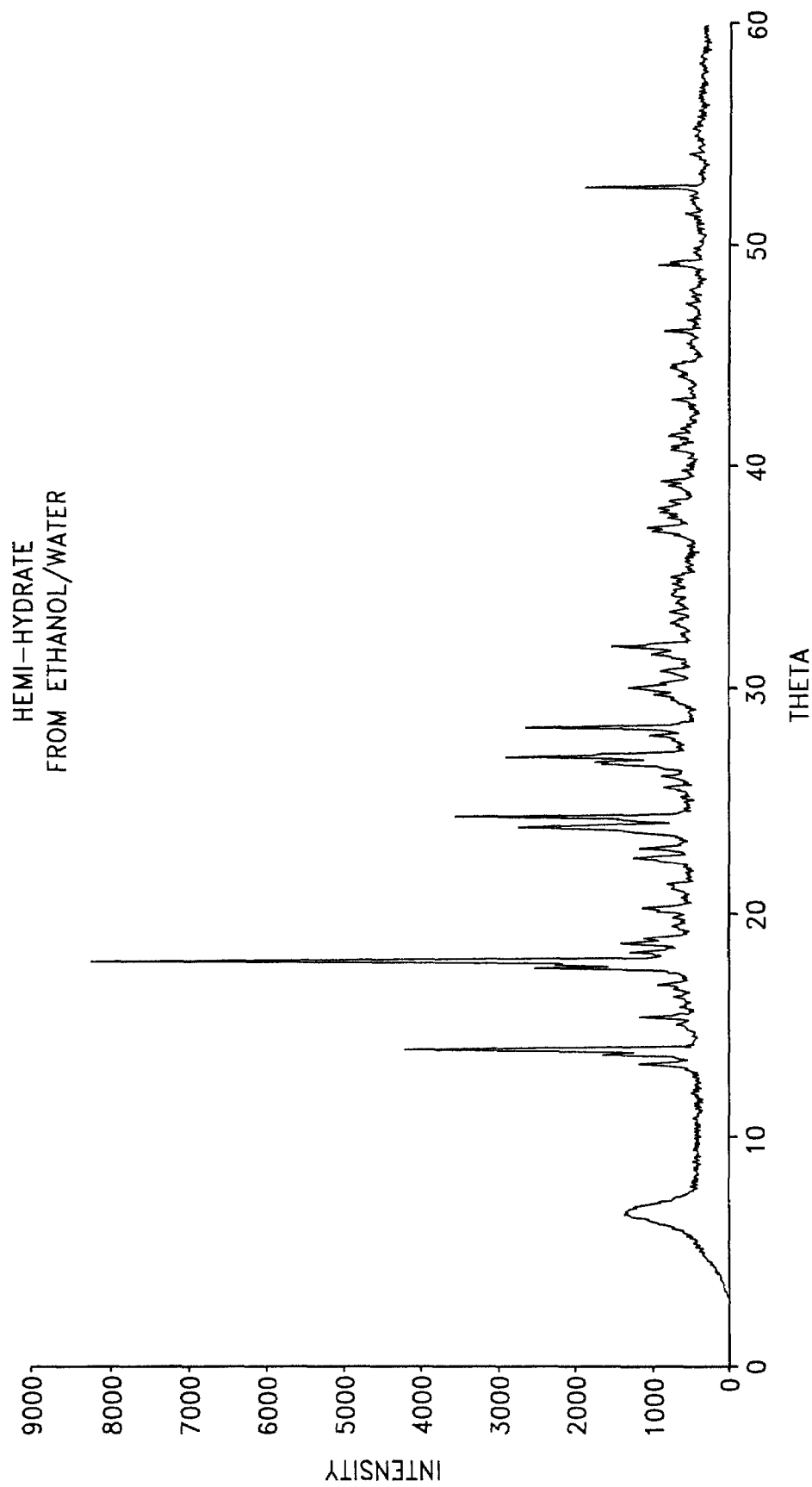
FIG. 5 is an XRD (powder X-ray diffraction) spectrum of BrEA hemihydrate that was prepared by precipitation of BrEA from ethanol and water.
Figure 6:
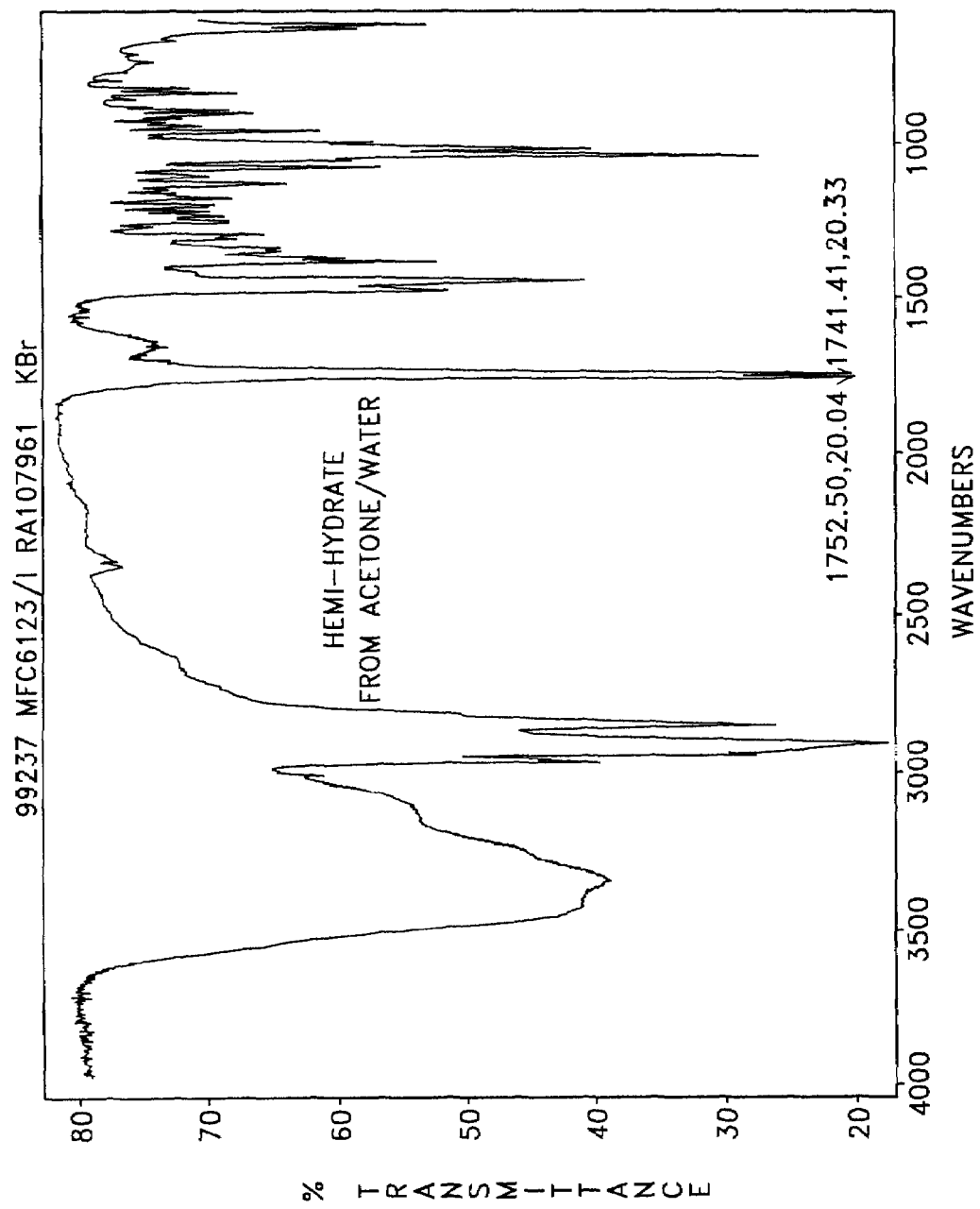
FIG. 6 is a FTIR spectrum obtained by USP method <197> of BrEA hemihydrate that was prepared by precipitation of BrEA from acetone and water.

In accordance with the objects, the invention provides BrEA hemihydrate

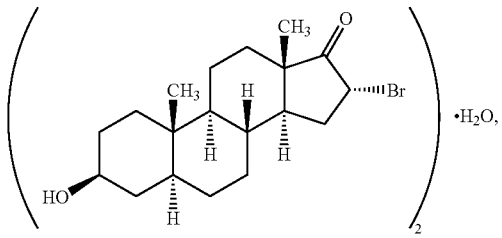

which is optionally characterized by reference to one or more physical properties such as its melting point, infrared absorption spectrum or its powder X-ray diffraction spectrum.

Related embodiments include BrEA hemihydrate and one or more excipients suitable for human pharmaceutical use or for veterinary use. Another related embodiment is a method to make BrEA hemihydrate comprising precipitating BrEA from a solution comprising ethanol and water.

Invention embodiments include a composition comprising a compound of formula 1

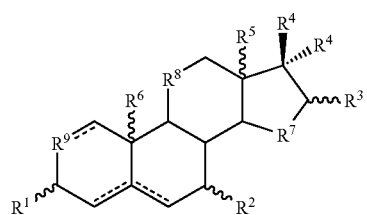

and one or more nonaqueous liquid excipients, wherein the composition comprises less than about 3% v/v water and wherein, $R^1$, $R^2$, $R^3$, $R^4$, $R^5$, $R^6$ and $R^{10}$ independently are —H, —$OR^{PR}$, —$SR^{PR}$, —$N(R^{PR})_2$, —O—Si—$(R^{13})_3$, —CN, —$NO_2$, an ester, a thioester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide, a polymer, or, one more of $R^1$, $R^2$, $R^3$, $R^4$, $R^5$, $R^6$, $R^{10}$, $R^{15}$, $R^{17}$ and $R^{18}$ are =O or =S and the hydrogen atom that is bonded to the same carbon atom is absent, or, $R^3$ and both $R^4$ together comprise a structure of formula 2

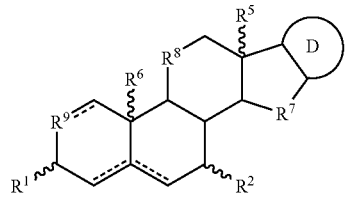

$R^7$ is —$CHR^{10}$—, —$CHR^{10}$—$CHR^{10}$—, —$CHR^{10}$—$CHR^{10}$—$CHR^{10}$—, —$CHR^{10}$—O—$CHR^{10}$—, —$CHR^{10}$—S—$CHR^{10}$—, —$CHR^{10}$—$NR^{PR}$—$CHR^{10}$—, —O—, —O—$CHR^{10}$—, —S—, —S—$CHR^{10}$—, —$NR^{PR}$— or —$NR^{PR}$—$CHR^{10}$—;

$R^8$ and $R^9$ independently are —$CHR^{10}$—, —$CHR^{10}$—$CHR^{10}$—, —O—, —O—$CHR^{10}$—, —S—, —S—$CHR^{10}$—, —$NR^{PR}$— or —$NR^{PR}$—$CHR^{10}$—, or $R^8$ or $R^9$ independently is absent, leaving a 5-membered ring;

$R^{13}$ independently is $C_{1-6}$ alkyl;

$R^{16}$ independently are —$CH_2$—, —O—, —S— or —NH—;

D is a heterocycle or a 4-, 5-, 6- or 7-membered ring that comprises saturated carbon atoms, wherein 1, 2 or 3 ring carbon atoms of the 4-, 5-, 6- or 7-membered ring are optionally independently substituted with —O—, —S— or —$NR^{PR}$— or where 1, 2 or 3 hydrogen atoms of the heterocycle or where 1 or 2 hydrogen atoms of the 4-, 5-, 6- or 7-membered ring are substituted with —$OR^{PR}$, —$SR^{PR}$, —$N(R^{PR})_2$, —O—Si—$(R^{13})_3$, —CN, —$NO_2$, an ester, a thioester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide or a polymer, or, one more of the ring carbons are substituted with =O or =S, or D comprises two 5- or 6-membered rings, wherein the rings are fused or are linked by 1 or 2 bonds.

In other embodiments, the invention provides a compound of formula 1, wherein two or three of $R^7$, $R^8$ and $R^9$ independently are not —$CHR^{10}$—, wherein the compound is optionally present in a composition that comprises one or more excipients suitable for human pharmaceutical use or for veterinary use.

Invention embodiments also include a compound of formula 1

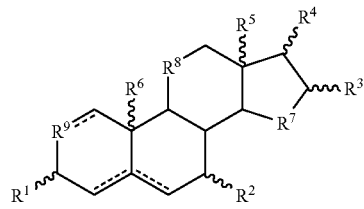

wherein, $R^1$, $R^2$, $R^3$, $R^4$, $R^5$, $R^6$ and $R^{10}$ independently are —H, —$OR^{PR}$, —$SR^{PR}$, —$N(R^{PR})_2$, —O—Si—$(R^{13})_3$, —CN, —$NO_2$, an ester, a thioester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide, a polymer, or, one, two or more of $R^1$, $R^2$, $R^3$, $R^4$, $R^5$, $R^6$ and $R^{10}$ independently are =O or =S and the hydrogen atom that is bonded to the same carbon atom is absent, or, $R^3$ and $R^4$ together comprise a structure of formula 2

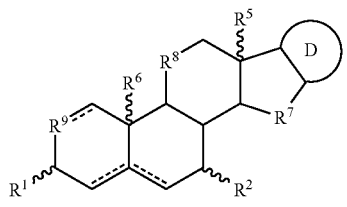

$R^7$ is —$CHR^{10}$—, —$CHR^{10}$—$CHR^{10}$—, —$CHR^{10}$—$CHR^{10}$—$CHR^{10}$—, —$CHR^{10}$—O—$CHR^{10}$—, —$CHR^{10}$—S—$CHR^{10}$—, —$CHR^{10}$—$NR^{PR}$—$CHR^{10}$—, —O—, —O—$CHR^{10}$—, —S—, —S—$CHR^{10}$—, —$NR^{PR}$— or —$NR^{PR}$—$CHR^{10}$—;

$R^8$ and $R^9$ independently are —$CHR^{10}$—, —$CHR^{10}$—$CHR^{10}$—, —O—, —O—$CHR^{10}$—, —S—, —S—$CHR^{10}$—, —$NR^{PR}$— or —$NR^{PR}$—$CHR^{10}$—, or $R^3$ or $R^9$ independently is absent, leaving a 5-membered ring;

$R^{13}$ independently is $C_{1-6}$ alkyl;

D is a heterocycle or a 4-, 5-, 6- or 7-membered ring that comprises saturated carbon atoms, wherein 1, 2 or 3 ring carbon atoms of the 4-, 5-, 6- or 7-membered ring are optionally independently substituted with —O—, —S— or —$NR^{PR}$— or where 1, 2 or 3 hydrogen atoms of the heterocycle or where 1 or 2 hydrogen atoms of the 4-, 5-, 6- or 7-membered ring are substituted with —$OR^{PR}$, —$SR^{PR}$, —N($R^{PR}$)$_2$, —O—Si—($R^{13}$)$_3$, —CN, —NO$_2$, an ester, a thioester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate, a carbamate, a thioacetal, a halogen, an optionally substituted alkyl group, an optionally substituted alkenyl group, an optionally substituted alkynyl group, an optionally substituted aryl moiety, an optionally substituted heteroaryl moiety, an optionally substituted monosaccharide, an optionally substituted oligosaccharide, a nucleoside, a nucleotide, an oligonucleotide or a polymer, or, one or more of the ring carbons are substituted with =O or =S, or D comprises two 5- or 6-membered rings, wherein the rings are fused or are linked by 1 or 2 bonds, wherein one, two or three of $R^7$, $R^8$ and $R^9$ are not —CH$R^{10}$—.

Other embodiments include a method to enhance the expression of one or more cytokines or interleukins that facilitate Th1 immune responses in a subject or to reduce the expression of one or more cytokines or interleukins that facilitate Th2 immune response in a subject comprising administering to the subject an effective amount of the composition, whereby the subject's Th1 immune response is enhanced or the subject's undesired Th2 immune response is reduced.

Embodiments include liquid formulations that comprise a formula 1 compound, one or more excipients and less than about 3% water, wherein the formulation is optionally disposed in containers that exclude water.

Another embodiment is a method comprising intermittent administration of a formula 1 compound, to a subject having a pathological condition, such as a viral or parasite infection.

A further embodiment is a method to modulate a subject's innate immunity, Th1 immune responses or Th2 immune responses comprising administering a formula 1 compound to a subject.

Other embodiments are as described in the specification including the appended numbered embodiments and the claims.

DETAILED DESCRIPTION OF THE INVENTION

Definitions. As used herein and unless otherwise stated or implied by context, the following terms have the meanings defined here.

An "invention formulation" or "formulation" means an invention composition that one can administer parenterally to a human or animal without further manipulations that change the ingredients or the ingredient proportions that are present. Formulations are suitable for human or veterinary applications.

An "invention composition" is a composition, that is an intermediate one can use to make the invention formulations, i.e., a change(s) in an ingredient(s) or its amount(s) is needed to make a formulation. Thus, invention compositions include compositions where further processing is required before it is a formulation, e.g., mixing or addition of a desired amount of an ingredient.

An "excipient" means a component or an ingredient that is acceptable in the sense of being compatible with the other ingredients of invention compositions or formulations and not overly deleterious to the patient or animal to which the formulation is to be administered. As used here, "excipients" include liquids, such as benzyl benzoate, cottonseed oil, N,N-dimethylacetamide, a $C_{2-12}$ alcohol (e.g., ethanol), glycerol, peanut oil, a polyethylene glycol ("PEG"), vitamin E, poppyseed oil, propylene glycol, safflower oil, sesame oil, soybean oil and vegetable oil. Excipients, as used herein will optionally exclude chloroform, dioxane, vegetable oil, DMSO or any combination of these. Excipients comprise one or more components typically used in the pharmaceutical formulation arts, e.g., fillers, binders, disintegrants and lubricants.

A "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, felines, e.g., domestic cat, canines, e.g., dog, avians, e.g., chicken, emu, ostrich, and fish, e.g., trout, catfish and salmon. Subject includes any subset of the foregoing, e.g., all of the above, but excluding one or more groups or species such as humans, primates or rodents.

Expressions that refer to "a formula 1 compound(s)" or "a formula 1 compound" mean invention compositions or formulations where one or more than one formula 1 compound is present, typically 1, 2, 3 or 4, usually 1.

"Alkyl" as used here means linked normal, secondary, tertiary or cyclic carbon atoms, i.e., linear, branched or cyclic. The number of carbon atoms in an alkyl group or moiety is 1 to about 20, unless otherwise specified, e.g., $C_{1-8}$ alkyl means an alkyl moiety containing 1, 2, 3, 4, 5, 6, 7 or 8 carbon atoms. Examples include methyl, ethyl, 1-propyl (n-propyl), 2-propyl (1-propyl, —CH(CH$_3$)$_2$), 1-butyl (n-butyl), 2-methyl-1-propyl (i-butyl, —CH$_2$CH(CH$_3$)$_2$), 2-butyl (s-butyl, —CH(CH$_3$)CH$_2$CH$_3$), 2-methyl-2-propyl (t-butyl, —C(CH$_3$)$_3$), 1-pentyl (n-pentyl), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl, 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), cyclopropyl, cyclobutyl, cyclopentyl and cyclohexyl.

"Alkenyl" means linked normal, secondary, tertiary or cyclic carbon atoms where one or more double bonds (e.g., —CH=CH—) are present, typically 1, 2 or 3, usually 1 or 2. The number of carbon atoms in an alkenyl group or moiety is 2 to about 20, unless otherwise specified, e.g., $C_{1-8}$ alkenyl means an alkenyl moiety containing 1, 2, 3, 4, 5, 6, 7 or 8 carbon atoms.

"Alkynyl" means linked normal, secondary, tertiary or cyclic carbon atoms where one or more triple bonds (—C≡C—) are present, typically 1, 2 or 3, usually 1. The number of carbon atoms in an alkynyl group or moiety is 2 to about 20, unless otherwise specified, e.g., $C_{1-8}$ alkynyl means an alkynyl moiety containing 1, 2, 3, 4, 5, 6, 7 or 8 carbon atoms.

"Aryl" means phenyl or naphthyl.

"Substituted alkyl", "substituted alkenyl" and "substituted alkynyl" mean an alkyl, alkenyl or alkynyl group that has a substituent(s) linked to a carbon atom or substituent(s) that interrupt a carbon atom chain. Substituents include ethers (—O—), ketones (—C(O)—), —O$R^{PR}$, —C(O)O$R^{PR}$, —C(O)O—, —C(S)O$R^{PR}$, —C(S)O—, —OC(O)—, —C(O)H, —OCH$_2$—, —OCH$_2$CH$_2$—, —OCH$_2$O—, —OCH$_2$CH$_2$O—, —NR$^{PR}$—, —N(R$^{PR}$)$_2$, —NHR$^{PR}$, —NHC(O)—, —CH$_2$—NR$^{PR}$—, —CH$_2$—NHR$^{PR}$, —CH$_2$—NHC(O)—, —C(O)NH—, —C(O)NHR$^{PR}$, —OC(O)NR$^{PR}$—, —OC(O)NHR$^{PR}$, —NR$^{PR}$C(O)NR$^{PR}$—, —NR$^{PR}$C(O)NHR$^{PR}$, —NR$^{PR}$CH$_2$—, —NR$^{PR}$CH$_2$CH$_2$, —S—SR$^{PR}$, —S(O)—, —S(O)(O)—, —S(O)OR$^{PR}$, —S(O)H, —CN, —NO$_2$, halogen, and combinations of these moieties where R$^{PR}$ independently is hydrogen, a protecting group or both R$^{PR}$ together are a protecting group. Substituents are independently chosen when more than one is present. Alkenyl and alkynyl groups that comprise a substituent(s), are typically substituted at a carbon that is one or more methylene moiety removed from the double bond, e.g., separated at least by one, two or more —CH$_2$— moieties.

Heterocycle. "Heterocycle" or "heterocyclic" includes by way of example and not limitation the heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5566.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl.

"Heteroaryl" means an aromatic ring or two or more fused rings that contain one or more aromatic rings where the ring or fused rings comprise 1, 2, 3 or more heteroatoms, usually oxygen (—O—), nitrogen (—NX—) or sulfur (—S—) where X is —H, a protecting group or C$_{1-6}$ alkyl, usually —H. Examples are as described for heterocycle.

"Alcohol" as used herein, usually in the context of excipients, means an alcohol that comprises a C$_{2-12}$ alkyl moiety substituted at a hydrogen atom with one hydroxyl group. Alcohols include ethanol, n-propanol, i-propanol, n-butanol, i-butanol, s-butanol, t-butanol, n-pentanol, i-pentanol, n-hexanol, cyclohexanol, n-heptanol, n-octanol, n-nonanol and n-decanol. The carbon atoms in alcohols can be straight, branched or cyclic. Alcohol includes any subset of the foregoing, e.g., C$_{2-4}$ alcohols (alcohols having 2, 3 or 4 carbon atoms).

"Halogen" means fluorine, chlorine, bromine or iodine.

"Protecting group" means a moiety that prevents the atom to which it is linked from participating in unwanted reactions. For example, for —OR$^{PR}$, R$^{PR}$ may be hydrogen or a protecting group for the oxygen atom found in a hydroxyl, while for —C(O)—OR$^{PR}$, R$^{PR}$ may be hydrogen or a carboxyl protecting group, for —SR$^{PR}$, R$^{PR}$ may be hydrogen or a protecting group for sulfur in thiols for instance, and for —NHR$^{PR}$ or —N(R$^{PR}$)$_2$—, R$^{PR}$ may be hydrogen or a nitrogen atom protecting group for primary or secondary amines. Hydroxyl, amine and other reactive groups are found in formula 1 compounds at, e.g., R$^1$ or R$^2$. These groups may require protection against reactions taking place elsewhere in the molecule. The protecting groups for oxygen, sulfur or nitrogen atoms are usually used to prevent unwanted reactions with electrophilic compounds, such as acylating used, e.g., in steroid chemistry.

"Ester" means a moiety that comprises a —C(O)—O— structure. Typically, esters as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a formula 1 steroid nucleus at, e.g., R$^1$ or R$^2$ through the —C(O)—O— structure, e.g., organic moiety-C(O)—O-steroid or organic moiety-O—C(O)-steroid. The organic moiety usually comprises one or more of any of the organic groups described above, e.g., C$_{1-20}$ alkyl moieties, C$_{2-20}$ alkenyl moieties, C$_{2-20}$ alkynyl moieties, aryl moieties, C$_{2-9}$ heterocycles or substituted derivatives of any of these, e.g., comprising 1, 2, 3, 4 or more substituents, where each substituent is independently chosen. Typical substitutions for hydrogen or carbon atoms in these organic groups include 1, 2, 3, 4 or more, usually 1, 2, or 3-O—, —S—, —NR$^{PR}$— (including —NH—), —C(O)—, =O, =S, —N(R$^{PR}$)$_2$ (including —NH$_2$), —C(O)OR$^{PR}$ (including —C(O)OH), —OC(O)R$^{PR}$ (including —O—C(O)—H), —OR$^{PR}$ (including —OH), —SR$^{PR}$ (including —SH), —NO$_2$, —CN, —NHC(O)—, —C(O)NH—, —OC(O)—, —C(O)O—, —O-A8, —S-A8, —C(O)-A8, —OC(O)-A8, —C(O)O-A8, =N—, —N=, =N—OH, —OPO$_3$(R$^{PR}$)$_2$, —OSO$_3$H$_2$ or halogen moieties or atoms, where each R$^{PR}$ is —H, an independently selected protecting group or both R$^{PR}$ together comprise a protecting group, and A8 is C$_{1-8}$ alkyl, C$_{2-8}$ alkenyl, C$_{2-8}$ alkynyl, C$_{1-4}$ alkyl-aryl (e.g., benzyl), aryl (e.g. phenyl) or C$_{0-4}$ alkyl-C$_{2-9}$ heterocycle. Substitutions are independently chosen. The organic moiety includes compounds defined by the R$_4$ variable. The organic moieties exclude obviously unstable moieties, e.g., —O—O—, except where such unstable moieties are transient species that one can use to make a compound with sufficient chemical stability for one or more of the uses described herein. The substitutions listed above are typically substituents that one can use to replace one or more carbon atoms, e.g., —O— or —C(O)—, or one or more hydrogen atom, e.g., halogen, —NH$_2$ or —OH.

"Thioester" means a moiety that comprises a —C(S)—O— structure. Typically, thioesters as used here comprise an organic moiety containing about 1-50 carbon atoms (e.g., about 2-20 carbon atoms) and 0 to about 10 heteroatoms (e.g., O, S, N, P, Si), where the organic moiety is bonded to a formula 1 steroid nucleus at R$^2$ through the —C(S)—O— structure, e.g., organic moiety-C(S)—O-steroid or organic moiety-O—C(S)-steroid. The organic moiety is as described above for esters.

"Thioacetal" means a moiety that comprises a —C(O)—S— structure. Typically, thioacetals as used here comprise an organic moiety containing about 1-50 carbon atoms (e.g., about 2-20 carbon atoms) and 0 to about 10 heteroatoms (e.g., O, S, N, P, Si), where the organic moiety is bonded to a formula 1 steroid nucleus at R$^2$ through the —C(O)—S— structure, e.g., organic moiety-C(O)—S-steroid or organic moiety-S—C(O)-steroid. The organic moiety is as described above for esters.

"Phosphoester" or "phosphate ester" means a moiety that comprises a —O—P(OR$^{PR}$)(O)—O— structure where R$^{PR}$ is hydrogen (—H), a protecting group or an organic moiety as described for esters. Typically, phosphoesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —O—P(O)(O)—O— structure, e.g., organic moiety-O—P(O)(OH)—O-steroid. The organic moiety is as described above for esters.

"Phosphothioester" means a moiety that comprises a —O—P(SR$^{PR}$)(O)—O— structure where R$^{PR}$ is —H, a protecting group or an organic moiety as described for esters. Typically, phosphothioesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —O—P(O)(O)—O— structure, e.g., organic moiety-O—P(O)(SH)—O-steroid. The organic moiety is as described above for esters.

"Phosphonoester" means a moiety that comprises a —P(OR$^{PR}$)(O)—O— structure where R$^{PR}$ is —H, a protecting group or an organic moiety as described for esters. Typically, phosphonoesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —P(OR$^{PR}$)(O)—O— structure, i.e., organic moiety-P(OR$^{PR}$)(O)—O-steroid or steroid-P(OR$^{PR}$)(O)—O-organic moiety. The organic moiety is as described above for esters.

"Phosphiniester" means a moiety that comprises a —P(OR$^{PR}$)—O— structure where R$^{PR}$ is —H, a protecting group or an organic moiety as described for esters. Typically, phosphiniesters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —P(OR$^{PR}$)—O— structure, i.e., organic moiety-P(OR$^{PR}$)—O-steroid or steroid-P(OR$^{PR}$)—O-organic moiety. The organic moiety is as described above for esters.

"Sulfate ester" means a moiety that comprises a —O—S(O)(O)—O— structure. Typically, sulfate esters as used here comprise a hydrogen atom, a protecting group or an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —O—S(O)(O)—O— structure, e.g., organic moiety-O—S(O)(O)—O-steroid. The organic moiety is as described above for esters.

"Sulfite ester" means a moiety that comprises a —O—S(O)—O— structure. Typically, sulfite esters as used here comprise an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —O—S(O)—O— structure, e.g., organic moiety-O—S(O)—O-steroid. The organic moiety is as described above for esters.

"Thioacetal" means a moiety that comprises a —S—C(O)— structure. Typically, thioacetal groups as used here comprise an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —S—C(O)— structure, e.g., organic moiety-S—C(O)-steroid or steroid-S—C(O)-organic moiety. The organic moiety is as described above for esters.

"Amide" means an organic moiety as described for ester that comprises 1, 2, 3, 4 or more —C(O)—NR$^{PR}$— moieties, usually 1 or 2, where R$^{PR}$ is —H or a protecting group, R$^{PR}$ is usually H. In some embodiments, the —C(O)NR$^{PR}$— group is linked to the steroid nucleus at R$^1$-R$^6$, R$^{10}$, R$^{15}$, R$^{17}$ or R$^{18}$, i.e., organic moiety-C(O)NR$^{PR}$-steroid or steroid-C(O)NR$^{PR}$-organic moiety.

"Ether" means an organic moiety as described for ester that comprises 1, 2, 3, 4 or more —O— moieties, usually 1 or 2. In some embodiments, the —O— group is linked to the steroid nucleus at R$^1$-R$^6$, R$^{10}$, R$^{15}$, R$^{17}$ or R$^{18}$, e.g., organic moiety-O-steroid.

"Thioether" means an organic moiety as described for ester that comprises 1, 2, 3, 4 or more —S— moieties, usually 1 or 2. In some embodiments, the —S— group is linked to the steroid nucleus at R$^1$-R$^6$, R$^{10}$, R$^{15}$, R$^{17}$ or R$^{18}$, e.g., organic moiety-S-steroid.

"Acyl group" means an organic moiety as described for ester that comprises 1, 2, 3, 4 or more —C(O)— groups. In some embodiments, the —C(O)— group is linked to the steroid nucleus at R$^1$-R$^6$, R$^{10}$, R$^{15}$, R$^{17}$ or R$^{18}$, e.g., organic moiety-C(O)-steroid.

"Thioacyl" means an organic moiety as described for ester that comprises 1, 2, 3, 4 or more —C(S)— groups. In some embodiments, the —C(S)— group is linked to the steroid nucleus at R$^1$-R$^6$, R$^{10}$, R$^{15}$, R$^{17}$ or R$^{18}$, e.g., organic moiety-C(S)-steroid.

"Carbonate" means an organic moiety as described for ester that comprises 1, 2, 3, 4 or more —O—C(O)—O— structures. Typically, carbonate groups as used here comprise an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, R$^{17}$ or R$^{18}$ through the —O—C(O)—O— structure, e.g., organic moiety-O—C(O)—O-steroid.

"Carbamate" means an organic moiety as described for ester that comprises 1, 2, 3, 4 or more —O—C(O)NR$^{PR}$— structures where R$^{PR}$ is —H, a protecting group or an organic moiety as described for ester. Typically, carbamate groups as used here comprise an organic moiety containing about 1-50 carbon atoms and 0 to about 10 heteroatoms (e.g., O, S, N, P, Si) linked to a formula 1 steroid nucleus at R$^1$-R$^6$, R$^{10}$, R$^{15}$, $R^{17}$ or $R^{18}$ through the —O—C(O)—$NR^{PR}$— structure, e.g., organic moiety-O—C(O)—$NR^{PR}$-steroid or steroid-O—C(O)—$NR^{PR}$-organic moiety.

As used herein, "monosaccharide" means a polyhydroxy aldehyde or ketone having the empirical formula $(CH_2O)_n$ where n is 3, 4, 5, 6 or 7. Monosaccharide includes open chain and closed chain forms, but will usually be closed chain forms. Monosaccharide includes hexofuranose and pentofuranose sugars such as 2'-deoxyribose, ribose, arabinose, xylose, their 2'-deoxy and 3'-deoxy derivatives and their 2',3'-dideoxy derivatives. Monosaccharide also includes the 2',3' dideoxydidehydro derivative of ribose. Monosaccharides include the D-, L- and DL-isomers of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone and their monodeoxy derivatives such as rhamnose. Monosaccharides are optionally protected or partially protected.

Optionally substituted alkyl group, optionally substituted alkenyl group, optionally substituted alkynyl group, optionally substituted aryl moiety and optionally substituted heterocycle mean substitutions that include $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these. Typical substitutions for these organic groups include 1, 2, 3, 4 or more, usually 1 or 2, —O—, —S—, —$NR^{PR}$—, —C(O)—, —$N(R^{PR})_2$, —C(O)$OR^{PR}$, —OC(O)$R^{PR}$, —$OR^{PR}$, —$SR^{PR}$, —$NO_2$, —CN, —NHC(O)—, —C(O)NH—, —OC(O)—, —C(O)O—, —O-A8, —S-A8, —C(O)-A8, —OC(O)-A8, —C(O)O-A8, =N—, —N=, —$OPO_2R^{PR}$, —$OSO_3H$ or halogen moieties or atoms, where $R^{PR}$ independently is —H, a protecting group or both $R^{PR}$ together are a protecting group and A8 is $C_{1-8}$ alkyl, $C_{1-8}$ alkenyl, $C_{1-8}$ alkynyl, $C_{1-4}$ alkyl-aryl (e.g., benzyl), aryl (e.g. phenyl) or $C_{1-4}$ alkyl-$C_{1-5}$ heterocycle. Substitutions are independently chosen. The organic moieties as described here, and for other any other moieties described herein, exclude obviously unstable moieties, e.g., —O—O—, except where such unstable moieties are transient species that one can use to make a compound with sufficient chemical stability for the one or more of the uses described herein.

Optionally substituted "monosaccharide" comprise any C3-C7 sugar, D-, L- or DL-configurations, e.g., erythrose, glycerol, ribose, deoxyribose, arabinose, glucose, mannose, galactose, fucose, mannose, glucosamine, N-acetylneuraminic acid, N-acetylglucosamine, N-acetylgalactosamine that is optionally substituted at one or more hydroxyl groups. Suitable substitutions include hydrogen, protected hydroxyl, carboxyl, azido, cyano, —O—$C_{1-6}$ alkyl, —S—$C_{1-6}$alkyl, —O—$C_{2-6}$ alkenyl, —S—$C_{2-6}$ alkenyl, optionally protected amine, optionally protected carboxyl, halogen, thiol or protected thiol. The linkage between the monosaccharide the steroid is α or β.

Optionally substituted "oligosaccharide" comprises two, three, four or more of any $C_3$-$C_7$ sugars that are covalently linked to each other. The linked sugars may have D-, L- or DL-configurations. Suitable sugars and substitutions are as described for monosaccharides. The linkage between the oligosaccharide and the steroid is α or β, as are the linkages between the monosaccharides that comprise the oligosaccharide.

Nucleoside includes 3TC, AZT, D4T, ddI, ddC, G, A, U, C, T, dG, dA, dT and dC.

Polymer includes biocompatible organic polymers, e.g., PEGs and polyhydroxyalkyl polymers.

PEG means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG 200, PEG 300, PEG400, PEG500, PEG600, PEG1000, PEG1500, PEG2000, PEG 3350, PEG4000, PEG4600, PEG5000, PEG6000, PEG8000, PEG11000, PEG12000, PEG2000000 and any mixtures thereof.

Amino acid. "Amino acid" means an amino acid moiety that comprises any naturally-occurring or synthetic amino acid residue, i.e., any moiety comprising at least one carboxyl and at least one amino residue directly linked by one, two three or more carbon atoms, typically one (α) carbon atom. The nature and identity of the intervening structure located between the carboxyl and amino groups can have a variety of structures including those described herein. Typically, amino acids linked to the steroid through the amine group have sufficient conformation and length to be capable of autocatalytic hydrolysis of the amino acid-steroid bond and release of the steroid. This can occur when the free carboxyl is generated in vivo by deesterification, deamidation or peptidolytic cleavage of the precursor containing a linkage between the amino acid's amine group and the steroid. Hydrolysis of the bond between an amino acid's carboxyl or amino group and the steroid can also occur by chemical or enzymatic activity, e.g., esterase cleavage or non-enzymatic hydrolysis.

In general, the amino acids corresponding to the residues employed in the invention compounds are naturally occurring and have no significant pharmacological activity per se. However, optimal pharmacokinetic activity, (substantially complete hydrolysis upon hydrolysis of the distal amide or ester bond) may be achieved by using non-naturally occurring amino acid residues. The intervening structure may be as simple as methylene when the amino acid residue is glycyl, or substituted methylene for other α amino acids. The structure ordinarily contains up to about 5 carbon or heteroatoms in the direct linkage between the amino acid's carboxyl carbon and the amine nitrogen. Thus, amino acids can comprise intervening ethylene, propylene, butylene, or pentylene groups or their substituted analogs, such as for example, oxyesters or ethers in which oxygen replaces carbon and, as appropriate, hydrogen. An example of such an intervening structure would be —CH—O—C($R^{22}$)($R^{23}$)—, where $R^{22}$ and $R^{23}$ are independently selected hydrogen or organic moieties as described above for esters. In some embodiments one of $R^{22}$ and $R^{23}$ is hydrogen and the other is a C2-20 organic moiety. Typically the organic moieties contain about 1-20 carbon atoms and 0, 1, 2, 3, 4 or 5 independently selected heteroatoms, which are typically selected from oxygen, nitrogen, sulfur and phosphorus. In general, fewer intervening atoms are used when more rapid hydrolysis is desired, although larger structures are suitable if, e.g., they possess sufficient flexibility or have conformations to allow positioning of the carboxyl group in proximity to the amino acid-steroid bond.

Ordinarily, $R^{22}$ is —H, methyl or hydroxymethyl, usually —H, and $R^{23}$ is a side chain or group of a naturally occurring amino acid. Amino acid side chains include analogs where the side chain is a $C_{1-15}$ homolog of the corresponding natural compound, e.g., methylene, ethylene, propylene, butylene or a substituted derivative thereof, e.g., an alkyl, ether or alkoxy (e.g., methoxy, ethoxy, propoxy) substituted derivative. In general, for carboxyl-containing side chains, if the C atom of the side chain carboxyl is linked by 5 or less atoms to the N then the carboxyl optionally will be blocked, e.g. by esterification or amidation wherein the ester or amide bonds are hydrolyzable in vivo. $R^{22}$ also is taken together with $R^{30}$ to form a proline residue $(-CH_2-)_3$. Thus, $R^{23}$ is generally a side group such as —H, —CH$_3$, —CH(CH$_3$)$_2$, —CH$_2$—CH (CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. $R^{23}$ also includes 1-guanidinoprop-3-yl, benzyl, 4-hydroxybenzyl, imidazol-4-yl, indol-3-yl, methoxyphenyl and ethoxyphenyl. The optimal $R^{30}$ group is readily selected using routine assays.

In general, the amino acid residue has the structure shown in the formulas below. Ordinarily, n is 1 or 2, $R^{22}$ is —H and $R^{23}$ is a moiety containing one or more of the following groups: amino, carboxyl, amide, carboxyl ester, hydroxyl, $C_6$-$C_7$ aryl, ether (—O—), thioether (—S—), n-, s- or t-alkyl ($C_1$-$C_6$), guanidinyl, imidazolyl, indolyl, sulfhydryl, sulfoxide, and phosphoryl. The $R^{22}$ and $R^{23}$ substituents can have a wide variety of structures including those disclosed herein, e.g., esters, ethers or carbonates.

When the amino acid residues contain one or more chiral centers, any of the D, L, meso, threo or erythro (as appropriate) racemates or mixtures thereof, fall within the scope of this invention. In general, if it is desired to rely on non-enzymatic means of hydrolysis, D isomers should be used. On the other hand, L isomers may be more versatile since they can be susceptible to both non-enzymatic as well as potential targeted enzymatic hydrolysis, and are more efficiently transported by amino acid or dipeptidyl transport systems in the gastrointestinal tract.

Examples of suitable amino acid residues include the following: Glycyl; aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues; amino acid amides such as glutaminyl and asparaginyl; polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine) and diaminobutyric acid residues; other basic amino acid residues such as histidinyl; diaminodicarboxylic acids such as α, α'-diaminosuccinic acid, α, α'-diaminoglutaric acid, α, α'-diaminoadipic acid, α, α'-diaminopimelic acid, α, α'-diamino-β-hydroxypimelic acid, α, α'-diaminosuberic acid, α, α'-diaminoazelaic acid, and α, α'-diaminosebacic acid residues; imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH$_2$]$_n$ COOR$^{PR}$)$_2$, wherein n is 1, 2, 3, 4, 5 or 6 and R$^{PR}$ is —H or a protecting group, and azetidine-2-carboxylic acid residues; a mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl; aliphatic α-amino-β-hydroxy acids such as serine, β-hydroxyleucine, β-hydroxynorleucine, β-hydroxynorvaline, and α-amino-β-hydroxystearic acid residues; α-Amino, α-, γ-, δ- or ε-hydroxy acids such as homoserine, γ-hydroxynorvaline, δ-hydroxynorvaline and epsilon-hydroxynorleucine residues; canavinyl and canalinyl; γ-hydroxyornithinyl; 2-Hexosaminic acids such as D-glucosaminic acid or D-galactosaminic acid residues; α-amino-β-thiols such as penicillamine, β-thiolnorvaline or β-thiolbutyrine residues; other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine; phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro, 2-hydroxy-5-nitro and p-nitro-phenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues; α-amino substituted amino acid residues including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention. Typically amino acids are capable of autocatalytically hydrolyzing the amino acid-steroid bond. Thus, they typically contain, or upon being hydrolyzed in vivo, contain a free carboxyl group or amine group.

Also of interest are hydrophobic amino acids such as mono- or di-alkyl or aryl amino acids, cycloalkylamino acids and the like. These residues, together with $R^{29}$-$R^{34}$ ($R^{31}$-$R^{34}$ are defined below) can contribute to cell permeability by modulating the lipophilicity of a formula 1 or formula 2 compound. Typically, the residue does not contain a sulfhydryl or guanidino substituent.

Peptide. One, 2, 3 or more of $R^1$-$R^4$ can comprise a "peptide", i.e., two or more amino acids as defined above. Typically the amino acids are linked through normal peptide bonds, i.e., —CO—NH—, between adjacent amino acid residues. Peptides comprise dipeptides (dimers), tripeptides (trimers), short peptides of 4, 5, 6, 8, 10 or 15 residues, and longer peptides or proteins having about 100 or more residues. Invention compounds that comprise a peptide can be used as immunogens, prodrugs or as synthetic precursors for other steroid derivatives. In one embodiment, the peptide will contain a peptidolytic enzyme cleavage site at the peptide bond linking the first residue and the next residue distal to the steroid residue. Such cleavage sites are optionally flanked by enzymatic recognition structures, e.g. particular residues recognized by a hydrolytic enzyme, e.g., a peptidase located in the serum or in cells.

Peptidolytic enzymes are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide having a given pair of residues and a free carboxyl terminus is covalently bonded through its α-amino group to the steroid nucleus. It is expected that the peptide will be cleaved by the appropriate dipeptidase, protease or by chemical hydrolysis, leaving the carboxyl of the proximal amino acid residue to autocatalytically cleave the amidate bond.

Examples of suitable dipeptidyl groups (designated by their single letter symbols) are shown in the table below.

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

Dipeptides

AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY, VV

Such dipeptides include species where both amino acids are in the L configuration, the D configuration or mixtures of configurations.

Tripeptides, i.e., 3 linked amino acid residues, are also useful embodiments. Tripeptides include those where A, C, D, E, F, G, H, I, K, L, M, N, P, Q, R, S, T, V, W or Y is linked by a standard peptide bond to the amino or the carboxyl terminus of any of the dipeptides listed above. The sequence —X1-pro-X2-(where X1 is any amino acid and X2 is hydrogen, any amino acid residue or a carboxyl ester of proline) will be cleaved by luminal carboxypeptidase to yield X1 with a free carboxyl, which in turn autocatalytically cleaves the amidate bond. X2 usually will be a benzyl ester of the carboxy group of X2. Other embodiments include tetrapeptides such as ones where any two of the dipeptides listed above, which may be the same or different dipeptides (e.g., AA and AA linked together or, e.g., AA and GI linked together), are linked to each other by a peptide bond through the amino terminus or carboxyl terminus. One, 2 or more tetrapeptides may bond to the formula 1 or formula 2 compound through the tetrapeptide's amino or carboxyl terminus.

In some embodiments, the formula 1 or formula 2 compound comprises one or more amino acids or peptides having the structure (A), (B) or (C): (A) $R^{32}$—NH-$\{[C(R^{29})(R^{30})]_b$—C(O)—N(R$^{31}$)$\}_f$—[C(R$^{29}$)(R$^{30}$)]$_a$—C(O)—O-steroid, (B) $R^{33}$—O—$\{$C(O)—[C(R$^{29}$)(R$^{30}$)]$_d$—N(R$^{31}$)$\}_g$—C(O)—[C(R$^{29}$)(R$^{30}$)]$_c$—N(R$^{31}$)—O-steroid, or (C) $R^{33}$—O—$\{$C(O)—[C(R$^{29}$)(R$^{30}$)]$_d$—N(R$^{31}$)$\}_e$—C(O)—[C(R$^{29}$)(R$^{30}$)]$_c$—N(R$^{31}$)—C(O)—O-steroid, wherein (A), (B) or (C) are independently selected and they are bonded to 1, 2, 3 or more of $R^1$ through $R^4$, where each $R^{29}$-$R^{31}$ is independently selected; $R^{29}$ independently are —H or a $C_{1-20}$ organic moiety (e.g., $C_{1-6}$ alkyl, e.g. —CH$_3$ or —C$_2$H$_5$); $R^{30}$ independently are the side chain of an amino acid, including the side chain of naturally occurring amino acids as described above, e.g., —H, —CH$_3$, —CH$_2$C$_6$H$_5$; $R^{31}$ is —H or a protecting group;

$R^{32}$ and $R^{33}$ independently comprise —H, a protecting group, an ester or an amide where each atom or group is independently chosen; a, b, c and d independently are 1, 2, 3, 4 or 5, usually 1; e, f and g independently are an integer from 0 to about 1000, typically they independently are 0, 1, 2, 3, 4, 5, 6, 7 or 8; a, b, c and d independently are 1 or 2; e, f and g independently are 0, 1, 2, 3, 4 or 5.

If the amino acid(s) or residue(s) has 2 or more amine groups, e.g., a lysinyl or arginyl, or ornithinyl residue, then $R^{29}$ is usually —H and $R^{30}$ may comprise —$[C(R^{34})_2]_{n2}N$ ($R^{PR}$)— where n2 is 0, 1, 2, 3, 4, 5 or 6, $R^{PR}$ is —H or a protecting group and each $R^{34}$ independently is —H, $C_1$-$C_{20}$ optionally substituted alkyl, $C_6$-$C_{20}$ optionally substituted aryl, $C_7$-$C_{20}$ optionally substituted alkylaryl, $C_7$-$C_{20}$ optionally substituted arylalkyl, $C_1$-$C_{20}$ optionally substituted alkoxy, $C_6$-$C_{20}$ optionally substituted aryloxy or hydroxyl. Such compounds will contain a plurality of steroid moieties. For example when both the epsilon (ε) or delta (δ) and alpha (α) amino groups of lysine or ornithine are substituted with steroid moieties the amidate is believed to be capable of releasing two molecules of active drug, each expected to emerge under different pharmacokinetics and therefore further sustaining the drug release.

Salt. Invention embodiments include salts and complexes of invention compounds (formula 1 compounds), including pharmaceutically acceptable or salts that are relatively non-toxic. Some of the invention compounds have one or more moieties that carry at least a partial positive or negative charge in aqueous solutions, typically at a pH of about 4-10, that can participate in forming a salt, a complex, a composition with partial salt and partial complex properties or other noncovalent interactions, all of which we refer to as a "salt(s)". Salts are usually biologically compatible or pharmaceutically acceptable or non-toxic, particularly for mammalian cells. Salts that are biologically toxic are optionally used with synthetic intermediates of invention compounds. When a water-soluble composition is desired, monovalent salts are usually used.

Metal salts typically are prepared by reacting the metal hydroxide with a compound of this invention. Examples of metal salts that are optionally prepared in this way are salts containing $Li^+$, $Na^+$, and $K^+$. A less soluble metal salt can be precipitated from the solution of a more soluble salt by adding a suitable metal compound. Invention salts may be formed from acid addition of certain organic acids, such as organic carboxylic acids, and inorganic acids, such as alkylsulfonic acids or hydrogen halide acids, to acidic or basic centers on invention compounds, such as basic centers on the invention pyrimidine base analogs. Metal salts include ones containing $Na^+$, $Li^+$, $K^+$, $Ca^{++}$ or $Mg^{++}$. Other metal salts may contain aluminum, barium, strontium, cadmium, bismuth, arsenic or zinc ion.

Salt(s) of invention compounds may comprise a combination of appropriate cations such as alkali and alkaline earth metal ions or ammonium and quaternary ammonium ions with the acid anion moiety of the phosphoric acid or phosphonic acid group, which may be present in invention polymers or monomers.

Salts are produced by standard methods, including dissolving free base in an aqueous, aqueous-alcohol or aqueous-organic solution containing the selected acid, optionally followed by evaporating the solution. The free base is reacted in an organic solution containing the acid, in which case the salt usually separates directly or one can concentrate the solution.

Suitable amine salts include amines having sufficient basicity to form a stable salt, usually amines of low toxicity including trialkyl amines (tripropylamine, triethylamine, trimethylamine), procaine, dibenzylamine, N-benzyl-betaphenethylamine, ephenamine, N,N'-dibenzylethylenediamine, N-ethylpiperidine, benzylamine and dicyclohexylamine.

Salts include organic sulfonic acid or organic carboxylic acid salts, made for example by addition of the acids to basic centers, typically amines. Exemplary sulfonic acids include $C_{6-16}$ aryl sulfonic acids, $C_{6-16}$ heteroaryl sulfonic acids and $C_{1-16}$ alkyl sulfonic acids such as phenyl sulfonic acid, α-naphthalene sulfonic acid, β-naphthalene sulfonic acid, (S)-camphorsulfonic acid, methyl ($CH_3SO_3H$), ethyl ($C_2H_5SO_3H$), n-propyl, i-propyl, n-butyl, s-butyl, i-butyl, t-butyl, pentyl and hexyl sulfonic acids. Exemplary organic carboxylic acids include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic and 2-phenoxybenzoic.

Invention salts include those made from inorganic acids, e.g., HF, HCl, HBr, $H_1$, $H_2SO_4$, $H_3PO_4$, $Na_2CO_3$, $K_2CO_3$, $CaCO_3$, $MgCO_3$ and $NaClO_3$. Suitable anions, which are optionally present with a cation such a $Ca^{++}$, $Mg^{++}$, $Li^+$, $Na^+$ or $K^+$, include arsenate, arsenite formate, sorbate, chlorate, perchlorate, periodate, dichromate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, thiocyanate, silicate, metasilicate, $CN^-$, gluconate, gulcuronate, hippurate, picrate, hydrosulfite, hexafluorophosphate, hypochlorite, hypochlorate, borate, metaborate, tungstate and urate.

Salts also include the invention compound salts with one or more amino acids. Many amino acids are suitable, especially the naturally-occurring amino acids found as protein components, although the amino acid typically is one bearing a side chain with a basic or acidic group, e.g., lysine, arginine, histidine or glutamic acid, or a neutral group such as glycine, serine, threonine, alanine, isoleucine, or leucine.

The invention compositions include compounds in their un-ionized, as well as zwitterionic form, and combinations with stoiochimetric amounts of water as in hydrates.

Stereoisomers. The compounds of the invention (formula 1 compounds) include enriched or resolved optical isomers at any or all asymmetric atoms as are apparent from the depictions. Both racemic and diasteromeric mixtures, as well as the individual optical isomers can be isolated or synthesized so as to be substantially free of their enantiomeric or diastereomeric partners, and these are all within the scope of the invention. Chiral centers may be found in invention compounds at, for example, $R^1$, $R^2$, $R^3$ and $R^4$.

One or more of the following methods are used to prepare the enantiomerically enriched or pure isomers herein. The methods are listed in approximately their order of preference, i.e., one ordinarily should employ stereospecific synthesis from chiral precursors before chromatographic resolution before spontaneous crystallization.

Stereospecific synthesis is described in the examples. Methods of this type conveniently are used when the appropriate chiral starting material is available and reaction steps are chosen do not result in undesired racemization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis.

If a suitable stereospecific synthesis cannot be empirically designed or determined with routine experimentation then those skilled in the art would turn to other methods. One method of general utility is chromatographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—International Symposium on Chiral Separations, Sep. 3-4, 1987. Examples of chiral columns that could be used to screen for the optimal separation technique would include Diacel Chriacel OD, Regis Pirkle Covalent D-phenylglycine, Regis Pirkle Type 1A, Astec Cyclobond II, Astec Cyclobond III, Serva Chiral D-DL=Daltosil 100, Bakerbond DNBLeu, Sumipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desirable to employ embodiments of the compounds of this invention in which the charges are not neutralized, e.g., where acidic functionalities such as carboxyl are not esterified or amidated.

Another method entails converting the enantiomers in the mixture to diasteriomers with chiral auxiliaries and then separating the conjugates by ordinary column chromatography. This is a very suitable method, particularly when the embodiment contains free carboxyl, amino or hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group. For example, pure D or L amino acids can be used to amidate the carboxyl group of invention embodiments that comprise a carboxyl group and then separated by chromatography.

Enzymatic resolution is another method of potential value. In such methods one prepares covalent derivatives of the enantiomers in the racemic mixture, generally lower alkyl esters (for example of carboxyl), and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enantiomeric mixture separates from solution or a melt as a conglomerate, i.e., a mixture of enantiomerically pure crystals, then the crystals can be mechanically separated, thereby producing the enantiomerically enriched preparation. This method, however, is not practical for large-scale preparations and is of limited value for true racemic compounds.

Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Further guidance in the separation of enantiomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4): Part 2, Resolution of Enantiomer Mixture, pages 217-435; more particularly, section 4, Resolution by Direct Crystallization, pages 217-251, section 5, Formation and Separation of Diastereomers, pages 251-369, section 6, Crystallization-Induced Asymmetric Transformations, pages 369-378, and section 7, Experimental Aspects and Art of Resolutions, pages 378-435; still more particularly, section 5.1.4, Resolution of Alcohols, Transformation of Alcohols into Salt—Forming Derivatives, pages 263-266, section 5.2.3, Covalent Derivatives of Alcohols, Thiols, and Phenols, pages 332-335, section 5.1.1, Resolution of Acids, pages 257-259, section 5.1.2, Resolution of Bases, pages 259-260, section 5.1.3, Resolution of Amino Acids, page 261-263, section 5.2.1, Covalent Derivatives of Acids, page 329, section 5.2.2, Covalent derivatives of Amines, pages 330-331, section 5.2.4, Covalent Derivatives of Aldehydes, Ketones, and Sulfoxides, pages 335-339, and section 5.2.7, Chromatographic Behavior of Covalent Diastereomers, pages 348-354.

Unless otherwise stated or implied by context, expressions of a percentage of a liquid ingredient, e.g., an excipient, in an invention composition or formulation mean the ingredient's percent by volume (v/v). Thus, 20% propylene glycol means 20% v/v propylene glycol is present in an invention composition or formulation. The amount of excipient indicated in invention compositions is not affected by the form used, e.g., NF or USP grade solvent or excipient. Thus, an invention composition that comprises about 30% polyethylene glycol 300 NF can instead comprise a USP counterpart, provided that other limitations, such as the amount of water present, are not exceeded.

As used herein, "innate immunity" refers to one or more components typically associated with nonspecific immune defense mechanisms in a subject. These components include the alternate complement pathway, e.g., Factor B, Factor D and properdin; NK cells, phagocytes (monocytes, macrophages), neutrophils, eosinophils, dendritic cells, fibrocytes; anti-microbial chemicals, e.g., defensins; physical barriers—skin, mucosal epithelium; and certain interleukins, chemokines and cytokines. Innate immunity plays a role in resistance to intracellular parasite infections, e.g., white blood cell infection, a liver infection, and other infections, e.g., lymph node infections. Enhancement of innate immunity mechanism by formula 1 compounds or method described herein may enhance phagolysosome fusion or movement, which some pathogens, e.g., intracellular bacteria such as mycobacteria, or *Listeria* inhibit.

As used herein, references to CD molecules, specific immune cell subsets, immune responses and the like, generally use nomenclature that applies to molecules, cells or the like that are found in humans. Analogs or counterparts of such molecules, cells or the like in other species may have a differing nomenclature, but are included in this invention. A description of the nomenclature and function of various CD molecules and immune cell subsets are as found in the scientific literature. References to Th0, Th1 or Th2 cells and references to Th1 or Th2 immune responses in the context of human patients refers to the human counterparts of the murine Th0, Th1 or Th2 immune cells or responses. For reviews see, e.g., A. K. Abbas et al., editors, *Cellular and Molecular Immunology*, W.B. Saunders Company, third edition, 1997, ISBN 0-7216-4024-9, pages 4-469, and 1. Kimber and M. K. Selgrade, editors, *T Lymphocyte Subpopulations in Immunotoxicology*, John Wiley & Sons Ltd., 1998, ISBN 0-471-97194-4, pages 1-53.

"Immunosuppressive molecule" means molecules such as cyclosporin, cyclohexamide, mitomycin C, adriamycin, taxol and amphotericin B. These molecules tend to have toxicities toward the immune system and are directly or indirectly immunosuppressive, i.e., toxic to dividing cells or they can downregulate immunity.

"Steroid receptor" means a gene product, typically a protein monomer or dimer that can bind to a ligand, e.g., a natural steroid or an analog thereof, such as formula 1 compounds. Steroid receptors include orphan steroid receptors. Orphan steroid receptors are proteins for which the natural ligand or biological function is at least partially unknown. As used here, steroid receptors include homodimers, e.g., SXR and $(CAR\beta)_2$, and heterodimers, e.g., PXR-CAR$\beta$ or RXR-CAR$\beta$. Steroid receptors also include isoforms, e.g., PXR.1 and PXR.2 for the PXR receptor, and homologs of the steroid receptors, e.g., the homolog of CAR$\beta$ known as MB67. Isoforms are typically generated by different splicing pathways for a nuclear RNA from one gene, while homologs are typically a distinct copy of a steroid receptor gene, where the gene copy encodes only relatively small differences compared to the reference steroid receptor gene product. Such differences are most often found in areas other than the dimerization region and the steroid binding region of the steroid receptor's structure. Typically isoforms and homologs bind the same or similar ligands as the reference gene product or steroid receptor. Steroid receptors may be of human or animal origin, e.g., obtained from cells, tissues or cDNA expression libraries derived from cells or tissues of any primate, rodent (including murine), avian, ovine, bovine, equine, canine or feline species or any of the species or any species within any group (e.g., Family or Genus) of species mentioned elsewhere herein or in any reference cited herein.

In the context of a combination of molecules that includes a steroid receptor and a formula 1 compound, "invention complexes" or "complexes" means a complex that comprises a steroid receptor and a formula 1 compound and optionally other molecules. These other molecules include (i) a DNA recognition sequence ("DNARS" hereafter), i.e., a sequence that the steroid receptor specifically recognizes and binds to and (ii) a transcription factor that can bind to the steroid receptor-formula 1 compound complex. As used herein, these complexes can arise in cells in vitro or in vivo, or in cell-free systems. Complexes include, for example, steroid receptor heterodimer-formula 1 compound combinations, steroid receptor homodimer-formula 1 compound combinations, steroid receptor monomer-formula 1 compound combinations, steroid receptor heterodimer-formula 1 compound-DNA (or DNARS) combinations, steroid receptor homodimer-formula 1 compound-DNA (or DNARS) combinations, steroid receptor heterodimer-formula 1 compound-transcription factor combinations, steroid receptor homodimer-formula 1 compound-transcription factor combinations, steroid receptor heterodimer-formula 1 compound-DNA (or DNARS)-transcription factor combinations and steroid receptor homodimer-formula 1 compound-DNA (or DNARS)-transcription factor combinations.

An "agonist" or an "antagonist" is a compound or composition that respectively, either increases or decreases the activity of a receptor, which can lead to increased or decreased transcription of a regulated gene. Receptors (and transcription factors) can modulate transcription of their target gene(s) by enhancing transcription or decreasing it.

General methods. Methods have been described, for example Karl Fischer (KF) and loss on drying (LOD), to determine the content of water or solvents in various compositions. LOD measures all volatiles in a sample, while KF is typically used to measure all water. When water is the only volatile present, LOD values are equal to or less than KF values for a given composition. KF measures water in hydrates of a compound and LOD determines both water and the amount of other volatiles that may be present. Invention compositions and formulations are conveniently assayed for water content by KF titration (e.g., using a Metrohm 684 KF Coulometer or equivalent) according to a published procedure (*U.S. Pharmacopoeia*, vol. 23, 1995, chapter <921>, U.S. Pharmacopeial Convention, Inc., Rockville, Md.) and manufacturer's Coulometer instructions. The amount of material used in the assay, about 50-100 mg, is measured using a five place analytical balance (Sartorius, Model RC210D, or a suitable equivalent). The amounts of water specified in invention compositions and formulations is the amount obtained by KF analysis.

Powder X-ray diffraction (XRD) methods have been used to characterize various crystalline compounds (see, e.g., U.S. Pharmacopoeia, volume 23, 1995, <941>, p. 1843-1845, U.S. Pharmacopeial Convention, Inc., Rockville, Md.; Stout et al., *X-Ray Structure Determination; A Practical Guide*, MacMillan Co., New York, N.Y., 1986). The diffraction pattern, or portions thereof, obtained from a crystalline compound is usually diagnostic for a given crystal form, although weak or very weak diffraction peaks may not always appear in replicate diffraction patterns obtained from successive batches of crystals. Also, the relative intensities of XRD bands, particularly at low angle X-ray incidence values (low Theta), may vary due to preferred orientation effects arising from differences in, e.g., crystal habit, particle size or other measurement conditions. Peaks on XRD spectra are typically defined at a given Theta value +/−about 0.1 to 0.2. XRD information from the 1, 2, 3, 4, 5 or more main intensity XRD peaks, optionally combined with one or more other diagnostic data (melting point, DSC, IR), is usually suitable to characterize or describe a crystalline material such as BrEA hemihydrate from other crystal forms that contain the same compound.

Other techniques that are used to identify or describe a crystalline material such as BrEA hemihydrate include melting point (MP), differential scanning calorimetry (DSC) and infrared absorption spectroscopy (IR) data. DSC measures thermal transition temperatures at which a crystal absorbs or releases heat when its crystal structure changes or it melts. MP data and DSC thermal transition temperatures are typically reproducible within about 1 or 2° C. on successive analyses. IR measures absorption of infrared light that is associated with the presence of particular chemical bonds that are associated with groups, e.g., hydroxyl, that vibrate in response to particular light wavelengths.

INVENTION EMBODIMENTS

The invention provides BrEA hemihydrate, which is typically substantially free of other forms of BrEA, such as amorphous BrEA or anhydrous BrEA. As used herein, BrEA hemihydrate or crystalline BrEA hemihydrate refers to solid BrEA and water having an ordered arrangement of substantially all of the constituent molecules in a defined three-dimensional spatial pattern or lattice. Crystalline BrEA hemihydrate may comprise one or more crystal habits, e.g., tablets, rods, plates or needles. BrEA hemihydrate that is substantially free of other forms of BrEA means a dry or substantially dry (where a liquid(s) comprises less than about 10% w/w of the total weight) solid preparation where more than about 55% w/w of the BrEA in the preparation is present as BrEA hemihydrate. Such compositions typically comprise at least about 60% w/w, or at least about 70% w/w, or at least about 80% w/w, usually at least about 90% w/w or at least about 95% w/w, or at least about 98% w/w of BrEA hemihydrate, with the remaining BrEA being present as other forms of BrEA such as the amorphous or anhydrous BrEA. Solid BrEA hemihydrate will typically comprise at least about 90% w/w, usually at least about 97% or about 98% w/w of the compound and less than about 10% w/w, usually less than about 3% or 2% w/w of by-products, which may include the 16β isomer of BrEA or one or more by-products of BrEA synthesis. Often the amount of solid BrEA that is present in a solid or a liquid medium will not contain detectable amounts of other forms of BrEA (using standard analytical methods such as, e.g., FTIR, DSC or XRD) and the hemihydrate will may thus comprise about 99-100% w/w of the total amount of BrEA that is present.

Other invention embodiments include compositions that comprise a substantial amount of BrEA hemihydrate that is present in compositions that comprise one or more other forms of BrEA, e.g., amorphous BrEA or anhydrous BrEA, and optionally one or more additional components, such as any excipient described herein. As used herein, the "substantial amount" of BrEA hemihydrate in these compositions comprises at least about 15-20% w/w or at least about 20% w/w of BrEA hemihydrate of the total amount of BrEA that is present, typically at least about 25% w/w, more typically at least about 30% w/w, often at least about 35% w/w and usually at least about 45% w/w. These compositions are generally solids, e.g., formulations or unit dosages, but they also include suspensions, precipitates, gels and colloids that contain solid BrEA. Such suspensions or precipitates may arise from, e.g., precipitation of BrEA hemihydrate from a solution that contains water or from addition of solid BrEA to a liquid excipient(s). Obviously, compositions that comprise a substantial amount of BrEA may be substantially free of other forms of solid BrEA as discussed above.

BrEA hemihydrate may conveniently be identified by reference to BrEA hemihydrate characterized by one or more of (1) its melting or decomposition point or range (optionally expressed as +/−2° C.), (2) one or more BrEA hemihydrate DSC transition temperatures or ranges (any of which may be optionally expressed as +/−2° C.), (3) one or more characteristic BrEA hemihydrate IR absorption bands, (4) 1, 2, 3, 4, 5, 6 or more of the highest intensity XRD peaks (any one or more of which are optionally expressed as +/−0.1° Theta or +/−0.2° Theta) obtained from an XRD spectrum of BrEA hemihydrate using Cu—Kα radiation (e.g., obtained essentially according to the method described at U.S. Pharmacopoeia, volume 23, 1995, <941>, p. 1843-1845), (5) the presence of less than about 3% or less than about 2% w/w of other compounds, (6) a water content of dry BrEA hemihydrate of about 2.5% w/w (e.g., 2.3-2.7% w/w), where dry BrEA hemihydrate means compound dried by filtration, optionally washed once with an anhydrous solvent such as hexane, filtered again and dried in vacuo at about 60° C. until no further weight loss occurs over 24 hours at about 60° C. (e.g., where water content is determined essentially by the Karl Fisher or other method described at U.S. Pharmacopoeia, vol. 23, 1995, p 1801-1802 or 1840-1843 methods <731> or <921>), (7) cell constants and the orientation matrix obtained from single crystal X-ray crystallography of BrEA hemihydrate (obtained, e.g., essentially as described in WO 99/04774 at example 13), (8) a description of crystal shapes as observed at about 100× magnification to about 150× magnification by polarized light microscopy or (9) average BrEA hemihydrate crystal size and shape descriptions.

Thus, for example, BrEA hemihydrate may be characterized by or one or more of its IR absorption bands, e.g., the carbonyl peaks at 1741 cm$^{-1}$ and 1752 cm$^{-1}$, and either its melting or decomposition point or range and/or 1, 2, 3, 4, 5, 6 or more of the XRD peaks (usually the highest intensity peaks) at Theta (X-ray diffraction angle) values of 17.8, 23.8, 24.2, 26.9-27.2, 28.6, 30.1 and 32.2.

BrEA hemihydrate is suitable to prepare compositions comprising an excipient(s) suitable for human pharmaceutical use or for veterinary use. Such compositions are used to prepare formulations and unit dosages. Unit dosages typically comprise tablets, capsules, lozenges or sterile solutions, including sterile solutions for parenteral administration. Solid unit dosage forms typically comprise about 5-1000 mg of BrEA hemihydrate, typically about 20-400 mg, e.g., about 25 mg, about 50 mg, about 100 mg, about 150 mg or about 250 mg per unit dose.

The invention provides a method to make BrEA hemihydrate comprising contacting water, 16α-bromo-3β-hydroxy-5α-androstan-17-one and a C1-C6 alcohol (e.g., methanol, ethanol, propanol, isopropanol, butanol) and water. Typically the only one $C_1$-$C_6$ alcohol is present, e.g., ethanol, which is anhydrous or which may comprise up to about 2% w/w water. In some embodiments, the method utilizes a solution that comprises about 5-25% w/w water, about 30-45% w/w ethanol and about 30-45% w/w of a BrEA preparation. Typical BrEA preparations are solid preparations that comprise at least about 80% w/w, usually at least about 90% w/w or at least about 95% w/w of BrEA. The solutions may comprise about 18-22% w/w water, about 37-43% w/w ethanol and about 37-43% w/w of a BrEA preparation. In conducting the precipitation or crystallization method, the solution will typically be at a temperature of about −20° C. to about 45° C., usually at about 0° C. to about 20° C. The solution is maintained at this temperature range for about 30 minutes to about 12 hours and the solution is optionally agitated using slow to moderate agitation during crystallization.

A related embodiment comprises a method to prepare BrEA hemihydrate comprising precipitating BrEA from a solution comprising at least about 15-25% w/w water, about 35-45% w/w of a BrEA preparation and at least about 35-45% w/w of one or more water-miscible solvents, typically $C_{1-6}$ alcohols (methanol, ethanol, propanol, isopropanol, butanol). The BrEA preparation may optionally comprise one or more by-products of BrEA synthesis. Typical BrEA hemihydrate preparations or batches comprise less than about 5% w/w, usually less than about 3% or about 2% w/w of other compounds, such as by-products of BrEA synthesis. Aspects of this method include contacting water with an organic solution that comprises BrEA and an organic solvent such as a $C_1$-$C_6$ alcohol (e.g., ethanol) or acetone. Addition of water to such solutions leads to precipitation of BrEA hemihydrate. Solutions that contain BrEA hemihydrate crystals or precipitate are invention embodiments that are used to prepare solid BrEA that is later dried and stored, typically at ambient temperatures.

Precipitation of BrEA hemihydrate from water-containing solutions is accomplished by known methods, e.g., reducing the solution's temperature, using saturated or nearly saturated BrEA solutions, vacuum concentration of saturated or nearly saturated BrEA solutions (which is typically conducted at a relatively low temperature, usually about 15-25° C.), seeding with saturated or nearly saturated BrEA solutions with BrEA hemihydrate crystals (e.g., about 10-100 mg per 1-10 L of solution), by heating a saturated or nearly saturated BrEA solution (about 25-35° C. for a few minutes followed by allowing the temperature to fall or by actively cooling the solution) and optionally seeding the solution with BrEA hemihydrate crystals or by addition of a liquid, e.g., additional water or ethanol, to a saturated or nearly saturated BrEA ethanol-water solution, which causes the solution to become supersaturated. BrEA may also be precipitated from other solvents or solvent systems, including acetone and acetone-ethanol. Such solvents are typically water miscible. Two-stage precipitation of BrEA may also be used to recover solid BrEA hemihydrate, e.g., initial precipitation and recovery of the solid, followed by either cooling and seeding of the mother liquor or by allowing the mother liquor to stand, e.g., for about one, two or more days at ambient temperature, to obtain a second crop of crystals. Also, BrEA hemihydrate crystals may optionally be recrystallized, essentially as described herein, to further increase the purity of the final solid. Methods for crystallizing organic compounds have been described, e.g., A. S. Myerson, *Handbook of Industrial Crystallization*, 1993, Butterworth—Heinemann, Stoneham, Mass., p 1-101.

Other related embodiments comprise a product produced by the process of contacting a solution comprising BrEA and an organic solvent with water. Typically the solutions are as described above, e.g., a solution comprising about 3-5% v/v water and at least about 40% v/v of one or more water-miscible solvents, typically polar solvents such as $C_{1-6}$ alcohols or ketones (e.g., methanol, ethanol, propanol, isopropanol, butanol, typically ethanol or acetone). Such processes are accomplished by any one or more of the techniques described in the paragraph above, e.g., cooling of a saturated or nearly saturated BrEA water-ethanol solution and optionally seeding the cooled solution with BrEA hemihydrate. An embodiment related to this comprises solutions or solids that comprise wet BrEA hemihydrate crystals or wet filtered or centrifuged BrEA hemihydrate cakes, which may be obtained after crystallization. Examples of these embodiments include adding water to a BrEA-alcohol solution, e.g., slow addition of about 0.5-1.5 volumes or about 0.8-1.2 volumes of water to about 6 volumes of a BrEA-ethanol solution to obtain BrEA hemihydrate. Other examples of these embodiments include adding water to a BrEA-ketone solvent solution, e.g., slow addition of about 0.5-1.5 volumes or about 0.8-1.2 volumes of water to about 10 volumes of a BrEA-acetone solution to obtain BrEA hemihydrate.

Another related embodiment is BrEA hemihydrate that is milled to an average particle size of about 0.01-200 μM, or about 0.1-10 μM or about 0.5-5 μM. Average particle size or diameter for milled BrEA hemihydrate may thus be relatively small, e.g., about 0.03-2.0 μM or about 0.1-1.0 μM, or somewhat larger, e.g., about 0.5-5.0 μM or about 1-5.0 μM. Milled BrEA hemihydrate is suitable for preparing solid formulations and parenteral formulations for human or veterinary use. The milled material facilitates dissolution of BrEA hemihydrate in solvents or excipients and facilitates mixing with solids or solid excipients.

While it is possible to administer BrEA hemihydrate as a pure compound to a subject, it is usually presented as a solid formulation or used to prepare a liquid formulation. Formulations will typically be used to prepare unit dosages, e.g., tablets, capsules or lozenges for oral, buccal or sublingual administration, that comprise about 10-1000 mg or typically about 25-400 mg of BrEA hemihydrate. Alternatively, embodiments include a product for parenteral (e.g., subcutaneous, subdermal, intravenous, intramuscular, intraperitoneal) administration made by the process of contacting BrEA hemihydrate and a liquid excipient, e.g., any one, two, three or more of PEG 100, PEG 200, PEG 300, PEG 400, propylene glycol, benzyl benzoate, benzyl alcohol or ethanol, and optionally sterilizing the solution and optionally dispensing the solution into vials or ampules (typically amber glass), which may be single-use or multi-use and optionally storing the formulation at reduced temperature (about 0-12° C., or about 2-10° C.). Such products for parenteral administration typically comprise BrEA at a concentration of about 10-170 mg/mL, usually at about 20-110 mg/mL or about 30-100 mg/mL, and optionally one or more of a salt, buffer or bacteriostat or preservative (e.g., NaCl, BHA, BHT or EDTA).

Other embodiments include a product produced by the process of contacting BrEA hemihydrate, which may be substantially free of other forms of BrEA, with an excipient suitable for human pharmaceutical use or for veterinary use. The product is useful to make formulations or unit dosage forms that contain the hemihydrate.

Formulations made from or containing BrEA hemihydrate will usually be stored under conditions that limit the amount of water that reaches the formulation, e.g., silica gel in a sealed container that holds a formulation. Water permeation characteristics of containers have been described, e.g., Containers—Permeation, Chapter, USP 23, 1995, U.S. Pharmacopeial Convention, Inc., Rockville, Md., p. 1787.

Embodiments include invention compositions that transiently occur when a method step or operation is performed. For example, when a formula 1 compound such as BrEA, containing less than about 3% water is contacted with an excipient, e.g., a PEG, an alcohol, propylene glycol or benzyl benzoate, the composition before addition of one ingredient with another is a non-homogenous mixture. As the ingredients are contacted, the mixture's homogeneity increases and the proportion of ingredients relative to each other approaches a desired value. Thus, invention compositions, which contain less than about 3% water can comprise about 0.0001-99% of a formula 1 compound such as BrEA and one or more excipients. These transient compositions are intermediates that necessarily arise when one makes an invention composition or formulation and they are included in invention embodiments to the extent that they are patentable.

In general, the formula 1 compound that is present in invention compositions and formulations is completely dissolved in the non-aqueous excipients. However, in some embodiments, e.g., transient compositions and some formulations, the formula 1 compound is partially dissolved while the remaining portion is present as a solid, which can be a suspension or a colloid.

Invention compositions and formulations suitable for parenteral delivery of formula 1 compounds to humans or animals typically comprise two, three or more excipients. Exemplary embodiments include (1) any two, three or four of propylene glycol, PEG200, PEG300, ethanol and benzyl benzoate and (2) any two, three or four of propylene glycol, PEG100, PEG200, PEG300, PEG400 and benzyl benzoate.

Invention compositions and formulations generally comprise about 0.01-10% of BrEA, usually about 1-5%, and about 0.01-3% water, typically about 0.05-3%, usually about 0.1-1%. The invention formulations are usually presented as unit or multi-unit dosages suitable for parenteral administration once or twice per day or once per 2-3 days. Unit dosages comprise about 3-1000 mg of BrEA per unit dose, typically about 5-500 mg, usually about 10-200 mg. For treating retroviruses such as HIV in humans, a unit dose usually comprises about 10-250 mg of BrEA, usually about 100-200 mg, in a volume of about 1-6 mL, usually about 2-4 mL.

Invention embodiments include the product made by a process of combining, mixing or otherwise contacting BrEA and one, two or more excipients. Such products are produced by routine methods of contacting the ingredients. Such products optionally also contain a diluent, a disintegrant and a binder, or other excipients described herein or in references cited herein.

BrEA in the presence of significant amounts of water was found to epimerize at the bromine atom, leading to a mixture of the 16α- and 16β—BrEA isomers. Invention compositions and formulations comprising BrEA or BrEA hemihydrate will usually have a water content of less than about 3%, typically less than about 0.3%, usually less than about 0.1%. These compositions and formulations were found to have a good stability when stored at ambient temperature (about 5-40° C. as used herein) in closed containers compared to control compositions and formulations having more water. Such liquids are also characterized by an unexpected reduction in precipitation of the compound, which water appears to induce.

Invention embodiments include compositions that comprise less than about 3% water, a formula 1 compound and a compound that is not generally considered suitable for human use but is useful to make an invention formulation for veterinary use. Veterinary formulations are compositions useful for the purpose of administering invention compositions to primates, cats, dogs, horses, cows, rabbits and other subjects and may contain excipients acceptable in the veterinary art and are compatible with formula 1 compounds such as BrEA. These veterinary compositions may not always be suitable for human use because they contain an excipient that is not suitable for human use, e.g., an alcohol other than ethanol such as methanol, propanol or butanol. Typically such excipients will be present at relatively low levels, e.g., about 1-30%, usually about 1-5%.

Invention embodiments include compositions and formulations, e.g., unit dosage forms and sterile solutions, that comprise (1) about 1-100 mg/mL of a formula 1 compound(s), about 57.5% propylene glycol, about 25% PEG300, about 12.5% ethanol and about 5% benzyl benzoate; (2) about 1-60 mg/mL of a formula 1 compound(s), about 70% propylene glycol, about 25% PEG300 and about 5% benzyl benzoate; (3) about 1-60 mg/mL of a formula 1 compound(s), about 25% PEG300, about 35% propylene glycol, about 35% mannitol and about 5% benzyl benzoate; (4) about 1-60 mg/mL of a formula 1 compound(s), about 57.5% propylene glycol, a mixture comprising about 25% PEG300 and PEG200 (e.g., PEG300:PEG200 in a ratio of about 1:10 to about 10:1), about 12.5% ethanol and about 5% benzyl benzoate; (5) about 1-60 mg/mL of a formula 1 compound(s), about 75% propylene glycol, a mixture comprising about 25% PEG300 and PEG200 (e.g., a PEG300:PEG200 in a ratio of about 1:10 to about 10:1) and about 5% benzyl benzoate; (6) about 1-60 mg/mL of a formula 1 compound(s), about 25% PEG300 and PEG200 (e.g., PEG300:PEG200 in a ratio of about 1:10 to about 10:1), about 35% propylene glycol, about 35% mannitol and about 5% benzyl benzoate; (7) any of formulations (1) through (6) where the formula 1 compound(s) is about 40-55 mg/mL; (8) any of formulations (1) through (6) where the formula 1 compound(s) is about 30-100 mg/mL; (9) any of formulations (1) through (8) where 1, 2, 3 or 4 formula 1 compounds are present; (10) any of formulations (1) through (8) where 1 or 2 formula 1 compounds are present; (11) any of formulations (1) through (8) where 1 formula 1 compound is present; (12) any of formulations (1) through (11) where the formula 1 compound comprises independently at 1, 2 or 3 of any of $R^1$-$R^6$, $R^{10}$, $R^{15}$, $R^{17}$ or $R^{18}$ an independently selected ester, thioester, carbonate, carbamate, amino acid or peptide of 1 or 2 independently selected formula 1 compounds; (13) any of formulations (1) through (12) where the formula 1 compound comprises or is BrEA or BrEA hemihydrate; (14) any of formulations (1) through (13) where the formula 1 compound comprises or is an ester, a sulfate ester or phosphoester of BrEA.

Other embodiments include the product obtained by storing invention compositions or formulations, e.g., unit dosage forms, any of embodiments (1)-(14) above, or compositions used to make formulations, at about 10-40° C. for at least about 3 days, e.g., storage at ambient temperature for about 1-24 months. Invention formulations will typically be stored in hermetically or induction sealed containers for these time periods. Invention compositions will typically be held in closed containers. The specification and claims disclose exemplary suitable formulations and unit dosage forms for these embodiments.

Other embodiments include compounds compositions and formulations where one or more of $R^1$-$R^6$, $R^{10}$, $R^{15}$, $R^{17}$ and $R^{18}$ comprise an amino acid or a peptide, e.g., $R^1$, $R^2$ or $R^4$ comprises an amino acid or a peptide, $R^3$ is a halogen and $R^5$ and $R^6$ are both —$CH_3$. The peptide at one or more of $R^1$-$R^6$ can comprise a cell surface binding peptide such as the entire protein or a sequence from fibronectin or retronectin, e.g., KQAGDV (SEQ ID NO 1).

In the formula 1 compounds, each $R^4$ is independently selected. In some embodiments one $R^4$ is hydrogen and the other is another moiety. In other embodiments, both $R^4$ are independently selected moieties other than hydrogen, e.g., a C1 to C20 organic moiety.

$R^1$-$R^6$, $R^{10}$, $R^{15}$, $R^{17}$ and $R^{18}$ include moieties, e.g., esters, thioesters, carbonates, amino acids, peptides and/or carbamates, that are chemically and/or enzymatically hydrolyzable, often under physiological conditions. Such moieties are independently chosen. Typically these moieties will give rise to —OH, —SH or —$NH_2$ at the $R^1$-$R^6$ positions of the steroid nucleus. Embodiments of formula 1 compounds include ones where (1) one of $R^1$, $R^2$ and $R^4$ is a hydrolyzable moiety (e.g., ester, thioester, carbonate, amino acid, peptide or carbamate), the other two of $R^1$, $R^2$ and $R^4$ are —H, $R^3$ is not hydrogen and $R^5$ and $R^6$ are both —$CH_3$, (2) two of $R^1$, $R^2$ and $R^4$ are hydrolyzable moieties (e.g., independently chosen esters, thioesters, carbonates, amino acids, peptides and/or carbamates), the other of $R^1$, $R^2$ and $R^4$ is —H, $R^3$ is not hydrogen and $R^5$ and $R^6$ are both —$CH_3$, (3) $R^1$, $R^2$ and $R^4$ are hydrolyzable moieties, $R^3$ is not hydrogen and $R^5$ and $R^6$ are both —$CH_3$. In these embodiments, the $R^3$ group is typically in the β-configuration and the $R^1$, $R^2$ and $R^4$-$R^6$ groups are typically in the α-configuration.

In other embodiments, one or more of $R^1$-$R^6$, $R^{10}$, $R^{15}$, $R^{17}$ and $R^{18}$, usually one, comprises an amino acid or a peptide, while the remaining groups are independently selected from the moieties defined herein. In these embodiments, the peptides are typically dimers (dipeptides) or trimers (tripeptides). For example one of $R^1$, $R^2$ or $R^4$ comprises an amino acid, the remaining of $R^1$, $R^2$ or $R^4$ independently comprise —OH, =O, an ester, a carbonate or a carbamate, while $R^3$ is a halogen, hydroxyl or an ester and $R^5$ and $R^6$ independently are —H, —$(CH_2)_n$—$CH_3$, —$(CH_2)_n$—$CH_2OH$, or —$(CH_2)_n$—$CH_2F$, —$(CH_2)_{2-4}$—O—$(CH_2)_{2-4}$—$CH_3$, where n is 0, 1, 2, 3, 4, 5, 6, 7 or 8 often 0, 1, or 2, usually 0. Typically the ester, carbonate or carbamate are hydrolyzable under physiological conditions.

Hydrolyzable moieties typically comprise acyl groups, esters, ethers, thioethers, amides, amino acids, peptides, carbonates and/or carbamates. In general, the structure of hydrolyzable moieties is not critical and can vary. In some embodiments, these moieties contain a total of about 4 to about 10 carbon atoms. These hydrolyzable moieties in other embodiments comprise an organic moiety, as described above for ester, that contains 2, 3, 4, 5, 6, 7, 8, 9, 10, 11 or 12 carbon atoms and 1, 2, 3, 4, 5 or 6 heteroatoms, e.g., oxygen, nitrogen or sulfur. These hydrolyzable moieties can comprise no groups that are charged in plasma, blood, intracellular cytoplasm or in the gut, or they can comprise 1, 2, 3 or more positive, negative or positive and negative charges under one or more of these conditions. The charges may be fractional depending on the group and the conditions it is under. These hydrolyzable moieties may comprise 1, 2, 3, 4 or more substitutions at a hydrogen atom(s) and/or a carbon atom(s), e.g., —OH, protected hydroxyl, —SH, protected thiol, carboxyl, protected carboxyl, amine, protected amine, —O—, —S—, —CO—, —CS—, alkoxy, alkylthio, alkenyloxy, aryl, —OP(O)(O)—O—, —OS(O)(O)—O— and/or heterocycle. Such substitutions are independently selected.

Formula 1 compounds that comprise a hydrolyzable moiety(ies) may include one or more independently chosen —O—CHR$^{24}$C(O)OR$^{25}$, —S—CHR$^{24}$C(O)OR$^{25}$, —NH—CHR$^{24}$C(O)OR$^{25}$, O—CHR$^{24}$C(S)OR$^{25}$, —S—CHR$^{24}$C(S)OR$^{25}$, —NH—CHR$^{24}$C(S)OR$^{25}$, —O—CHR$^{24}$OC(O)R$^{25}$, —S—CHR$^{24}$OC(O)R$^{25}$, —NH—CHR$^{24}$OC(O)R$^{25}$, —O—CHR$^{24}$C(O)N(R$^{25}$)$_2$, —S—CHR$^{24}$C(O)N(R$^{25}$)$_2$, —NH—CHR$^{24}$C(O)N(R$^{25}$)$_2$, —O—CHR$^{24}$OR$^{25}$, —S—CHR$^{24}$OR$^{25}$—NH—CHR$^{24}$OR$^{25}$, —O—CHR$^{24}$C(R$^{25}$)$_2$CH$_2$OX, —S—CHR$^{24}$C(R$^{25}$)$_2$CH$_2$OX, —NH—CHR$^{24}$C(R$^{25}$)$_2$CH$_2$OX, —O—CHR$^{24}$C(R$^{25}$)$_2$OX, —S—CHR$^{24}$C(R$^{25}$)$_2$OX or —NH—CHR$^{24}$C(R$^{25}$)$_2$OX, groups that one or more of R$^1$-R$^6$, R$^{10}$, R$^{15}$, R$^{17}$ and R$^{18}$ comprise. For these hydrolyzable moieties, R$^{24}$ independently is —H, —CH$_2$—C$_6$H$_5$, —CH$_2$CH$_2$—C$_6$H$_5$, C$_{1-8}$ alkyl, C$_{2-8}$ alkenyl, aryl or heterocycle where each alkyl, alkenyl, aryl and heterocycle moiety is independently optionally substituted with 1, 2, or 3, usually 1, —O—, —S—, —NH—, halogen, aryl, —OX, —SX, —NHX, ketone (═O) or —CN moieties or the C$_{1-8}$ alkyl is optionally substituted with 3, 4, 5 or 6 halogens, and X is —H or a protecting group. Exemplary R$^{24}$ are —H, —CH$_3$, —C$_2$H$_5$, —CH$_2$—C$_{1-5}$ optionally substituted alkyl, —CH$_2$CH$_2$—C$_{1-4}$ optionally substituted alkyl and —CH$_2$CH$_2$—O—C$_{1-4}$ optionally substituted alkyl. R$^{25}$ independently is —H, —CH$_2$—C$_6$H$_5$, —CH$_2$CH$_2$—C$_6$H$_5$, C$_{1-12}$ alkyl, C$_{2-12}$ alkenyl, aryl, heterocycle, —CH$_2$-heterocycle or —CH$_2$-aryl, where each alkyl alkenyl, aryl, heterocycle, —CH$_2$-heterocycle or —CH$_2$-aryl moiety is independently optionally substituted with 1 or 2, usually 1, —O—, —S—, —NH—, halogen, aryl, —OX, —SX, —NHX, ketone (═O), —C(O)OX or —CN moieties or the C$_{1-12}$ alkyl, C$_{2-12}$ alkenyl or aryl, are optionally independently substituted with 3, 4, 5 or 6 halogens, where X is —H or a protecting group, or the aryl, heterocycle, —CH$_2$-heterocycle or —CH$_2$-aryl moieties are optionally independently substituted with 1, 2 or 3 C$_{1-4}$ alkyl moieties or with 1, 2 or 3 C$_{1-4}$ alkoxy moieties at the aryl moiety or at the heterocycle, usually at a ring carbon. Exemplary R$^{25}$ are —H, —CH$_3$, —C$_2$H$_5$, —C$_3$H$_7$, —C$_4$H$_9$, —C$_6$H$_{13}$, —C$_6$H$_5$, —C$_6$H$_4$OH, —C$_6$H$_4$OCH$_3$, —C$_6$H$_4$F, —CH$_2$—C115 optionally substituted alkyl, —CH$_2$CH$_2$—C$_{1-4}$ optionally substituted alkyl and —CH$_2$CH$_2$—O—C$_{1-4}$ optionally substituted alkyl.

Embodiments of formula 1 compounds include or exclude any subset of compounds within the definition of formula 1, provided that at least one compound remains. For example, a subset of formula 1 compounds that are usually included, for example in the invention nonaqueous formulations and in the invention intermittent dosing protocols and immune modulation methods, are formula 1 compounds where R$^2$ is hydroxyl, or a group that can hydrolyze to hydroxyl, in either configuration and R$^5$ and R$^6$ are methyl in the α-configuration. A subset compounds that are optionally excluded from formula 1 compounds comprises one or all compounds that are disclosed in one or more prior art references or publications, e.g., one or more compounds that are disclosed in one or more of the references cited herein, especially for those compounds that can render any claim or embodiment unpatentable for novelty, obviousness and/or inventive step reasons.

Exemplary embodiments of species and genera of formula 1 compounds are named as described below.

Group 1. Exemplary embodiments include the formula 1 compounds named according to the compound structure designations given in Tables A and B below. Each compound named in Table B is depicted as a compound having formula B

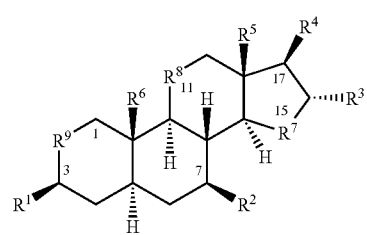

where R$^5$ and R$^5$ are both —CH$_3$, there is no double bond at the 1-2-, 4-5- or 5-6-positions, one R$^4$ is hydrogen, R$^7$, R$^3$ and R$^9$ are all —CH$_2$— and R$^1$, R$^2$, R$^3$ and R$^4$ are the substituents designated in Table A. The compounds named according to Tables A and B are referred to as "group 1" compounds.

Compounds named in Table B are named by numbers assigned to R$^1$, R$^2$, R$^3$ and R$^4$ according to the following compound naming convention, R$^1$.R$^2$.R$^3$.R$^4$, based on the numbered chemical substituents depicted in Table A. Each Table A number specifies a different structure for each of R$^1$, R$^2$, R$^3$ and R$^4$. When R$^1$, R$^2$, R$^3$ or R$^4$ is a divalent moiety, e.g., ═O, the hydrogen at the corresponding position is absent. Thus, the group 1 compound named 1.2.1.1 is a formula B structure with a β-hydroxyl bonded to carbons at the 3- and 7-positions (the variable groups R$^1$ and R$^2$ respectively), an α-bromine bonded to carbon 16 (the variable group R$^3$) and double bonded oxygen (═O) at carbon 17 (the variable group R$^4$), i.e., 1.2.1.1 has the structure shown below.

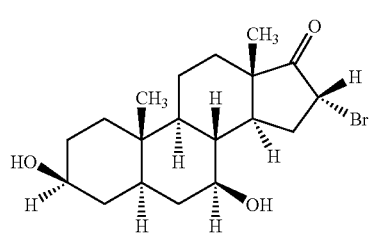

1.2.1.1

TABLE A

| | R¹ | | R² |
|---|---|---|---|
| 1 | —OH | 1 | —H |
| 2 | =O | 2 | —OH |
| 3 | —SH | 3 | =O |
| 4 | =S | 4 | —CH₃ |
| 5 | —O—CH₃ | 5 | —OCH₃ |
| 6 | —O—S(O)(O)—O⁻Na⁺ | 6 | —OC₂H₅ |
| 7 | —O—S(O)(O)—OC₂H₅ | 7 | —OCH₂CH₂CH₃ |
| 8 | —CH₃ | 8 | —OCH₂CH₂CH₂CH₃ |
| 9 | —H | 9 | —Cl |
| 10 | —OC(O)C(CH₃)₃ | 10 | —Br |

TABLE A-continued

| | R³ | | R⁴ |
|---|---|---|---|
| 1 | —Br | 1 | =O |
| 2 | —Cl | 2 | —OH |
| 3 | —I | 3 | —H |
| 4 | —F | 4 | —F |
| 5 | —H | 5 | —Cl |
| 6 | —OH | 6 | —Br |
| 7 | =O | 7 | —I |
| 8 | —O—C(O)—CH₃ | 8 | —O—C(O)—CH₃ |
| 9 | —O—C(O)—CH₂CH₃ | 9 | —O—C(O)—CH₂CH₃ |
| 10 | —O—C(O)—CH₂CH₂CH₃ | 10 | —O—C(O)—CH₂CH₂CH₃ |

TABLE B 1.1.1.1, 1.1.1.2, 1.1.1.3, 1.1.1.4, 1.1.1.5, 1.1.1.6, 1.1.1.7, 1.1.1.8, 1.1.1.9, 1.1.1.10, 1.1.2.1, 1.1.2.2, 1.1.2.3, 1.1.2.4, 1.1.2.5, 1.1.2.6, 1.1.2.7, 1.1.2.8, 1.1.2.9, 1.1.2.10, 1.1.3.1, 1.1.3.2, 1.1.3.3, 1.1.3.4, 1.1.3.5, 1.1.3.6, 1.1.3.7, 1.1.3.8, 1.1.3.9, 1.1.3.10, 1.1.4.1, 1.1.4.2, 1.1.4.3, 1.1.4.4, 1.1.4.5, 1.1.4.6, 1.1.4.7, 1.1.4.8, 1.1.4.9, 1.1.4.10, 1.1.5.1, 1.1.5.2, 1.1.5.3, 1.1.5.4, 1.1.5.5, 1.1.5.6, 1.1.5.7, 1.1.5.8, 1.1.5.9, 1.1.5.10, 1.1.6.1, 1.1.6.2, 1.1.6.3, 1.1.6.4, 1.1.6.5, 1.1.6.6, 1.1.6.7, 1.1.6.8, 1.1.6.9, 1.1.6.10, 1.1.7.1, 1.1.7.2, 1.1.7.3, 1.1.7.4, 1.1.7.5, 1.1.7.6, 1.1.7.7, 1.1.7.8, 1.1.7.9, 1.1.7.10, 1.1.8.1, 1.1.8.2, 1.1.8.3, 1.1.8.4, 1.1.8.5, 1.1.8.6, 1.1.8.7, 1.1.8.8, 1.1.8.9, 1.1.8.10, 1.1.9.1, 1.1.9.2, 1.1.9.3, 1.1.9.4, 1.1.9.5, 1.1.9.6, 1.1.9.7, 1.1.9.8, 1.1.9.9, 1.1.9.10, 1.1.10.1, 1.1.10.2, 1.1.10.3, 1.1.10.4, 1.1.10.5, 1.1.10.6, 1.1.10.7, 1.1.10.8, 1.1.10.9, 1.1.10.10, 1.2.1.1, 1.2.1.2, 1.2.1.3, 1.2.1.4, 1.2.1.5, 1.2.1.6, 1.2.1.7, 1.2.1.8, 1.2.1.9, 1.2.1.10, 1.2.2.1, 1.2.2.2, 1.2.2.3, 1.2.2.4, 1.2.2.5, 1.2.2.6, 1.2.2.7, 1.2.2.8, 1.2.2.9, 1.2.2.10, 1.2.3.1, 1.2.3.2, 1.2.3.3, 1.2.3.4, 1.2.3.5, 1.2.3.6, 1.2.3.7, 1.2.3.8, 1.2.3.9, 1.2.3.10, 1.2.4.1, 1.2.4.2, 1.2.4.3, 1.2.4.4, 1.2.4.5, 1.2.4.6, 1.2.4.7, 1.2.4.8, 1.2.4.9, 1.2.4.10, 1.2.5.1, 1.2.5.2, 1.2.5.3, 1.2.5.4, 1.2.5.5, 1.2.5.6, 1.2.5.7, 1.2.5.8, 1.2.5.9, 1.2.5.10, 1.2.6.1, 1.2.6.2, 1.2.6.3, 1.2.6.4, 1.2.6.5, 1.2.6.6, 1.2.6.7, 1.2.6.8, 1.2.6.9, 1.2.6.10, 1.2.7.1, 1.2.7.2, 1.2.7.3, 1.2.7.4, 1.2.7.5, 1.2.7.6, 1.2.7.7, 1.2.7.8, 1.2.7.9, 1.2.7.10, 1.2.8.1, 1.2.8.2, 1.2.8.3, 1.2.8.4, 1.2.8.5, 1.2.8.6, 1.2.8.7, 1.2.8.8, 1.2.8.9, 1.2.8.10, 1.2.9.1, 1.2.9.2, 1.2.9.3, 1.2.9.4, 1.2.9.5, 1.2.9.6, 1.2.9.7, 1.2.9.8, 1.2.9.9, 1.2.9.10, 1.2.10.1, 1.2.10.2, 1.2.10.3, 1.2.10.4, 1.2.10.5, 1.2.10.6, 1.2.10.7, 1.2.10.8, 1.2.10.9, 1.2.10.10, 1.3.1.1, 1.3.1.2, 1.3.1.3, 1.3.1.4, 1.3.1.5, 1.3.1.6, 1.3.1.7, 1.3.1.8, 1.3.1.9, 1.3.1.10, 1.3.2.1, 1.3.2.2, 1.3.2.3, 1.3.2.4, 1.3.2.5, 1.3.2.6, 1.3.2.7, 1.3.2.8, 1.3.2.9, 1.3.2.10, 1.3.3.1, 1.3.3.2, 1.3.3.3, 1.3.3.4, 1.3.3.5, 1.3.3.6, 1.3.3.7, 1.3.3.8, 1.3.3.9, 1.3.3.10, 1.3.4.1, 1.3.4.2, 1.3.4.3, 1.3.4.4, 1.3.4.5, 1.3.4.6, 1.3.4.7, 1.3.4.8, 1.3.4.9, 1.3.4.10, 1.3.5.1, 1.3.5.2, 1.3.5.3, 1.3.5.4, 1.3.5.5, 1.3.5.6, 1.3.5.7, 1.3.5.8, 1.3.5.9, 1.3.5.10, 1.3.6.1, 1.3.6.2, 1.3.6.3, 1.3.6.4, 1.3.6.5, 1.3.6.6, 1.3.6.7, 1.3.6.8, 1.3.6.9, 1.3.6.10, 1.3.7.1, 1.3.7.2, 1.3.7.3, 1.3.7.4, 1.3.7.5, 1.3.7.6, 1.3.7.7, 1.3.7.8, 1.3.7.9, 1.3.7.10, 1.3.8.1, 1.3.8.2, 1.3.8.3, 1.3.8.4, 1.3.8.5, 1.3.8.6, 1.3.8.7, 1.3.8.8, 1.3.8.9, 1.3.8.10, 1.3.9.1, 1.3.9.2, 1.3.9.3, 1.3.9.4, 1.3.9.5, 1.3.9.6, 1.3.9.7, 1.3.9.8, 1.3.9.9, 1.3.9.10, 1.3.10.1, 1.3.10.2, 1.3.10.3, 1.3.10.4, 1.3.10.5, 1.3.10.6, 1.3.10.7, 1.3.10.8, 1.3.10.9, 1.3.10.10, 1.4.1.1, 1.4.1.2, 1.4.1.3, 1.4.1.4, 1.4.1.5, 1.4.1.6, 1.4.1.7, 1.4.1.8, 1.4.1.9, 1.4.1.10, 1.4.2.1, 1.4.2.2, 1.4.2.3, 1.4.2.4, 1.4.2.5, 1.4.2.6, 1.4.2.7, 1.4.2.8, 1.4.2.9, 1.4.2.10, 1.4.3.1, 1.4.3.2, 1.4.3.3, 1.4.3.4, 1.4.3.5, 1.4.3.6, 1.4.3.7, 1.4.3.8, 1.4.3.9, 1.4.3.10, 1.4.4.1, 1.4.4.2, 1.4.4.3, 1.4.4.4, 1.4.4.5, 1.4.4.6, 1.4.4.7, 1.4.4.8, 1.4.4.9, 1.4.4.10, 1.4.5.1, 1.4.5.2, 1.4.5.3, 1.4.5.4, 1.4.5.5, 1.4.5.6, 1.4.5.7, 1.4.5.8, 1.4.5.9, 1.4.5.10, 1.4.6.1, 1.4.6.2, 1.4.6.3, 1.4.6.4, 1.4.6.5, 1.4.6.6, 1.4.6.7, 1.4.6.8, 1.4.6.9, 1.4.6.10, 1.4.7.1, 1.4.7.2, 1.4.7.3, 1.4.7.4, 1.4.7.5, 1.4.7.6, 1.4.7.7, 1.4.7.8, 1.4.7.9, 1.4.7.10, 1.4.8.1, 1.4.8.2, 1.4.8.3, 1.4.8.4, 1.4.8.5, 1.4.8.6, 1.4.8.7, 1.4.8.8, 1.4.8.9, 1.4.8.10, 1.4.9.1, 1.4.9.2, 1.4.9.3, 1.4.9.4, 1.4.9.5, 1.4.9.6, 1.4.9.7, 1.4.9.8, 1.4.9.9, 1.4.9.10, 1.4.10.1, 1.4.10.2, 1.4.10.3, 1.4.10.4, 1.4.10.5, 1.4.10.6, 1.4.10.7, 1.4.10.8, 1.4.10.9, 1.4.10.10, 1.5.1.1, 1.5.1.2, 1.5.1.3, 1.5.1.4, 1.5.1.5, 1.5.1.6, 1.5.1.7, 1.5.1.8, 1.5.1.9, 1.5.1.10, 1.5.2.1, 1.5.2.2, 1.5.2.3, 1.5.2.4, 1.5.2.5, 1.5.2.6, 1.5.2.7, 1.5.2.8, 1.5.2.9, 1.5.2.10, 1.5.3.1, 1.5.3.2, 1.5.3.3, 1.5.3.4, 1.5.3.5, 1.5.3.6, 1.5.3.7, 1.5.3.8, 1.5.3.9, 1.5.3.10, 1.5.4.1, 1.5.4.2, 1.5.4.3, 1.5.4.4, 1.5.4.5, 1.5.4.6, 1.5.4.7, 1.5.4.8, 1.5.4.9, 1.5.4.10, 1.5.5.1, 1.5.5.2, 1.5.5.3, 1.5.5.4, 1.5.5.5, 1.5.5.6, 1.5.5.7, 1.5.5.8, 1.5.5.9, 1.5.5.10, 1.5.6.1, 1.5.6.2, 1.5.6.3, 1.5.6.4, 1.5.6.5, 1.5.6.6, 1.5.6.7, 1.5.6.8, 1.5.6.9, 1.5.6.10, 1.5.7.1, 1.5.7.2, 1.5.7.3, 1.5.7.4, 1.5.7.5, 1.5.7.6, 1.5.7.7, 1.5.7.8, 1.5.7.9, 1.5.7.10, 1.5.8.1, 1.5.8.2, 1.5.8.3, 1.5.8.4, 1.5.8.5, 1.5.8.6, 1.5.8.7, 1.5.8.8, 1.5.8.9, 1.5.8.10, 1.5.9.1, 1.5.9.2, 1.5.9.3, 1.5.9.4, 1.5.9.5, 1.5.9.6, 1.5.9.7, 1.5.9.8, 1.5.9.9, 1.5.9.10, 1.5.10.1, 1.5.10.2, 1.5.10.3, 1.5.10.4, 1.5.10.5, 1.5.10.6, 1.5.10.7, 1.5.10.8, 1.5.10.9, 1.5.10.10, 1.6.1.1, 1.6.1.2, 1.6.1.3, 1.6.1.4, 1.6.1.5, 1.6.1.6, 1.6.1.7, 1.6.1.8, 1.6.1.9, 1.6.1.10, 1.6.2.1, 1.6.2.2, 1.6.2.3, 1.6.2.4, 1.6.2.5, 1.6.2.6, 1.6.2.7, 1.6.2.8, 1.6.2.9, 1.6.2.10, 1.6.3.1, 1.6.3.2, 1.6.3.3, 1.6.3.4, 1.6.3.5, 1.6.3.6, 1.6.3.7, 1.6.3.8, 1.6.3.9, 1.6.3.10, 1.6.4.1, 1.6.4.2, 1.6.4.3, 1.6.4.4, 1.6.4.5, 1.6.4.6, 1.6.4.7, 1.6.4.8, 1.6.4.9, 1.6.4.10, 1.6.5.1, 1.6.5.2, 1.6.5.3, 1.6.5.4, 1.6.5.5, 1.6.5.6, 1.6.5.7, 1.6.5.8, 1.6.5.9, 1.6.5.10, 1.6.6.1, 1.6.6.2, 1.6.6.3, 1.6.6.4, 1.6.6.5, 1.6.6.6, 1.6.6.7, 1.6.6.8, 1.6.6.9, 1.6.6.10, 1.6.7.1, 1.6.7.2, 1.6.7.3, 1.6.7.4, 1.6.7.5, 1.6.7.6, 1.6.7.7, 1.6.7.8, 1.6.7.9, 1.6.7.10, 1.6.8.1, 1.6.8.2, 1.6.8.3, 1.6.8.4, 1.6.8.5, 1.6.8.6, 1.6.8.7, 1.6.8.8, 1.6.8.9, 1.6.8.10, 1.6.9.1, 1.6.9.2, 1.6.9.3, 1.6.9.4, 1.6.9.5, 1.6.9.6, 1.6.9.7, 1.6.9.8, 1.6.9.9, 1.6.9.10, 1.6.10.1, 1.6.10.2, 1.6.10.3, 1.6.10.4, 1.6.10.5, 1.6.10.6, 1.6.10.7, 1.6.10.8, 1.6.10.9, 1.6.10.10, 1.7.1.1, 1.7.1.2, 1.7.1.3, 1.7.1.4, 1.7.1.5, 1.7.1.6, 1.7.1.7, 1.7.1.8, 1.7.1.9, 1.7.1.10, 1.7.2.1, 1.7.2.2, 1.7.2.3, 1.7.2.4, 1.7.2.5, 1.7.2.6, 1.7.2.7, 1.7.2.8, 1.7.2.9, 1.7.2.10, 1.7.3.1, 1.7.3.2, 1.7.3.3, 1.7.3.4, 1.7.3.5, 1.7.3.6, 1.7.3.7, 1.7.3.8, 1.7.3.9, 1.7.3.10, 1.7.4.1, 1.7.4.2, 1.7.4.3, 1.7.4.4, 1.7.4.5, 1.7.4.6, 1.7.4.7, 1.7.4.8, 1.7.4.9, 1.7.4.10, 1.7.5.1, 1.7.5.2, 1.7.5.3, 1.7.5.4, 1.7.5.5, 1.7.5.6, 1.7.5.7, 1.7.5.8, 1.7.5.9, 1.7.5.10, 1.7.6.1, 1.7.6.2, 1.7.6.3, 1.7.6.4, 1.7.6.5, 1.7.6.6, 1.7.6.7, 1.7.6.8, 1.7.6.9, 1.7.6.10, 1.7.7.1, 1.7.7.2, 1.7.7.3, 1.7.7.4, 1.7.7.5, 1.7.7.6, 1.7.7.7, 1.7.7.8, 1.7.7.9, 1.7.7.10, 1.7.8.1, 1.7.8.2, 1.7.8.3, 1.7.8.4, 1.7.8.5, 1.7.8.6, 1.7.8.7, 1.7.8.8, 1.7.8.9, 1.7.8.10, 1.7.9.1, 1.7.9.2, 1.7.9.3, 1.7.9.4, 1.7.9.5, 1.7.9.6, 1.7.9.7, 1.7.9.8, 1.7.9.9, 1.7.9.10, 1.7.10.1, 1.7.10.2, 1.7.10.3, 1.7.10.4, 1.7.10.5, 1.7.10.6, 1.7.10.7, 1.7.10.8, 1.7.10.9, 1.7.10.10, 1.8.1.1, 1.8.1.2, 1.8.1.3, 1.8.1.4, 1.8.1.5, 1.8.1.6, 1.8.1.7, 1.8.1.8, 1.8.1.9, 1.8.1.10, 1.8.2.1, 1.8.2.2, 1.8.2.3, 1.8.2.4, 1.8.2.5, 1.8.2.6, 1.8.2.7, 1.8.2.8, 1.8.2.9, 1.8.2.10, 1.8.3.1, 1.8.3.2, 1.8.3.3, 1.8.3.4, 1.8.3.5, 1.8.3.6, 1.8.3.7, 1.8.3.8, 1.8.3.9, 1.8.3.10, 1.8.4.1, 1.8.4.2, 1.8.4.3, 1.8.4.4, 1.8.4.5, 1.8.4.6, 1.8.4.7, 1.8.4.8, 1.8.4.9, 1.8.4.10, 1.8.5.1, 1.8.5.2, 1.8.5.3, 1.8.5.4, 1.8.5.5, 1.8.5.6, 1.8.5.7, 1.8.5.8, 1.8.5.9, 1.8.5.10, 1.8.6.1, 1.8.6.2, 1.8.6.3, 1.8.6.4, 1.8.6.5, 1.8.6.6, 1.8.6.7, 1.8.6.8, 1.8.6.9, 1.8.6.10, 1.8.7.1, 1.8.7.2, 1.8.7.3, 1.8.7.4, 1.8.7.5, 1.8.7.6, 1.8.7.7, 1.8.7.8, 1.8.7.9, 1.8.7.10, 1.8.8.1, 1.8.8.2, 1.8.8.3, 1.8.8.4, 1.8.8.5, 1.8.8.6, 1.8.8.7, 1.8.8.8, 1.8.8.9, 1.8.8.10, 1.8.9.1, 1.8.9.2, 1.8.9.3, 1.8.9.4, 1.8.9.5, 1.8.9.6, 1.8.9.7, 1.8.9.8, 1.8.9.9, 1.8.9.10, 1.8.10.1, 1.8.10.2, 1.8.10.3, 1.8.10.4, 1.8.10.5, 1.8.10.6, 1.8.10.7, 1.8.10.8, 1.8.10.9, 1.8.10.10, 1.9.1.1, 1.9.1.2, 1.9.1.3, 1.9.1.4, 1.9.1.5, 1.9.1.6, 1.9.1.7, 1.9.1.8, 1.9.1.9, 1.9.1.10, 1.9.2.1, 1.9.2.2, 1.9.2.3, 1.9.2.4, 1.9.2.5,

TABLE B-continued 1.9.2.6, 1.9.2.7, 1.9.2.8, 1.9.2.9, 1.9.2.10, 1.9.3.1, 1.9.3.2, 1.9.3.3, 1.9.3.4, 1.9.3.5, 1.9.3.6, 1.9.3.7, 1.9.3.8, 1.9.3.9, 1.9.3.10, 1.9.4.1, 1.9.4.2, 1.9.4.3, 1.9.4.4, 1.9.4.5, 1.9.4.6, 1.9.4.7, 1.9.4.8, 1.9.4.9, 1.9.4.10, 1.9.5.1, 1.9.5.2, 1.9.5.3, 1.9.5.4, 1.9.5.5, 1.9.5.6, 1.9.5.7, 1.9.5.8, 1.9.5.9, 1.9.5.10, 1.9.6.1, 1.9.6.2, 1.9.6.3, 1.9.6.4, 1.9.6.5, 1.9.6.6, 1.9.6.7, 1.9.6.8, 1.9.6.9, 1.9.6.10, 1.9.7.1, 1.9.7.2, 1.9.7.3, 1.9.7.4, 1.9.7.5, 1.9.7.6, 1.9.7.7, 1.9.7.8, 1.9.7.9, 1.9.7.10, 1.9.8.1, 1.9.8.2, 1.9.8.3, 1.9.8.4, 1.9.8.5, 1.9.8.6, 1.9.8.7, 1.9.8.8, 1.9.8.9, 1.9.8.10, 1.9.9.1, 1.9.9.2, 1.9.9.3, 1.9.9.4, 1.9.9.5, 1.9.9.6, 1.9.9.7, 1.9.9.8, 1.9.9.9, 1.9.9.10, 1.9.10.1, 1.9.10.2, 1.9.10.3, 1.9.10.4, 1.9.10.5, 1.9.10.6, 1.9.10.7, 1.9.10.8, 1.9.10.9, 1.9.10.10, 1.10.1.1, 1.10.1.2, 1.10.1.3, 1.10.1.4, 1.10.1.5, 1.10.1.6, 1.10.1.7, 1.10.1.8, 1.10.1.9, 1.10.1.10, 1.10.2.1, 1.10.2.2, 1.10.2.3, 1.10.2.4, 1.10.2.5, 1.10.2.6, 1.10.2.7, 1.10.2.8, 1.10.2.9, 1.10.2.10, 1.10.3.1, 1.10.3.2, 1.10.3.3, 1.10.3.4, 1.10.3.5, 1.10.3.6, 1.10.3.7, 1.10.3.8, 1.10.3.9, 1.10.3.10, 1.10.4.1, 1.10.4.2, 1.10.4.3, 1.10.4.4, 1.10.4.5, 1.10.4.6, 1.10.4.7, 1.10.4.8, 1.10.4.9, 1.10.4.10, 1.10.5.1, 1.10.5.2, 1.10.5.3, 1.10.5.4, 1.10.5.5, 1.10.5.6, 1.10.5.7, 1.10.5.8, 1.10.5.9, 1.10.5.10, 1.10.6.1, 1.10.6.2, 1.10.6.3, 1.10.6.4, 1.10.6.5, 1.10.6.6, 1.10.6.7, 1.10.6.8, 1.10.6.9, 1.10.6.10, 1.10.7.1, 1.10.7.2, 1.10.7.3, 1.10.7.4, 1.10.7.5, 1.10.7.6, 1.10.7.7, 1.10.7.8, 1.10.7.9, 1.10.7.10, 1.10.8.1, 1.10.8.2, 1.10.8.3, 1.10.8.4, 1.10.8.5, 1.10.8.6, 1.10.8.7, 1.10.8.8, 1.10.8.9, 1.10.8.10, 1.10.9.1, 1.10.9.2, 1.10.9.3, 1.10.9.4, 1.10.9.5, 1.10.9.6, 1.10.9.7, 1.10.9.8, 1.10.9.9, 1.10.9.10, 1.10.10.1, 1.10.10.2, 1.10.10.3, 1.10.10.4, 1.10.10.5, 1.10.10.6, 1.10.10.7, 1.10.10.8, 1.10.10.9, 1.10.10.10, 2.1.1.1, 2.1.1.2, 2.1.1.3, 2.1.1.4, 2.1.1.5, 2.1.1.6, 2.1.1.7, 2.1.1.8, 2.1.1.9, 2.1.1.10, 2.1.2.1, 2.1.2.2, 2.1.2.3, 2.1.2.4, 2.1.2.5, 2.1.2.6, 2.1.2.7, 2.1.2.8, 2.1.2.9, 2.1.2.10, 2.1.3.1, 2.1.3.2, 2.1.3.3, 2.1.3.4, 2.1.3.5, 2.1.3.6, 2.1.3.7, 2.1.3.8, 2.1.3.9, 2.1.3.10, 2.1.4.1, 2.1.4.2, 2.1.4.3, 2.1.4.4, 2.1.4.5, 2.1.4.6, 2.1.4.7, 2.1.4.8, 2.1.4.9, 2.1.4.10, 2.1.5.1, 2.1.5.2, 2.1.5.3, 2.1.5.4, 2.1.5.5, 2.1.5.6, 2.1.5.7, 2.1.5.8, 2.1.5.9, 2.1.5.10, 2.1.6.1, 2.1.6.2, 2.1.6.3, 2.1.6.4, 2.1.6.5, 2.1.6.6, 2.1.6.7, 2.1.6.8, 2.1.6.9, 2.1.6.10, 2.1.7.1, 2.1.7.2, 2.1.7.3, 2.1.7.4, 2.1.7.5, 2.1.7.6, 2.1.7.7, 2.1.7.8, 2.1.7.9, 2.1.7.10, 2.1.8.1, 2.1.8.2, 2.1.8.3, 2.1.8.4, 2.1.8.5, 2.1.8.6, 2.1.8.7, 2.1.8.8, 2.1.8.9, 2.1.8.10, 2.1.9.1, 2.1.9.2, 2.1.9.3, 2.1.9.4, 2.1.9.5, 2.1.9.6, 2.1.9.7, 2.1.9.8, 2.1.9.9, 2.1.9.10, 2.1.10.1, 2.1.10.2, 2.1.10.3, 2.1.10.4, 2.1.10.5, 2.1.10.6, 2.1.10.7, 2.1.10.8, 2.1.10.9, 2.1.10.10, 2.2.1.1, 2.2.1.2, 2.2.1.3, 2.2.1.4, 2.2.1.5, 2.2.1.6, 2.2.1.7, 2.2.1.8, 2.2.1.9, 2.2.1.10, 2.2.2.1, 2.2.2.2, 2.2.2.3, 2.2.2.4, 2.2.2.5, 2.2.2.6, 2.2.2.7, 2.2.2.8, 2.2.2.9, 2.2.2.10, 2.2.3.1, 2.2.3.2, 2.2.3.3, 2.2.3.4, 2.2.3.5, 2.2.3.6, 2.2.3.7, 2.2.3.8, 2.2.3.9, 2.2.3.10, 2.2.4.1, 2.2.4.2, 2.2.4.3, 2.2.4.4, 2.2.4.5, 2.2.4.6, 2.2.4.7, 2.2.4.8, 2.2.4.9, 2.2.4.10, 2.2.5.1, 2.2.5.2, 2.2.5.3, 2.2.5.4, 2.2.5.5, 2.2.5.6, 2.2.5.7, 2.2.5.8, 2.2.5.9, 2.2.5.10, 2.2.6.1, 2.2.6.2, 2.2.6.3, 2.2.6.4, 2.2.6.5, 2.2.6.6, 2.2.6.7, 2.2.6.8, 2.2.6.9, 2.2.6.10, 2.2.7.1, 2.2.7.2, 2.2.7.3, 2.2.7.4, 2.2.7.5, 2.2.7.6, 2.2.7.7, 2.2.7.8, 2.2.7.9, 2.2.7.10, 2.2.8.1, 2.2.8.2, 2.2.8.3, 2.2.8.4, 2.2.8.5, 2.2.8.6, 2.2.8.7, 2.2.8.8, 2.2.8.9, 2.2.8.10, 2.2.9.1, 2.2.9.2, 2.2.9.3, 2.2.9.4, 2.2.9.5, 2.2.9.6, 2.2.9.7, 2.2.9.8, 2.2.9.9, 2.2.9.10, 2.2.10.1, 2.2.10.2, 2.2.10.3, 2.2.10.4, 2.2.10.5, 2.2.10.6, 2.2.10.7, 2.2.10.8, 2.2.10.9, 2.2.10.10, 2.3.1.1, 2.3.1.2, 2.3.1.3, 2.3.1.4, 2.3.1.5, 2.3.1.6, 2.3.1.7, 2.3.1.8, 2.3.1.9, 2.3.1.10, 2.3.2.1, 2.3.2.2, 2.3.2.3, 2.3.2.4, 2.3.2.5, 2.3.2.6, 2.3.2.7, 2.3.2.8, 2.3.2.9, 2.3.2.10, 2.3.3.1, 2.3.3.2, 2.3.3.3, 2.3.3.4, 2.3.3.5, 2.3.3.6, 2.3.3.7, 2.3.3.8, 2.3.3.9, 2.3.3.10, 2.3.4.1, 2.3.4.2, 2.3.4.3, 2.3.4.4, 2.3.4.5, 2.3.4.6, 2.3.4.7, 2.3.4.8, 2.3.4.9, 2.3.4.10, 2.3.5.1, 2.3.5.2, 2.3.5.3, 2.3.5.4, 2.3.5.5, 2.3.5.6, 2.3.5.7, 2.3.5.8, 2.3.5.9, 2.3.5.10, 2.3.6.1, 2.3.6.2, 2.3.6.3, 2.3.6.4, 2.3.6.5, 2.3.6.6, 2.3.6.7, 2.3.6.8, 2.3.6.9, 2.3.6.10, 2.3.7.1, 2.3.7.2, 2.3.7.3, 2.3.7.4, 2.3.7.5, 2.3.7.6, 2.3.7.7, 2.3.7.8, 2.3.7.9, 2.3.7.10, 2.3.8.1, 2.3.8.2, 2.3.8.3, 2.3.8.4, 2.3.8.5, 2.3.8.6, 2.3.8.7, 2.3.8.8, 2.3.8.9, 2.3.8.10, 2.3.9.1, 2.3.9.2, 2.3.9.3, 2.3.9.4, 2.3.9.5, 2.3.9.6, 2.3.9.7, 2.3.9.8, 2.3.9.9, 2.3.9.10, 2.3.10.1, 2.3.10.2, 2.3.10.3, 2.3.10.4, 2.3.10.5, 2.3.10.6, 2.3.10.7, 2.3.10.8, 2.3.10.9, 2.3.10.10, 2.4.1.1, 2.4.1.2, 2.4.1.3, 2.4.1.4, 2.4.1.5, 2.4.1.6, 2.4.1.7, 2.4.1.8, 2.4.1.9, 2.4.1.10, 2.4.2.1, 2.4.2.2, 2.4.2.3, 2.4.2.4, 2.4.2.5, 2.4.2.6, 2.4.2.7, 2.4.2.8, 2.4.2.9, 2.4.2.10, 2.4.3.1, 2.4.3.2, 2.4.3.3, 2.4.3.4, 2.4.3.5, 2.4.3.6, 2.4.3.7, 2.4.3.8, 2.4.3.9, 2.4.3.10, 2.4.4.1, 2.4.4.2, 2.4.4.3, 2.4.4.4, 2.4.4.5, 2.4.4.6, 2.4.4.7, 2.4.4.8, 2.4.4.9, 2.4.4.10, 2.4.5.1, 2.4.5.2, 2.4.5.3, 2.4.5.4, 2.4.5.5, 2.4.5.6, 2.4.5.7, 2.4.5.8, 2.4.5.9, 2.4.5.10, 2.4.6.1, 2.4.6.2, 2.4.6.3, 2.4.6.4, 2.4.6.5, 2.4.6.6, 2.4.6.7, 2.4.6.8, 2.4.6.9, 2.4.6.10, 2.4.7.1, 2.4.7.2, 2.4.7.3, 2.4.7.4, 2.4.7.5, 2.4.7.6, 2.4.7.7, 2.4.7.8, 2.4.7.9, 2.4.7.10, 2.4.8.1, 2.4.8.2, 2.4.8.3, 2.4.8.4, 2.4.8.5, 2.4.8.6, 2.4.8.7, 2.4.8.8, 2.4.8.9, 2.4.8.10, 2.4.9.1, 2.4.9.2, 2.4.9.3, 2.4.9.4, 2.4.9.5, 2.4.9.6, 2.4.9.7, 2.4.9.8, 2.4.9.9, 2.4.9.10, 2.4.10.1, 2.4.10.2, 2.4.10.3, 2.4.10.4, 2.4.10.5, 2.4.10.6, 2.4.10.7, 2.4.10.8, 2.4.10.9, 2.4.10.10, 2.5.1.1, 2.5.1.2, 2.5.1.3, 2.5.1.4, 2.5.1.5, 2.5.1.6, 2.5.1.7, 2.5.1.8, 2.5.1.9, 2.5.1.10, 2.5.2.1, 2.5.2.2, 2.5.2.3, 2.5.2.4, 2.5.2.5, 2.5.2.6, 2.5.2.7, 2.5.2.8, 2.5.2.9, 2.5.2.10, 2.5.3.1, 2.5.3.2, 2.5.3.3, 2.5.3.4, 2.5.3.5, 2.5.3.6, 2.5.3.7, 2.5.3.8, 2.5.3.9, 2.5.3.10, 2.5.4.1, 2.5.4.2, 2.5.4.3, 2.5.4.4, 2.5.4.5, 2.5.4.6, 2.5.4.7, 2.5.4.8, 2.5.4.9, 2.5.4.10, 2.5.5.1, 2.5.5.2, 2.5.5.3, 2.5.5.4, 2.5.5.5, 2.5.5.6, 2.5.5.7, 2.5.5.8, 2.5.5.9, 2.5.5.10, 2.5.6.1, 2.5.6.2, 2.5.6.3, 2.5.6.4, 2.5.6.5, 2.5.6.6, 2.5.6.7, 2.5.6.8, 2.5.6.9, 2.5.6.10, 2.5.7.1, 2.5.7.2, 2.5.7.3, 2.5.7.4, 2.5.7.5, 2.5.7.6, 2.5.7.7, 2.5.7.8, 2.5.7.9, 2.5.7.10, 2.5.8.1, 2.5.8.2, 2.5.8.3, 2.5.8.4, 2.5.8.5, 2.5.8.6, 2.5.8.7, 2.5.8.8, 2.5.8.9, 2.5.8.10, 2.5.9.1, 2.5.9.2, 2.5.9.3, 2.5.9.4, 2.5.9.5, 2.5.9.6, 2.5.9.7, 2.5.9.8, 2.5.9.9, 2.5.9.10, 2.5.10.1, 2.5.10.2, 2.5.10.3, 2.5.10.4, 2.5.10.5, 2.5.10.6, 2.5.10.7, 2.5.10.8, 2.5.10.9, 2.5.10.10, 2.6.1.1, 2.6.1.2, 2.6.1.3, 2.6.1.4, 2.6.1.5, 2.6.1.6, 2.6.1.7, 2.6.1.8, 2.6.1.9, 2.6.1.10, 2.6.2.1, 2.6.2.2, 2.6.2.3, 2.6.2.4, 2.6.2.5, 2.6.2.6, 2.6.2.7, 2.6.2.8, 2.6.2.9, 2.6.2.10, 2.6.3.1, 2.6.3.2, 2.6.3.3, 2.6.3.4, 2.6.3.5, 2.6.3.6, 2.6.3.7, 2.6.3.8, 2.6.3.9, 2.6.3.10, 2.6.4.1, 2.6.4.2, 2.6.4.3, 2.6.4.4, 2.6.4.5, 2.6.4.6, 2.6.4.7, 2.6.4.8, 2.6.4.9, 2.6.4.10, 2.6.5.1, 2.6.5.2, 2.6.5.3, 2.6.5.4, 2.6.5.5, 2.6.5.6, 2.6.5.7, 2.6.5.8, 2.6.5.9, 2.6.5.10, 2.6.6.1, 2.6.6.2, 2.6.6.3, 2.6.6.4, 2.6.6.5, 2.6.6.6, 2.6.6.7, 2.6.6.8, 2.6.6.9, 2.6.6.10, 2.6.7.1, 2.6.7.2, 2.6.7.3, 2.6.7.4, 2.6.7.5, 2.6.7.6, 2.6.7.7, 2.6.7.8, 2.6.7.9, 2.6.7.10, 2.6.8.1, 2.6.8.2, 2.6.8.3, 2.6.8.4, 2.6.8.5, 2.6.8.6, 2.6.8.7, 2.6.8.8, 2.6.8.9, 2.6.8.10, 2.6.9.1, 2.6.9.2, 2.6.9.3, 2.6.9.4, 2.6.9.5, 2.6.9.6, 2.6.9.7, 2.6.9.8, 2.6.9.9, 2.6.9.10, 2.6.10.1, 2.6.10.2, 2.6.10.3, 2.6.10.4, 2.6.10.5, 2.6.10.6, 2.6.10.7, 2.6.10.8, 2.6.10.9, 2.6.10.10, 2.7.1.1, 2.7.1.2, 2.7.1.3, 2.7.1.4, 2.7.1.5, 2.7.1.6, 2.7.1.7, 2.7.1.8, 2.7.1.9, 2.7.1.10, 2.7.2.1, 2.7.2.2, 2.7.2.3, 2.7.2.4, 2.7.2.5, 2.7.2.6, 2.7.2.7, 2.7.2.8, 2.7.2.9, 2.7.2.10, 2.7.3.1, 2.7.3.2, 2.7.3.3, 2.7.3.4, 2.7.3.5, 2.7.3.6, 2.7.3.7, 2.7.3.8, 2.7.3.9, 2.7.3.10, 2.7.4.1, 2.7.4.2, 2.7.4.3, 2.7.4.4, 2.7.4.5, 2.7.4.6, 2.7.4.7, 2.7.4.8, 2.7.4.9, 2.7.4.10, 2.7.5.1, 2.7.5.2, 2.7.5.3, 2.7.5.4, 2.7.5.5, 2.7.5.6, 2.7.5.7, 2.7.5.8, 2.7.5.9, 2.7.5.10, 2.7.6.1, 2.7.6.2, 2.7.6.3, 2.7.6.4, 2.7.6.5, 2.7.6.6, 2.7.6.7, 2.7.6.8, 2.7.6.9, 2.7.6.10, 2.7.7.1, 2.7.7.2, 2.7.7.3, 2.7.7.4, 2.7.7.5, 2.7.7.6, 2.7.7.7, 2.7.7.8, 2.7.7.9, 2.7.7.10, 2.7.8.1, 2.7.8.2, 2.7.8.3, 2.7.8.4, 2.7.8.5, 2.7.8.6, 2.7.8.7, 2.7.8.8, 2.7.8.9, 2.7.8.10, 2.7.9.1, 2.7.9.2, 2.7.9.3, 2.7.9.4, 2.7.9.5, 2.7.9.6, 2.7.9.7, 2.7.9.8, 2.7.9.9, 2.7.9.10, 2.7.10.1, 2.7.10.2, 2.7.10.3, 2.7.10.4, 2.7.10.5, 2.7.10.6, 2.7.10.7, 2.7.10.8, 2.7.10.9, 2.7.10.10, 2.8.1.1, 2.8.1.2, 2.8.1.3, 2.8.1.4, 2.8.1.5, 2.8.1.6, 2.8.1.7, 2.8.1.8, 2.8.1.9, 2.8.1.10, 2.8.2.1, 2.8.2.2, 2.8.2.3, 2.8.2.4, 2.8.2.5, 2.8.2.6, 2.8.2.7, 2.8.2.8, 2.8.2.9, 2.8.2.10, 2.8.3.1, 2.8.3.2, 2.8.3.3, 2.8.3.4, 2.8.3.5, 2.8.3.6, 2.8.3.7, 2.8.3.8, 2.8.3.9, 2.8.3.10, 2.8.4.1, 2.8.4.2, 2.8.4.3, 2.8.4.4, 2.8.4.5, 2.8.4.6, 2.8.4.7, 2.8.4.8, 2.8.4.9, 2.8.4.10, 2.8.5.1, 2.8.5.2, 2.8.5.3, 2.8.5.4, 2.8.5.5, 2.8.5.6, 2.8.5.7, 2.8.5.8, 2.8.5.9, 2.8.5.10, 2.8.6.1, 2.8.6.2, 2.8.6.3, 2.8.6.4, 2.8.6.5, 2.8.6.6, 2.8.6.7, 2.8.6.8, 2.8.6.9, 2.8.6.10, 2.8.7.1, 2.8.7.2, 2.8.7.3, 2.8.7.4, 2.8.7.5, 2.8.7.6, 2.8.7.7, 2.8.7.8, 2.8.7.9, 2.8.7.10, 2.8.8.1, 2.8.8.2, 2.8.8.3, 2.8.8.4, 2.8.8.5, 2.8.8.6, 2.8.8.7, 2.8.8.8, 2.8.8.9, 2.8.8.10, 2.8.9.1, 2.8.9.2, 2.8.9.3, 2.8.9.4, 2.8.9.5, 2.8.9.6, 2.8.9.7, 2.8.9.8, 2.8.9.9, 2.8.9.10, 2.8.10.1, 2.8.10.2, 2.8.10.3, 2.8.10.4, 2.8.10.5, 2.8.10.6, 2.8.10.7, 2.8.10.8, 2.8.10.9, 2.8.10.10, 2.9.1.1, 2.9.1.2, 2.9.1.3, 2.9.1.4, 2.9.1.5, 2.9.1.6, 2.9.1.7, 2.9.1.8, 2.9.1.9, 2.9.1.10, 2.9.2.1, 2.9.2.2, 2.9.2.3, 2.9.2.4, 2.9.2.5, 2.9.2.6, 2.9.2.7, 2.9.2.8, 2.9.2.9, 2.9.2.10, 2.9.3.1, 2.9.3.2, 2.9.3.3, 2.9.3.4, 2.9.3.5, 2.9.3.6, 2.9.3.7, 2.9.3.8, 2.9.3.9, 2.9.3.10, 2.9.4.1, 2.9.4.2, 2.9.4.3, 2.9.4.4, 2.9.4.5, 2.9.4.6, 2.9.4.7, 2.9.4.8, 2.9.4.9, 2.9.4.10, 2.9.5.1, 2.9.5.2, 2.9.5.3, 2.9.5.4, 2.9.5.5, 2.9.5.6, 2.9.5.7, 2.9.5.8, 2.9.5.9, 2.9.5.10, 2.9.6.1, 2.9.6.2, 2.9.6.3, 2.9.6.4, 2.9.6.5, 2.9.6.6, 2.9.6.7, 2.9.6.8, 2.9.6.9, 2.9.6.10, 2.9.7.1, 2.9.7.2, 2.9.7.3, 2.9.7.4, 2.9.7.5, 2.9.7.6, 2.9.7.7, 2.9.7.8, 2.9.7.9, TABLE B-continued 2.9.7.10, 2.9.8.1, 2.9.8.2, 2.9.8.3, 2.9.8.4, 2.9.8.5, 2.9.8.6, 2.9.8.7, 2.9.8.8, 2.9.8.9, 2.9.8.10, 2.9.9.1, 2.9.9.2, 2.9.9.3, 2.9.9.4, 2.9.9.5, 2.9.9.6, 2.9.9.7, 2.9.9.8, 2.9.9.9, 2.9.9.10, 2.9.10.1, 2.9.10.2, 2.9.10.3, 2.9.10.4, 2.9.10.5, 2.9.10.6, 2.9.10.7, 2.9.10.8, 2.9.10.9, 2.9.10.10, 2.10.1.1, 2.10.1.2, 2.10.1.3, 2.10.1.4, 2.10.1.5, 2.10.1.6, 2.10.1.7, 2.10.1.8, 2.10.1.9, 2.10.1.10, 2.10.2.1, 2.10.2.2, 2.10.2.3, 2.10.2.4, 2.10.2.5, 2.10.2.6, 2.10.2.7, 2.10.2.8, 2.10.2.9, 2.10.2.10, 2.10.3.1, 2.10.3.2, 2.10.3.3, 2.10.3.4, 2.10.3.5, 2.10.3.6, 2.10.3.7, 2.10.3.8, 2.10.3.9, 2.10.3.10, 2.10.4.1, 2.10.4.2, 2.10.4.3, 2.10.4.4, 2.10.4.5, 2.10.4.6, 2.10.4.7, 2.10.4.8, 2.10.4.9, 2.10.4.10, 2.10.5.1, 2.10.5.2, 2.10.5.3, 2.10.5.4, 2.10.5.5, 2.10.5.6, 2.10.5.7, 2.10.5.8, 2.10.5.9, 2.10.5.10, 2.10.6.1, 2.10.6.2, 2.10.6.3, 2.10.6.4, 2.10.6.5, 2.10.6.6, 2.10.6.7, 2.10.6.8, 2.10.6.9, 2.10.6.10, 2.10.7.1, 2.10.7.2, 2.10.7.3, 2.10.7.4, 2.10.7.5, 2.10.7.6, 2.10.7.7, 2.10.7.8, 2.10.7.9, 2.10.7.10, 2.10.8.1, 2.10.8.2, 2.10.8.3, 2.10.8.4, 2.10.8.5, 2.10.8.6, 2.10.8.7, 2.10.8.8, 2.10.8.9, 2.10.8.10, 2.10.9.1, 2.10.9.2, 2.10.9.3, 2.10.9.4, 2.10.9.5, 2.10.9.6, 2.10.9.7, 2.10.9.8, 2.10.9.9, 2.10.9.10, 2.10.10.1, 2.10.10.2, 2.10.10.3, 2.10.10.4, 2.10.10.5, 2.10.10.6, 2.10.10.7, 2.10.10.8, 2.10.10.9, 2.10.10.10, 3.1.1.1, 3.1.1.2, 3.1.1.3, 3.1.1.4, 3.1.1.5, 3.1.1.6, 3.1.1.7, 3.1.1.8, 3.1.1.9, 3.1.1.10, 3.1.2.1, 3.1.2.2, 3.1.2.3, 3.1.2.4, 3.1.2.5, 3.1.2.6, 3.1.2.7, 3.1.2.8, 3.1.2.9, 3.1.2.10, 3.1.3.1, 3.1.3.2, 3.1.3.3, 3.1.3.4, 3.1.3.5, 3.1.3.6, 3.1.3.7, 3.1.3.8, 3.1.3.9, 3.1.3.10, 3.1.4.1, 3.1.4.2, 3.1.4.3, 3.1.4.4, 3.1.4.5, 3.1.4.6, 3.1.4.7, 3.1.4.8, 3.1.4.9, 3.1.4.10, 3.1.5.1, 3.1.5.2, 3.1.5.3, 3.1.5.4, 3.1.5.5, 3.1.5.6, 3.1.5.7, 3.1.5.8, 3.1.5.9, 3.1.5.10, 3.1.6.1, 3.1.6.2, 3.1.6.3, 3.1.6.4, 3.1.6.5, 3.1.6.6, 3.1.6.7, 3.1.6.8, 3.1.6.9, 3.1.6.10, 3.1.7.1, 3.1.7.2, 3.1.7.3, 3.1.7.4, 3.1.7.5, 3.1.7.6, 3.1.7.7, 3.1.7.8, 3.1.7.9, 3.1.7.10, 3.1.8.1, 3.1.8.2, 3.1.8.3, 3.1.8.4, 3.1.8.5, 3.1.8.6, 3.1.8.7, 3.1.8.8, 3.1.8.9, 3.1.8.10, 3.1.9.1, 3.1.9.2, 3.1.9.3, 3.1.9.4, 3.1.9.5, 3.1.9.6, 3.1.9.7, 3.1.9.8, 3.1.9.9, 3.1.9.10, 3.1.10.1, 3.1.10.2, 3.1.10.3, 3.1.10.4, 3.1.10.5, 3.1.10.6, 3.1.10.7, 3.1.10.8, 3.1.10.9, 3.1.10.10, 3.2.1.1, 3.2.1.2, 3.2.1.3, 3.2.1.4, 3.2.1.5, 3.2.1.6, 3.2.1.7, 3.2.1.8, 3.2.1.9, 3.2.1.10, 3.2.2.1, 3.2.2.2, 3.2.2.3, 3.2.2.4, 3.2.2.5, 3.2.2.6, 3.2.2.7, 3.2.2.8, 3.2.2.9, 3.2.2.10, 3.2.3.1, 3.2.3.2, 3.2.3.3, 3.2.3.4, 3.2.3.5, 3.2.3.6, 3.2.3.7, 3.2.3.8, 3.2.3.9, 3.2.3.10, 3.2.4.1, 3.2.4.2, 3.2.4.3, 3.2.4.4, 3.2.4.5, 3.2.4.6, 3.2.4.7, 3.2.4.8, 3.2.4.9, 3.2.4.10, 3.2.5.1, 3.2.5.2, 3.2.5.3, 3.2.5.4, 3.2.5.5, 3.2.5.6, 3.2.5.7, 3.2.5.8, 3.2.5.9, 3.2.5.10, 3.2.6.1, 3.2.6.2, 3.2.6.3, 3.2.6.4, 3.2.6.5, 3.2.6.6, 3.2.6.7, 3.2.6.8, 3.2.6.9, 3.2.6.10, 3.2.7.1, 3.2.7.2, 3.2.7.3, 3.2.7.4, 3.2.7.5, 3.2.7.6, 3.2.7.7, 3.2.7.8, 3.2.7.9, 3.2.7.10, 3.2.8.1, 3.2.8.2, 3.2.8.3, 3.2.8.4, 3.2.8.5, 3.2.8.6, 3.2.8.7, 3.2.8.8, 3.2.8.9, 3.2.8.10, 3.2.9.1, 3.2.9.2, 3.2.9.3, 3.2.9.4, 3.2.9.5, 3.2.9.6, 3.2.9.7, 3.2.9.8, 3.2.9.9, 3.2.9.10, 3.2.10.1, 3.2.10.2, 3.2.10.3, 3.2.10.4, 3.2.10.5, 3.2.10.6, 3.2.10.7, 3.2.10.8, 3.2.10.9, 3.2.10.10, 3.3.1.1, 3.3.1.2, 3.3.1.3, 3.3.1.4, 3.3.1.5, 3.3.1.6, 3.3.1.7, 3.3.1.8, 3.3.1.9, 3.3.1.10, 3.3.2.1, 3.3.2.2, 3.3.2.3, 3.3.2.4, 3.3.2.5, 3.3.2.6, 3.3.2.7, 3.3.2.8, 3.3.2.9, 3.3.2.10, 3.3.3.1, 3.3.3.2, 3.3.3.3, 3.3.3.4, 3.3.3.5, 3.3.3.6, 3.3.3.7, 3.3.3.8, 3.3.3.9, 3.3.3.10, 3.3.4.1, 3.3.4.2, 3.3.4.3, 3.3.4.4, 3.3.4.5, 3.3.4.6, 3.3.4.7, 3.3.4.8, 3.3.4.9, 3.3.4.10, 3.3.5.1, 3.3.5.2, 3.3.5.3, 3.3.5.4, 3.3.5.5, 3.3.5.6, 3.3.5.7, 3.3.5.8, 3.3.5.9, 3.3.5.10, 3.3.6.1, 3.3.6.2, 3.3.6.3, 3.3.6.4, 3.3.6.5, 3.3.6.6, 3.3.6.7, 3.3.6.8, 3.3.6.9, 3.3.6.10, 3.3.7.1, 3.3.7.2, 3.3.7.3, 3.3.7.4, 3.3.7.5, 3.3.7.6, 3.3.7.7, 3.3.7.8, 3.3.7.9, 3.3.7.10, 3.3.8.1, 3.3.8.2, 3.3.8.3, 3.3.8.4, 3.3.8.5, 3.3.8.6, 3.3.8.7, 3.3.8.8, 3.3.8.9, 3.3.8.10, 3.3.9.1, 3.3.9.2, 3.3.9.3, 3.3.9.4, 3.3.9.5, 3.3.9.6, 3.3.9.7, 3.3.9.8, 3.3.9.9, 3.3.9.10, 3.3.10.1, 3.3.10.2, 3.3.10.3, 3.3.10.4, 3.3.10.5, 3.3.10.6, 3.3.10.7, 3.3.10.8, 3.3.10.9, 3.3.10.10, 3.4.1.1, 3.4.1.2, 3.4.1.3, 3.4.1.4, 3.4.1.5, 3.4.1.6, 3.4.1.7, 3.4.1.8, 3.4.1.9, 3.4.1.10, 3.4.2.1, 3.4.2.2, 3.4.2.3, 3.4.2.4, 3.4.2.5, 3.4.2.6, 3.4.2.7, 3.4.2.8, 3.4.2.9, 3.4.2.10, 3.4.3.1, 3.4.3.2, 3.4.3.3, 3.4.3.4, 3.4.3.5, 3.4.3.6, 3.4.3.7, 3.4.3.8, 3.4.3.9, 3.4.3.10, 3.4.4.1, 3.4.4.2, 3.4.4.3, 3.4.4.4, 3.4.4.5, 3.4.4.6, 3.4.4.7, 3.4.4.8, 3.4.4.9, 3.4.4.10, 3.4.5.1, 3.4.5.2, 3.4.5.3, 3.4.5.4, 3.4.5.5, 3.4.5.6, 3.4.5.7, 3.4.5.8, 3.4.5.9, 3.4.5.10, 3.4.6.1, 3.4.6.2, 3.4.6.3, 3.4.6.4, 3.4.6.5, 3.4.6.6, 3.4.6.7, 3.4.6.8, 3.4.6.9, 3.4.6.10, 3.4.7.1, 3.4.7.2, 3.4.7.3, 3.4.7.4, 3.4.7.5, 3.4.7.6, 3.4.7.7, 3.4.7.8, 3.4.7.9, 3.4.7.10, 3.4.8.1, 3.4.8.2, 3.4.8.3, 3.4.8.4, 3.4.8.5, 3.4.8.6, 3.4.8.7, 3.4.8.8, 3.4.8.9, 3.4.8.10, 3.4.9.1, 3.4.9.2, 3.4.9.3, 3.4.9.4, 3.4.9.5, 3.4.9.6, 3.4.9.7, 3.4.9.8, 3.4.9.9, 3.4.9.10, 3.4.10.1, 3.4.10.2, 3.4.10.3, 3.4.10.4, 3.4.10.5, 3.4.10.6, 3.4.10.7, 3.4.10.8, 3.4.10.9, 3.4.10.10, 3.5.1.1, 3.5.1.2, 3.5.1.3, 3.5.1.4, 3.5.1.5, 3.5.1.6, 3.5.1.7, 3.5.1.8, 3.5.1.9, 3.5.1.10, 3.5.2.1, 3.5.2.2, 3.5.2.3, 3.5.2.4, 3.5.2.5, 3.5.2.6, 3.5.2.7, 3.5.2.8, 3.5.2.9, 3.5.2.10, 3.5.3.1, 3.5.3.2, 3.5.3.3, 3.5.3.4, 3.5.3.5, 3.5.3.6, 3.5.3.7, 3.5.3.8, 3.5.3.9, 3.5.3.10, 3.5.4.1, 3.5.4.2, 3.5.4.3, 3.5.4.4, 3.5.4.5, 3.5.4.6, 3.5.4.7, 3.5.4.8, 3.5.4.9, 3.5.4.10, 3.5.5.1, 3.5.5.2, 3.5.5.3, 3.5.5.4, 3.5.5.5, 3.5.5.6, 3.5.5.7, 3.5.5.8, 3.5.5.9, 3.5.5.10, 3.5.6.1, 3.5.6.2, 3.5.6.3, 3.5.6.4, 3.5.6.5, 3.5.6.6, 3.5.6.7, 3.5.6.8, 3.5.6.9, 3.5.6.10, 3.5.7.1, 3.5.7.2, 3.5.7.3, 3.5.7.4, 3.5.7.5, 3.5.7.6, 3.5.7.7, 3.5.7.8, 3.5.7.9, 3.5.7.10, 3.5.8.1, 3.5.8.2, 3.5.8.3, 3.5.8.4, 3.5.8.5, 3.5.8.6, 3.5.8.7, 3.5.8.8, 3.5.8.9, 3.5.8.10, 3.5.9.1, 3.5.9.2, 3.5.9.3, 3.5.9.4, 3.5.9.5, 3.5.9.6, 3.5.9.7, 3.5.9.8, 3.5.9.9, 3.5.9.10, 3.5.10.1, 3.5.10.2, 3.5.10.3, 3.5.10.4, 3.5.10.5, 3.5.10.6, 3.5.10.7, 3.5.10.8, 3.5.10.9, 3.5.10.10, 3.6.1.1, 3.6.1.2, 3.6.1.3, 3.6.1.4, 3.6.1.5, 3.6.1.6, 3.6.1.7, 3.6.1.8, 3.6.1.9, 3.6.1.10, 3.6.2.1, 3.6.2.2, 3.6.2.3, 3.6.2.4, 3.6.2.5, 3.6.2.6, 3.6.2.7, 3.6.2.8, 3.6.2.9, 3.6.2.10, 3.6.3.1, 3.6.3.2, 3.6.3.3, 3.6.3.4, 3.6.3.5, 3.6.3.6, 3.6.3.7, 3.6.3.8, 3.6.3.9, 3.6.3.10, 3.6.4.1, 3.6.4.2, 3.6.4.3, 3.6.4.4, 3.6.4.5, 3.6.4.6, 3.6.4.7, 3.6.4.8, 3.6.4.9, 3.6.4.10, 3.6.5.1, 3.6.5.2, 3.6.5.3, 3.6.5.4, 3.6.5.5, 3.6.5.6, 3.6.5.7, 3.6.5.8, 3.6.5.9, 3.6.5.10, 3.6.6.1, 3.6.6.2, 3.6.6.3, 3.6.6.4, 3.6.6.5, 3.6.6.6, 3.6.6.7, 3.6.6.8, 3.6.6.9, 3.6.6.10, 3.6.7.1, 3.6.7.2, 3.6.7.3, 3.6.7.4, 3.6.7.5, 3.6.7.6, 3.6.7.7, 3.6.7.8, 3.6.7.9, 3.6.7.10, 3.6.8.1, 3.6.8.2, 3.6.8.3, 3.6.8.4, 3.6.8.5, 3.6.8.6, 3.6.8.7, 3.6.8.8, 3.6.8.9, 3.6.8.10, 3.6.9.1, 3.6.9.2, 3.6.9.3, 3.6.9.4, 3.6.9.5, 3.6.9.6, 3.6.9.7, 3.6.9.8, 3.6.9.9, 3.6.9.10, 3.6.10.1, 3.6.10.2, 3.6.10.3, 3.6.10.4, 3.6.10.5, 3.6.10.6, 3.6.10.7, 3.6.10.8, 3.6.10.9, 3.6.10.10, 3.7.1.1, 3.7.1.2, 3.7.1.3, 3.7.1.4, 3.7.1.5, 3.7.1.6, 3.7.1.7, 3.7.1.8, 3.7.1.9, 3.7.1.10, 3.7.2.1, 3.7.2.2, 3.7.2.3, 3.7.2.4, 3.7.2.5, 3.7.2.6, 3.7.2.7, 3.7.2.8, 3.7.2.9, 3.7.2.10, 3.7.3.1, 3.7.3.2, 3.7.3.3, 3.7.3.4, 3.7.3.5, 3.7.3.6, 3.7.3.7, 3.7.3.8, 3.7.3.9, 3.7.3.10, 3.7.4.1, 3.7.4.2, 3.7.4.3, 3.7.4.4, 3.7.4.5, 3.7.4.6, 3.7.4.7, 3.7.4.8, 3.7.4.9, 3.7.4.10, 3.7.5.1, 3.7.5.2, 3.7.5.3, 3.7.5.4, 3.7.5.5, 3.7.5.6, 3.7.5.7, 3.7.5.8, 3.7.5.9, 3.7.5.10, 3.7.6.1, 3.7.6.2, 3.7.6.3, 3.7.6.4, 3.7.6.5, 3.7.6.6, 3.7.6.7, 3.7.6.8, 3.7.6.9, 3.7.6.10, 3.7.7.1, 3.7.7.2, 3.7.7.3, 3.7.7.4, 3.7.7.5, 3.7.7.6, 3.7.7.7, 3.7.7.8, 3.7.7.9, 3.7.7.10, 3.7.8.1, 3.7.8.2, 3.7.8.3, 3.7.8.4, 3.7.8.5, 3.7.8.6, 3.7.8.7, 3.7.8.8, 3.7.8.9, 3.7.8.10, 3.7.9.1, 3.7.9.2, 3.7.9.3, 3.7.9.4, 3.7.9.5, 3.7.9.6, 3.7.9.7, 3.7.9.8, 3.7.9.9, 3.7.9.10, 3.7.10.1, 3.7.10.2, 3.7.10.3, 3.7.10.4, 3.7.10.5, 3.7.10.6, 3.7.10.7, 3.7.10.8, 3.7.10.9, 3.7.10.10, 3.8.1.1, 3.8.1.2, 3.8.1.3, 3.8.1.4, 3.8.1.5, 3.8.1.6, 3.8.1.7, 3.8.1.8, 3.8.1.9, 3.8.1.10, 3.8.2.1, 3.8.2.2, 3.8.2.3, 3.8.2.4, 3.8.2.5, 3.8.2.6, 3.8.2.7, 3.8.2.8, 3.8.2.9, 3.8.2.10, 3.8.3.1, 3.8.3.2, 3.8.3.3, 3.8.3.4, 3.8.3.5, 3.8.3.6, 3.8.3.7, 3.8.3.8, 3.8.3.9, 3.8.3.10, 3.8.4.1, 3.8.4.2, 3.8.4.3, 3.8.4.4, 3.8.4.5, 3.8.4.6, 3.8.4.7, 3.8.4.8, 3.8.4.9, 3.8.4.10, 3.8.5.1, 3.8.5.2, 3.8.5.3, 3.8.5.4, 3.8.5.5, 3.8.5.6, 3.8.5.7, 3.8.5.8, 3.8.5.9, 3.8.5.10, 3.8.6.1, 3.8.6.2, 3.8.6.3, 3.8.6.4, 3.8.6.5, 3.8.6.6, 3.8.6.7, 3.8.6.8, 3.8.6.9, 3.8.6.10, 3.8.7.1, 3.8.7.2, 3.8.7.3, 3.8.7.4, 3.8.7.5, 3.8.7.6, 3.8.7.7, 3.8.7.8, 3.8.7.9, 3.8.7.10, 3.8.8.1, 3.8.8.2, 3.8.8.3, 3.8.8.4, 3.8.8.5, 3.8.8.6, 3.8.8.7, 3.8.8.8, 3.8.8.9, 3.8.8.10, 3.8.9.1, 3.8.9.2, 3.8.9.3, 3.8.9.4, 3.8.9.5, 3.8.9.6, 3.8.9.7, 3.8.9.8, 3.8.9.9, 3.8.9.10, 3.8.10.1, 3.8.10.2, 3.8.10.3, 3.8.10.4, 3.8.10.5, 3.8.10.6, 3.8.10.7, 3.8.10.8, 3.8.10.9, 3.8.10.10, 3.9.1.1, 3.9.1.2, 3.9.1.3, 3.9.1.4, 3.9.1.5, 3.9.1.6, 3.9.1.7, 3.9.1.8, 3.9.1.9, 3.9.1.10, 3.9.2.1, 3.9.2.2, 3.9.2.3, 3.9.2.4, 3.9.2.5, 3.9.2.6, 3.9.2.7, 3.9.2.8, 3.9.2.9, 3.9.2.10, 3.9.3.1, 3.9.3.2, 3.9.3.3, 3.9.3.4, 3.9.3.5, 3.9.3.6, 3.9.3.7, 3.9.3.8, 3.9.3.9, 3.9.3.10, 3.9.4.1, 3.9.4.2, 3.9.4.3, 3.9.4.4, 3.9.4.5, 3.9.4.6, 3.9.4.7, 3.9.4.8, 3.9.4.9, 3.9.4.10, 3.9.5.1, 3.9.5.2, 3.9.5.3, 3.9.5.4, 3.9.5.5, 3.9.5.6, 3.9.5.7, 3.9.5.8, 3.9.5.9, 3.9.5.10, 3.9.6.1, 3.9.6.2, 3.9.6.3, 3.9.6.4, 3.9.6.5, 3.9.6.6, 3.9.6.7, 3.9.6.8, 3.9.6.9, 3.9.6.10, 3.9.7.1, 3.9.7.2, 3.9.7.3, 3.9.7.4, 3.9.7.5, 3.9.7.6, 3.9.7.7, 3.9.7.8, 3.9.7.9, 3.9.7.10, 3.9.8.1, 3.9.8.2, 3.9.8.3, 3.9.8.4, 3.9.8.5, 3.9.8.6, 3.9.8.7, 3.9.8.8, 3.9.8.9, 3.9.8.10, 3.9.9.1, 3.9.9.2, 3.9.9.3, 3.9.9.4, 3.9.9.5, 3.9.9.6, 3.9.9.7, 3.9.9.8, 3.9.9.9, 3.9.9.10, 3.9.10.1, 3.9.10.2, 3.9.10.3, 3.9.10.4, 3.9.10.5, 3.9.10.6, 3.9.10.7, 3.9.10.8, 3.9.10.9, 3.9.10.10, 3.10.1.1, 3.10.1.2, 3.10.1.3, 3.10.1.4, 3.10.1.5, 3.10.1.6, 3.10.1.7, 3.10.1.8, 3.10.1.9, 3.10.1.10, 3.10.2.1, 3.10.2.2, 3.10.2.3, 3.10.2.4, 3.10.2.5, 3.10.2.6, 3.10.2.7, 3.10.2.8, 3.10.2.9, TABLE B-continued 3.10.2.10, 3.10.3.1, 3.10.3.2, 3.10.3.3, 3.10.3.4, 3.10.3.5, 3.10.3.6, 3.10.3.7, 3.10.3.8, 3.10.3.9, 3.10.3.10, 3.10.4.1, 3.10.4.2, 3.10.4.3, 3.10.4.4, 3.10.4.5, 3.10.4.6, 3.10.4.7, 3.10.4.8, 3.10.4.9, 3.10.4.10, 3.10.5.1, 3.10.5.2, 3.10.5.3, 3.10.5.4, 3.10.5.5, 3.10.5.6, 3.10.5.7, 3.10.5.8, 3.10.5.9, 3.10.5.10, 3.10.6.1, 3.10.6.2, 3.10.6.3, 3.10.6.4, 3.10.6.5, 3.10.6.6, 3.10.6.7, 3.10.6.8, 3.10.6.9, 3.10.6.10, 3.10.7.1, 3.10.7.2, 3.10.7.3, 3.10.7.4, 3.10.7.5, 3.10.7.6, 3.10.7.7, 3.10.7.8, 3.10.7.9, 3.10.7.10, 3.10.8.1, 3.10.8.2, 3.10.8.3, 3.10.8.4, 3.10.8.5, 3.10.8.6, 3.10.8.7, 3.10.8.8, 3.10.8.9, 3.10.8.10, 3.10.9.1, 3.10.9.2, 3.10.9.3, 3.10.9.4, 3.10.9.5, 3.10.9.6, 3.10.9.7, 3.10.9.8, 3.10.9.9, 3.10.9.10, 3.10.10.1, 3.10.10.2, 3.10.10.3, 3.10.10.4, 3.10.10.5, 3.10.10.6, 3.10.10.7, 3.10.10.8, 3.10.10.9, 3.10.10.10, 4.1.1.1, 4.1.1.2, 4.1.1.3, 4.1.1.4, 4.1.1.5, 4.1.1.6, 4.1.1.7, 4.1.1.8, 4.1.1.9, 4.1.1.10, 4.1.2.1, 4.1.2.2, 4.1.2.3, 4.1.2.4, 4.1.2.5, 4.1.2.6, 4.1.2.7, 4.1.2.8, 4.1.2.9, 4.1.2.10, 4.1.3.1, 4.1.3.2, 4.1.3.3, 4.1.3.4, 4.1.3.5, 4.1.3.6, 4.1.3.7, 4.1.3.8, 4.1.3.9, 4.1.3.10, 4.1.4.1, 4.1.4.2, 4.1.4.3, 4.1.4.4, 4.1.4.5, 4.1.4.6, 4.1.4.7, 4.1.4.8, 4.1.4.9, 4.1.4.10, 4.1.5.1, 4.1.5.2, 4.1.5.3, 4.1.5.4, 4.1.5.5, 4.1.5.6, 4.1.5.7, 4.1.5.8, 4.1.5.9, 4.1.5.10, 4.1.6.1, 4.1.6.2, 4.1.6.3, 4.1.6.4, 4.1.6.5, 4.1.6.6, 4.1.6.7, 4.1.6.8, 4.1.6.9, 4.1.6.10, 4.1.7.1, 4.1.7.2, 4.1.7.3, 4.1.7.4, 4.1.7.5, 4.1.7.6, 4.1.7.7, 4.1.7.8, 4.1.7.9, 4.1.7.10, 4.1.8.1, 4.1.8.2, 4.1.8.3, 4.1.8.4, 4.1.8.5, 4.1.8.6, 4.1.8.7, 4.1.8.8, 4.1.8.9, 4.1.8.10, 4.1.9.1, 4.1.9.2, 4.1.9.3, 4.1.9.4, 4.1.9.5, 4.1.9.6, 4.1.9.7, 4.1.9.8, 4.1.9.9, 4.1.9.10, 4.1.10.1, 4.1.10.2, 4.1.10.3, 4.1.10.4, 4.1.10.5, 4.1.10.6, 4.1.10.7, 4.1.10.8, 4.1.10.9, 4.1.10.10, 4.2.1.1, 4.2.1.2, 4.2.1.3, 4.2.1.4, 4.2.1.5, 4.2.1.6, 4.2.1.7, 4.2.1.8, 4.2.1.9, 4.2.1.10, 4.2.2.1, 4.2.2.2, 4.2.2.3, 4.2.2.4, 4.2.2.5, 4.2.2.6, 4.2.2.7, 4.2.2.8, 4.2.2.9, 4.2.2.10, 4.2.3.1, 4.2.3.2, 4.2.3.3, 4.2.3.4, 4.2.3.5, 4.2.3.6, 4.2.3.7, 4.2.3.8, 4.2.3.9, 4.2.3.10, 4.2.4.1, 4.2.4.2, 4.2.4.3, 4.2.4.4, 4.2.4.5, 4.2.4.6, 4.2.4.7, 4.2.4.8, 4.2.4.9, 4.2.4.10, 4.2.5.1, 4.2.5.2, 4.2.5.3, 4.2.5.4, 4.2.5.5, 4.2.5.6, 4.2.5.7, 4.2.5.8, 4.2.5.9, 4.2.5.10, 4.2.6.1, 4.2.6.2, 4.2.6.3, 4.2.6.4, 4.2.6.5, 4.2.6.6, 4.2.6.7, 4.2.6.8, 4.2.6.9, 4.2.6.10, 4.2.7.1, 4.2.7.2, 4.2.7.3, 4.2.7.4, 4.2.7.5, 4.2.7.6, 4.2.7.7, 4.2.7.8, 4.2.7.9, 4.2.7.10, 4.2.8.1, 4.2.8.2, 4.2.8.3, 4.2.8.4, 4.2.8.5, 4.2.8.6, 4.2.8.7, 4.2.8.8, 4.2.8.9, 4.2.8.10, 4.2.9.1, 4.2.9.2, 4.2.9.3, 4.2.9.4, 4.2.9.5, 4.2.9.6, 4.2.9.7, 4.2.9.8, 4.2.9.9, 4.2.9.10, 4.2.10.1, 4.2.10.2, 4.2.10.3, 4.2.10.4, 4.2.10.5, 4.2.10.6, 4.2.10.7, 4.2.10.8, 4.2.10.9, 4.2.10.10, 4.3.1.1, 4.3.1.2, 4.3.1.3, 4.3.1.4, 4.3.1.5, 4.3.1.6, 4.3.1.7, 4.3.1.8, 4.3.1.9, 4.3.1.10, 4.3.2.1, 4.3.2.2, 4.3.2.3, 4.3.2.4, 4.3.2.5, 4.3.2.6, 4.3.2.7, 4.3.2.8, 4.3.2.9, 4.3.2.10, 4.3.3.1, 4.3.3.2, 4.3.3.3, 4.3.3.4, 4.3.3.5, 4.3.3.6, 4.3.3.7, 4.3.3.8, 4.3.3.9, 4.3.3.10, 4.3.4.1, 4.3.4.2, 4.3.4.3, 4.3.4.4, 4.3.4.5, 4.3.4.6, 4.3.4.7, 4.3.4.8, 4.3.4.9, 4.3.4.10, 4.3.5.1, 4.3.5.2, 4.3.5.3, 4.3.5.4, 4.3.5.5, 4.3.5.6, 4.3.5.7, 4.3.5.8, 4.3.5.9, 4.3.5.10, 4.3.6.1, 4.3.6.2, 4.3.6.3, 4.3.6.4, 4.3.6.5, 4.3.6.6, 4.3.6.7, 4.3.6.8, 4.3.6.9, 4.3.6.10, 4.3.7.1, 4.3.7.2, 4.3.7.3, 4.3.7.4, 4.3.7.5, 4.3.7.6, 4.3.7.7, 4.3.7.8, 4.3.7.9, 4.3.7.10, 4.3.8.1, 4.3.8.2, 4.3.8.3, 4.3.8.4, 4.3.8.5, 4.3.8.6, 4.3.8.7, 4.3.8.8, 4.3.8.9, 4.3.8.10, 4.3.9.1, 4.3.9.2, 4.3.9.3, 4.3.9.4, 4.3.9.5, 4.3.9.6, 4.3.9.7, 4.3.9.8, 4.3.9.9, 4.3.9.10, 4.3.10.1, 4.3.10.2, 4.3.10.3, 4.3.10.4, 4.3.10.5, 4.3.10.6, 4.3.10.7, 4.3.10.8, 4.3.10.9, 4.3.10.10, 4.4.1.1, 4.4.1.2, 4.4.1.3, 4.4.1.4, 4.4.1.5, 4.4.1.6, 4.4.1.7, 4.4.1.8, 4.4.1.9, 4.4.1.10, 4.4.2.1, 4.4.2.2, 4.4.2.3, 4.4.2.4, 4.4.2.5, 4.4.2.6, 4.4.2.7, 4.4.2.8, 4.4.2.9, 4.4.2.10, 4.4.3.1, 4.4.3.2, 4.4.3.3, 4.4.3.4, 4.4.3.5, 4.4.3.6, 4.4.3.7, 4.4.3.8, 4.4.3.9, 4.4.3.10, 4.4.4.1, 4.4.4.2, 4.4.4.3, 4.4.4.4, 4.4.4.5, 4.4.4.6, 4.4.4.7, 4.4.4.8, 4.4.4.9, 4.4.4.10, 4.4.5.1, 4.4.5.2, 4.4.5.3, 4.4.5.4, 4.4.5.5, 4.4.5.6, 4.4.5.7, 4.4.5.8, 4.4.5.9, 4.4.5.10, 4.4.6.1, 4.4.6.2, 4.4.6.3, 4.4.6.4, 4.4.6.5, 4.4.6.6, 4.4.6.7, 4.4.6.8, 4.4.6.9, 4.4.6.10, 4.4.7.1, 4.4.7.2, 4.4.7.3, 4.4.7.4, 4.4.7.5, 4.4.7.6, 4.4.7.7, 4.4.7.8, 4.4.7.9, 4.4.7.10, 4.4.8.1, 4.4.8.2, 4.4.8.3, 4.4.8.4, 4.4.8.5, 4.4.8.6, 4.4.8.7, 4.4.8.8, 4.4.8.9, 4.4.8.10, 4.4.9.1, 4.4.9.2, 4.4.9.3, 4.4.9.4, 4.4.9.5, 4.4.9.6, 4.4.9.7, 4.4.9.8, 4.4.9.9, 4.4.9.10, 4.4.10.1, 4.4.10.2, 4.4.10.3, 4.4.10.4, 4.4.10.5, 4.4.10.6, 4.4.10.7, 4.4.10.8, 4.4.10.9, 4.4.10.10, 4.5.1.1, 4.5.1.2, 4.5.1.3, 4.5.1.4, 4.5.1.5, 4.5.1.6, 4.5.1.7, 4.5.1.8, 4.5.1.9, 4.5.1.10, 4.5.2.1, 4.5.2.2, 4.5.2.3, 4.5.2.4, 4.5.2.5, 4.5.2.6, 4.5.2.7, 4.5.2.8, 4.5.2.9, 4.5.2.10, 4.5.3.1, 4.5.3.2, 4.5.3.3, 4.5.3.4, 4.5.3.5, 4.5.3.6, 4.5.3.7, 4.5.3.8, 4.5.3.9, 4.5.3.10, 4.5.4.1, 4.5.4.2, 4.5.4.3, 4.5.4.4, 4.5.4.5, 4.5.4.6, 4.5.4.7, 4.5.4.8, 4.5.4.9, 4.5.4.10, 4.5.5.1, 4.5.5.2, 4.5.5.3, 4.5.5.4, 4.5.5.5, 4.5.5.6, 4.5.5.7, 4.5.5.8, 4.5.5.9, 4.5.5.10, 4.5.6.1, 4.5.6.2, 4.5.6.3, 4.5.6.4, 4.5.6.5, 4.5.6.6, 4.5.6.7, 4.5.6.8, 4.5.6.9, 4.5.6.10, 4.5.7.1, 4.5.7.2, 4.5.7.3, 4.5.7.4, 4.5.7.5, 4.5.7.6, 4.5.7.7, 4.5.7.8, 4.5.7.9, 4.5.7.10, 4.5.8.1, 4.5.8.2, 4.5.8.3, 4.5.8.4, 4.5.8.5, 4.5.8.6, 4.5.8.7, 4.5.8.8, 4.5.8.9, 4.5.8.10, 4.5.9.1, 4.5.9.2, 4.5.9.3, 4.5.9.4, 4.5.9.5, 4.5.9.6, 4.5.9.7, 4.5.9.8, 4.5.9.9, 4.5.9.10, 4.5.10.1, 4.5.10.2, 4.5.10.3, 4.5.10.4, 4.5.10.5, 4.5.10.6, 4.5.10.7, 4.5.10.8, 4.5.10.9, 4.5.10.10, 4.6.1.1, 4.6.1.2, 4.6.1.3, 4.6.1.4, 4.6.1.5, 4.6.1.6, 4.6.1.7, 4.6.1.8, 4.6.1.9, 4.6.1.10, 4.6.2.1, 4.6.2.2, 4.6.2.3, 4.6.2.4, 4.6.2.5, 4.6.2.6, 4.6.2.7, 4.6.2.8, 4.6.2.9, 4.6.2.10, 4.6.3.1, 4.6.3.2, 4.6.3.3, 4.6.3.4, 4.6.3.5, 4.6.3.6, 4.6.3.7, 4.6.3.8, 4.6.3.9, 4.6.3.10, 4.6.4.1, 4.6.4.2, 4.6.4.3, 4.6.4.4, 4.6.4.5, 4.6.4.6, 4.6.4.7, 4.6.4.8, 4.6.4.9, 4.6.4.10, 4.6.5.1, 4.6.5.2, 4.6.5.3, 4.6.5.4, 4.6.5.5, 4.6.5.6, 4.6.5.7, 4.6.5.8, 4.6.5.9, 4.6.5.10, 4.6.6.1, 4.6.6.2, 4.6.6.3, 4.6.6.4, 4.6.6.5, 4.6.6.6, 4.6.6.7, 4.6.6.8, 4.6.6.9, 4.6.6.10, 4.6.7.1, 4.6.7.2, 4.6.7.3, 4.6.7.4, 4.6.7.5, 4.6.7.6, 4.6.7.7, 4.6.7.8, 4.6.7.9, 4.6.7.10, 4.6.8.1, 4.6.8.2, 4.6.8.3, 4.6.8.4, 4.6.8.5, 4.6.8.6, 4.6.8.7, 4.6.8.8, 4.6.8.9, 4.6.8.10, 4.6.9.1, 4.6.9.2, 4.6.9.3, 4.6.9.4, 4.6.9.5, 4.6.9.6, 4.6.9.7, 4.6.9.8, 4.6.9.9, 4.6.9.10, 4.6.10.1, 4.6.10.2, 4.6.10.3, 4.6.10.4, 4.6.10.5, 4.6.10.6, 4.6.10.7, 4.6.10.8, 4.6.10.9, 4.6.10.10, 4.7.1.1, 4.7.1.2, 4.7.1.3, 4.7.1.4, 4.7.1.5, 4.7.1.6, 4.7.1.7, 4.7.1.8, 4.7.1.9, 4.7.1.10, 4.7.2.1, 4.7.2.2, 4.7.2.3, 4.7.2.4, 4.7.2.5, 4.7.2.6, 4.7.2.7, 4.7.2.8, 4.7.2.9, 4.7.2.10, 4.7.3.1, 4.7.3.2, 4.7.3.3, 4.7.3.4, 4.7.3.5, 4.7.3.6, 4.7.3.7, 4.7.3.8, 4.7.3.9, 4.7.3.10, 4.7.4.1, 4.7.4.2, 4.7.4.3, 4.7.4.4, 4.7.4.5, 4.7.4.6, 4.7.4.7, 4.7.4.8, 4.7.4.9, 4.7.4.10, 4.7.5.1, 4.7.5.2, 4.7.5.3, 4.7.5.4, 4.7.5.5, 4.7.5.6, 4.7.5.7, 4.7.5.8, 4.7.5.9, 4.7.5.10, 4.7.6.1, 4.7.6.2, 4.7.6.3, 4.7.6.4, 4.7.6.5, 4.7.6.6, 4.7.6.7, 4.7.6.8, 4.7.6.9, 4.7.6.10, 4.7.7.1, 4.7.7.2, 4.7.7.3, 4.7.7.4, 4.7.7.5, 4.7.7.6, 4.7.7.7, 4.7.7.8, 4.7.7.9, 4.7.7.10, 4.7.8.1, 4.7.8.2, 4.7.8.3, 4.7.8.4, 4.7.8.5, 4.7.8.6, 4.7.8.7, 4.7.8.8, 4.7.8.9, 4.7.8.10, 4.7.9.1, 4.7.9.2, 4.7.9.3, 4.7.9.4, 4.7.9.5, 4.7.9.6, 4.7.9.7, 4.7.9.8, 4.7.9.9, 4.7.9.10, 4.7.10.1, 4.7.10.2, 4.7.10.3, 4.7.10.4, 4.7.10.5, 4.7.10.6, 4.7.10.7, 4.7.10.8, 4.7.10.9, 4.7.10.10, 4.8.1.1, 4.8.1.2, 4.8.1.3, 4.8.1.4, 4.8.1.5, 4.8.1.6, 4.8.1.7, 4.8.1.8, 4.8.1.9, 4.8.1.10, 4.8.2.1, 4.8.2.2, 4.8.2.3, 4.8.2.4, 4.8.2.5, 4.8.2.6, 4.8.2.7, 4.8.2.8, 4.8.2.9, 4.8.2.10, 4.8.3.1, 4.8.3.2, 4.8.3.3, 4.8.3.4, 4.8.3.5, 4.8.3.6, 4.8.3.7, 4.8.3.8, 4.8.3.9, 4.8.3.10, 4.8.4.1, 4.8.4.2, 4.8.4.3, 4.8.4.4, 4.8.4.5, 4.8.4.6, 4.8.4.7, 4.8.4.8, 4.8.4.9, 4.8.4.10, 4.8.5.1, 4.8.5.2, 4.8.5.3, 4.8.5.4, 4.8.5.5, 4.8.5.6, 4.8.5.7, 4.8.5.8, 4.8.5.9, 4.8.5.10, 4.8.6.1, 4.8.6.2, 4.8.6.3, 4.8.6.4, 4.8.6.5, 4.8.6.6, 4.8.6.7, 4.8.6.8, 4.8.6.9, 4.8.6.10, 4.8.7.1, 4.8.7.2, 4.8.7.3, 4.8.7.4, 4.8.7.5, 4.8.7.6, 4.8.7.7, 4.8.7.8, 4.8.7.9, 4.8.7.10, 4.8.8.1, 4.8.8.2, 4.8.8.3, 4.8.8.4, 4.8.8.5, 4.8.8.6, 4.8.8.7, 4.8.8.8, 4.8.8.9, 4.8.8.10, 4.8.9.1, 4.8.9.2, 4.8.9.3, 4.8.9.4, 4.8.9.5, 4.8.9.6, 4.8.9.7, 4.8.9.8, 4.8.9.9, 4.8.9.10, 4.8.10.1, 4.8.10.2, 4.8.10.3, 4.8.10.4, 4.8.10.5, 4.8.10.6, 4.8.10.7, 4.8.10.8, 4.8.10.9, 4.8.10.10, 4.9.1.1, 4.9.1.2, 4.9.1.3, 4.9.1.4, 4.9.1.5, 4.9.1.6, 4.9.1.7, 4.9.1.8, 4.9.1.9, 4.9.1.10, 4.9.2.1, 4.9.2.2, 4.9.2.3, 4.9.2.4, 4.9.2.5, 4.9.2.6, 4.9.2.7, 4.9.2.8, 4.9.2.9, 4.9.2.10, 4.9.3.1, 4.9.3.2, 4.9.3.3, 4.9.3.4, 4.9.3.5, 4.9.3.6, 4.9.3.7, 4.9.3.8, 4.9.3.9, 4.9.3.10, 4.9.4.1, 4.9.4.2, 4.9.4.3, 4.9.4.4, 4.9.4.5, 4.9.4.6, 4.9.4.7, 4.9.4.8, 4.9.4.9, 4.9.4.10, 4.9.5.1, 4.9.5.2, 4.9.5.3, 4.9.5.4, 4.9.5.5, 4.9.5.6, 4.9.5.7, 4.9.5.8, 4.9.5.9, 4.9.5.10, 4.9.6.1, 4.9.6.2, 4.9.6.3, 4.9.6.4, 4.9.6.5, 4.9.6.6, 4.9.6.7, 4.9.6.8, 4.9.6.9, 4.9.6.10, 4.9.7.1, 4.9.7.2, 4.9.7.3, 4.9.7.4, 4.9.7.5, 4.9.7.6, 4.9.7.7, 4.9.7.8, 4.9.7.9, 4.9.7.10, 4.9.8.1, 4.9.8.2, 4.9.8.3, 4.9.8.4, 4.9.8.5, 4.9.8.6, 4.9.8.7, 4.9.8.8, 4.9.8.9, 4.9.8.10, 4.9.9.1, 4.9.9.2, 4.9.9.3, 4.9.9.4, 4.9.9.5, 4.9.9.6, 4.9.9.7, 4.9.9.8, 4.9.9.9, 4.9.9.10, 4.9.10.1, 4.9.10.2, 4.9.10.3, 4.9.10.4, 4.9.10.5, 4.9.10.6, 4.9.10.7, 4.9.10.8, 4.9.10.9, 4.9.10.10, 4.10.1.1, 4.10.1.2, 4.10.1.3, 4.10.1.4, 4.10.1.5, 4.10.1.6, 4.10.1.7, 4.10.1.8, 4.10.1.9, 4.10.1.10, 4.10.2.1, 4.10.2.2, 4.10.2.3, 4.10.2.4, 4.10.2.5, 4.10.2.6, 4.10.2.7, 4.10.2.8, 4.10.2.9, 4.10.2.10, 4.10.3.1, 4.10.3.2, 4.10.3.3, 4.10.3.4, 4.10.3.5, 4.10.3.6, 4.10.3.7, 4.10.3.8, 4.10.3.9, 4.10.3.10, 4.10.4.1, 4.10.4.2, 4.10.4.3, 4.10.4.4, 4.10.4.5, 4.10.4.6, 4.10.4.7, 4.10.4.8, 4.10.4.9, 4.10.4.10, 4.10.5.1, 4.10.5.2, 4.10.5.3, 4.10.5.4, 4.10.5.5, 4.10.5.6, 4.10.5.7, 4.10.5.8, 4.10.5.9, 4.10.5.10, 4.10.6.1, 4.10.6.2, 4.10.6.3, 4.10.6.4, 4.10.6.5, 4.10.6.6, 4.10.6.7, 4.10.6.8, 4.10.6.9, 4.10.6.10, 4.10.7.1, 4.10.7.2, 4.10.7.3, 4.10.7.4, 4.10.7.5, 4.10.7.6, 4.10.7.7, TABLE B-continued 4.10.7.8, 4.10.7.9, 4.10.7.10, 4.10.8.1, 4.10.8.2, 4.10.8.3, 4.10.8.4, 4.10.8.5, 4.10.8.6, 4.10.8.7, 4.10.8.8, 4.10.8.9, 4.10.8.10, 4.10.9.1, 4.10.9.2, 4.10.9.3, 4.10.9.4, 4.10.9.5, 4.10.9.6, 4.10.9.7, 4.10.9.8, 4.10.9.9, 4.10.9.10, 4.10.10.1, 4.10.10.2, 4.10.10.3, 4.10.10.4, 4.10.10.5, 4.10.10.6, 4.10.10.7, 4.10.10.8, 4.10.10.9, 4.10.10.10, 5.1.1.1, 5.1.1.2, 5.1.1.3, 5.1.1.4, 5.1.1.5, 5.1.1.6, 5.1.1.7, 5.1.1.8, 5.1.1.9, 5.1.1.10, 5.1.2.1, 5.1.2.2, 5.1.2.3, 5.1.2.4, 5.1.2.5, 5.1.2.6, 5.1.2.7, 5.1.2.8, 5.1.2.9, 5.1.2.10, 5.1.3.1, 5.1.3.2, 5.1.3.3, 5.1.3.4, 5.1.3.5, 5.1.3.6, 5.1.3.7, 5.1.3.8, 5.1.3.9, 5.1.3.10, 5.1.4.1, 5.1.4.2, 5.1.4.3, 5.1.4.4, 5.1.4.5, 5.1.4.6, 5.1.4.7, 5.1.4.8, 5.1.4.9, 5.1.4.10, 5.1.5.1, 5.1.5.2, 5.1.5.3, 5.1.5.4, 5.1.5.5, 5.1.5.6, 5.1.5.7, 5.1.5.8, 5.1.5.9, 5.1.5.10, 5.1.6.1, 5.1.6.2, 5.1.6.3, 5.1.6.4, 5.1.6.5, 5.1.6.6, 5.1.6.7, 5.1.6.8, 5.1.6.9, 5.1.6.10, 5.1.7.1, 5.1.7.2, 5.1.7.3, 5.1.7.4, 5.1.7.5, 5.1.7.6, 5.1.7.7, 5.1.7.8, 5.1.7.9, 5.1.7.10, 5.1.8.1, 5.1.8.2, 5.1.8.3, 5.1.8.4, 5.1.8.5, 5.1.8.6, 5.1.8.7, 5.1.8.8, 5.1.8.9, 5.1.8.10, 5.1.9.1, 5.1.9.2, 5.1.9.3, 5.1.9.4, 5.1.9.5, 5.1.9.6, 5.1.9.7, 5.1.9.8, 5.1.9.9, 5.1.9.10, 5.1.10.1, 5.1.10.2, 5.1.10.3, 5.1.10.4, 5.1.10.5, 5.1.10.6, 5.1.10.7, 5.1.10.8, 5.1.10.9, 5.1.10.10, 5.2.1.1, 5.2.1.2, 5.2.1.3, 5.2.1.4, 5.2.1.5, 5.2.1.6, 5.2.1.7, 5.2.1.8, 5.2.1.9, 5.2.1.10, 5.2.2.1, 5.2.2.2, 5.2.2.3, 5.2.2.4, 5.2.2.5, 5.2.2.6, 5.2.2.7, 5.2.2.8, 5.2.2.9, 5.2.2.10, 5.2.3.1, 5.2.3.2, 5.2.3.3, 5.2.3.4, 5.2.3.5, 5.2.3.6, 5.2.3.7, 5.2.3.8, 5.2.3.9, 5.2.3.10, 5.2.4.1, 5.2.4.2, 5.2.4.3, 5.2.4.4, 5.2.4.5, 5.2.4.6, 5.2.4.7, 5.2.4.8, 5.2.4.9, 5.2.4.10, 5.2.5.1, 5.2.5.2, 5.2.5.3, 5.2.5.4, 5.2.5.5, 5.2.5.6, 5.2.5.7, 5.2.5.8, 5.2.5.9, 5.2.5.10, 5.2.6.1, 5.2.6.2, 5.2.6.3, 5.2.6.4, 5.2.6.5, 5.2.6.6, 5.2.6.7, 5.2.6.8, 5.2.6.9, 5.2.6.10, 5.2.7.1, 5.2.7.2, 5.2.7.3, 5.2.7.4, 5.2.7.5, 5.2.7.6, 5.2.7.7, 5.2.7.8, 5.2.7.9, 5.2.7.10, 5.2.8.1, 5.2.8.2, 5.2.8.3, 5.2.8.4, 5.2.8.5, 5.2.8.6, 5.2.8.7, 5.2.8.8, 5.2.8.9, 5.2.8.10, 5.2.9.1, 5.2.9.2, 5.2.9.3, 5.2.9.4, 5.2.9.5, 5.2.9.6, 5.2.9.7, 5.2.9.8, 5.2.9.9, 5.2.9.10, 5.2.10.1, 5.2.10.2, 5.2.10.3, 5.2.10.4, 5.2.10.5, 5.2.10.6, 5.2.10.7, 5.2.10.8, 5.2.10.9, 5.2.10.10, 5.3.1.1, 5.3.1.2, 5.3.1.3, 5.3.1.4, 5.3.1.5, 5.3.1.6, 5.3.1.7, 5.3.1.8, 5.3.1.9, 5.3.1.10, 5.3.2.1, 5.3.2.2, 5.3.2.3, 5.3.2.4, 5.3.2.5, 5.3.2.6, 5.3.2.7, 5.3.2.8, 5.3.2.9, 5.3.2.10, 5.3.3.1, 5.3.3.2, 5.3.3.3, 5.3.3.4, 5.3.3.5, 5.3.3.6, 5.3.3.7, 5.3.3.8, 5.3.3.9, 5.3.3.10, 5.3.4.1, 5.3.4.2, 5.3.4.3, 5.3.4.4, 5.3.4.5, 5.3.4.6, 5.3.4.7, 5.3.4.8, 5.3.4.9, 5.3.4.10, 5.3.5.1, 5.3.5.2, 5.3.5.3, 5.3.5.4, 5.3.5.5, 5.3.5.6, 5.3.5.7, 5.3.5.8, 5.3.5.9, 5.3.5.10, 5.3.6.1, 5.3.6.2, 5.3.6.3, 5.3.6.4, 5.3.6.5, 5.3.6.6, 5.3.6.7, 5.3.6.8, 5.3.6.9, 5.3.6.10, 5.3.7.1, 5.3.7.2, 5.3.7.3, 5.3.7.4, 5.3.7.5, 5.3.7.6, 5.3.7.7, 5.3.7.8, 5.3.7.9, 5.3.7.10, 5.3.8.1, 5.3.8.2, 5.3.8.3, 5.3.8.4, 5.3.8.5, 5.3.8.6, 5.3.8.7, 5.3.8.8, 5.3.8.9, 5.3.8.10, 5.3.9.1, 5.3.9.2, 5.3.9.3, 5.3.9.4, 5.3.9.5, 5.3.9.6, 5.3.9.7, 5.3.9.8, 5.3.9.9, 5.3.9.10, 5.3.10.1, 5.3.10.2, 5.3.10.3, 5.3.10.4, 5.3.10.5, 5.3.10.6, 5.3.10.7, 5.3.10.8, 5.3.10.9, 5.3.10.10, 5.4.1.1, 5.4.1.2, 5.4.1.3, 5.4.1.4, 5.4.1.5, 5.4.1.6, 5.4.1.7, 5.4.1.8, 5.4.1.9, 5.4.1.10, 5.4.2.1, 5.4.2.2, 5.4.2.3, 5.4.2.4, 5.4.2.5, 5.4.2.6, 5.4.2.7, 5.4.2.8, 5.4.2.9, 5.4.2.10, 5.4.3.1, 5.4.3.2, 5.4.3.3, 5.4.3.4, 5.4.3.5, 5.4.3.6, 5.4.3.7, 5.4.3.8, 5.4.3.9, 5.4.3.10, 5.4.4.1, 5.4.4.2, 5.4.4.3, 5.4.4.4, 5.4.4.5, 5.4.4.6, 5.4.4.7, 5.4.4.8, 5.4.4.9, 5.4.4.10, 5.4.5.1, 5.4.5.2, 5.4.5.3, 5.4.5.4, 5.4.5.5, 5.4.5.6, 5.4.5.7, 5.4.5.8, 5.4.5.9, 5.4.5.10, 5.4.6.1, 5.4.6.2, 5.4.6.3, 5.4.6.4, 5.4.6.5, 5.4.6.6, 5.4.6.7, 5.4.6.8, 5.4.6.9, 5.4.6.10, 5.4.7.1, 5.4.7.2, 5.4.7.3, 5.4.7.4, 5.4.7.5, 5.4.7.6, 5.4.7.7, 5.4.7.8, 5.4.7.9, 5.4.7.10, 5.4.8.1, 5.4.8.2, 5.4.8.3, 5.4.8.4, 5.4.8.5, 5.4.8.6, 5.4.8.7, 5.4.8.8, 5.4.8.9, 5.4.8.10, 5.4.9.1, 5.4.9.2, 5.4.9.3, 5.4.9.4, 5.4.9.5, 5.4.9.6, 5.4.9.7, 5.4.9.8, 5.4.9.9, 5.4.9.10, 5.4.10.1, 5.4.10.2, 5.4.10.3, 5.4.10.4, 5.4.10.5, 5.4.10.6, 5.4.10.7, 5.4.10.8, 5.4.10.9, 5.4.10.10, 5.5.1.1, 5.5.1.2, 5.5.1.3, 5.5.1.4, 5.5.1.5, 5.5.1.6, 5.5.1.7, 5.5.1.8, 5.5.1.9, 5.5.1.10, 5.5.2.1, 5.5.2.2, 5.5.2.3, 5.5.2.4, 5.5.2.5, 5.5.2.6, 5.5.2.7, 5.5.2.8, 5.5.2.9, 5.5.2.10, 5.5.3.1, 5.5.3.2, 5.5.3.3, 5.5.3.4, 5.5.3.5, 5.5.3.6, 5.5.3.7, 5.5.3.8, 5.5.3.9, 5.5.3.10, 5.5.4.1, 5.5.4.2, 5.5.4.3, 5.5.4.4, 5.5.4.5, 5.5.4.6, 5.5.4.7, 5.5.4.8, 5.5.4.9, 5.5.4.10, 5.5.5.1, 5.5.5.2, 5.5.5.3, 5.5.5.4, 5.5.5.5, 5.5.5.6, 5.5.5.7, 5.5.5.8, 5.5.5.9, 5.5.5.10, 5.5.6.1, 5.5.6.2, 5.5.6.3, 5.5.6.4, 5.5.6.5, 5.5.6.6, 5.5.6.7, 5.5.6.8, 5.5.6.9, 5.5.6.10, 5.5.7.1, 5.5.7.2, 5.5.7.3, 5.5.7.4, 5.5.7.5, 5.5.7.6, 5.5.7.7, 5.5.7.8, 5.5.7.9, 5.5.7.10, 5.5.8.1, 5.5.8.2, 5.5.8.3, 5.5.8.4, 5.5.8.5, 5.5.8.6, 5.5.8.7, 5.5.8.8, 5.5.8.9, 5.5.8.10, 5.5.9.1, 5.5.9.2, 5.5.9.3, 5.5.9.4, 5.5.9.5, 5.5.9.6, 5.5.9.7, 5.5.9.8, 5.5.9.9, 5.5.9.10, 5.5.10.1, 5.5.10.2, 5.5.10.3, 5.5.10.4, 5.5.10.5, 5.5.10.6, 5.5.10.7, 5.5.10.8, 5.5.10.9, 5.5.10.10, 5.6.1.1, 5.6.1.2, 5.6.1.3, 5.6.1.4, 5.6.1.5, 5.6.1.6, 5.6.1.7, 5.6.1.8, 5.6.1.9, 5.6.1.10, 5.6.2.1, 5.6.2.2, 5.6.2.3, 5.6.2.4, 5.6.2.5, 5.6.2.6, 5.6.2.7, 5.6.2.8, 5.6.2.9, 5.6.2.10, 5.6.3.1, 5.6.3.2, 5.6.3.3, 5.6.3.4, 5.6.3.5, 5.6.3.6, 5.6.3.7, 5.6.3.8, 5.6.3.9, 5.6.3.10, 5.6.4.1, 5.6.4.2, 5.6.4.3, 5.6.4.4, 5.6.4.5, 5.6.4.6, 5.6.4.7, 5.6.4.8, 5.6.4.9, 5.6.4.10, 5.6.5.1, 5.6.5.2, 5.6.5.3, 5.6.5.4, 5.6.5.5, 5.6.5.6, 5.6.5.7, 5.6.5.8, 5.6.5.9, 5.6.5.10, 5.6.6.1, 5.6.6.2, 5.6.6.3, 5.6.6.4, 5.6.6.5, 5.6.6.6, 5.6.6.7, 5.6.6.8, 5.6.6.9, 5.6.6.10, 5.6.7.1, 5.6.7.2, 5.6.7.3, 5.6.7.4, 5.6.7.5, 5.6.7.6, 5.6.7.7, 5.6.7.8, 5.6.7.9, 5.6.7.10, 5.6.8.1, 5.6.8.2, 5.6.8.3, 5.6.8.4, 5.6.8.5, 5.6.8.6, 5.6.8.7, 5.6.8.8, 5.6.8.9, 5.6.8.10, 5.6.9.1, 5.6.9.2, 5.6.9.3, 5.6.9.4, 5.6.9.5, 5.6.9.6, 5.6.9.7, 5.6.9.8, 5.6.9.9, 5.6.9.10, 5.6.10.1, 5.6.10.2, 5.6.10.3, 5.6.10.4, 5.6.10.5, 5.6.10.6, 5.6.10.7, 5.6.10.8, 5.6.10.9, 5.6.10.10, 5.7.1.1, 5.7.1.2, 5.7.1.3, 5.7.1.4, 5.7.1.5, 5.7.1.6, 5.7.1.7, 5.7.1.8, 5.7.1.9, 5.7.1.10, 5.7.2.1, 5.7.2.2, 5.7.2.3, 5.7.2.4, 5.7.2.5, 5.7.2.6, 5.7.2.7, 5.7.2.8, 5.7.2.9, 5.7.2.10, 5.7.3.1, 5.7.3.2, 5.7.3.3, 5.7.3.4, 5.7.3.5, 5.7.3.6, 5.7.3.7, 5.7.3.8, 5.7.3.9, 5.7.3.10, 5.7.4.1, 5.7.4.2, 5.7.4.3, 5.7.4.4, 5.7.4.5, 5.7.4.6, 5.7.4.7, 5.7.4.8, 5.7.4.9, 5.7.4.10, 5.7.5.1, 5.7.5.2, 5.7.5.3, 5.7.5.4, 5.7.5.5, 5.7.5.6, 5.7.5.7, 5.7.5.8, 5.7.5.9, 5.7.5.10, 5.7.6.1, 5.7.6.2, 5.7.6.3, 5.7.6.4, 5.7.6.5, 5.7.6.6, 5.7.6.7, 5.7.6.8, 5.7.6.9, 5.7.6.10, 5.7.7.1, 5.7.7.2, 5.7.7.3, 5.7.7.4, 5.7.7.5, 5.7.7.6, 5.7.7.7, 5.7.7.8, 5.7.7.9, 5.7.7.10, 5.7.8.1, 5.7.8.2, 5.7.8.3, 5.7.8.4, 5.7.8.5, 5.7.8.6, 5.7.8.7, 5.7.8.8, 5.7.8.9, 5.7.8.10, 5.7.9.1, 5.7.9.2, 5.7.9.3, 5.7.9.4, 5.7.9.5, 5.7.9.6, 5.7.9.7, 5.7.9.8, 5.7.9.9, 5.7.9.10, 5.7.10.1, 5.7.10.2, 5.7.10.3, 5.7.10.4, 5.7.10.5, 5.7.10.6, 5.7.10.7, 5.7.10.8, 5.7.10.9, 5.7.10.10, 5.8.1.1, 5.8.1.2, 5.8.1.3, 5.8.1.4, 5.8.1.5, 5.8.1.6, 5.8.1.7, 5.8.1.8, 5.8.1.9, 5.8.1.10, 5.8.2.1, 5.8.2.2, 5.8.2.3, 5.8.2.4, 5.8.2.5, 5.8.2.6, 5.8.2.7, 5.8.2.8, 5.8.2.9, 5.8.2.10, 5.8.3.1, 5.8.3.2, 5.8.3.3, 5.8.3.4, 5.8.3.5, 5.8.3.6, 5.8.3.7, 5.8.3.8, 5.8.3.9, 5.8.3.10, 5.8.4.1, 5.8.4.2, 5.8.4.3, 5.8.4.4, 5.8.4.5, 5.8.4.6, 5.8.4.7, 5.8.4.8, 5.8.4.9, 5.8.4.10, 5.8.5.1, 5.8.5.2, 5.8.5.3, 5.8.5.4, 5.8.5.5, 5.8.5.6, 5.8.5.7, 5.8.5.8, 5.8.5.9, 5.8.5.10, 5.8.6.1, 5.8.6.2, 5.8.6.3, 5.8.6.4, 5.8.6.5, 5.8.6.6, 5.8.6.7, 5.8.6.8, 5.8.6.9, 5.8.6.10, 5.8.7.1, 5.8.7.2, 5.8.7.3, 5.8.7.4, 5.8.7.5, 5.8.7.6, 5.8.7.7, 5.8.7.8, 5.8.7.9, 5.8.7.10, 5.8.8.1, 5.8.8.2, 5.8.8.3, 5.8.8.4, 5.8.8.5, 5.8.8.6, 5.8.8.7, 5.8.8.8, 5.8.8.9, 5.8.8.10, 5.8.9.1, 5.8.9.2, 5.8.9.3, 5.8.9.4, 5.8.9.5, 5.8.9.6, 5.8.9.7, 5.8.9.8, 5.8.9.9, 5.8.9.10, 5.8.10.1, 5.8.10.2, 5.8.10.3, 5.8.10.4, 5.8.10.5, 5.8.10.6, 5.8.10.7, 5.8.10.8, 5.8.10.9, 5.8.10.10, 5.9.1.1, 5.9.1.2, 5.9.1.3, 5.9.1.4, 5.9.1.5, 5.9.1.6, 5.9.1.7, 5.9.1.8, 5.9.1.9, 5.9.1.10, 5.9.2.1, 5.9.2.2, 5.9.2.3, 5.9.2.4, 5.9.2.5, 5.9.2.6, 5.9.2.7, 5.9.2.8, 5.9.2.9, 5.9.2.10, 5.9.3.1, 5.9.3.2, 5.9.3.3, 5.9.3.4, 5.9.3.5, 5.9.3.6, 5.9.3.7, 5.9.3.8, 5.9.3.9, 5.9.3.10, 5.9.4.1, 5.9.4.2, 5.9.4.3, 5.9.4.4, 5.9.4.5, 5.9.4.6, 5.9.4.7, 5.9.4.8, 5.9.4.9, 5.9.4.10, 5.9.5.1, 5.9.5.2, 5.9.5.3, 5.9.5.4, 5.9.5.5, 5.9.5.6, 5.9.5.7, 5.9.5.8, 5.9.5.9, 5.9.5.10, 5.9.6.1, 5.9.6.2, 5.9.6.3, 5.9.6.4, 5.9.6.5, 5.9.6.6, 5.9.6.7, 5.9.6.8, 5.9.6.9, 5.9.6.10, 5.9.7.1, 5.9.7.2, 5.9.7.3, 5.9.7.4, 5.9.7.5, 5.9.7.6, 5.9.7.7, 5.9.7.8, 5.9.7.9, 5.9.7.10, 5.9.8.1, 5.9.8.2, 5.9.8.3, 5.9.8.4, 5.9.8.5, 5.9.8.6, 5.9.8.7, 5.9.8.8, 5.9.8.9, 5.9.8.10, 5.9.9.1, 5.9.9.2, 5.9.9.3, 5.9.9.4, 5.9.9.5, 5.9.9.6, 5.9.9.7, 5.9.9.8, 5.9.9.9, 5.9.9.10, 5.9.10.1, 5.9.10.2, 5.9.10.3, 5.9.10.4, 5.9.10.5, 5.9.10.6, 5.9.10.7, 5.9.10.8, 5.9.10.9, 5.9.10.10, 5.10.1.1, 5.10.1.2, 5.10.1.3, 5.10.1.4, 5.10.1.5, 5.10.1.6, 5.10.1.7, 5.10.1.8, 5.10.1.9, 5.10.1.10, 5.10.2.1, 5.10.2.2, 5.10.2.3, 5.10.2.4, 5.10.2.5, 5.10.2.6, 5.10.2.7, 5.10.2.8, 5.10.2.9, 5.10.2.10, 5.10.3.1, 5.10.3.2, 5.10.3.3, 5.10.3.4, 5.10.3.5, 5.10.3.6, 5.10.3.7, 5.10.3.8, 5.10.3.9, 5.10.3.10, 5.10.4.1, 5.10.4.2, 5.10.4.3, 5.10.4.4, 5.10.4.5, 5.10.4.6, 5.10.4.7, 5.10.4.8, 5.10.4.9, 5.10.4.10, 5.10.5.1, 5.10.5.2, 5.10.5.3, 5.10.5.4, 5.10.5.5, 5.10.5.6, 5.10.5.7, 5.10.5.8, 5.10.5.9, 5.10.5.10, 5.10.6.1, 5.10.6.2, 5.10.6.3, 5.10.6.4, 5.10.6.5, 5.10.6.6, 5.10.6.7, 5.10.6.8, 5.10.6.9, 5.10.6.10, 5.10.7.1, 5.10.7.2, 5.10.7.3, 5.10.7.4, 5.10.7.5, 5.10.7.6, 5.10.7.7, 5.10.7.8, 5.10.7.9, 5.10.7.10, 5.10.8.1, 5.10.8.2, 5.10.8.3, 5.10.8.4, 5.10.8.5, 5.10.8.6, 5.10.8.7, 5.10.8.8, 5.10.8.9, 5.10.8.10, 5.10.9.1, 5.10.9.2, 5.10.9.3, 5.10.9.4, 5.10.9.5, 5.10.9.6, 5.10.9.7, 5.10.9.8, 5.10.9.9, 5.10.9.10, 5.10.10.1, 5.10.10.2, 5.10.10.3, 5.10.10.4, 5.10.10.5, 5.10.10.6, 5.10.10.7, 5.10.10.8, 5.10.10.9, 5.10.10.10, 6.1.1.1, 6.1.1.2, 6.1.1.3, 6.1.1.4, 6.1.1.5, 6.1.1.6, 6.1.1.7, 6.1.1.8, 6.1.1.9, 6.1.1.10, 6.1.2.1, 6.1.2.2, 6.1.2.3, 6.1.2.4, 6.1.2.5, TABLE B-continued 6.1.2.6, 6.1.2.7, 6.1.2.8, 6.1.2.9, 6.1.2.10, 6.1.3.1, 6.1.3.2, 6.1.3.3, 6.1.3.4, 6.1.3.5, 6.1.3.6, 6.1.3.7, 6.1.3.8, 6.1.3.9, 6.1.3.10, 6.1.4.1, 6.1.4.2, 6.1.4.3, 6.1.4.4, 6.1.4.5, 6.1.4.6, 6.1.4.7, 6.1.4.8, 6.1.4.9, 6.1.4.10, 6.1.5.1, 6.1.5.2, 6.1.5.3, 6.1.5.4, 6.1.5.5, 6.1.5.6, 6.1.5.7, 6.1.5.8, 6.1.5.9, 6.1.5.10, 6.1.6.1, 6.1.6.2, 6.1.6.3, 6.1.6.4, 6.1.6.5, 6.1.6.6, 6.1.6.7, 6.1.6.8, 6.1.6.9, 6.1.6.10, 6.1.7.1, 6.1.7.2, 6.1.7.3, 6.1.7.4, 6.1.7.5, 6.1.7.6, 6.1.7.7, 6.1.7.8, 6.1.7.9, 6.1.7.10, 6.1.8.1, 6.1.8.2, 6.1.8.3, 6.1.8.4, 6.1.8.5, 6.1.8.6, 6.1.8.7, 6.1.8.8, 6.1.8.9, 6.1.8.10, 6.1.9.1, 6.1.9.2, 6.1.9.3, 6.1.9.4, 6.1.9.5, 6.1.9.6, 6.1.9.7, 6.1.9.8, 6.1.9.9, 6.1.9.10, 6.1.10.1, 6.1.10.2, 6.1.10.3, 6.1.10.4, 6.1.10.5, 6.1.10.6, 6.1.10.7, 6.1.10.8, 6.1.10.9, 6.1.10.10, 6.2.1.1, 6.2.1.2, 6.2.1.3, 6.2.1.4, 6.2.1.5, 6.2.1.6, 6.2.1.7, 6.2.1.8, 6.2.1.9, 6.2.1.10, 6.2.2.1, 6.2.2.2, 6.2.2.3, 6.2.2.4, 6.2.2.5, 6.2.2.6, 6.2.2.7, 6.2.2.8, 6.2.2.9, 6.2.2.10, 6.2.3.1, 6.2.3.2, 6.2.3.3, 6.2.3.4, 6.2.3.5, 6.2.3.6, 6.2.3.7, 6.2.3.8, 6.2.3.9, 6.2.3.10, 6.2.4.1, 6.2.4.2, 6.2.4.3, 6.2.4.4, 6.2.4.5, 6.2.4.6, 6.2.4.7, 6.2.4.8, 6.2.4.9, 6.2.4.10, 6.2.5.1, 6.2.5.2, 6.2.5.3, 6.2.5.4, 6.2.5.5, 6.2.5.6, 6.2.5.7, 6.2.5.8, 6.2.5.9, 6.2.5.10, 6.2.6.1, 6.2.6.2, 6.2.6.3, 6.2.6.4, 6.2.6.5, 6.2.6.6, 6.2.6.7, 6.2.6.8, 6.2.6.9, 6.2.6.10, 6.2.7.1, 6.2.7.2, 6.2.7.3, 6.2.7.4, 6.2.7.5, 6.2.7.6, 6.2.7.7, 6.2.7.8, 6.2.7.9, 6.2.7.10, 6.2.8.1, 6.2.8.2, 6.2.8.3, 6.2.8.4, 6.2.8.5, 6.2.8.6, 6.2.8.7, 6.2.8.8, 6.2.8.9, 6.2.8.10, 6.2.9.1, 6.2.9.2, 6.2.9.3, 6.2.9.4, 6.2.9.5, 6.2.9.6, 6.2.9.7, 6.2.9.8, 6.2.9.9, 6.2.9.10, 6.2.10.1, 6.2.10.2, 6.2.10.3, 6.2.10.4, 6.2.10.5, 6.2.10.6, 6.2.10.7, 6.2.10.8, 6.2.10.9, 6.2.10.10, 6.3.1.1, 6.3.1.2, 6.3.1.3, 6.3.1.4, 6.3.1.5, 6.3.1.6, 6.3.1.7, 6.3.1.8, 6.3.1.9, 6.3.1.10, 6.3.2.1, 6.3.2.2, 6.3.2.3, 6.3.2.4, 6.3.2.5, 6.3.2.6, 6.3.2.7, 6.3.2.8, 6.3.2.9, 6.3.2.10, 6.3.3.1, 6.3.3.2, 6.3.3.3, 6.3.3.4, 6.3.3.5, 6.3.3.6, 6.3.3.7, 6.3.3.8, 6.3.3.9, 6.3.3.10, 6.3.4.1, 6.3.4.2, 6.3.4.3, 6.3.4.4, 6.3.4.5, 6.3.4.6, 6.3.4.7, 6.3.4.8, 6.3.4.9, 6.3.4.10, 6.3.5.1, 6.3.5.2, 6.3.5.3, 6.3.5.4, 6.3.5.5, 6.3.5.6, 6.3.5.7, 6.3.5.8, 6.3.5.9, 6.3.5.10, 6.3.6.1, 6.3.6.2, 6.3.6.3, 6.3.6.4, 6.3.6.5, 6.3.6.6, 6.3.6.7, 6.3.6.8, 6.3.6.9, 6.3.6.10, 6.3.7.1, 6.3.7.2, 6.3.7.3, 6.3.7.4, 6.3.7.5, 6.3.7.6, 6.3.7.7, 6.3.7.8, 6.3.7.9, 6.3.7.10, 6.3.8.1, 6.3.8.2, 6.3.8.3, 6.3.8.4, 6.3.8.5, 6.3.8.6, 6.3.8.7, 6.3.8.8, 6.3.8.9, 6.3.8.10, 6.3.9.1, 6.3.9.2, 6.3.9.3, 6.3.9.4, 6.3.9.5, 6.3.9.6, 6.3.9.7, 6.3.9.8, 6.3.9.9, 6.3.9.10, 6.3.10.1, 6.3.10.2, 6.3.10.3, 6.3.10.4, 6.3.10.5, 6.3.10.6, 6.3.10.7, 6.3.10.8, 6.3.10.9, 6.3.10.10, 6.4.1.1, 6.4.1.2, 6.4.1.3, 6.4.1.4, 6.4.1.5, 6.4.1.6, 6.4.1.7, 6.4.1.8, 6.4.1.9, 6.4.1.10, 6.4.2.1, 6.4.2.2, 6.4.2.3, 6.4.2.4, 6.4.2.5, 6.4.2.6, 6.4.2.7, 6.4.2.8, 6.4.2.9, 6.4.2.10, 6.4.3.1, 6.4.3.2, 6.4.3.3, 6.4.3.4, 6.4.3.5, 6.4.3.6, 6.4.3.7, 6.4.3.8, 6.4.3.9, 6.4.3.10, 6.4.4.1, 6.4.4.2, 6.4.4.3, 6.4.4.4, 6.4.4.5, 6.4.4.6, 6.4.4.7, 6.4.4.8, 6.4.4.9, 6.4.4.10, 6.4.5.1, 6.4.5.2, 6.4.5.3, 6.4.5.4, 6.4.5.5, 6.4.5.6, 6.4.5.7, 6.4.5.8, 6.4.5.9, 6.4.5.10, 6.4.6.1, 6.4.6.2, 6.4.6.3, 6.4.6.4, 6.4.6.5, 6.4.6.6, 6.4.6.7, 6.4.6.8, 6.4.6.9, 6.4.6.10, 6.4.7.1, 6.4.7.2, 6.4.7.3, 6.4.7.4, 6.4.7.5, 6.4.7.6, 6.4.7.7, 6.4.7.8, 6.4.7.9, 6.4.7.10, 6.4.8.1, 6.4.8.2, 6.4.8.3, 6.4.8.4, 6.4.8.5, 6.4.8.6, 6.4.8.7, 6.4.8.8, 6.4.8.9, 6.4.8.10, 6.4.9.1, 6.4.9.2, 6.4.9.3, 6.4.9.4, 6.4.9.5, 6.4.9.6, 6.4.9.7, 6.4.9.8, 6.4.9.9, 6.4.9.10, 6.4.10.1, 6.4.10.2, 6.4.10.3, 6.4.10.4, 6.4.10.5, 6.4.10.6, 6.4.10.7, 6.4.10.8, 6.4.10.9, 6.5.1.1, 6.5.1.2, 6.5.1.3, 6.5.1.4, 6.5.1.5, 6.5.1.6, 6.5.1.7, 6.5.1.8, 6.5.1.9, 6.5.1.10, 6.5.2.1, 6.5.2.2, 6.5.2.3, 6.5.2.4, 6.5.2.5, 6.5.2.6, 6.5.2.7, 6.5.2.8, 6.5.2.9, 6.5.2.10, 6.5.3.1, 6.5.3.2, 6.5.3.3, 6.5.3.4, 6.5.3.5, 6.5.3.6, 6.5.3.7, 6.5.3.8, 6.5.3.9, 6.5.3.10, 6.5.4.1, 6.5.4.2, 6.5.4.3, 6.5.4.4, 6.5.4.5, 6.5.4.6, 6.5.4.7, 6.5.4.8, 6.5.4.9, 6.5.4.10, 6.5.5.1, 6.5.5.2, 6.5.5.3, 6.5.5.4, 6.5.5.5, 6.5.5.6, 6.5.5.7, 6.5.5.8, 6.5.5.9, 6.5.5.10, 6.5.6.1, 6.5.6.2, 6.5.6.3, 6.5.6.4, 6.5.6.5, 6.5.6.6, 6.5.6.7, 6.5.6.8, 6.5.6.9, 6.5.6.10, 6.5.7.1, 6.5.7.2, 6.5.7.3, 6.5.7.4, 6.5.7.5, 6.5.7.6, 6.5.7.7, 6.5.7.8, 6.5.7.9, 6.5.7.10, 6.5.8.1, 6.5.8.2, 6.5.8.3, 6.5.8.4, 6.5.8.5, 6.5.8.6, 6.5.8.7, 6.5.8.8, 6.5.8.9, 6.5.8.10, 6.5.9.1, 6.5.9.2, 6.5.9.3, 6.5.9.4, 6.5.9.5, 6.5.9.6, 6.5.9.7, 6.5.9.8, 6.5.9.9, 6.5.9.10, 6.5.10.1, 6.5.10.2, 6.5.10.3, 6.5.10.4, 6.5.10.5, 6.5.10.6, 6.5.10.7, 6.5.10.8, 6.5.10.9, 6.5.10.10, 6.6.1.1, 6.6.1.2, 6.6.1.3, 6.6.1.4, 6.6.1.5, 6.6.1.6, 6.6.1.7, 6.6.1.8, 6.6.1.9, 6.6.1.10, 6.6.2.1, 6.6.2.2, 6.6.2.3, 6.6.2.4, 6.6.2.5, 6.6.2.6, 6.6.2.7, 6.6.2.8, 6.6.2.9, 6.6.2.10, 6.6.3.1, 6.6.3.2, 6.6.3.3, 6.6.3.4, 6.6.3.5, 6.6.3.6, 6.6.3.7, 6.6.3.8, 6.6.3.9, 6.6.3.10, 6.6.4.1, 6.6.4.2, 6.6.4.3, 6.6.4.4, 6.6.4.5, 6.6.4.6, 6.6.4.7, 6.6.4.8, 6.6.4.9, 6.6.4.10, 6.6.5.1, 6.6.5.2, 6.6.5.3, 6.6.5.4, 6.6.5.5, 6.6.5.6, 6.6.5.7, 6.6.5.8, 6.6.5.9, 6.6.5.10, 6.6.6.1, 6.6.6.2, 6.6.6.3, 6.6.6.4, 6.6.6.5, 6.6.6.6, 6.6.6.7, 6.6.6.8, 6.6.6.9, 6.6.6.10, 6.6.7.1, 6.6.7.2, 6.6.7.3, 6.6.7.4, 6.6.7.5, 6.6.7.6, 6.6.7.7, 6.6.7.8, 6.6.7.9, 6.6.7.10, 6.6.8.1, 6.6.8.2, 6.6.8.3, 6.6.8.4, 6.6.8.5, 6.6.8.6, 6.6.8.7, 6.6.8.8, 6.6.8.9, 6.6.8.10, 6.6.9.1, 6.6.9.2, 6.6.9.3, 6.6.9.4, 6.6.9.5, 6.6.9.6, 6.6.9.7, 6.6.9.8, 6.6.9.9, 6.6.9.10, 6.6.10.1, 6.6.10.2, 6.6.10.3, 6.6.10.4, 6.6.10.5, 6.6.10.6, 6.6.10.7, 6.6.10.8, 6.6.10.9, 6.6.10.10, 6.7.1.1, 6.7.1.2, 6.7.1.3, 6.7.1.4, 6.7.1.5, 6.7.1.6, 6.7.1.7, 6.7.1.8, 6.7.1.9, 6.7.1.10, 6.7.2.1, 6.7.2.2, 6.7.2.3, 6.7.2.4, 6.7.2.5, 6.7.2.6, 6.7.2.7, 6.7.2.8, 6.7.2.9, 6.7.2.10, 6.7.3.1, 6.7.3.2, 6.7.3.3, 6.7.3.4, 6.7.3.5, 6.7.3.6, 6.7.3.7, 6.7.3.8, 6.7.3.9, 6.7.3.10, 6.7.4.1, 6.7.4.2, 6.7.4.3, 6.7.4.4, 6.7.4.5, 6.7.4.6, 6.7.4.7, 6.7.4.8, 6.7.4.9, 6.7.4.10, 6.7.5.1, 6.7.5.2, 6.7.5.3, 6.7.5.4, 6.7.5.5, 6.7.5.6, 6.7.5.7, 6.7.5.8, 6.7.5.9, 6.7.5.10, 6.7.6.1, 6.7.6.2, 6.7.6.3, 6.7.6.4, 6.7.6.5, 6.7.6.6, 6.7.6.7, 6.7.6.8, 6.7.6.9, 6.7.6.10, 6.7.7.1, 6.7.7.2, 6.7.7.3, 6.7.7.4, 6.7.7.5, 6.7.7.6, 6.7.7.7, 6.7.7.8, 6.7.7.9, 6.7.7.10, 6.7.8.1, 6.7.8.2, 6.7.8.3, 6.7.8.4, 6.7.8.5, 6.7.8.6, 6.7.8.7, 6.7.8.8, 6.7.8.9, 6.7.8.10, 6.7.9.1, 6.7.9.2, 6.7.9.3, 6.7.9.4, 6.7.9.5, 6.7.9.6, 6.7.9.7, 6.7.9.8, 6.7.9.9, 6.7.9.10, 6.7.10.1, 6.7.10.2, 6.7.10.3, 6.7.10.4, 6.7.10.5, 6.7.10.6, 6.7.10.7, 6.7.10.8, 6.7.10.9, 6.7.10.10, 6.8.1.1, 6.8.1.2, 6.8.1.3, 6.8.1.4, 6.8.1.5, 6.8.1.6, 6.8.1.7, 6.8.1.8, 6.8.1.9, 6.8.1.10, 6.8.2.1, 6.8.2.2, 6.8.2.3, 6.8.2.4, 6.8.2.5, 6.8.2.6, 6.8.2.7, 6.8.2.8, 6.8.2.9, 6.8.2.10, 6.8.3.1, 6.8.3.2, 6.8.3.3, 6.8.3.4, 6.8.3.5, 6.8.3.6, 6.8.3.7, 6.8.3.8, 6.8.3.9, 6.8.3.10, 6.8.4.1, 6.8.4.2, 6.8.4.3, 6.8.4.4, 6.8.4.5, 6.8.4.6, 6.8.4.7, 6.8.4.8, 6.8.4.9, 6.8.4.10, 6.8.5.1, 6.8.5.2, 6.8.5.3, 6.8.5.4, 6.8.5.5, 6.8.5.6, 6.8.5.7, 6.8.5.8, 6.8.5.9, 6.8.5.10, 6.8.6.1, 6.8.6.2, 6.8.6.3, 6.8.6.4, 6.8.6.5, 6.8.6.6, 6.8.6.7, 6.8.6.8, 6.8.6.9, 6.8.6.10, 6.8.7.1, 6.8.7.2, 6.8.7.3, 6.8.7.4, 6.8.7.5, 6.8.7.6, 6.8.7.7, 6.8.7.8, 6.8.7.9, 6.8.7.10, 6.8.8.1, 6.8.8.2, 6.8.8.3, 6.8.8.4, 6.8.8.5, 6.8.8.6, 6.8.8.7, 6.8.8.8, 6.8.8.9, 6.8.8.10, 6.8.9.1, 6.8.9.2, 6.8.9.3, 6.8.9.4, 6.8.9.5, 6.8.9.6, 6.8.9.7, 6.8.9.8, 6.8.9.9, 6.8.9.10, 6.8.10.1, 6.8.10.2, 6.8.10.3, 6.8.10.4, 6.8.10.5, 6.8.10.6, 6.8.10.7, 6.8.10.8, 6.8.10.9, 6.8.10.10, 6.9.1.1, 6.9.1.2, 6.9.1.3, 6.9.1.4, 6.9.1.5, 6.9.1.6, 6.9.1.7, 6.9.1.8, 6.9.1.9, 6.9.1.10, 6.9.2.1, 6.9.2.2, 6.9.2.3, 6.9.2.4, 6.9.2.5, 6.9.2.6, 6.9.2.7, 6.9.2.8, 6.9.2.9, 6.9.2.10, 6.9.3.1, 6.9.3.2, 6.9.3.3, 6.9.3.4, 6.9.3.5, 6.9.3.6, 6.9.3.7, 6.9.3.8, 6.9.3.9, 6.9.3.10, 6.9.4.1, 6.9.4.2, 6.9.4.3, 6.9.4.4, 6.9.4.5, 6.9.4.6, 6.9.4.7, 6.9.4.8, 6.9.4.9, 6.9.4.10, 6.9.5.1, 6.9.5.2, 6.9.5.3, 6.9.5.4, 6.9.5.5, 6.9.5.6, 6.9.5.7, 6.9.5.8, 6.9.5.9, 6.9.5.10, 6.9.6.1, 6.9.6.2, 6.9.6.3, 6.9.6.4, 6.9.6.5, 6.9.6.6, 6.9.6.7, 6.9.6.8, 6.9.6.9, 6.9.6.10, 6.9.7.1, 6.9.7.2, 6.9.7.3, 6.9.7.4, 6.9.7.5, 6.9.7.6, 6.9.7.7, 6.9.7.8, 6.9.7.9, 6.9.7.10, 6.9.8.1, 6.9.8.2, 6.9.8.3, 6.9.8.4, 6.9.8.5, 6.9.8.6, 6.9.8.7, 6.9.8.8, 6.9.8.9, 6.9.8.10, 6.9.9.1, 6.9.9.2, 6.9.9.3, 6.9.9.4, 6.9.9.5, 6.9.9.6, 6.9.9.7, 6.9.9.8, 6.9.9.9, 6.9.9.10, 6.9.10.1, 6.9.10.2, 6.9.10.3, 6.9.10.4, 6.9.10.5, 6.9.10.6, 6.9.10.7, 6.9.10.8, 6.9.10.9, 6.9.10.10, 6.10.1.1, 6.10.1.2, 6.10.1.3, 6.10.1.4, 6.10.1.5, 6.10.1.6, 6.10.1.7, 6.10.1.8, 6.10.1.9, 6.10.1.10, 6.10.2.1, 6.10.2.2, 6.10.2.3, 6.10.2.4, 6.10.2.5, 6.10.2.6, 6.10.2.7, 6.10.2.8, 6.10.2.9, 6.10.2.10, 6.10.3.1, 6.10.3.2, 6.10.3.3, 6.10.3.4, 6.10.3.5, 6.10.3.6, 6.10.3.7, 6.10.3.8, 6.10.3.9, 6.10.3.10, 6.10.4.1, 6.10.4.2, 6.10.4.3, 6.10.4.4, 6.10.4.5, 6.10.4.6, 6.10.4.7, 6.10.4.8, 6.10.4.9, 6.10.4.10, 6.10.5.1, 6.10.5.2, 6.10.5.3, 6.10.5.4, 6.10.5.5, 6.10.5.6, 6.10.5.7, 6.10.5.8, 6.10.5.9, 6.10.5.10, 6.10.6.1, 6.10.6.2, 6.10.6.3, 6.10.6.4, 6.10.6.5, 6.10.6.6, 6.10.6.7, 6.10.6.8, 6.10.6.9, 6.10.6.10, 6.10.7.1, 6.10.7.2, 6.10.7.3, 6.10.7.4, 6.10.7.5, 6.10.7.6, 6.10.7.7, 6.10.7.8, 6.10.7.9, 6.10.7.10, 6.10.8.1, 6.10.8.2, 6.10.8.3, 6.10.8.4, 6.10.8.5, 6.10.8.6, 6.10.8.7, 6.10.8.8, 6.10.8.9, 6.10.8.10, 6.10.9.1, 6.10.9.2, 6.10.9.3, 6.10.9.4, 6.10.9.5, 6.10.9.6, 6.10.9.7, 6.10.9.8, 6.10.9.9, 6.10.9.10, 6.10.10.1, 6.10.10.2, 6.10.10.3, 6.10.10.4, 6.10.10.5, 6.10.10.6, 6.10.10.7, 6.10.10.8, 6.10.10.9, 6.10.10.10, 7.1.1.1, 7.1.1.2, 7.1.1.3, 7.1.1.4, 7.1.1.5, 7.1.1.6, 7.1.1.7, 7.1.1.8, 7.1.1.9, 7.1.1.10, 7.1.2.1, 7.1.2.2, 7.1.2.3, 7.1.2.4, 7.1.2.5, 7.1.2.6, 7.1.2.7, 7.1.2.8, 7.1.2.9, 7.1.2.10, 7.1.3.1, 7.1.3.2, 7.1.3.3, 7.1.3.4, 7.1.3.5, 7.1.3.6, 7.1.3.7, 7.1.3.8, 7.1.3.9, 7.1.3.10, 7.1.4.1, 7.1.4.2, 7.1.4.3, 7.1.4.4, 7.1.4.5, 7.1.4.6, 7.1.4.7, 7.1.4.8, 7.1.4.9, 7.1.4.10, 7.1.5.1, 7.1.5.2, 7.1.5.3, 7.1.5.4, 7.1.5.5, 7.1.5.6, 7.1.5.7, 7.1.5.8, 7.1.5.9, 7.1.5.10, 7.1.6.1, 7.1.6.2, 7.1.6.3, 7.1.6.4, 7.1.6.5, 7.1.6.6, 7.1.6.7, 7.1.6.8, 7.1.6.9, 7.1.6.10, 7.1.7.1, 7.1.7.2, 7.1.7.3, 7.1.7.4, 7.1.7.5, 7.1.7.6, 7.1.7.7, 7.1.7.8, 7.1.7.9, TABLE B-continued 7.1.7.10, 7.1.8.1, 7.1.8.2, 7.1.8.3, 7.1.8.4, 7.1.8.5, 7.1.8.6, 7.1.8.7, 7.1.8.8, 7.1.8.9, 7.1.8.10, 7.1.9.1, 7.1.9.2,
7.1.9.3, 7.1.9.4, 7.1.9.5, 7.1.9.6, 7.1.9.7, 7.1.9.8, 7.1.9.9, 7.1.9.10, 7.1.10.1, 7.1.10.2, 7.1.10.3, 7.1.10.4, 7.1.10.5,
7.1.10.6, 7.1.10.7, 7.1.10.8, 7.1.10.9, 7.1.10.10, 7.2.1.1, 7.2.1.2, 7.2.1.3, 7.2.1.4, 7.2.1.5, 7.2.1.6, 7.2.1.7, 7.2.1.8,
7.2.1.9, 7.2.1.10, 7.2.2.1, 7.2.2.2, 7.2.2.3, 7.2.2.4, 7.2.2.5, 7.2.2.6, 7.2.2.7, 7.2.2.8, 7.2.2.9, 7.2.2.10, 7.2.3.1,
7.2.3.2, 7.2.3.3, 7.2.3.4, 7.2.3.5, 7.2.3.6, 7.2.3.7, 7.2.3.8, 7.2.3.9, 7.2.3.10, 7.2.4.1, 7.2.4.2, 7.2.4.3, 7.2.4.4, 7.2.4.5,
7.2.4.6, 7.2.4.7, 7.2.4.8, 7.2.4.9, 7.2.4.10, 7.2.5.1, 7.2.5.2, 7.2.5.3, 7.2.5.4, 7.2.5.5, 7.2.5.6, 7.2.5.7, 7.2.5.8, 7.2.5.9,
7.2.5.10, 7.2.6.1, 7.2.6.2, 7.2.6.3, 7.2.6.4, 7.2.6.5, 7.2.6.6, 7.2.6.7, 7.2.6.8, 7.2.6.9, 7.2.6.10, 7.2.7.1, 7.2.7.2,
7.2.7.3, 7.2.7.4, 7.2.7.5, 7.2.7.6, 7.2.7.7, 7.2.7.8, 7.2.7.9, 7.2.7.10, 7.2.8.1, 7.2.8.2, 7.2.8.3, 7.2.8.4, 7.2.8.5, 7.2.8.6,
7.2.8.7, 7.2.8.8, 7.2.8.9, 7.2.8.10, 7.2.9.1, 7.2.9.2, 7.2.9.3, 7.2.9.4, 7.2.9.5, 7.2.9.6, 7.2.9.7, 7.2.9.8, 7.2.9.9,
7.2.9.10, 7.2.10.1, 7.2.10.2, 7.2.10.3, 7.2.10.4, 7.2.10.5, 7.2.10.6, 7.2.10.7, 7.2.10.8, 7.2.10.9, 7.2.10.10, 7.3.1.1,
7.3.1.2, 7.3.1.3, 7.3.1.4, 7.3.1.5, 7.3.1.6, 7.3.1.7, 7.3.1.8, 7.3.1.9, 7.3.1.10, 7.3.2.1, 7.3.2.2, 7.3.2.3, 7.3.2.4, 7.3.2.5,
7.3.2.6, 7.3.2.7, 7.3.2.8, 7.3.2.9, 7.3.2.10, 7.3.3.1, 7.3.3.2, 7.3.3.3, 7.3.3.4, 7.3.3.5, 7.3.3.6, 7.3.3.7, 7.3.3.8, 7.3.3.9,
7.3.3.10, 7.3.4.1, 7.3.4.2, 7.3.4.3, 7.3.4.4, 7.3.4.5, 7.3.4.6, 7.3.4.7, 7.3.4.8, 7.3.4.9, 7.3.4.10, 7.3.5.1, 7.3.5.2,
7.3.5.3, 7.3.5.4, 7.3.5.5, 7.3.5.6, 7.3.5.7, 7.3.5.8, 7.3.5.9, 7.3.5.10, 7.3.6.1, 7.3.6.2, 7.3.6.3, 7.3.6.4, 7.3.6.5, 7.3.6.6,
7.3.6.7, 7.3.6.8, 7.3.6.9, 7.3.6.10, 7.3.7.1, 7.3.7.2, 7.3.7.3, 7.3.7.4, 7.3.7.5, 7.3.7.6, 7.3.7.7, 7.3.7.8, 7.3.7.9,
7.3.7.10, 7.3.8.1, 7.3.8.2, 7.3.8.3, 7.3.8.4, 7.3.8.5, 7.3.8.6, 7.3.8.7, 7.3.8.8, 7.3.8.9, 7.3.8.10, 7.3.9.1, 7.3.9.2,
7.3.9.3, 7.3.9.4, 7.3.9.5, 7.3.9.6, 7.3.9.7, 7.3.9.8, 7.3.9.9, 7.3.10.1, 7.3.10.2, 7.3.10.3, 7.3.10.4, 7.3.10.5,
7.3.10.6, 7.3.10.7, 7.3.10.8, 7.3.10.9, 7.3.10.10, 7.4.1.1, 7.4.1.2, 7.4.1.3, 7.4.1.4, 7.4.1.5, 7.4.1.6, 7.4.1.7, 7.4.1.8,
7.4.1.9, 7.4.1.10, 7.4.2.1, 7.4.2.2, 7.4.2.3, 7.4.2.4, 7.4.2.5, 7.4.2.6, 7.4.2.7, 7.4.2.8, 7.4.2.9, 7.4.2.10, 7.4.3.1,
7.4.3.2, 7.4.3.3, 7.4.3.4, 7.4.3.5, 7.4.3.6, 7.4.3.7, 7.4.3.8, 7.4.3.9, 7.4.3.10, 7.4.4.1, 7.4.4.2, 7.4.4.3, 7.4.4.4, 7.4.4.5,
7.4.4.6, 7.4.4.7, 7.4.4.8, 7.4.4.9, 7.4.4.10, 7.4.5.1, 7.4.5.2, 7.4.5.3, 7.4.5.4, 7.4.5.5, 7.4.5.6, 7.4.5.7, 7.4.5.8, 7.4.5.9,
7.4.5.10, 7.4.6.1, 7.4.6.2, 7.4.6.3, 7.4.6.4, 7.4.6.5, 7.4.6.6, 7.4.6.7, 7.4.6.8, 7.4.6.9, 7.4.6.10, 7.4.7.1, 7.4.7.2,
7.4.7.3, 7.4.7.4, 7.4.7.5, 7.4.7.6, 7.4.7.7, 7.4.7.8, 7.4.7.9, 7.4.7.10, 7.4.8.1, 7.4.8.2, 7.4.8.3, 7.4.8.4, 7.4.8.5, 7.4.8.6,
7.4.8.7, 7.4.8.8, 7.4.8.9, 7.4.8.10, 7.4.9.1, 7.4.9.2, 7.4.9.3, 7.4.9.4, 7.4.9.5, 7.4.9.6, 7.4.9.7, 7.4.9.8, 7.4.9.9,
7.4.9.10, 7.4.10.1, 7.4.10.2, 7.4.10.3, 7.4.10.4, 7.4.10.5, 7.4.10.6, 7.4.10.7, 7.4.10.8, 7.4.10.9, 7.4.10.10, 7.5.1.1,
7.5.1.2, 7.5.1.3, 7.5.1.4, 7.5.1.5, 7.5.1.6, 7.5.1.7, 7.5.1.8, 7.5.1.9, 7.5.1.10, 7.5.2.1, 7.5.2.2, 7.5.2.3, 7.5.2.4, 7.5.2.5,
7.5.2.6, 7.5.2.7, 7.5.2.8, 7.5.2.9, 7.5.2.10, 7.5.3.1, 7.5.3.2, 7.5.3.3, 7.5.3.4, 7.5.3.5, 7.5.3.6, 7.5.3.7, 7.5.3.8, 7.5.3.9,
7.5.3.10, 7.5.4.1, 7.5.4.2, 7.5.4.3, 7.5.4.4, 7.5.4.5, 7.5.4.6, 7.5.4.7, 7.5.4.8, 7.5.4.9, 7.5.4.10, 7.5.5.1, 7.5.5.2,
7.5.5.3, 7.5.5.4, 7.5.5.5, 7.5.5.6, 7.5.5.7, 7.5.5.8, 7.5.5.9, 7.5.5.10, 7.5.6.1, 7.5.6.2, 7.5.6.3, 7.5.6.4, 7.5.6.5, 7.5.6.6,
7.5.6.7, 7.5.6.8, 7.5.6.9, 7.5.6.10, 7.5.7.1, 7.5.7.2, 7.5.7.3, 7.5.7.4, 7.5.7.5, 7.5.7.6, 7.5.7.7, 7.5.7.8, 7.5.7.9,
7.5.7.10, 7.5.8.1, 7.5.8.2, 7.5.8.3, 7.5.8.4, 7.5.8.5, 7.5.8.6, 7.5.8.7, 7.5.8.8, 7.5.8.9, 7.5.8.10, 7.5.9.1, 7.5.9.2,
7.5.9.3, 7.5.9.4, 7.5.9.5, 7.5.9.6, 7.5.9.7, 7.5.9.8, 7.5.9.9, 7.5.9.10, 7.5.10.1, 7.5.10.2, 7.5.10.3, 7.5.10.4, 7.5.10.5,
7.5.10.6, 7.5.10.7, 7.5.10.8, 7.5.10.9, 7.5.10.10, 7.6.1.1, 7.6.1.2, 7.6.1.3, 7.6.1.4, 7.6.1.5, 7.6.1.6, 7.6.1.7, 7.6.1.8,
7.6.1.9, 7.6.1.10, 7.6.2.1, 7.6.2.2, 7.6.2.3, 7.6.2.4, 7.6.2.5, 7.6.2.6, 7.6.2.7, 7.6.2.8, 7.6.2.9, 7.6.2.10, 7.6.3.1,
7.6.3.2, 7.6.3.3, 7.6.3.4, 7.6.3.5, 7.6.3.6, 7.6.3.7, 7.6.3.8, 7.6.3.9, 7.6.3.10, 7.6.4.1, 7.6.4.2, 7.6.4.3, 7.6.4.4, 7.6.4.5,
7.6.4.6, 7.6.4.7, 7.6.4.8, 7.6.4.9, 7.6.4.10, 7.6.5.1, 7.6.5.2, 7.6.5.3, 7.6.5.4, 7.6.5.5, 7.6.5.6, 7.6.5.7, 7.6.5.8, 7.6.5.9,
7.6.5.10, 7.6.6.1, 7.6.6.2, 7.6.6.3, 7.6.6.4, 7.6.6.5, 7.6.6.6, 7.6.6.7, 7.6.6.8, 7.6.6.9, 7.6.6.10, 7.6.7.1, 7.6.7.2,
7.6.7.3, 7.6.7.4, 7.6.7.5, 7.6.7.6, 7.6.7.7, 7.6.7.8, 7.6.7.9, 7.6.7.10, 7.6.8.1, 7.6.8.2, 7.6.8.3, 7.6.8.4, 7.6.8.5, 7.6.8.6,
7.6.8.7, 7.6.8.8, 7.6.8.9, 7.6.8.10, 7.6.9.1, 7.6.9.2, 7.6.9.3, 7.6.9.4, 7.6.9.5, 7.6.9.6, 7.6.9.7, 7.6.9.8, 7.6.9.9,
7.6.9.10, 7.6.10.1, 7.6.10.2, 7.6.10.3, 7.6.10.4, 7.6.10.5, 7.6.10.6, 7.6.10.7, 7.6.10.8, 7.6.10.9, 7.6.10.10, 7.7.1.1,
7.7.1.2, 7.7.1.3, 7.7.1.4, 7.7.1.5, 7.7.1.6, 7.7.1.7, 7.7.1.8, 7.7.1.9, 7.7.1.10, 7.7.2.1, 7.7.2.2, 7.7.2.3, 7.7.2.4, 7.7.2.5,
7.7.2.6, 7.7.2.7, 7.7.2.8, 7.7.2.9, 7.7.2.10, 7.7.3.1, 7.7.3.2, 7.7.3.3, 7.7.3.4, 7.7.3.5, 7.7.3.6, 7.7.3.7, 7.7.3.8, 7.7.3.9,
7.7.3.10, 7.7.4.1, 7.7.4.2, 7.7.4.3, 7.7.4.4, 7.7.4.5, 7.7.4.6, 7.7.4.7, 7.7.4.8, 7.7.4.9, 7.7.4.10, 7.7.5.1, 7.7.5.2,
7.7.5.3, 7.7.5.4, 7.7.5.5, 7.7.5.6, 7.7.5.7, 7.7.5.8, 7.7.5.9, 7.7.5.10, 7.7.6.1, 7.7.6.2, 7.7.6.3, 7.7.6.4, 7.7.6.5, 7.7.6.6,
7.7.6.7, 7.7.6.8, 7.7.6.9, 7.7.6.10, 7.7.7.1, 7.7.7.2, 7.7.7.3, 7.7.7.4, 7.7.7.5, 7.7.7.6, 7.7.7.7, 7.7.7.8, 7.7.7.9,
7.7.7.10, 7.7.8.1, 7.7.8.2, 7.7.8.3, 7.7.8.4, 7.7.8.5, 7.7.8.6, 7.7.8.7, 7.7.8.8, 7.7.8.9, 7.7.8.10, 7.7.9.1, 7.7.9.2,
7.7.9.3, 7.7.9.4, 7.7.9.5, 7.7.9.6, 7.7.9.7, 7.7.9.8, 7.7.9.9, 7.7.9.10, 7.7.10.1, 7.7.10.2, 7.7.10.3, 7.7.10.4, 7.7.10.5,
7.7.10.6, 7.7.10.7, 7.7.10.8, 7.7.10.9, 7.7.10.10, 7.8.1.1, 7.8.1.2, 7.8.1.3, 7.8.1.4, 7.8.1.5, 7.8.1.6, 7.8.1.7, 7.8.1.8,
7.8.1.9, 7.8.1.10, 7.8.2.1, 7.8.2.2, 7.8.2.3, 7.8.2.4, 7.8.2.5, 7.8.2.6, 7.8.2.7, 7.8.2.8, 7.8.2.9, 7.8.2.10, 7.8.3.1,
7.8.3.2, 7.8.3.3, 7.8.3.4, 7.8.3.5, 7.8.3.6, 7.8.3.7, 7.8.3.8, 7.8.3.9, 7.8.3.10, 7.8.4.1, 7.8.4.2, 7.8.4.3, 7.8.4.4, 7.8.4.5,
7.8.4.6, 7.8.4.7, 7.8.4.8, 7.8.4.9, 7.8.4.10, 7.8.5.1, 7.8.5.2, 7.8.5.3, 7.8.5.4, 7.8.5.5, 7.8.5.6, 7.8.5.7, 7.8.5.8, 7.8.5.9,
7.8.5.10, 7.8.6.1, 7.8.6.2, 7.8.6.3, 7.8.6.4, 7.8.6.5, 7.8.6.6, 7.8.6.7, 7.8.6.8, 7.8.6.9, 7.8.6.10, 7.8.7.1, 7.8.7.2,
7.8.7.3, 7.8.7.4, 7.8.7.5, 7.8.7.6, 7.8.7.7, 7.8.7.8, 7.8.7.9, 7.8.7.10, 7.8.8.1, 7.8.8.2, 7.8.8.3, 7.8.8.4, 7.8.8.5, 7.8.8.6,
7.8.8.7, 7.8.8.8, 7.8.8.9, 7.8.8.10, 7.8.9.1, 7.8.9.2, 7.8.9.3, 7.8.9.4, 7.8.9.5, 7.8.9.6, 7.8.9.7, 7.8.9.8, 7.8.9.9,
7.8.9.10, 7.8.10.1, 7.8.10.2, 7.8.10.3, 7.8.10.4, 7.8.10.5, 7.8.10.6, 7.8.10.7, 7.8.10.8, 7.8.10.9, 7.8.10.10, 7.9.1.1,
7.9.1.2, 7.9.1.3, 7.9.1.4, 7.9.1.5, 7.9.1.6, 7.9.1.7, 7.9.1.8, 7.9.1.9, 7.9.1.10, 7.9.2.1, 7.9.2.2, 7.9.2.3, 7.9.2.4, 7.9.2.5,
7.9.2.6, 7.9.2.7, 7.9.2.8, 7.9.2.9, 7.9.2.10, 7.9.3.1, 7.9.3.2, 7.9.3.3, 7.9.3.4, 7.9.3.5, 7.9.3.6, 7.9.3.7, 7.9.3.8, 7.9.3.9,
7.9.3.10, 7.9.4.1, 7.9.4.2, 7.9.4.3, 7.9.4.4, 7.9.4.5, 7.9.4.6, 7.9.4.7, 7.9.4.8, 7.9.4.9, 7.9.4.10, 7.9.5.1, 7.9.5.2,
7.9.5.3, 7.9.5.4, 7.9.5.5, 7.9.5.6, 7.9.5.7, 7.9.5.8, 7.9.5.9, 7.9.5.10, 7.9.6.1, 7.9.6.2, 7.9.6.3, 7.9.6.4, 7.9.6.5, 7.9.6.6,
7.9.6.7, 7.9.6.8, 7.9.6.9, 7.9.6.10, 7.9.7.1, 7.9.7.2, 7.9.7.3, 7.9.7.4, 7.9.7.5, 7.9.7.6, 7.9.7.7, 7.9.7.8, 7.9.7.9,
7.9.7.10, 7.9.8.1, 7.9.8.2, 7.9.8.3, 7.9.8.4, 7.9.8.5, 7.9.8.6, 7.9.8.7, 7.9.8.8, 7.9.8.9, 7.9.8.10, 7.9.9.1, 7.9.9.2,
7.9.9.3, 7.9.9.4, 7.9.9.5, 7.9.9.6, 7.9.9.7, 7.9.9.8, 7.9.9.9, 7.9.9.10, 7.9.10.1, 7.9.10.2, 7.9.10.3, 7.9.10.4, 7.9.10.5,
7.9.10.6, 7.9.10.7, 7.9.10.8, 7.9.10.9, 7.9.10.10, 7.10.1.1, 7.10.1.2, 7.10.1.3, 7.10.1.4, 7.10.1.5, 7.10.1.6, 7.10.1.7,
7.10.1.8, 7.10.1.9, 7.10.1.10, 7.10.2.1, 7.10.2.2, 7.10.2.3, 7.10.2.4, 7.10.2.5, 7.10.2.6, 7.10.2.7, 7.10.2.8, 7.10.2.9,
7.10.2.10, 7.10.3.1, 7.10.3.2, 7.10.3.3, 7.10.3.4, 7.10.3.5, 7.10.3.6, 7.10.3.7, 7.10.3.8, 7.10.3.9, 7.10.3.10, 7.10.4.1,
7.10.4.2, 7.10.4.3, 7.10.4.4, 7.10.4.5, 7.10.4.6, 7.10.4.7, 7.10.4.8, 7.10.4.9, 7.10.4.10, 7.10.5.1, 7.10.5.2, 7.10.5.3,
7.10.5.4, 7.10.5.5, 7.10.5.6, 7.10.5.7, 7.10.5.8, 7.10.5.9, 7.10.5.10, 7.10.6.1, 7.10.6.2, 7.10.6.3, 7.10.6.4, 7.10.6.5,
7.10.6.6, 7.10.6.7, 7.10.6.8, 7.10.6.9, 7.10.6.10, 7.10.7.1, 7.10.7.2, 7.10.7.3, 7.10.7.4, 7.10.7.5, 7.10.7.6, 7.10.7.7,
7.10.7.8, 7.10.7.9, 7.10.7.10, 7.10.8.1, 7.10.8.2, 7.10.8.3, 7.10.8.4, 7.10.8.5, 7.10.8.6, 7.10.8.7, 7.10.8.8, 7.10.8.9,
7.10.8.10, 7.10.9.1, 7.10.9.2, 7.10.9.3, 7.10.9.4, 7.10.9.5, 7.10.9.6, 7.10.9.7, 7.10.9.8, 7.10.9.9, 7.10.9.10,
7.10.10.1, 7.10.10.2, 7.10.10.3, 7.10.10.4, 7.10.10.5, 7.10.10.6, 7.10.10.7, 7.10.10.8, 7.10.10.9, 7.10.10.10, 8.1.1.1,
8.1.1.2, 8.1.1.3, 8.1.1.4, 8.1.1.5, 8.1.1.6, 8.1.1.7, 8.1.1.8, 8.1.1.9, 8.1.1.10, 8.1.2.1, 8.1.2.2, 8.1.2.3, 8.1.2.4, 8.1.2.5,
8.1.2.6, 8.1.2.7, 8.1.2.8, 8.1.2.9, 8.1.2.10, 8.1.3.1, 8.1.3.2, 8.1.3.3, 8.1.3.4, 8.1.3.5, 8.1.3.6, 8.1.3.7, 8.1.3.8, 8.1.3.9,
8.1.3.10, 8.1.4.1, 8.1.4.2, 8.1.4.3, 8.1.4.4, 8.1.4.5, 8.1.4.6, 8.1.4.7, 8.1.4.8, 8.1.4.9, 8.1.4.10, 8.1.5.1, 8.1.5.2,
8.1.5.3, 8.1.5.4, 8.1.5.5, 8.1.5.6, 8.1.5.7, 8.1.5.8, 8.1.5.9, 8.1.5.10, 8.1.6.1, 8.1.6.2, 8.1.6.3, 8.1.6.4, 8.1.6.5, 8.1.6.6,
8.1.6.7, 8.1.6.8, 8.1.6.9, 8.1.6.10, 8.1.7.1, 8.1.7.2, 8.1.7.3, 8.1.7.4, 8.1.7.5, 8.1.7.6, 8.1.7.7, 8.1.7.8, 8.1.7.9,
8.1.7.10, 8.1.8.1, 8.1.8.2, 8.1.8.3, 8.1.8.4, 8.1.8.5, 8.1.8.6, 8.1.8.7, 8.1.8.8, 8.1.8.9, 8.1.8.10, 8.1.9.1, 8.1.9.2,
8.1.9.3, 8.1.9.4, 8.1.9.5, 8.1.9.6, 8.1.9.7, 8.1.9.8, 8.1.9.9, 8.1.9.10, 8.1.10.1, 8.1.10.2, 8.1.10.3, 8.1.10.4, 8.1.10.5,
8.1.10.6, 8.1.10.7, 8.1.10.8, 8.1.10.9, 8.1.10.10, 8.2.1.1, 8.2.1.2, 8.2.1.3, 8.2.1.4, 8.2.1.5, 8.2.1.6, 8.2.1.7, 8.2.1.8,
8.2.1.9, 8.2.1.10, 8.2.2.1, 8.2.2.2, 8.2.2.3, 8.2.2.4, 8.2.2.5, 8.2.2.6, 8.2.2.7, 8.2.2.8, 8.2.2.9, 8.2.2.10, 8.2.3.1, TABLE B-continued 8.2.3.2, 8.2.3.3, 8.2.3.4, 8.2.3.5, 8.2.3.6, 8.2.3.7, 8.2.3.8, 8.2.3.9, 8.2.3.10, 8.2.4.1, 8.2.4.2, 8.2.4.3, 8.2.4.4, 8.2.4.5,
8.2.4.6, 8.2.4.7, 8.2.4.8, 8.2.4.9, 8.2.4.10, 8.2.5.1, 8.2.5.2, 8.2.5.3, 8.2.5.4, 8.2.5.5, 8.2.5.6, 8.2.5.7, 8.2.5.8, 8.2.5.9,
8.2.5.10, 8.2.6.1, 8.2.6.2, 8.2.6.3, 8.2.6.4, 8.2.6.5, 8.2.6.6, 8.2.6.7, 8.2.6.8, 8.2.6.9, 8.2.6.10, 8.2.7.1, 8.2.7.2,
8.2.7.3, 8.2.7.4, 8.2.7.5, 8.2.7.6, 8.2.7.7, 8.2.7.8, 8.2.7.9, 8.2.7.10, 8.2.8.1, 8.2.8.2, 8.2.8.3, 8.2.8.4, 8.2.8.5, 8.2.8.6,
8.2.8.7, 8.2.8.8, 8.2.8.9, 8.2.8.10, 8.2.9.1, 8.2.9.2, 8.2.9.3, 8.2.9.4, 8.2.9.5, 8.2.9.6, 8.2.9.7, 8.2.9.8, 8.2.9.9,
8.2.9.10, 8.2.10.1, 8.2.10.2, 8.2.10.3, 8.2.10.4, 8.2.10.5, 8.2.10.6, 8.2.10.7, 8.2.10.8, 8.2.10.9, 8.2.10.10, 8.3.1.1,
8.3.1.2, 8.3.1.3, 8.3.1.4, 8.3.1.5, 8.3.1.6, 8.3.1.7, 8.3.1.8, 8.3.1.9, 8.3.1.10, 8.3.2.1, 8.3.2.2, 8.3.2.3, 8.3.2.4, 8.3.2.5,
8.3.2.6, 8.3.2.7, 8.3.2.8, 8.3.2.9, 8.3.2.10, 8.3.3.1, 8.3.3.2, 8.3.3.3, 8.3.3.4, 8.3.3.5, 8.3.3.6, 8.3.3.7, 8.3.3.8, 8.3.3.9,
8.3.3.10, 8.3.4.1, 8.3.4.2, 8.3.4.3, 8.3.4.4, 8.3.4.5, 8.3.4.6, 8.3.4.7, 8.3.4.8, 8.3.4.9, 8.3.4.10, 8.3.5.1, 8.3.5.2,
8.3.5.3, 8.3.5.4, 8.3.5.5, 8.3.5.6, 8.3.5.7, 8.3.5.8, 8.3.5.9, 8.3.5.10, 8.3.6.1, 8.3.6.2, 8.3.6.3, 8.3.6.4, 8.3.6.5, 8.3.6.6,
8.3.6.7, 8.3.6.8, 8.3.6.9, 8.3.6.10, 8.3.7.1, 8.3.7.2, 8.3.7.3, 8.3.7.4, 8.3.7.5, 8.3.7.6, 8.3.7.7, 8.3.7.8, 8.3.7.9,
8.3.7.10, 8.3.8.1, 8.3.8.2, 8.3.8.3, 8.3.8.4, 8.3.8.5, 8.3.8.6, 8.3.8.7, 8.3.8.8, 8.3.8.9, 8.3.8.10, 8.3.9.1, 8.3.9.2,
8.3.9.3, 8.3.9.4, 8.3.9.5, 8.3.9.6, 8.3.9.7, 8.3.9.8, 8.3.9.9, 8.3.9.10, 8.3.10.1, 8.3.10.2, 8.3.10.3, 8.3.10.4, 8.3.10.5,
8.3.10.6, 8.3.10.7, 8.3.10.8, 8.3.10.9, 8.3.10.10, 8.4.1.1, 8.4.1.2, 8.4.1.3, 8.4.1.4, 8.4.1.5, 8.4.1.6, 8.4.1.7, 8.4.1.8,
8.4.1.9, 8.4.1.10, 8.4.2.1, 8.4.2.2, 8.4.2.3, 8.4.2.4, 8.4.2.5, 8.4.2.6, 8.4.2.7, 8.4.2.8, 8.4.2.9, 8.4.2.10, 8.4.3.1,
8.4.3.2, 8.4.3.3, 8.4.3.4, 8.4.3.5, 8.4.3.6, 8.4.3.7, 8.4.3.8, 8.4.3.9, 8.4.3.10, 8.4.4.1, 8.4.4.2, 8.4.4.3, 8.4.4.4, 8.4.4.5,
8.4.4.6, 8.4.4.7, 8.4.4.8, 8.4.4.9, 8.4.4.10, 8.4.5.1, 8.4.5.2, 8.4.5.3, 8.4.5.4, 8.4.5.5, 8.4.5.6, 8.4.5.7, 8.4.5.8, 8.4.5.9,
8.4.5.10, 8.4.6.1, 8.4.6.2, 8.4.6.3, 8.4.6.4, 8.4.6.5, 8.4.6.6, 8.4.6.7, 8.4.6.8, 8.4.6.9, 8.4.6.10, 8.4.7.1, 8.4.7.2,
8.4.7.3, 8.4.7.4, 8.4.7.5, 8.4.7.6, 8.4.7.7, 8.4.7.8, 8.4.7.9, 8.4.7.10, 8.4.8.1, 8.4.8.2, 8.4.8.3, 8.4.8.4, 8.4.8.5, 8.4.8.6,
8.4.8.7, 8.4.8.8, 8.4.8.9, 8.4.8.10, 8.4.9.1, 8.4.9.2, 8.4.9.3, 8.4.9.4, 8.4.9.5, 8.4.9.6, 8.4.9.7, 8.4.9.8, 8.4.9.9,
8.4.9.10, 8.4.10.1, 8.4.10.2, 8.4.10.3, 8.4.10.4, 8.4.10.5, 8.4.10.6, 8.4.10.7, 8.4.10.8, 8.4.10.9, 8.4.10.10, 8.5.1.1,
8.5.1.2, 8.5.1.3, 8.5.1.4, 8.5.1.5, 8.5.1.6, 8.5.1.7, 8.5.1.8, 8.5.1.9, 8.5.1.10, 8.5.2.1, 8.5.2.2, 8.5.2.3, 8.5.2.4, 8.5.2.5,
8.5.2.6, 8.5.2.7, 8.5.2.8, 8.5.2.9, 8.5.2.10, 8.5.3.1, 8.5.3.2, 8.5.3.3, 8.5.3.4, 8.5.3.5, 8.5.3.6, 8.5.3.7, 8.5.3.8, 8.5.3.9,
8.5.3.10, 8.5.4.1, 8.5.4.2, 8.5.4.3, 8.5.4.4, 8.5.4.5, 8.5.4.6, 8.5.4.7, 8.5.4.8, 8.5.4.9, 8.5.4.10, 8.5.5.1, 8.5.5.2,
8.5.5.3, 8.5.5.4, 8.5.5.5, 8.5.5.6, 8.5.5.7, 8.5.5.8, 8.5.5.9, 8.5.5.10, 8.5.6.1, 8.5.6.2, 8.5.6.3, 8.5.6.4, 8.5.6.5, 8.5.6.6,
8.5.6.7, 8.5.6.8, 8.5.6.9, 8.5.6.10, 8.5.7.1, 8.5.7.2, 8.5.7.3, 8.5.7.4, 8.5.7.5, 8.5.7.6, 8.5.7.7, 8.5.7.8, 8.5.7.9,
8.5.7.10, 8.5.8.1, 8.5.8.2, 8.5.8.3, 8.5.8.4, 8.5.8.5, 8.5.8.6, 8.5.8.7, 8.5.8.8, 8.5.8.9, 8.5.8.10, 8.5.9.1, 8.5.9.2,
8.5.9.3, 8.5.9.4, 8.5.9.5, 8.5.9.6, 8.5.9.7, 8.5.9.8, 8.5.9.9, 8.5.9.10, 8.5.10.1, 8.5.10.2, 8.5.10.3, 8.5.10.4, 8.5.10.5,
8.5.10.6, 8.5.10.7, 8.5.10.8, 8.5.10.9, 8.5.10.10, 8.6.1.1, 8.6.1.2, 8.6.1.3, 8.6.1.4, 8.6.1.5, 8.6.1.6, 8.6.1.7, 8.6.1.8,
8.6.1.9, 8.6.1.10, 8.6.2.1, 8.6.2.2, 8.6.2.3, 8.6.2.4, 8.6.2.5, 8.6.2.6, 8.6.2.7, 8.6.2.8, 8.6.2.9, 8.6.2.10, 8.6.3.1,
8.6.3.2, 8.6.3.3, 8.6.3.4, 8.6.3.5, 8.6.3.6, 8.6.3.7, 8.6.3.8, 8.6.3.9, 8.6.3.10, 8.6.4.1, 8.6.4.2, 8.6.4.3, 8.6.4.4, 8.6.4.5,
8.6.4.6, 8.6.4.7, 8.6.4.8, 8.6.4.9, 8.6.4.10, 8.6.5.1, 8.6.5.2, 8.6.5.3, 8.6.5.4, 8.6.5.5, 8.6.5.6, 8.6.5.7, 8.6.5.8, 8.6.5.9,
8.6.5.10, 8.6.6.1, 8.6.6.2, 8.6.6.3, 8.6.6.4, 8.6.6.5, 8.6.6.6, 8.6.6.7, 8.6.6.8, 8.6.6.9, 8.6.6.10, 8.6.7.1, 8.6.7.2,
8.6.7.3, 8.6.7.4, 8.6.7.5, 8.6.7.6, 8.6.7.7, 8.6.7.8, 8.6.7.9, 8.6.7.10, 8.6.8.1, 8.6.8.2, 8.6.8.3, 8.6.8.4, 8.6.8.5, 8.6.8.6,
8.6.8.7, 8.6.8.8, 8.6.8.9, 8.6.8.10, 8.6.9.1, 8.6.9.2, 8.6.9.3, 8.6.9.4, 8.6.9.5, 8.6.9.6, 8.6.9.7, 8.6.9.8, 8.6.9.9,
8.6.9.10, 8.6.10.1, 8.6.10.2, 8.6.10.3, 8.6.10.4, 8.6.10.5, 8.6.10.6, 8.6.10.7, 8.6.10.8, 8.6.10.9, 8.6.10.10, 8.7.1.1,
8.7.1.2, 8.7.1.3, 8.7.1.4, 8.7.1.5, 8.7.1.6, 8.7.1.7, 8.7.1.8, 8.7.1.9, 8.7.1.10, 8.7.2.1, 8.7.2.2, 8.7.2.3, 8.7.2.4, 8.7.2.5,
8.7.2.6, 8.7.2.7, 8.7.2.8, 8.7.2.9, 8.7.2.10, 8.7.3.1, 8.7.3.2, 8.7.3.3, 8.7.3.4, 8.7.3.5, 8.7.3.6, 8.7.3.7, 8.7.3.8, 8.7.3.9,
8.7.3.10, 8.7.4.1, 8.7.4.2, 8.7.4.3, 8.7.4.4, 8.7.4.5, 8.7.4.6, 8.7.4.7, 8.7.4.8, 8.7.4.9, 8.7.4.10, 8.7.5.1, 8.7.5.2,
8.7.5.3, 8.7.5.4, 8.7.5.5, 8.7.5.6, 8.7.5.7, 8.7.5.8, 8.7.5.9, 8.7.5.10, 8.7.6.1, 8.7.6.2, 8.7.6.3, 8.7.6.4, 8.7.6.5, 8.7.6.6,
8.7.6.7, 8.7.6.8, 8.7.6.9, 8.7.6.10, 8.7.7.1, 8.7.7.2, 8.7.7.3, 8.7.7.4, 8.7.7.5, 8.7.7.6, 8.7.7.7, 8.7.7.8, 8.7.7.9,
8.7.7.10, 8.7.8.1, 8.7.8.2, 8.7.8.3, 8.7.8.4, 8.7.8.5, 8.7.8.6, 8.7.8.7, 8.7.8.8, 8.7.8.9, 8.7.8.10, 8.7.9.1, 8.7.9.2,
8.7.9.3, 8.7.9.4, 8.7.9.5, 8.7.9.6, 8.7.9.7, 8.7.9.8, 8.7.9.9, 8.7.9.10, 8.7.10.1, 8.7.10.2, 8.7.10.3, 8.7.10.4, 8.7.10.5,
8.7.10.6, 8.7.10.7, 8.7.10.8, 8.7.10.9, 8.7.10.10, 8.8.1.1, 8.8.1.2, 8.8.1.3, 8.8.1.4, 8.8.1.5, 8.8.1.6, 8.8.1.7, 8.8.1.8,
8.8.1.9, 8.8.1.10, 8.8.2.1, 8.8.2.2, 8.8.2.3, 8.8.2.4, 8.8.2.5, 8.8.2.6, 8.8.2.7, 8.8.2.8, 8.8.2.9, 8.8.2.10, 8.8.3.1,
8.8.3.2, 8.8.3.3, 8.8.3.4, 8.8.3.5, 8.8.3.6, 8.8.3.7, 8.8.3.8, 8.8.3.9, 8.8.3.10, 8.8.4.1, 8.8.4.2, 8.8.4.3, 8.8.4.4, 8.8.4.5,
8.8.4.6, 8.8.4.7, 8.8.4.8, 8.8.4.9, 8.8.4.10, 8.8.5.1, 8.8.5.2, 8.8.5.3, 8.8.5.4, 8.8.5.5, 8.8.5.6, 8.8.5.7, 8.8.5.8, 8.8.5.9,
8.8.5.10, 8.8.6.1, 8.8.6.2, 8.8.6.3, 8.8.6.4, 8.8.6.5, 8.8.6.6, 8.8.6.7, 8.8.6.8, 8.8.6.9, 8.8.6.10, 8.8.7.1, 8.8.7.2,
8.8.7.3, 8.8.7.4, 8.8.7.5, 8.8.7.6, 8.8.7.7, 8.8.7.8, 8.8.7.9, 8.8.7.10, 8.8.8.1, 8.8.8.2, 8.8.8.3, 8.8.8.4, 8.8.8.5, 8.8.8.6,
8.8.8.7, 8.8.8.8, 8.8.8.9, 8.8.8.10, 8.8.9.1, 8.8.9.2, 8.8.9.3, 8.8.9.4, 8.8.9.5, 8.8.9.6, 8.8.9.7, 8.8.9.8, 8.8.9.9,
8.8.9.10, 8.8.10.1, 8.8.10.2, 8.8.10.3, 8.8.10.4, 8.8.10.5, 8.8.10.6, 8.8.10.7, 8.8.10.8, 8.8.10.9, 8.8.10.10, 8.9.1.1,
8.9.1.2, 8.9.1.3, 8.9.1.4, 8.9.1.5, 8.9.1.6, 8.9.1.7, 8.9.1.8, 8.9.1.9, 8.9.1.10, 8.9.2.1, 8.9.2.2, 8.9.2.3, 8.9.2.4, 8.9.2.5,
8.9.2.6, 8.9.2.7, 8.9.2.8, 8.9.2.9, 8.9.2.10, 8.9.3.1, 8.9.3.2, 8.9.3.3, 8.9.3.4, 8.9.3.5, 8.9.3.6, 8.9.3.7, 8.9.3.8, 8.9.3.9,
8.9.3.10, 8.9.4.1, 8.9.4.2, 8.9.4.3, 8.9.4.4, 8.9.4.5, 8.9.4.6, 8.9.4.7, 8.9.4.8, 8.9.4.9, 8.9.4.10, 8.9.5.1, 8.9.5.2,
8.9.5.3, 8.9.5.4, 8.9.5.5, 8.9.5.6, 8.9.5.7, 8.9.5.8, 8.9.5.9, 8.9.5.10, 8.9.6.1, 8.9.6.2, 8.9.6.3, 8.9.6.4, 8.9.6.5, 8.9.6.6,
8.9.6.7, 8.9.6.8, 8.9.6.9, 8.9.6.10, 8.9.7.1, 8.9.7.2, 8.9.7.3, 8.9.7.4, 8.9.7.5, 8.9.7.6, 8.9.7.7, 8.9.7.8, 8.9.7.9,
8.9.7.10, 8.9.8.1, 8.9.8.2, 8.9.8.3, 8.9.8.4, 8.9.8.5, 8.9.8.6, 8.9.8.7, 8.9.8.8, 8.9.8.9, 8.9.8.10, 8.9.9.1, 8.9.9.2,
8.9.9.3, 8.9.9.4, 8.9.9.5, 8.9.9.6, 8.9.9.7, 8.9.9.8, 8.9.9.9, 8.9.9.10, 8.9.10.1, 8.9.10.2, 8.9.10.3, 8.9.10.4, 8.9.10.5,
8.9.10.6, 8.9.10.7, 8.9.10.8, 8.9.10.9, 8.9.10.10, 8.10.1.1, 8.10.1.2, 8.10.1.3, 8.10.1.4, 8.10.1.5, 8.10.1.6, 8.10.1.7,
8.10.1.8, 8.10.1.9, 8.10.1.10, 8.10.2.1, 8.10.2.2, 8.10.2.3, 8.10.2.4, 8.10.2.5, 8.10.2.6, 8.10.2.7, 8.10.2.8, 8.10.2.9,
8.10.2.10, 8.10.3.1, 8.10.3.2, 8.10.3.3, 8.10.3.4, 8.10.3.5, 8.10.3.6, 8.10.3.7, 8.10.3.8, 8.10.3.9, 8.10.3.10, 8.10.4.1,
8.10.4.2, 8.10.4.3, 8.10.4.4, 8.10.4.5, 8.10.4.6, 8.10.4.7, 8.10.4.8, 8.10.4.9, 8.10.4.10, 8.10.5.1, 8.10.5.2, 8.10.5.3,
8.10.5.4, 8.10.5.5, 8.10.5.6, 8.10.5.7, 8.10.5.8, 8.10.5.9, 8.10.5.10, 8.10.6.1, 8.10.6.2, 8.10.6.3, 8.10.6.4, 8.10.6.5,
8.10.6.6, 8.10.6.7, 8.10.6.8, 8.10.6.9, 8.10.6.10, 8.10.7.1, 8.10.7.2, 8.10.7.3, 8.10.7.4, 8.10.7.5, 8.10.7.6, 8.10.7.7,
8.10.7.8, 8.10.7.9, 8.10.7.10, 8.10.8.1, 8.10.8.2, 8.10.8.3, 8.10.8.4, 8.10.8.5, 8.10.8.6, 8.10.8.7, 8.10.8.8, 8.10.8.9,
8.10.8.10, 8.10.9.1, 8.10.9.2, 8.10.9.3, 8.10.9.4, 8.10.9.5, 8.10.9.6, 8.10.9.7, 8.10.9.8, 8.10.9.9, 8.10.9.10,
8.10.10.1, 8.10.10.2, 8.10.10.3, 8.10.10.4, 8.10.10.5, 8.10.10.6, 8.10.10.7, 8.10.10.8, 8.10.10.9, 8.10.10.10, 9.1.1.1,
9.1.1.2, 9.1.1.3, 9.1.1.4, 9.1.1.5, 9.1.1.6, 9.1.1.7, 9.1.1.8, 9.1.1.9, 9.1.1.10, 9.1.2.1, 9.1.2.2, 9.1.2.3, 9.1.2.4, 9.1.2.5,
9.1.2.6, 9.1.2.7, 9.1.2.8, 9.1.2.9, 9.1.2.10, 9.1.3.1, 9.1.3.2, 9.1.3.3, 9.1.3.4, 9.1.3.5, 9.1.3.6, 9.1.3.7, 9.1.3.8, 9.1.3.9,
9.1.3.10, 9.1.4.1, 9.1.4.2, 9.1.4.3, 9.1.4.4, 9.1.4.5, 9.1.4.6, 9.1.4.7, 9.1.4.8, 9.1.4.9, 9.1.4.10, 9.1.5.1, 9.1.5.2,
9.1.5.3, 9.1.5.4, 9.1.5.5, 9.1.5.6, 9.1.5.7, 9.1.5.8, 9.1.5.9, 9.1.5.10, 9.1.6.1, 9.1.6.2, 9.1.6.3, 9.1.6.4, 9.1.6.5, 9.1.6.6,
9.1.6.7, 9.1.6.8, 9.1.6.9, 9.1.6.10, 9.1.7.1, 9.1.7.2, 9.1.7.3, 9.1.7.4, 9.1.7.5, 9.1.7.6, 9.1.7.7, 9.1.7.8, 9.1.7.9,
9.1.7.10, 9.1.8.1, 9.1.8.2, 9.1.8.3, 9.1.8.4, 9.1.8.5, 9.1.8.6, 9.1.8.7, 9.1.8.8, 9.1.8.9, 9.1.8.10, 9.1.9.1, 9.1.9.2,
9.1.9.3, 9.1.9.4, 9.1.9.5, 9.1.9.6, 9.1.9.7, 9.1.9.8, 9.1.9.9, 9.1.9.10, 9.1.10.1, 9.1.10.2, 9.1.10.3, 9.1.10.4, 9.1.10.5,
9.1.10.6, 9.1.10.7, 9.1.10.8, 9.1.10.9, 9.1.10.10, 9.2.1.1, 9.2.1.2, 9.2.1.3, 9.2.1.4, 9.2.1.5, 9.2.1.6, 9.2.1.7, 9.2.1.8,
9.2.1.9, 9.2.1.10, 9.2.2.1, 9.2.2.2, 9.2.2.3, 9.2.2.4, 9.2.2.5, 9.2.2.6, 9.2.2.7, 9.2.2.8, 9.2.2.9, 9.2.2.10, 9.2.3.1,
9.2.3.2, 9.2.3.3, 9.2.3.4, 9.2.3.5, 9.2.3.6, 9.2.3.7, 9.2.3.8, 9.2.3.9, 9.2.3.10, 9.2.4.1, 9.2.4.2, 9.2.4.3, 9.2.4.4, 9.2.4.5,
9.2.4.6, 9.2.4.7, 9.2.4.8, 9.2.4.9, 9.2.4.10, 9.2.5.1, 9.2.5.2, 9.2.5.3, 9.2.5.4, 9.2.5.5, 9.2.5.6, 9.2.5.7, 9.2.5.8, 9.2.5.9,
9.2.5.10, 9.2.6.1, 9.2.6.2, 9.2.6.3, 9.2.6.4, 9.2.6.5, 9.2.6.6, 9.2.6.7, 9.2.6.8, 9.2.6.9, 9.2.6.10, 9.2.7.1, 9.2.7.2,
9.2.7.3, 9.2.7.4, 9.2.7.5, 9.2.7.6, 9.2.7.7, 9.2.7.8, 9.2.7.9, 9.2.7.10, 9.2.8.1, 9.2.8.2, 9.2.8.3, 9.2.8.4, 9.2.8.5, 9.2.8.6, TABLE B-continued 9.2.8.7, 9.2.8.8, 9.2.8.9, 9.2.8.10, 9.2.9.1, 9.2.9.2, 9.2.9.3, 9.2.9.4, 9.2.9.5, 9.2.9.6, 9.2.9.7, 9.2.9.8, 9.2.9.9, 9.2.9.10, 9.2.10.1, 9.2.10.2, 9.2.10.3, 9.2.10.4, 9.2.10.5, 9.2.10.6, 9.2.10.7, 9.2.10.8, 9.2.10.9, 9.2.10.10, 9.3.1.1, 9.3.1.2, 9.3.1.3, 9.3.1.4, 9.3.1.5, 9.3.1.6, 9.3.1.7, 9.3.1.8, 9.3.1.9, 9.3.1.10, 9.3.2.1, 9.3.2.2, 9.3.2.3, 9.3.2.4, 9.3.2.5, 9.3.2.6, 9.3.2.7, 9.3.2.8, 9.3.2.9, 9.3.2.10, 9.3.3.1, 9.3.3.2, 9.3.3.3, 9.3.3.4, 9.3.3.5, 9.3.3.6, 9.3.3.7, 9.3.3.8, 9.3.3.9, 9.3.3.10, 9.3.4.1, 9.3.4.2, 9.3.4.3, 9.3.4.4, 9.3.4.5, 9.3.4.6, 9.3.4.7, 9.3.4.8, 9.3.4.9, 9.3.4.10, 9.3.5.1, 9.3.5.2, 9.3.5.3, 9.3.5.4, 9.3.5.5, 9.3.5.6, 9.3.5.7, 9.3.5.8, 9.3.5.9, 9.3.5.10, 9.3.6.1, 9.3.6.2, 9.3.6.3, 9.3.6.4, 9.3.6.5, 9.3.6.6, 9.3.6.7, 9.3.6.8, 9.3.6.9, 9.3.6.10, 9.3.7.1, 9.3.7.2, 9.3.7.3, 9.3.7.4, 9.3.7.5, 9.3.7.6, 9.3.7.7, 9.3.7.8, 9.3.7.9, 9.3.7.10, 9.3.8.1, 9.3.8.2, 9.3.8.3, 9.3.8.4, 9.3.8.5, 9.3.8.6, 9.3.8.7, 9.3.8.8, 9.3.8.9, 9.3.8.10, 9.3.9.1, 9.3.9.2, 9.3.9.3, 9.3.9.4, 9.3.9.5, 9.3.9.6, 9.3.9.7, 9.3.9.8, 9.3.9.9, 9.3.9.10, 9.3.10.1, 9.3.10.2, 9.3.10.3, 9.3.10.4, 9.3.10.5, 9.3.10.6, 9.3.10.7, 9.3.10.8, 9.3.10.9, 9.3.10.10, 9.4.1.1, 9.4.1.2, 9.4.1.3, 9.4.1.4, 9.4.1.5, 9.4.1.6, 9.4.1.7, 9.4.1.8, 9.4.1.9, 9.4.1.10, 9.4.2.1, 9.4.2.2, 9.4.2.3, 9.4.2.4, 9.4.2.5, 9.4.2.6, 9.4.2.7, 9.4.2.8, 9.4.2.9, 9.4.2.10, 9.4.3.1, 9.4.3.2, 9.4.3.3, 9.4.3.4, 9.4.3.5, 9.4.3.6, 9.4.3.7, 9.4.3.8, 9.4.3.9, 9.4.3.10, 9.4.4.1, 9.4.4.2, 9.4.4.3, 9.4.4.4, 9.4.4.5, 9.4.4.6, 9.4.4.7, 9.4.4.8, 9.4.4.9, 9.4.4.10, 9.4.5.1, 9.4.5.2, 9.4.5.3, 9.4.5.4, 9.4.5.5, 9.4.5.6, 9.4.5.7, 9.4.5.8, 9.4.5.9, 9.4.5.10, 9.4.6.1, 9.4.6.2, 9.4.6.3, 9.4.6.4, 9.4.6.5, 9.4.6.6, 9.4.6.7, 9.4.6.8, 9.4.6.9, 9.4.6.10, 9.4.7.1, 9.4.7.2, 9.4.7.3, 9.4.7.4, 9.4.7.5, 9.4.7.6, 9.4.7.7, 9.4.7.8, 9.4.7.9, 9.4.7.10, 9.4.8.1, 9.4.8.2, 9.4.8.3, 9.4.8.4, 9.4.8.5, 9.4.8.6, 9.4.8.7, 9.4.8.8, 9.4.8.9, 9.4.8.10, 9.4.9.1, 9.4.9.2, 9.4.9.3, 9.4.9.4, 9.4.9.5, 9.4.9.6, 9.4.9.7, 9.4.9.8, 9.4.9.9, 9.4.9.10, 9.4.10.1, 9.4.10.2, 9.4.10.3, 9.4.10.4, 9.4.10.5, 9.4.10.6, 9.4.10.7, 9.4.10.8, 9.4.10.9, 9.4.10.10, 9.5.1.1, 9.5.1.2, 9.5.1.3, 9.5.1.4, 9.5.1.5, 9.5.1.6, 9.5.1.7, 9.5.1.8, 9.5.1.9, 9.5.1.10, 9.5.2.1, 9.5.2.2, 9.5.2.3, 9.5.2.4, 9.5.2.5, 9.5.2.6, 9.5.2.7, 9.5.2.8, 9.5.2.9, 9.5.2.10, 9.5.3.1, 9.5.3.2, 9.5.3.3, 9.5.3.4, 9.5.3.5, 9.5.3.6, 9.5.3.7, 9.5.3.8, 9.5.3.9, 9.5.3.10, 9.5.4.1, 9.5.4.2, 9.5.4.3, 9.5.4.4, 9.5.4.5, 9.5.4.6, 9.5.4.7, 9.5.4.8, 9.5.4.9, 9.5.4.10, 9.5.5.1, 9.5.5.2, 9.5.5.3, 9.5.5.4, 9.5.5.5, 9.5.5.6, 9.5.5.7, 9.5.5.8, 9.5.5.9, 9.5.5.10, 9.5.6.1, 9.5.6.2, 9.5.6.3, 9.5.6.4, 9.5.6.5, 9.5.6.6, 9.5.6.7, 9.5.6.8, 9.5.6.9, 9.5.6.10, 9.5.7.1, 9.5.7.2, 9.5.7.3, 9.5.7.4, 9.5.7.5, 9.5.7.6, 9.5.7.7, 9.5.7.8, 9.5.7.9, 9.5.7.10, 9.5.8.1, 9.5.8.2, 9.5.8.3, 9.5.8.4, 9.5.8.5, 9.5.8.6, 9.5.8.7, 9.5.8.8, 9.5.8.9, 9.5.8.10, 9.5.9.1, 9.5.9.2, 9.5.9.3, 9.5.9.4, 9.5.9.5, 9.5.9.6, 9.5.9.7, 9.5.9.8, 9.5.9.9, 9.5.9.10, 9.5.10.1, 9.5.10.2, 9.5.10.3, 9.5.10.4, 9.5.10.5, 9.5.10.6, 9.5.10.7, 9.5.10.8, 9.5.10.9, 9.5.10.10, 9.6.1.1, 9.6.1.2, 9.6.1.3, 9.6.1.4, 9.6.1.5, 9.6.1.6, 9.6.1.7, 9.6.1.8, 9.6.1.9, 9.6.1.10, 9.6.2.1, 9.6.2.2, 9.6.2.3, 9.6.2.4, 9.6.2.5, 9.6.2.6, 9.6.2.7, 9.6.2.8, 9.6.2.9, 9.6.2.10, 9.6.3.1, 9.6.3.2, 9.6.3.3, 9.6.3.4, 9.6.3.5, 9.6.3.6, 9.6.3.7, 9.6.3.8, 9.6.3.9, 9.6.3.10, 9.6.4.1, 9.6.4.2, 9.6.4.3, 9.6.4.4, 9.6.4.5, 9.6.4.6, 9.6.4.7, 9.6.4.8, 9.6.4.9, 9.6.4.10, 9.6.5.1, 9.6.5.2, 9.6.5.3, 9.6.5.4, 9.6.5.5, 9.6.5.6, 9.6.5.7, 9.6.5.8, 9.6.5.9, 9.6.5.10, 9.6.6.1, 9.6.6.2, 9.6.6.3, 9.6.6.4, 9.6.6.5, 9.6.6.6, 9.6.6.7, 9.6.6.8, 9.6.6.9, 9.6.6.10, 9.6.7.1, 9.6.7.2, 9.6.7.3, 9.6.7.4, 9.6.7.5, 9.6.7.6, 9.6.7.7, 9.6.7.8, 9.6.7.9, 9.6.7.10, 9.6.8.1, 9.6.8.2, 9.6.8.3, 9.6.8.4, 9.6.8.5, 9.6.8.6, 9.6.8.7, 9.6.8.8, 9.6.8.9, 9.6.8.10, 9.6.9.1, 9.6.9.2, 9.6.9.3, 9.6.9.4, 9.6.9.5, 9.6.9.6, 9.6.9.7, 9.6.9.8, 9.6.9.9, 9.6.9.10, 9.6.10.1, 9.6.10.2, 9.6.10.3, 9.6.10.4, 9.6.10.5, 9.6.10.6, 9.6.10.7, 9.6.10.8, 9.6.10.9, 9.6.10.10, 9.7.1.1, 9.7.1.2, 9.7.1.3, 9.7.1.4, 9.7.1.5, 9.7.1.6, 9.7.1.7, 9.7.1.8, 9.7.1.9, 9.7.1.10, 9.7.2.1, 9.7.2.2, 9.7.2.3, 9.7.2.4, 9.7.2.5, 9.7.2.6, 9.7.2.7, 9.7.2.8, 9.7.2.9, 9.7.2.10, 9.7.3.1, 9.7.3.2, 9.7.3.3, 9.7.3.4, 9.7.3.5, 9.7.3.6, 9.7.3.7, 9.7.3.8, 9.7.3.9, 9.7.3.10, 9.7.4.1, 9.7.4.2, 9.7.4.3, 9.7.4.4, 9.7.4.5, 9.7.4.6, 9.7.4.7, 9.7.4.8, 9.7.4.9, 9.7.4.10, 9.7.5.1, 9.7.5.2, 9.7.5.3, 9.7.5.4, 9.7.5.5, 9.7.5.6, 9.7.5.7, 9.7.5.8, 9.7.5.9, 9.7.5.10, 9.7.6.1, 9.7.6.2, 9.7.6.3, 9.7.6.4, 9.7.6.5, 9.7.6.6, 9.7.6.7, 9.7.6.8, 9.7.6.9, 9.7.6.10, 9.7.7.1, 9.7.7.2, 9.7.7.3, 9.7.7.4, 9.7.7.5, 9.7.7.6, 9.7.7.7, 9.7.7.8, 9.7.7.9, 9.7.7.10, 9.7.8.1, 9.7.8.2, 9.7.8.3, 9.7.8.4, 9.7.8.5, 9.7.8.6, 9.7.8.7, 9.7.8.8, 9.7.8.9, 9.7.8.10, 9.7.9.1, 9.7.9.2, 9.7.9.3, 9.7.9.4, 9.7.9.5, 9.7.9.6, 9.7.9.7, 9.7.9.8, 9.7.9.9, 9.7.9.10, 9.7.10.1, 9.7.10.2, 9.7.10.3, 9.7.10.4, 9.7.10.5, 9.7.10.6, 9.7.10.7, 9.7.10.8, 9.7.10.9, 9.7.10.10, 9.8.1.1, 9.8.1.2, 9.8.1.3, 9.8.1.4, 9.8.1.5, 9.8.1.6, 9.8.1.7, 9.8.1.8, 9.8.1.9, 9.8.1.10, 9.8.2.1, 9.8.2.2, 9.8.2.3, 9.8.2.4, 9.8.2.5, 9.8.2.6, 9.8.2.7, 9.8.2.8, 9.8.2.9, 9.8.2.10, 9.8.3.1, 9.8.3.2, 9.8.3.3, 9.8.3.4, 9.8.3.5, 9.8.3.6, 9.8.3.7, 9.8.3.8, 9.8.3.9, 9.8.3.10, 9.8.4.1, 9.8.4.2, 9.8.4.3, 9.8.4.4, 9.8.4.5, 9.8.4.6, 9.8.4.7, 9.8.4.8, 9.8.4.9, 9.8.4.10, 9.8.5.1, 9.8.5.2, 9.8.5.3, 9.8.5.4, 9.8.5.5, 9.8.5.6, 9.8.5.7, 9.8.5.8, 9.8.5.9, 9.8.5.10, 9.8.6.1, 9.8.6.2, 9.8.6.3, 9.8.6.4, 9.8.6.5, 9.8.6.6, 9.8.6.7, 9.8.6.8, 9.8.6.9, 9.8.6.10, 9.8.7.1, 9.8.7.2, 9.8.7.3, 9.8.7.4, 9.8.7.5, 9.8.7.6, 9.8.7.7, 9.8.7.8, 9.8.7.9, 9.8.7.10, 9.8.8.1, 9.8.8.2, 9.8.8.3, 9.8.8.4, 9.8.8.5, 9.8.8.6, 9.8.8.7, 9.8.8.8, 9.8.8.9, 9.8.8.10, 9.8.9.1, 9.8.9.2, 9.8.9.3, 9.8.9.4, 9.8.9.5, 9.8.9.6, 9.8.9.7, 9.8.9.8, 9.8.9.9, 9.8.9.10, 9.8.10.1, 9.8.10.2, 9.8.10.3, 9.8.10.4, 9.8.10.5, 9.8.10.6, 9.8.10.7, 9.8.10.8, 9.8.10.9, 9.8.10.10, 9.9.1.1, 9.9.1.2, 9.9.1.3, 9.9.1.4, 9.9.1.5, 9.9.1.6, 9.9.1.7, 9.9.1.8, 9.9.1.9, 9.9.1.10, 9.9.2.1, 9.9.2.2, 9.9.2.3, 9.9.2.4, 9.9.2.5, 9.9.2.6, 9.9.2.7, 9.9.2.8, 9.9.2.9, 9.9.2.10, 9.9.3.1, 9.9.3.2, 9.9.3.3, 9.9.3.4, 9.9.3.5, 9.9.3.6, 9.9.3.7, 9.9.3.8, 9.9.3.9, 9.9.3.10, 9.9.4.1, 9.9.4.2, 9.9.4.3, 9.9.4.4, 9.9.4.5, 9.9.4.6, 9.9.4.7, 9.9.4.8, 9.9.4.9, 9.9.4.10, 9.9.5.1, 9.9.5.2, 9.9.5.3, 9.9.5.4, 9.9.5.5, 9.9.5.6, 9.9.5.7, 9.9.5.8, 9.9.5.9, 9.9.5.10, 9.9.6.1, 9.9.6.2, 9.9.6.3, 9.9.6.4, 9.9.6.5, 9.9.6.6, 9.9.6.7, 9.9.6.8, 9.9.6.9, 9.9.6.10, 9.9.7.1, 9.9.7.2, 9.9.7.3, 9.9.7.4, 9.9.7.5, 9.9.7.6, 9.9.7.7, 9.9.7.8, 9.9.7.9, 9.9.7.10, 9.9.8.1, 9.9.8.2, 9.9.8.3, 9.9.8.4, 9.9.8.5, 9.9.8.6, 9.9.8.7, 9.9.8.8, 9.9.8.9, 9.9.8.10, 9.9.9.1, 9.9.9.2, 9.9.9.3, 9.9.9.4, 9.9.9.5, 9.9.9.6, 9.9.9.7, 9.9.9.8, 9.9.9.9, 9.9.9.10, 9.9.10.1, 9.9.10.2, 9.9.10.3, 9.9.10.4, 9.9.10.5, 9.9.10.6, 9.9.10.7, 9.9.10.8, 9.9.10.9, 9.9.10.10, 9.10.1.1, 9.10.1.2, 9.10.1.3, 9.10.1.4, 9.10.1.5, 9.10.1.6, 9.10.1.7, 9.10.1.8, 9.10.1.9, 9.10.1.10, 9.10.2.1, 9.10.2.2, 9.10.2.3, 9.10.2.4, 9.10.2.5, 9.10.2.6, 9.10.2.7, 9.10.2.8, 9.10.2.9, 9.10.2.10, 9.10.3.1, 9.10.3.2, 9.10.3.3, 9.10.3.4, 9.10.3.5, 9.10.3.6, 9.10.3.7, 9.10.3.8, 9.10.3.9, 9.10.3.10, 9.10.4.1, 9.10.4.2, 9.10.4.3, 9.10.4.4, 9.10.4.5, 9.10.4.6, 9.10.4.7, 9.10.4.8, 9.10.4.9, 9.10.4.10, 9.10.5.1, 9.10.5.2, 9.10.5.3, 9.10.5.4, 9.10.5.5, 9.10.5.6, 9.10.5.7, 9.10.5.8, 9.10.5.9, 9.10.5.10, 9.10.6.1, 9.10.6.2, 9.10.6.3, 9.10.6.4, 9.10.6.5, 9.10.6.6, 9.10.6.7, 9.10.6.8, 9.10.6.9, 9.10.6.10, 9.10.7.1, 9.10.7.2, 9.10.7.3, 9.10.7.4, 9.10.7.5, 9.10.7.6, 9.10.7.7, 9.10.7.8, 9.10.7.9, 9.10.7.10, 9.10.8.1, 9.10.8.2, 9.10.8.3, 9.10.8.4, 9.10.8.5, 9.10.8.6, 9.10.8.7, 9.10.8.8, 9.10.8.9, 9.10.8.10, 9.10.9.1, 9.10.9.2, 9.10.9.3, 9.10.9.4, 9.10.9.5, 9.10.9.6, 9.10.9.7, 9.10.9.8, 9.10.9.9, 9.10.9.10, 9.10.10.1, 9.10.10.2, 9.10.10.3, 9.10.10.4, 9.10.10.5, 9.10.10.6, 9.10.10.7, 9.10.10.8, 9.10.10.9, 9.10.10.10, 10.1.1.1, 10.1.1.2, 10.1.1.3, 10.1.1.4, 10.1.1.5, 10.1.1.6, 10.1.1.7, 10.1.1.8, 10.1.1.9, 10.1.1.10, 10.1.2.1, 10.1.2.2, 10.1.2.3, 10.1.2.4, 10.1.2.5, 10.1.2.6, 10.1.2.7, 10.1.2.8, 10.1.2.9, 10.1.2.10, 10.1.3.1, 10.1.3.2, 10.1.3.3, 10.1.3.4, 10.1.3.5, 10.1.3.6, 10.1.3.7, 10.1.3.8, 10.1.3.9, 10.1.3.10, 10.1.4.1, 10.1.4.2, 10.1.4.3, 10.1.4.4, 10.1.4.5, 10.1.4.6, 10.1.4.7, 10.1.4.8, 10.1.4.9, 10.1.4.10, 10.1.5.1, 10.1.5.2, 10.1.5.3, 10.1.5.4, 10.1.5.5, 10.1.5.6, 10.1.5.7, 10.1.5.8, 10.1.5.9, 10.1.5.10, 10.1.6.1, 10.1.6.2, 10.1.6.3, 10.1.6.4, 10.1.6.5, 10.1.6.6, 10.1.6.7, 10.1.6.8, 10.1.6.9, 10.1.6.10, 10.1.7.1, 10.1.7.2, 10.1.7.3, 10.1.7.4, 10.1.7.5, 10.1.7.6, 10.1.7.7, 10.1.7.8, 10.1.7.9, 10.1.7.10, 10.1.8.1, 10.1.8.2, 10.1.8.3, 10.1.8.4, 10.1.8.5, 10.1.8.6, 10.1.8.7, 10.1.8.8, 10.1.8.9, 10.1.8.10, 10.1.9.1, 10.1.9.2, 10.1.9.3, 10.1.9.4, 10.1.9.5, 10.1.9.6, 10.1.9.7, 10.1.9.8, 10.1.9.9, 10.1.9.10, 10.1.10.1, 10.1.10.2, 10.1.10.3, 10.1.10.4, 10.1.10.5, 10.1.10.6, 10.1.10.7, 10.1.10.8, 10.1.10.9, 10.1.10.10, 10.2.1.1, 10.2.1.2, 10.2.1.3, 10.2.1.4, 10.2.1.5, 10.2.1.6, 10.2.1.7, 10.2.1.8, 10.2.1.9, 10.2.1.10, 10.2.2.1, 10.2.2.2, 10.2.2.3, 10.2.2.4, 10.2.2.5, 10.2.2.6, 10.2.2.7, 10.2.2.8, 10.2.2.9, 10.2.2.10, 10.2.3.1, 10.2.3.2, 10.2.3.3, 10.2.3.4, 10.2.3.5, 10.2.3.6, 10.2.3.7, 10.2.3.8, 10.2.3.9, 10.2.3.10, 10.2.4.1, 10.2.4.2, 10.2.4.3, 10.2.4.4, 10.2.4.5, 10.2.4.6, 10.2.4.7, 10.2.4.8, 10.2.4.9, 10.2.4.10, 10.2.5.1, 10.2.5.2, 10.2.5.3, 10.2.5.4, 10.2.5.5, 10.2.5.6, 10.2.5.7, 10.2.5.8, 10.2.5.9, 10.2.5.10, 10.2.6.1, 10.2.6.2, 10.2.6.3, 10.2.6.4, 10.2.6.5, 10.2.6.6, 10.2.6.7, 10.2.6.8, 10.2.6.9, 10.2.6.10, 10.2.7.1, 10.2.7.2, 10.2.7.3, 10.2.7.4, 10.2.7.5, 10.2.7.6, 10.2.7.7, 10.2.7.8, 10.2.7.9, 10.2.7.10, 10.2.8.1, 10.2.8.2, 10.2.8.3, 10.2.8.4, 10.2.8.5, 10.2.8.6, 10.2.8.7, 10.2.8.8, 10.2.8.9, 10.2.8.10, 10.2.9.1, 10.2.9.2, 10.2.9.3, 10.2.9.4, 10.2.9.5, 10.2.9.6, 10.2.9.7, 10.2.9.8, 10.2.9.9, 10.2.9.10, 10.2.10.1, 10.2.10.2, 10.2.10.3, 10.2.10.4, 10.2.10.5, 10.2.10.6, 10.2.10.7, 10.2.10.8, 10.2.10.9, 10.2.10.10, TABLE B-continued 10.3.1.1, 10.3.1.2, 10.3.1.3, 10.3.1.4, 10.3.1.5, 10.3.1.6, 10.3.1.7, 10.3.1.8, 10.3.1.9, 10.3.1.10, 10.3.2.1, 10.3.2.2, 10.3.2.3, 10.3.2.4, 10.3.2.5, 10.3.2.6, 10.3.2.7, 10.3.2.8, 10.3.2.9, 10.3.2.10, 10.3.3.1, 10.3.3.2, 10.3.3.3, 10.3.3.4, 10.3.3.5, 10.3.3.6, 10.3.3.7, 10.3.3.8, 10.3.3.9, 10.3.3.10, 10.3.4.1, 10.3.4.2, 10.3.4.3, 10.3.4.4, 10.3.4.5, 10.3.4.6, 10.3.4.7, 10.3.4.8, 10.3.4.9, 10.3.4.10, 10.3.5.1, 10.3.5.2, 10.3.5.3, 10.3.5.4, 10.3.5.5, 10.3.5.6, 10.3.5.7, 10.3.5.8, 10.3.5.9, 10.3.5.10, 10.3.6.1, 10.3.6.2, 10.3.6.3, 10.3.6.4, 10.3.6.5, 10.3.6.6, 10.3.6.7, 10.3.6.8, 10.3.6.9, 10.3.6.10, 10.3.7.1, 10.3.7.2, 10.3.7.3, 10.3.7.4, 10.3.7.5, 10.3.7.6, 10.3.7.7, 10.3.7.8, 10.3.7.9, 10.3.7.10, 10.3.8.1, 10.3.8.2, 10.3.8.3, 10.3.8.4, 10.3.8.5, 10.3.8.6, 10.3.8.7, 10.3.8.8, 10.3.8.9, 10.3.8.10, 10.3.9.1, 10.3.9.2, 10.3.9.3, 10.3.9.4, 10.3.9.5, 10.3.9.6, 10.3.9.7, 10.3.9.8, 10.3.9.9, 10.3.9.10, 10.3.10.1, 10.3.10.2, 10.3.10.3, 10.3.10.4, 10.3.10.5, 10.3.10.6, 10.3.10.7, 10.3.10.8, 10.3.10.9, 10.3.10.10, 10.4.1.1, 10.4.1.2, 10.4.1.3, 10.4.1.4, 10.4.1.5, 10.4.1.6, 10.4.1.7, 10.4.1.8, 10.4.1.9, 10.4.1.10, 10.4.2.1, 10.4.2.2, 10.4.2.3, 10.4.2.4, 10.4.2.5, 10.4.2.6, 10.4.2.7, 10.4.2.8, 10.4.2.9, 10.4.2.10, 10.4.3.1, 10.4.3.2, 10.4.3.3, 10.4.3.4, 10.4.3.5, 10.4.3.6, 10.4.3.7, 10.4.3.8, 10.4.3.9, 10.4.3.10, 10.4.4.1, 10.4.4.2, 10.4.4.3, 10.4.4.4, 10.4.4.5, 10.4.4.6, 10.4.4.7, 10.4.4.8, 10.4.4.9, 10.4.4.10, 10.4.5.1, 10.4.5.2, 10.4.5.3, 10.4.5.4, 10.4.5.5, 10.4.5.6, 10.4.5.7, 10.4.5.8, 10.4.5.9, 10.4.5.10, 10.4.6.1, 10.4.6.2, 10.4.6.3, 10.4.6.4, 10.4.6.5, 10.4.6.6, 10.4.6.7, 10.4.6.8, 10.4.6.9, 10.4.6.10, 10.4.7.1, 10.4.7.2, 10.4.7.3, 10.4.7.4, 10.4.7.5, 10.4.7.6, 10.4.7.7, 10.4.7.8, 10.4.7.9, 10.4.7.10, 10.4.8.1, 10.4.8.2, 10.4.8.3, 10.4.8.4, 10.4.8.5, 10.4.8.6, 10.4.8.7, 10.4.8.8, 10.4.8.9, 10.4.8.10, 10.4.9.1, 10.4.9.2, 10.4.9.3, 10.4.9.4, 10.4.9.5, 10.4.9.6, 10.4.9.7, 10.4.9.8, 10.4.9.9, 10.4.9.10, 10.4.10.1, 10.4.10.2, 10.4.10.3, 10.4.10.4, 10.4.10.5, 10.4.10.6, 10.4.10.7, 10.4.10.8, 10.4.10.9, 10.4.10.10, 10.5.1.1, 10.5.1.2, 10.5.1.3, 10.5.1.4, 10.5.1.5, 10.5.1.6, 10.5.1.7, 10.5.1.8, 10.5.1.9, 10.5.1.10, 10.5.2.1, 10.5.2.2, 10.5.2.3, 10.5.2.4, 10.5.2.5, 10.5.2.6, 10.5.2.7, 10.5.2.8, 10.5.2.9, 10.5.2.10, 10.5.3.1, 10.5.3.2, 10.5.3.3, 10.5.3.4, 10.5.3.5, 10.5.3.6, 10.5.3.7, 10.5.3.8, 10.5.3.9, 10.5.3.10, 10.5.4.1, 10.5.4.2, 10.5.4.3, 10.5.4.4, 10.5.4.5, 10.5.4.6, 10.5.4.7, 10.5.4.8, 10.5.4.9, 10.5.4.10, 10.5.5.1, 10.5.5.2, 10.5.5.3, 10.5.5.4, 10.5.5.5, 10.5.5.6, 10.5.5.7, 10.5.5.8, 10.5.5.9, 10.5.5.10, 10.5.6.1, 10.5.6.2, 10.5.6.3, 10.5.6.4, 10.5.6.5, 10.5.6.6, 10.5.6.7, 10.5.6.8, 10.5.6.9, 10.5.6.10, 10.5.7.1, 10.5.7.2, 10.5.7.3, 10.5.7.4, 10.5.7.5, 10.5.7.6, 10.5.7.7, 10.5.7.8, 10.5.7.9, 10.5.7.10, 10.5.8.1, 10.5.8.2, 10.5.8.3, 10.5.8.4, 10.5.8.5, 10.5.8.6, 10.5.8.7, 10.5.8.8, 10.5.8.9, 10.5.8.10, 10.5.9.1, 10.5.9.2, 10.5.9.3, 10.5.9.4, 10.5.9.5, 10.5.9.6, 10.5.9.7, 10.5.9.8, 10.5.9.9, 10.5.9.10, 10.5.10.1, 10.5.10.2, 10.5.10.3, 10.5.10.4, 10.5.10.5, 10.5.10.6, 10.5.10.7, 10.5.10.8, 10.5.10.9, 10.5.10.10, 10.6.1.1, 10.6.1.2, 10.6.1.3, 10.6.1.4, 10.6.1.5, 10.6.1.6, 10.6.1.7, 10.6.1.8, 10.6.1.9, 10.6.1.10, 10.6.2.1, 10.6.2.2, 10.6.2.3, 10.6.2.4, 10.6.2.5, 10.6.2.6, 10.6.2.7, 10.6.2.8, 10.6.2.9, 10.6.2.10, 10.6.3.1, 10.6.3.2, 10.6.3.3, 10.6.3.4, 10.6.3.5, 10.6.3.6, 10.6.3.7, 10.6.3.8, 10.6.3.9, 10.6.3.10, 10.6.4.1, 10.6.4.2, 10.6.4.3, 10.6.4.4, 10.6.4.5, 10.6.4.6, 10.6.4.7, 10.6.4.8, 10.6.4.9, 10.6.4.10, 10.6.5.1, 10.6.5.2, 10.6.5.3, 10.6.5.4, 10.6.5.5, 10.6.5.6, 10.6.5.7, 10.6.5.8, 10.6.5.9, 10.6.5.10, 10.6.6.1, 10.6.6.2, 10.6.6.3, 10.6.6.4, 10.6.6.5, 10.6.6.6, 10.6.6.7, 10.6.6.8, 10.6.6.9, 10.6.6.10, 10.6.7.1, 10.6.7.2, 10.6.7.3, 10.6.7.4, 10.6.7.5, 10.6.7.6, 10.6.7.7, 10.6.7.8, 10.6.7.9, 10.6.7.10, 10.6.8.1, 10.6.8.2, 10.6.8.3, 10.6.8.4, 10.6.8.5, 10.6.8.6, 10.6.8.7, 10.6.8.8, 10.6.8.9, 10.6.8.10, 10.6.9.1, 10.6.9.2, 10.6.9.3, 10.6.9.4, 10.6.9.5, 10.6.9.6, 10.6.9.7, 10.6.9.8, 10.6.9.9, 10.6.9.10, 10.6.10.1, 10.6.10.2, 10.6.10.3, 10.6.10.4, 10.6.10.5, 10.6.10.6, 10.6.10.7, 10.6.10.8, 10.6.10.9, 10.6.10.10, 10.7.1.1, 10.7.1.2, 10.7.1.3, 10.7.1.4, 10.7.1.5, 10.7.1.6, 10.7.1.7, 10.7.1.8, 10.7.1.9, 10.7.1.10, 10.7.2.1, 10.7.2.2, 10.7.2.3, 10.7.2.4, 10.7.2.5, 10.7.2.6, 10.7.2.7, 10.7.2.8, 10.7.2.9, 10.7.2.10, 10.7.3.1, 10.7.3.2, 10.7.3.3, 10.7.3.4, 10.7.3.5, 10.7.3.6, 10.7.3.7, 10.7.3.8, 10.7.3.9, 10.7.3.10, 10.7.4.1, 10.7.4.2, 10.7.4.3, 10.7.4.4, 10.7.4.5, 10.7.4.6, 10.7.4.7, 10.7.4.8, 10.7.4.9, 10.7.4.10, 10.7.5.1, 10.7.5.2, 10.7.5.3, 10.7.5.4, 10.7.5.5, 10.7.5.6, 10.7.5.7, 10.7.5.8, 10.7.5.9, 10.7.5.10, 10.7.6.1, 10.7.6.2, 10.7.6.3, 10.7.6.4, 10.7.6.5, 10.7.6.6, 10.7.6.7, 10.7.6.8, 10.7.6.9, 10.7.6.10, 10.7.7.1, 10.7.7.2, 10.7.7.3, 10.7.7.4, 10.7.7.5, 10.7.7.6, 10.7.7.7, 10.7.7.8, 10.7.7.9, 10.7.7.10, 10.7.8.1, 10.7.8.2, 10.7.8.3, 10.7.8.4, 10.7.8.5, 10.7.8.6, 10.7.8.7, 10.7.8.8, 10.7.8.9, 10.7.8.10, 10.7.9.1, 10.7.9.2, 10.7.9.3, 10.7.9.4, 10.7.9.5, 10.7.9.6, 10.7.9.7, 10.7.9.8, 10.7.9.9, 10.7.9.10, 10.7.10.1, 10.7.10.2, 10.7.10.3, 10.7.10.4, 10.7.10.5, 10.7.10.6, 10.7.10.7, 10.7.10.8, 10.7.10.9, 10.7.10.10, 10.8.1.1, 10.8.1.2, 10.8.1.3, 10.8.1.4, 10.8.1.5, 10.8.1.6, 10.8.1.7, 10.8.1.8, 10.8.1.9, 10.8.1.10, 10.8.2.1, 10.8.2.2, 10.8.2.3, 10.8.2.4, 10.8.2.5, 10.8.2.6, 10.8.2.7, 10.8.2.8, 10.8.2.9, 10.8.2.10, 10.8.3.1, 10.8.3.2, 10.8.3.3, 10.8.3.4, 10.8.3.5, 10.8.3.6, 10.8.3.7, 10.8.3.8, 10.8.3.9, 10.8.3.10, 10.8.4.1, 10.8.4.2, 10.8.4.3, 10.8.4.4, 10.8.4.5, 10.8.4.6, 10.8.4.7, 10.8.4.8, 10.8.4.9, 10.8.4.10, 10.8.5.1, 10.8.5.2, 10.8.5.3, 10.8.5.4, 10.8.5.5, 10.8.5.6, 10.8.5.7, 10.8.5.8, 10.8.5.9, 10.8.5.10, 10.8.6.1, 10.8.6.2, 10.8.6.3, 10.8.6.4, 10.8.6.5, 10.8.6.6, 10.8.6.7, 10.8.6.8, 10.8.6.9, 10.8.6.10, 10.8.7.1, 10.8.7.2, 10.8.7.3, 10.8.7.4, 10.8.7.5, 10.8.7.6, 10.8.7.7, 10.8.7.8, 10.8.7.9, 10.8.7.10, 10.8.8.1, 10.8.8.2, 10.8.8.3, 10.8.8.4, 10.8.8.5, 10.8.8.6, 10.8.8.7, 10.8.8.8, 10.8.8.9, 10.8.8.10, 10.8.9.1, 10.8.9.2, 10.8.9.3, 10.8.9.4, 10.8.9.5, 10.8.9.6, 10.8.9.7, 10.8.9.8, 10.8.9.9, 10.8.9.10, 10.8.10.1, 10.8.10.2, 10.8.10.3, 10.8.10.4, 10.8.10.5, 10.8.10.6, 10.8.10.7, 10.8.10.8, 10.8.10.9, 10.8.10.10, 10.9.1.1, 10.9.1.2, 10.9.1.3, 10.9.1.4, 10.9.1.5, 10.9.1.6, 10.9.1.7, 10.9.1.8, 10.9.1.9, 10.9.1.10, 10.9.2.1, 10.9.2.2, 10.9.2.3, 10.9.2.4, 10.9.2.5, 10.9.2.6, 10.9.2.7, 10.9.2.8, 10.9.2.9, 10.9.2.10, 10.9.3.1, 10.9.3.2, 10.9.3.3, 10.9.3.4, 10.9.3.5, 10.9.3.6, 10.9.3.7, 10.9.3.8, 10.9.3.9, 10.9.3.10, 10.9.4.1, 10.9.4.2, 10.9.4.3, 10.9.4.4, 10.9.4.5, 10.9.4.6, 10.9.4.7, 10.9.4.8, 10.9.4.9, 10.9.4.10, 10.9.5.1, 10.9.5.2, 10.9.5.3, 10.9.5.4, 10.9.5.5, 10.9.5.6, 10.9.5.7, 10.9.5.8, 10.9.5.9, 10.9.5.10, 10.9.6.1, 10.9.6.2, 10.9.6.3, 10.9.6.4, 10.9.6.5, 10.9.6.6, 10.9.6.7, 10.9.6.8, 10.9.6.9, 10.9.6.10, 10.9.7.1, 10.9.7.2, 10.9.7.3, 10.9.7.4, 10.9.7.5, 10.9.7.6, 10.9.7.7, 10.9.7.8, 10.9.7.9, 10.9.7.10, 10.9.8.1, 10.9.8.2, 10.9.8.3, 10.9.8.4, 10.9.8.5, 10.9.8.6, 10.9.8.7, 10.9.8.8, 10.9.8.9, 10.9.8.10, 10.9.9.1, 10.9.9.2, 10.9.9.3, 10.9.9.4, 10.9.9.5, 10.9.9.6, 10.9.9.7, 10.9.9.8, 10.9.9.9, 10.9.9.10, 10.9.10.1, 10.9.10.2, 10.9.10.3, 10.9.10.4, 10.9.10.5, 10.9.10.6, 10.9.10.7, 10.9.10.8, 10.9.10.9, 10.9.10.10, 10.10.1.1, 10.10.1.2, 10.10.1.3, 10.10.1.4, 10.10.1.5, 10.10.1.6, 10.10.1.7, 10.10.1.8, 10.10.1.9, 10.10.1.10, 10.10.2.1, 10.10.2.2, 10.10.2.3, 10.10.2.4, 10.10.2.5, 10.10.2.6, 10.10.2.7, 10.10.2.8, 10.10.2.9, 10.10.2.10, 10.10.3.1, 10.10.3.2, 10.10.3.3, 10.10.3.4, 10.10.3.5, 10.10.3.6, 10.10.3.7, 10.10.3.8, 10.10.3.9, 10.10.3.10, 10.10.4.1, 10.10.4.2, 10.10.4.3, 10.10.4.4, 10.10.4.5, 10.10.4.6, 10.10.4.7, 10.10.4.8, 10.10.4.9, 10.10.4.10, 10.10.5.1, 10.10.5.2, 10.10.5.3, 10.10.5.4, 10.10.5.5, 10.10.5.6, 10.10.5.7, 10.10.5.8, 10.10.5.9, 10.10.5.10, 10.10.6.1, 10.10.6.2, 10.10.6.3, 10.10.6.4, 10.10.6.5, 10.10.6.6, 10.10.6.7, 10.10.6.8, 10.10.6.9, 10.10.6.10, 10.10.7.1, 10.10.7.2, 10.10.7.3, 10.10.7.4, 10.10.7.5, 10.10.7.6, 10.10.7.7, 10.10.7.8, 10.10.7.9, 10.10.7.10, 10.10.8.1, 10.10.8.2, 10.10.8.3, 10.10.8.4, 10.10.8.5, 10.10.8.6, 10.10.8.7, 10.10.8.8, 10.10.8.9, 10.10.8.10, 10.10.9.1, 10.10.9.2, 10.10.9.3, 10.10.9.4, 10.10.9.5, 10.10.9.6, 10.10.9.7, 10.10.9.8, 10.10.9.9, 10.10.9.10, 10.10.10.1, 10.10.10.2, 10.10.10.3, 10.10.10.4, 10.10.10.5, 10.10.10.6, 10.10.10.7, 10.10.10.8, 10.10.10.9, 10.10.10.10

Additional exemplary formula B compound groups include the following compound groups disclosed below. Unless otherwise specified, the configurations of all hydrogen atoms and R groups for the following compound groups are as defined for the group 1 compounds of formula B above.

Group 2. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 5-6 position is present. Thus, group 2 compound 1.3.1.1 has the structure

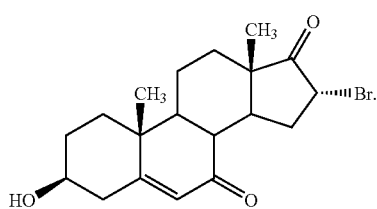

1.3.1.1

Group 3. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus as described for group 1 compounds, except that double bonds at the 1-2- and 5-6 positions are present. Thus, group 3 compound 2.2.5.1 has the structure

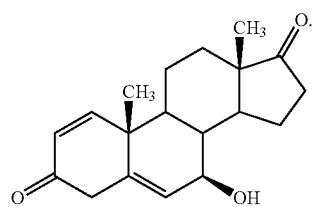

2.2.5.1

Group 4. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 1-2 position is present. Thus, group 4 compound 5.2.7.8 has the structure

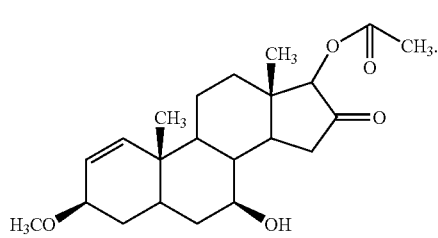

5.2.7.8

Group 5. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that a double bond at the 4-5 position is present. Thus, the group 5 compound named 3.5.2.9 has the structure

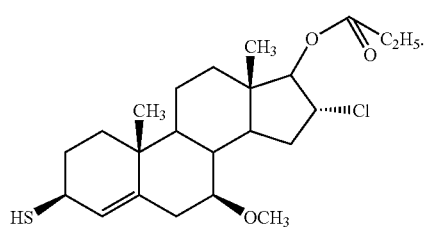

3.5.2.9

Group 6. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds at both the 1-2 and 4-5 positions are present. Thus, the group 6 compound named 10.2.7.8 has the structure

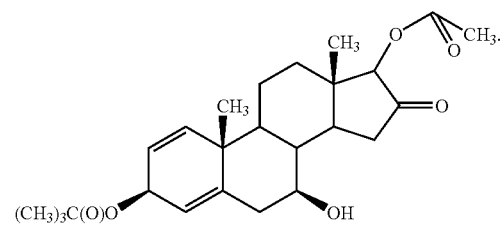

10.2.7.8

Groups 7-1 through 7-6. These groups comprise the 6 compound groups described above, except that $R^5$ is hydrogen instead of methyl. Thus, group 7-1 has the same steroid nucleus as group 1 above, i.e., no double bond is present, but $R^5$ is —H. Group 7-2 comprises the same steroid nucleus as group 2 above, i.e., a double bond is present at the 5-6-position, but $R^5$ is —H, Compound groups 7-3 through 7-6 are assigned a steroid nucleus in the same manner. Thus, the group 7-1 through group 7-6 compounds named 1.2.1.9 have the structures

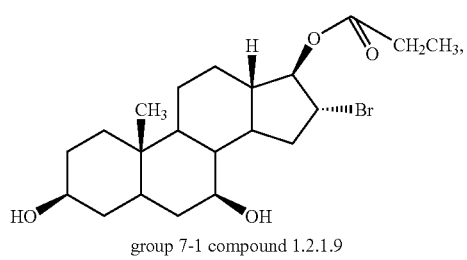

group 7-1 compound 1.2.1.9

-continued

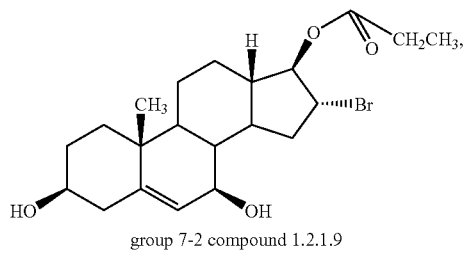
group 7-2 compound 1.2.1.9

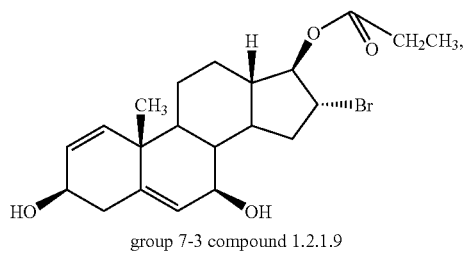
group 7-3 compound 1.2.1.9

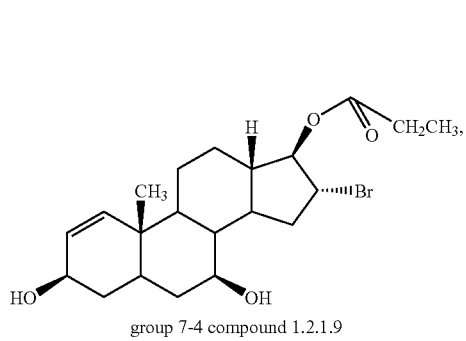
group 7-4 compound 1.2.1.9

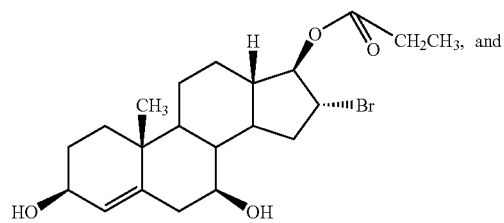
group 7-5 compound 1.2.1.9

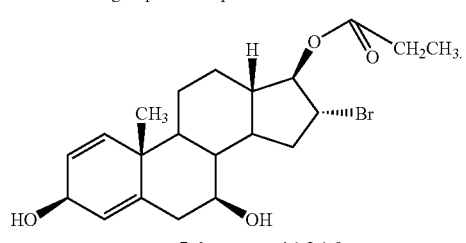
group 7-6 compound 1.2.1.9

Groups 8-1 through 8-6. These groups comprise each compound named in groups 1-6, except that $R^5$ of formula B is —$CH_2OH$ instead of methyl. The groups 8-1 through group 8-6 compounds have structures that are named in the same manner as group 1-6 compounds, except that —$CH_2OH$ instead of methyl is present at $R^5$. These groups are named in the same manner as groups 7-1 through 7-6. Thus, group 8-1 and group 8-2 compounds named 1.2.1.9 have the structures group 8-1 compound 1.2.1.9 group 8-2 compound 1.2.1.9

Groups 9-1 through 9-6. These groups comprise each compound named in compound groups 1-6, except that $R^6$ of formula B is hydrogen instead of methyl. The groups 9-1 through group 9-6 compounds have structures that are named in the same manner as group 7-1 through 7-6 compounds, except that —H instead of methyl is present at $R^6$. Thus, group 9-1 and group 9-2 compounds named 1.2.1.9 have the structures

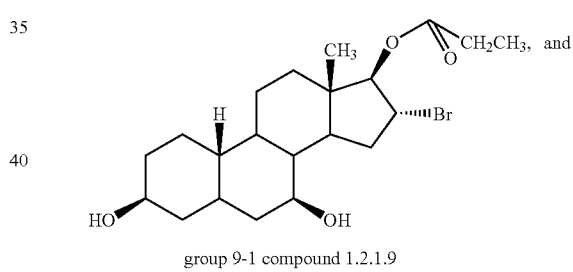
group 9-1 compound 1.2.1.9

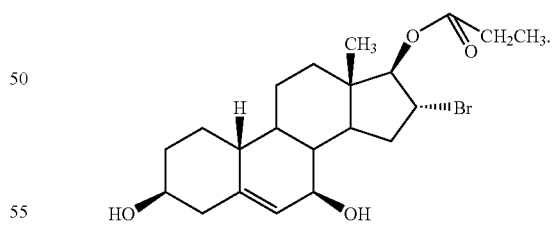
group 9-2 compound 1.2.1.9

Groups 10-1 through 10-6. These groups comprise each compound named in compound groups 1-6 where $R^6$ of formula 1 is —$CH_2OH$ instead of methyl. The groups 10-1 through group 10-6 compounds have structures that are named in the same manner as group 7-1 through 7-6 compounds, except that —$CH_2OH$ instead of methyl is present at $R^6$. Thus, group 10-6 and group 10-2 compounds named 1.2.1.9 have the structures

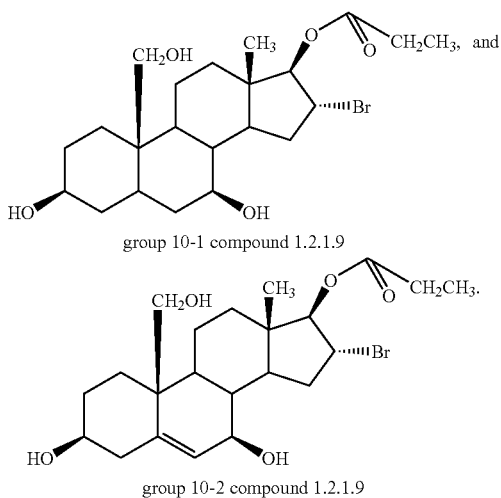

group 10-1 compound 1.2.1.9 group 10-2 compound 1.2.1.9

Groups 11-1 through 11-10-6. These groups comprise each compound named in compound groups 1 through 10-6 where $R^1$ substituents 1-10 listed in Table A are replaced with the following substituents:

1 —O—C(O)—CH$_2$CH$_2$CH$_2$CH$_3$ (—O—C(O)—CH$_2$CH$_2$CH$_2$CH$_3$ replaces —OH, which is $R^1$ substituent 1 in Table A)
2 —O—C(O)—CH$_2$CH$_2$CH$_2$CH$_2$CH$_2$CH$_3$
3 —O—C(O)—CH$_2$CH$_2$OCH$_2$CH$_3$
4 —O—C(O)—CH$_2$CH$_2$OCH$_2$CH$_2$OCH$_2$CH$_3$
5 —O—C(O)—CH$_2$CH$_2$CH$_2$CH$_2$OCH$_2$CH$_3$
6 —O—C(O)—CH$_2$CH$_2$OCH$_2$CH$_2$CH$_2$CH$_3$
7 —O—C$_6$H$_4$C$_{1-8}$
8 —O—C$_6$H$_3$F$_2$
9 —O—C$_6$H$_4$—O(CH$_2$)$_2$—O—CH$_2$CH$_3$
10 —O—C$_6$H$_4$—C(O)O(CH$_2$)$_{0-9}$CH$_3$ The group 11-1 through group 11-6 compounds have structures that are named in the same manner as group 7-1 through 7-6 compounds, except that substituents 1-10 of table A are replaced by the substituents 1-10 at $R^1$ listed above. Thus group 11-1 and 11-2 compounds named 1.2.1.9 have the structures

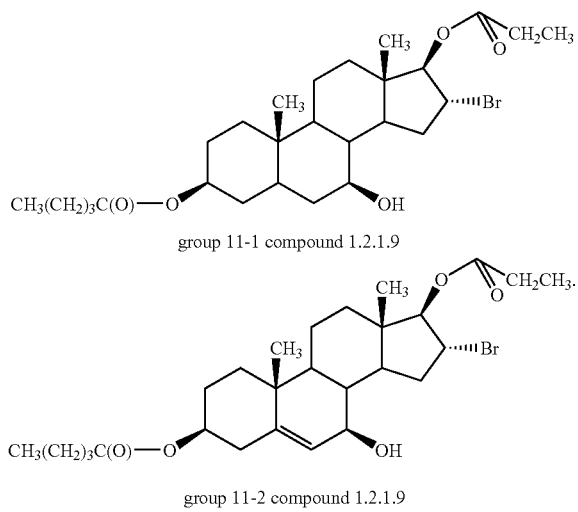

group 11-1 compound 1.2.1.9 group 11-2 compound 1.2.1.9

Group 11-7-1 and 11-7-2 compounds named 1.2.1.9 have the structures

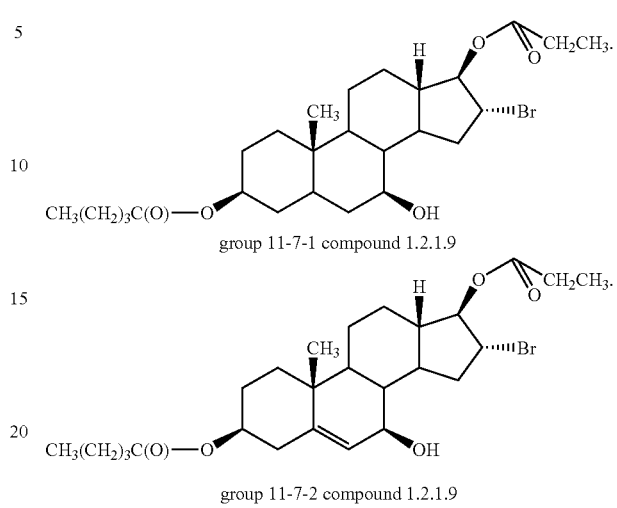

group 11-7-1 compound 1.2.1.9 group 11-7-2 compound 1.2.1.9

Group 11-8-1 and 11-8-2 compounds named 1.2.1.9 have the structures

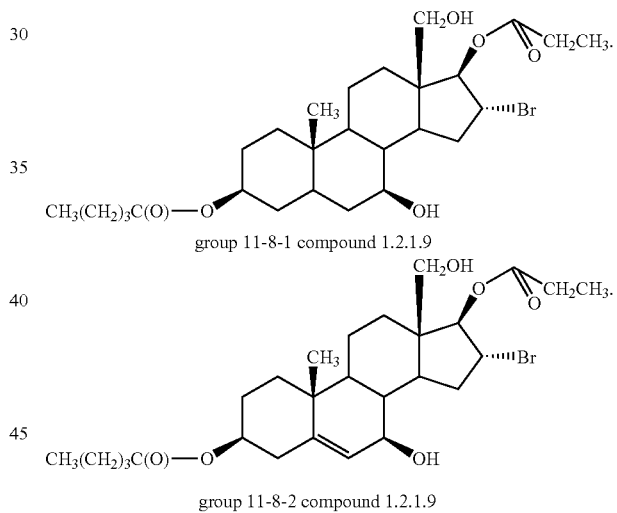

group 11-8-1 compound 1.2.1.9 group 11-8-2 compound 1.2.1.9

Groups 12-1 through 12-10-6. These groups comprise each compound named in groups 1 through 10-6 where $R^1$ substituents 1-10 listed in Table A are replaced with the following groups:

1 —O—P(O)(O)—OCH$_2$CH(CH$_3$)CH$_3$ (—O—P(O)(O)—OCH$_2$CH(CH$_3$)CH$_3$ replaces —OH, which is $R^1$ substituent 1 in Table A)
2 —O—P(O)(O)—OCH$_2$CH$_2$CH$_2$CH$_2$CH$_3$
3 —O—P(O)(O)—OCH$_2$CH$_2$CH$_2$CH$_2$CH$_2$CH$_3$
4 —O—P(O)(O)—OCH$_2$CH$_2$CH(CH$_2$CH$_2$)CH$_3$
5 —O—CH$_2$CH$_2$CH$_2$CH$_2$CH$_2$CH$_3$
6 —O—C$_2$H$_5$
7 —O—CH$_2$CH$_2$CH$_3$
8 —O—CH$_2$CH$_2$CH$_2$CH$_3$
9 —O—CH(CH$_3$)CHCH$_3$
10 —O—C(CH$_3$)$_3$ Groups 13-1 through 13-10-6. These groups comprise each compound named in groups 1 through 10-6 where $R^1$ substituents 1-10 listed in Table A are replaced with the following groups:
1 —O—(CH$_2$)$_4$—CH$_3$ (—O—(CH$_2$)$_4$—CH$_3$ replaces —OH, which is $R^1$ substituent 1 in Table A)
2 —O—C(O)—NH$_2$
3 —O—C(O)—NHCH$_3$
4 —O—C(O)—NHC$_2$H$_5$
5 —O—C(O)—NHCH$_2$CH$_2$CH$_3$
6 —O—C(O)—NHCH$_2$CH$_2$OCH$_2$CH$_3$
7 —O—C(O)—CH$_3$
8 —O—C(O)—C$_2$H$_5$
9 —O—C(O)—CH$_2$CH$_2$CH$_3$
10 —O—C(O)—CH$_2$CH$_2$CH$_2$CH$_3$ Groups 14-1 through 14-10-6. These groups comprise each compound named in groups 1 through 10-6 where $R^1$ substituents 1-10 listed in Table A are replaced with the following groups:
1 —O—CH$_2$C$_6$H$_5$
2 —O—CH$_2$C$_6$H$_5$
3 —O—CH$_2$C$_6$H$_4$OCH$_3$
4 —O—CH$_2$C$_6$H$_4$OCH$_3$
5 —O—CH$_2$C$_6$H$_4$F
6 —O—CH$_2$C$_6$H$_4$F
7 —O—CH$_2$C$_6$H$_3$(OCH$_3$)$_2$
8 —O—CH$_2$C$_6$H$_3$(OCH$_3$)$_2$
9 —O—CH$_2$C$_6$H$_4$OCH$_2$CH$_3$
10 —O—CH$_2$C$_6$H$_4$OCH$_2$CH$_3$ Groups 15-1 through 15-10-6. These groups comprise each compound named in groups 1 through 10-6 where $R^1$ substituents 1-10 listed in Table A are replaced with the following groups:
1 —O—C(O)—CH$_2$CH$_2$NH$_2$ (—O—C(O)—CH$_2$CH$_2$NH$_2$ replaces —OH, which is $R^1$ substituent 1 in Table A)
2 —O—C(O)—CH$_2$CH$_2$CH$_2$NH$_2$
3 —O—C(O)—CH$_2$OH
4 —O—C(O)—CH$_2$CH$_2$OH
5 —O—C(O)—CH$_2$CH$_2$CH$_2$OH
6 —O—C(O)—CH$_2$SH
7 —O—C(O)—CH$_2$CH$_2$SH
8 —O—C(O)—CH$_2$CH$_2$CH$_2$SH
9 —O—S(O)(O)—O—CH$_2$—CH(O—C(O)—OH)—CH$_2$—O—C(O)—C$_2$H$_5$
10 —O—P(O)(O)—O—CH$_2$—CH(O—C(O)—OH)—CH$_2$—O—C(O)—C$_2$H$_5$ Groups 16-1 through 16-10-6. These groups comprise each compound named in groups 1 through 10-6 where $R^1$ substituents 1-10 listed in Table A are replaced with the following groups:
1 —O—C(O)-A4-NH$_2$, where A4-NH$_2$ is a 4 carbon alkyl group substituted with —NH$_2$ (—O—C(O)-A4-NH$_2$ replaces —OH, which is $R^1$ substituent 1 in Table A)
2 —O—C(O)-A6-NH$_2$, where A6-NH$_2$ is a 6 carbon alkyl group substituted with —NH$_2$
3 —O—C(O)-A8-NH$_2$, where A8-NH$_2$ is a 8 carbon alkyl group substituted with —NH$_2$
4 —O—C(O)-A4-OH, where A4-OH is a 4 carbon alkyl group substituted with —OH or —O—
5 —O—C(O)-A6-OH, where A6-OH is a 6 carbon alkyl group substituted with —OH or —O—
6 —O—C(O)-A8-OH, where A8-OH is a 8 carbon alkyl group substituted with —OH or —O—
7 —O—S(O)(O)—O—CH$_2$—CH(O—C(O)—OH)—CH$_2$—O—C(O)—C$_3$H$_7$
8 —O—P(O)(O)—O—CH$_2$—CH(O—C(O)—OH)—CH$_2$—O—C(O)—C$_3$H$_7$
9 —O—S(O)(O)—O—CH$_2$—CH(O—C(O)—OH)—CH$_2$—O—C(O)—C$_4$H$_9$
10 —O—P(O)(O)—O—CH$_2$—CH(O—C(O)—OH)—CH$_2$—O—C(O)—C$_4$H$_9$ Groups 17-1 through 17-10-6. These groups comprise each compound named in compound groups 1 through 10-6 where $R^1$ substituents 1-10 listed in Table A are replaced with the following groups:
1 —O—S(O)(O)—O—CH$_2$—CH(O—C(O)—OH)—CH$_2$—O—C(O)—C$_6$H$_{13}$
2 —O—P(O)(O)—O—CH$_2$—CH(O—C(O)—OH)—CH$_2$—O—C(O)—C$_6$H$_{13}$
3 —O—S(O)(O)—O—CH$_2$—CH(O—C(O)—OH)—CH$_2$—O—C(O)—C$_8$H$_{17}$
4 —O—P(O)(O)—O—CH$_2$—CH(O—C(O)—OH)—CH$_2$—O—C(O)—C$_8$H$_{17}$
5 —O—S(O)(O)—O—CH$_2$—CH(O—C(O)—OH)—CH$_2$—O—C(O)—CH$_2$C$_5$H$_{10}$OH
6 —O—P(O)(O)—O—CH$_2$—CH(O—C(O)—OH)—CH$_2$—O—C(O)—CH$_2$C$_5$H$_{10}$OH
7 —O—S(O)(O)—O—CH$_2$—CH(O—C(O)—OH)—CH$_2$—O—C(O)—CH$_2$C$_3$H$_6$OH
8 —O—P(O)(O)—O—CH$_2$—CH(O—C(O)—OH)—CH$_2$—O—C(O)—CH$_2$C$_3$H$_6$OH
9 —O—S(O)(O)—O—CH$_2$—CH(O—C(O)—OH)—CH$_2$—O—C(O)—CH$_2$C$_7$H$_{14}$OH
10 —O—P(O)(O)—O—CH$_2$—CH(O—C(O)—OH)—CH$_2$—O—C(O)—CH$_2$C$_7$H$_{14}$OH Groups 18-1 through 18-10-6. These groups comprise each compound named in groups 1 through 10-6 where $R^4$ substituents 1-10 listed in Table A are replaced with the following groups:
1 —O—C(O)CH$_2$NH$_2$
2 —O—C(O)C(CH$_3$)H—NH$_2$
3 —O—C(O)C(CH$_2$C$_6$H$_5$)H—NH$_2$
4 —O—C(O)—O—NHC(CH$_3$)H—CO$_2$H
5 —O—C(O)—O—NHCH$_2$—CO$_2$H
6 —O—C(O)—O—NH(CH$_2$C$_6$H$_5$)H—CO$_2$H
7 —O—C(O)—CF$_3$
8 —O—C(O)—CH$_2$CF$_3$
9 —O—C(O)—(CH$_2$)$_3$CF$_3$
10 —O—C(O)—(CH$_2$)$_5$CH$_3$ Groups 19-1 through 19-10-6. These groups comprise each compound named in compound groups 1 through 10-6 where $R^4$ substituents 1-10 listed in Table A are replaced with the following groups:
1 —O—C(O)—O—CH$_3$
2 —O—C(O)—O—CH$_2$CH$_3$
3 —O—C(O)—O—C$_3$H$_7$
4 —O—C(O)—O—C$_4$H$_9$
5 —O—C(O)—O—C$_6$H$_{13}$
6 —O—C(O)—O—C$_6$H$_5$
7 —O—C(O)—O—C$_6$H$_4$OH
8 —O—C(O)—O—C$_6$H$_4$OCH$_3$
9 —O—C(O)—O—C$_6$H$_4$OCH$_2$CH$_3$
10 —O—C(O)—O—C$_6$H$_4$F Groups 20-1 through 20-10-6. These groups comprise each compound named in groups 1 through 10-6 where $R^4$ substituents 1-10 listed in Table A are replaced with the following groups:
1 —O—C(O)—S—CH$_3$
2 —O—C(O)—S—CH$_2$CH$_3$
3 —O—C(O)—S—C$_3$H$_7$
4 —O—C(O)—S—C$_4$H$_9$
5 —O—C(O)—S—C$_6$H$_{13}$
6 —O—C(O)—S—C$_6$H$_5$
7 —O—C(O)—S—C$_6$H$_4$OH 8 —O—C(O)—S—C$_6$H$_4$OCH$_3$
9 —O—C(O)—S—C$_6$H$_4$OCH$_2$CH$_3$
10 —O—C(O)—S—C$_6$H$_4$F Groups 21-1 through 21-10-6. These groups comprise each compound named in compound groups 1 through 10-6 where R$^4$ substituents 1-10 listed in Table A are replaced with the following groups:
1 —O—C(S)—O—CH$_3$
2 —O—C(S)—O—CH$_2$CH$_3$
3 —SH
4 =S
5 —O—C(S)—O—C$_6$H$_{13}$
6 —O—C(O)—O—CH$_2$C$_6$H$_5$
7 —O—C(O)—O—CH$_2$C$_6$H$_4$OH
8 —O—C(O)—O—CH$_2$C$_6$H$_4$OCH$_3$
9 —O—C(O)—O—CH$_2$C$_6$H$_4$OCH$_2$CH$_3$
10 —O—C(O)—O—CH$_2$C$_6$H$_4$F Groups 22-1 through 22-10-6. These groups comprise each compound named in compound groups 1 through 10-6 where R$^2$ substituents 1-10 listed in Table A are replaced with the following groups:
1 —O—C(S)—O—CH$_3$
2 —O—C(S)—O—CH$_2$CH$_3$
3 —O—C(S)—O—C$_3$H$_7$
4 —O—C(S)—O—C$_4$H$_9$
5 —C(S)—O—C$_6$H$_{13}$
6 —O—C(O)—O—CH$_2$C$_6$H$_5$
7 —O—C(O)—O—CH$_2$C$_6$H$_4$OH
8 —O—C(O)—O—CH$_2$C$_6$H$_4$OCH$_3$
9 —O—C(O)—O—CH$_2$C$_6$H$_4$OCH$_2$CH$_3$
10 —O—C(O)—O—CH$_2$C$_6$H$_4$F Groups 23-1 through 23-10-6. These groups comprise each compound named in compound groups 1 through 10-6 where R$^3$ substituents 1-10 listed in Table A are replaced with the following groups:
1 —O—C(S)—O—CH$_3$
2 —O—C(S)—O—CH$_2$CH$_3$
3 —O—C(S)—O—C$_3$H$_7$
4 —O—C(S)—O—C$_4$H$_9$
5 —O—C(S)—O—C$_6$H$_{13}$
6 —O—C(O)—O—CH$_2$C$_6$H$_5$
7 —O—C(O)—O—CH$_2$C$_6$H$_4$OH
8 —O—C(O)—O—CH$_2$C$_6$H$_4$OCH$_3$
9 —O—C(O)—O—CH$_2$C$_6$H$_4$OCH$_2$CH$_3$
10 —O—C(O)—O—CH$_2$C$_6$H$_4$F Groups 24-1 through 24-10-6. These groups comprise each compound named in compound groups 1 through 10-6 where R$^2$ substituents 1-10 listed in Table A are replaced with the following groups:
1 —O—C(O)—O—C$_6$H$_5$
2 —O—C(O)—O—C$_6$H$_4$OCH$_3$
3 —SH
4 =S
5 —O—CHR$^{24}$—C(O)—OR$^{25}$
6 —O—CHR$^{24}$—C(O)—R$^{25}$
7 —O—CHR$^{24}$—C(O)—N(R$^{25}$)$_2$
8 —O—CHR$^{24}$—C(O)—NHR$^{25}$
9 —O—CHR$^{24}$—C(O)—NH$_2$
10 —O—CHR$^{24}$—C(O)—OC$_6$H$_5$ Groups 25-1 through 25-10-6. These groups comprise each compound named in compound groups 1 through 10-6 where R$^3$ substituents 1-10 listed in Table A are replaced with the following groups:
1 —O—C(O)—O—C$_6$H$_5$
2 —O—C(O)—O—C$_6$H$_4$OCH$_3$
3 —SH
4 =S
5 —O—CHR$^{24}$C(O)—OR$^{25}$
6 —O—CHR$^{24}$—C(O)—R$^{25}$
7 —O—CHR$^{24}$—C(O)—N(R$^{25}$)$_2$
8 —O—CHR$^{24}$—C(O)—NHR$^{25}$
9 —O—CHR$^{24}$—C(O)—NH$_2$
10 —O—CHR$^{24}$—C(O)—OC$_6$H$_5$.

Groups 26-1 through 26-25-10-6. These groups comprise each compound named in compound groups 1 through 25-10-6 wherein R$^7$ in formula B is —O—, instead of —CH$_2$—. Thus the 26-1 and 26-2 compounds named 1.2.5.9 have the structures

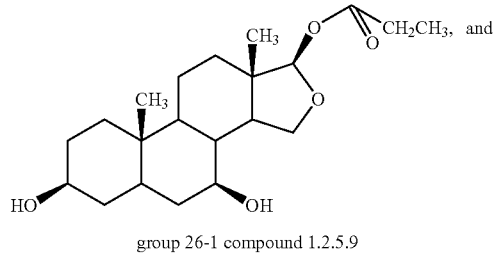

group 26-1 compound 1.2.5.9

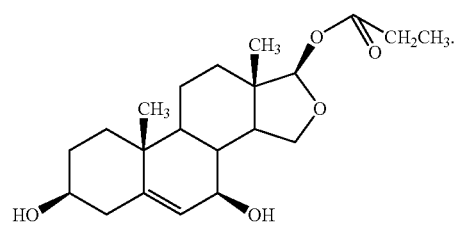

group 26-2 compound 1.2.5.9

The compound group 26-8-1 and compound group 26-8-2 compounds named 1.2.5.9 have the structures

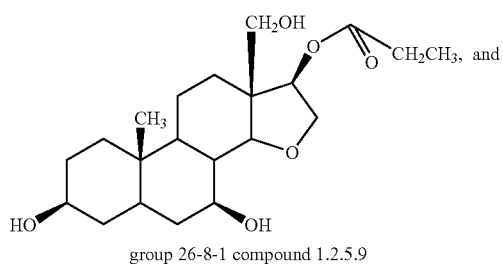

group 26-8-1 compound 1.2.5.9

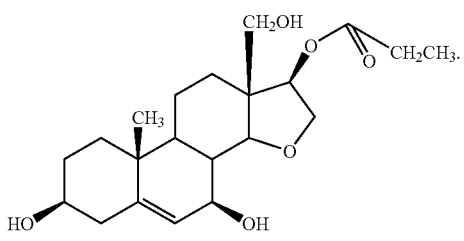

group 26-8-2 compound 1.2.5.9

The group 26-11-1 and 26-11-2 compounds named 1.2.5.9 have the structures

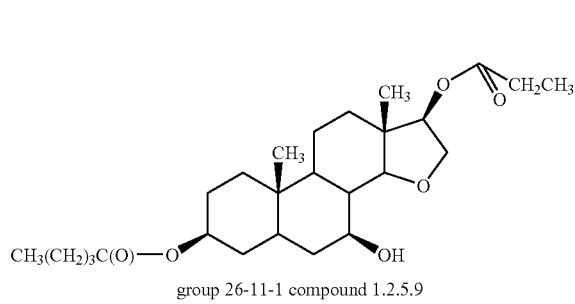

group 26-11-1 compound 1.2.5.9

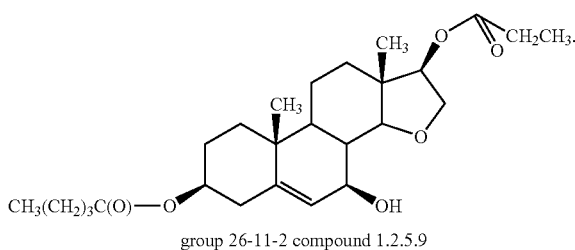

group 26-11-2 compound 1.2.5.9

Groups 27-1 through 27-25-10-6. These groups comprise each compound named in compound groups 1 through 25-10-6 wherein $R^8$ in formula B is —O—, instead of —CH$_2$—. Thus the 27-1 and 27-2 compounds named 1.2.5.9 have the structures

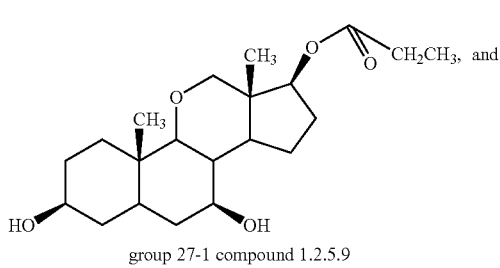

group 27-1 compound 1.2.5.9

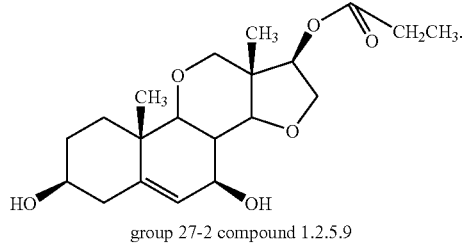

group 27-2 compound 1.2.5.9

The group 27-8-1 and group 27-8-2 compounds named 1.2.5.9 have the structures

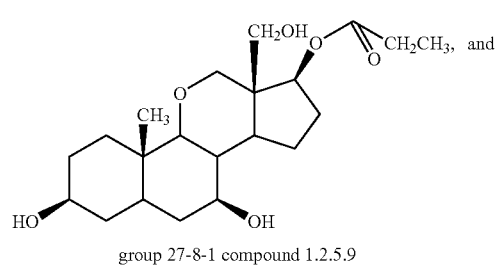

group 27-8-1 compound 1.2.5.9

-continued

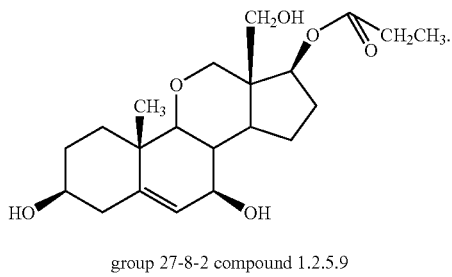

group 27-8-2 compound 1.2.5.9

The group 27-11-1 and 27-11-2 compounds named 1.2.5.9 have the structures

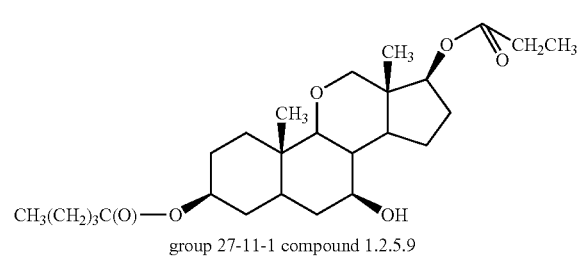

group 27-11-1 compound 1.2.5.9

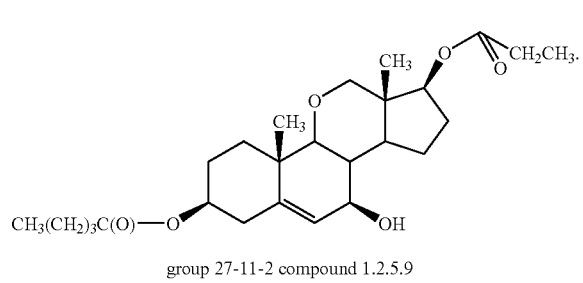

group 27-11-2 compound 1.2.5.9

Groups 28-1 through 28-25-10-6. These groups comprise each compound named in compound groups 1 through 25-10-6 wherein $R^9$ in formula B is —O—, instead of —CH$_2$— and no double bond is present at the 1-2 position. Thus, there is, e.g., no group 28-3, 28-4, 28-6, 28-8-3, 28-8-4 or 28-8-6, since a 1-2 double bond is present in these compounds and a ring oxygen at the 2 position would be charged. The 28-1, 28-2 and 28-5 compounds named 1.2.5.9 have the structures

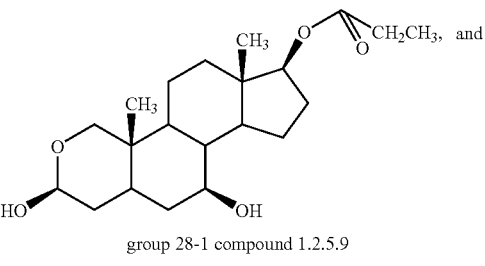

group 28-1 compound 1.2.5.9

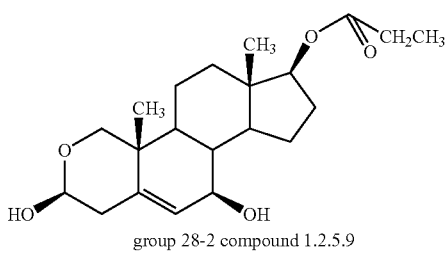

group 28-2 compound 1.2.5.9

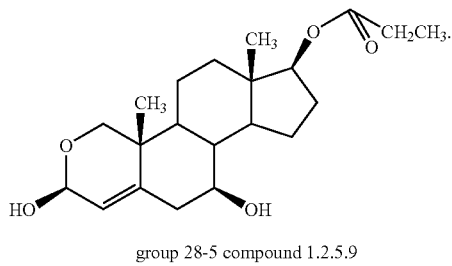

group 28-5 compound 1.2.5.9

The group 28-8-1 and group 28-8-2 compounds named 1.2.5.9 have the structures

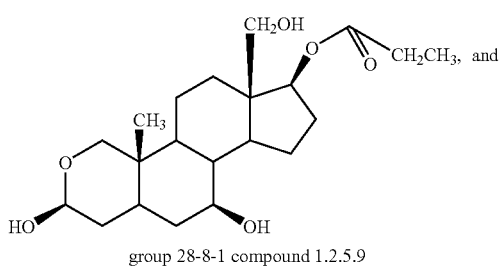

group 28-8-1 compound 1.2.5.9

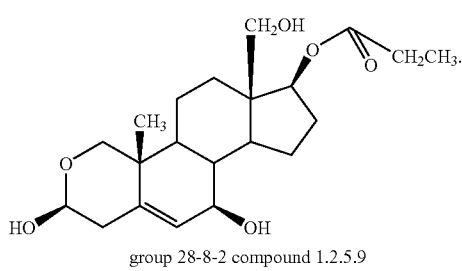

group 28-8-2 compound 1.2.5.9

The group 28-11-1 and 28-11-2 compounds named 1.2.5.9 have the structures

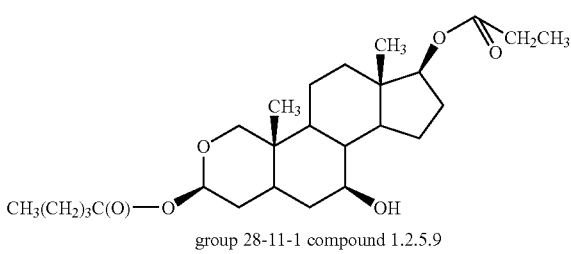

group 28-11-1 compound 1.2.5.9

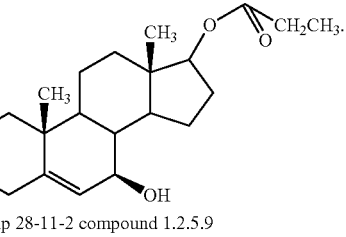

group 28-11-2 compound 1.2.5.9

Groups 29-1 through 29-25-10-6. These groups comprise each compound named in compound groups 1 through 25-10-6 wherein $R^7$ is —NH—, instead of —$CH_2$—. The compounds are named as described for compound groups 26-1 through 26-25-10-6.

Groups 30-1 through 30-25-10-6. These groups comprise each compound named in compound groups 1 through 25-10-6 wherein $R^8$ is —NH—, instead of —$CH_2$—. The compounds are named as described for compound groups 26-1 through 26-25-10-6.

Groups 31-1 through 31-25-10-6. These groups comprise each compound named in compound groups 1 through 25-10-6 wherein $R^9$ is —NH—, instead of —$CH_2$—. and no double bond is present at the 1-2 position. Thus, there is e.g., no group 31-3, 31-4, 31-6, 31-8-3, 31-8-4 or 31-8-6. The compounds are named as described for compound groups 26-1 through 26-25-10-6.

Groups 32-1 through 32-25-10-6. These groups comprise each compound named in compound groups 1 through 25-10-6 wherein two of $R^7$, $R^8$ and $R^9$ independently are —NH—, —O— or —S— instead of —$CH_2$—. The compounds are named as described for compound groups 26-1 through 26-25-10-6.

Groups 33-1 through 33-25-10-6. These groups comprise each compound named in compound groups 1 through 25-10-6 wherein each of $R^7 R^8$ and $R^9$ independently are —NH—, —O— or —S— instead of —$CH_2$—. The compounds are named as described for compound groups 26-1 through 26-25-10-6.

Groups 34-1 through 34-25-10-6. These groups comprise each compound named in compound groups 1 through 25-10-6 wherein $R^7$ is —S—, instead of —$CH_2$—. The compounds are named as described for compound groups 26-1 through 26-25-10-6.

Groups 35-1 through 35-25-10-6. These groups comprise each compound named in compound groups 1 through 25-10-6 wherein $R^3$ is —S—, instead of —$CH_2$—. The compounds are named as described for compound groups 26-1 through 26-25-10-6.

Groups 36-1 through 36-25-10-6. These groups comprise each compound named in compound groups 1 through 25-10-6 wherein $R^9$ is —S—, instead of —$CH_2$— and no double bond is present at the 1-2 position. There is, e.g., no group 36-3, 36-4, 36-6, 36-8-3, 36-8-4 or 36-8-6. The compounds are named as described for compound groups 26-1 through 26-25-10-6.

Groups 37-1 through 37-25-10-6. These groups comprise each compound named in all of the compound groups 1 through 36-25-10-6 described above wherein $R^1$ is not divalent, e.g., is not =O, and it is in the α-configuration, instead of the β-configuration as shown in formula B.

Groups 38-1 through 38-25-10-6. These groups comprise each compound named in all of the compound groups 1 through 36-25-10-6 described above wherein $R^2$ is not divalent, e.g., is not =O, and it is in the α-configuration, instead of the β-configuration as shown in formula B.

Groups 39-1 through 39-25-10-6. These groups comprise each compound named in all of the compound groups 1 through 36-25-10-6 described above wherein $R^3$ is not divalent, e.g., is not =O, and it is in the β-configuration, instead of the α-configuration as shown in formula B.

Groups 40-1 through 40-25-10-6. These groups comprise each compound named in all of the compound groups 1 through 36-25-10-6 described above wherein $R^4$ is not divalent, e.g., is not =O, and it is in the α-configuration, instead of the β-configuration as shown in formula B.

Groups 41-1 through 41-25-10-6. These groups comprise each compound named in all of the compound groups 1 through 36-25-10-6 described above wherein $R^2$ and $R^4$ is not divalent, e.g., they is not =O, and they are both in the α-configuration, instead of the β-configuration as shown in formula B.

Groups 42-1 through 42-25-10-6. These groups comprise each compound named in all of the compound groups 1 through 36-25-10-6 described above wherein, when hydrogen is present at the 5-position, it is in the β-configuration, instead of the α-configuration as shown in formula B.

Any of the compounds or general of compounds that are named in compound groups 1 through 42-25-10-6 are suitable for use in the methods described herein.

In some embodiments, one, or more of $R^1$-$R^6$, $R^{10}$, $R^{15}$, $R^{17}$ and $R^{18}$ independently have the structure(s) and/or independently comprise the named compounds, —H, —OH, =O, —SH, =S, —NH$_2$, —CN, —N$_3$, halogen, =CH$_2$, =NOH, =NOC(O)CH$_3$, —C(O)—CH$_3$, —C(O)—(CH$_2$)$_{1-4}$—CH$_3$, —CCH, —CCCH$_3$, —CH=CH$_2$, —CH=CH$_2$CH$_3$, —O—C(O)—(CH$_2$)$_m$—(CF$_2$)$_n$—CH$_3$, —O—C(O)—(CH$_2$)$_m$—(CF$_2$)$_n$—CF$_3$, —O—C(O)—(CH$_2$)$_m$—(CF$_2$)$_n$—CH$_2$F, —O—C(O)—O—(CH$_2$)$_m$—(CF$_2$)$_n$—CH$_3$, —O—C(O)—O—(CH$_2$)$_m$—(CF$_2$)$_n$—CF$_3$, —O—C(O)—O—(CH$_2$)$_m$—(CF$_2$)$_n$—CH$_2$F, —O—C(O)—NH—(CH$_2$)$_m$—(CF$_2$)$_n$—CH$_3$, —O—C(O)—NH—(CH$_2$)$_m$—(CF$_2$)$_n$—CF$_3$, —O—C(O)—NH—(CH$_2$)$_m$—(CF$_2$)$_n$—CH$_2$F (where m is 1, 2, 3, 4, 5, 6, 7, 8, 9 or 10, n is 0, 1, 2, 3, 4, 5, 6, 7, 8, 9 or 10, usually n is 0), —CH(CH$_3$)—(CH$_2$)$_2$—C(O)NH—CH$_2$COOH, —CH(CH$_3$)—(CH$_2$)$_2$—C(O)NH—CH$_2$SO$_3$H, —OSi(CH$_3$)$_2$C(CH$_3$)$_3$, —C(OH)=CHCH$_3$, =CH(CH$_2$)$_{0-15}$CH$_3$, —(CH$_2$)$_{0-14}$CH$_2$F, —(CH$_2$)$_{0-14}$CH$_2$Cl, —(CH$_2$)$_{0-14}$CH$_2$Br, —(CH$_2$)$_{0-14}$CH$_2$I, —(CH$_2$)$_{2-10}$—O—(CH$_2$)$_{0-4}$CH$_3$, —(CH$_2$)$_{2-10}$—S—(CH$_2$)$_{0-4}$CH$_3$, —(CH$_2$)$_{2-10}$—NH—(CH$_2$)$_{0-4}$CH$_3$, —O—(CH$_2$)$_{0-14}$—CH$_2$F, —O—(CH$_2$)$_{0-14}$CH$_2$Cl, —O—(CH$_2$)$_{0-14}$CH$_2$Br, —O—(CH$_2$)$_{0-14}$CH$_2$I, —O—(CH$_2$)$_{2-10}$—O—(CH$_2$)$_{0-4}$CH$_3$, —O—(CH$_2$)$_{2-10}$—S—(CH$_2$)$_{0-4}$CH$_3$, —O—(CH$_2$)$_{2-10}$—NH—(CH$_2$)$_{0-4}$CH$_3$, —O—C(O)—(CH$_2$)$_{0-14}$—CH$_2$F, —O—C(O)—(CH$_2$)$_{0-14}$—CH$_2$Cl, —O—C(O)—(CH$_2$)$_{0-14}$—CH$_2$Br, —O—C(O)—(CH$_2$)$_{0-14}$—CH$_2$I, —O—C(O)—(CH$_2$)$_{2-10}$—O—(CH$_2$)$_{0-4}$CH$_3$, —O—C(O)—(CH$_2$)$_{2-10}$—S—(CH$_2$)$_{0-4}$CH$_3$, —O—C(O)—(CH$_2$)$_{2-10}$—NH—(CH$_2$)$_{0-4}$CH$_3$, —O—C(S)—(CH$_2$)$_{0-14}$CH$_2$F, —O—C(S)—(CH$_2$)$_{0-14}$CH$_2$Cl, —O—C(S)—(CH$_2$)$_{0-14}$CH$_2$Br, —O—C(S)—(CH$_2$)$_{0-14}$CH$_2$I, —O—C(S)—(CH$_2$)$_{2-10}$—O—(CH$_2$)$_{0-4}$CH$_3$, —O—C(S)—(CH$_2$)$_{2-10}$—S—(CH$_2$)$_{0-4}$CH$_3$, —O—C(S)—(CH$_2$)$_{2-10}$—NH—(CH$_2$)$_{0-4}$CH$_3$, —(CH$_2$)$_{0-16}$NH$_2$, —(CH$_2$)$_{0-15}$CH$_3$, —(CH$_2$)$_{0-15}$CN, —(CH$_2$)$_{0-15}$CH=CH$_2$, —(CH$_2$)$_{0-15}$NHCH(O), —(CH$_2$)$_{0-16}$NH—(CH$_2$)$_{0-15}$CH$_3$, —(CH$_2$)$_{0-15}$CCH, —(CH$_2$)$_{0-15}$OC(O)CH$_3$, —(CH$_2$)$_{0-15}$OCH(OH)CH$_3$, —(CH$_2$)$_{0-15}$C(O)OCH$_3$, —(CH$_2$)$_{0-15}$C(O)OCH$_2$CH$_3$, —(CH$_2$)$_{0-15}$C(O)(CH$_2$)$_{0-15}$CH$_3$, —(CH$_2$)$_{0-15}$C(O)(CH$_2$)$_{0-15}$CH$_2$OH, —O(CH$_2$)$_{1-16}$NH$_2$, —O(CH$_2$)$_{1-15}$CH$_3$, —O(CH$_2$)$_{1-15}$CN, —O(CH$_2$)$_{1-15}$CH=CH$_2$, —O(CH$_2$)$_{1-15}$NHCH(O), —O(CH$_2$)$_{1-16}$NH—(CH$_2$)$_{1-15}$CH$_3$, —O(CH$_2$)$_{1-15}$CCH, —O(CH$_2$)$_{1-15}$OC(O)CH$_3$, —O(CH$_2$)$_{1-15}$OCH(OH)CH$_3$, —O(CH$_2$)$_{1-15}$C(O)OCH$_3$, —O(CH$_2$)$_{1-15}$C(O)OCH$_2$CH$_3$, —O(CH$_2$)$_{1-15}$C(O)(CH$_2$)$_{0-15}$CH$_3$, —O(CH$_2$)$_{1-15}$C(O)(CH$_2$)$_{0-15}$CH$_2$OH, —OC(O)(CH$_2$)$_{1-16}$NH$_2$, —OC(O)(CH$_2$)$_{1-15}$CH$_3$, —C(O)O(CH$_2$)$_{1-15}$CN, —C(O)O(CH$_2$)$_{1-15}$CH=CH$_2$, —OC(O)(CH$_2$)$_{1-15}$NHCH(O), —OC(O)(CH$_2$)$_{1-16}$NH—(CH$_2$)$_{1-15}$CH$_3$, —OC(O)(CH$_2$)$_{1-15}$CCH, —OC(O)(CH$_2$)$_{1-15}$OC(O)CH$_3$, —OC(O)(CH$_2$)$_{1-15}$OCH(OH)CH$_3$, —OC(O)(CH$_2$)$_{1-15}$C(O)OCH$_3$, —OC(O)(CH$_2$)$_{1-15}$C(O)OCH$_2$CH$_3$, —OC(O)(CH$_2$)$_{1-15}$C(O)(CH$_2$)$_{0-15}$CH$_3$, —OC(O)(CH$_2$)$_{1-15}$C(O)(CH$_2$)$_{0-15}$CH$_2$OH, phosphoenolpyruvate, D-glucosamine, glucholic acid, glucuronic acid, pantothenic acid, pyruvic acid, glucose, fructose, mannose, sucrose, lactose, fucose, rhamnose, galactose, ribose, 2'-deoxyribose, 3'-deoxyribose, glycerol, 3-phosphoglycerate, a PEG (PEG 20, PEG 100, PEG 200, PEG 10000), a polyoxyalkylene polymer, glycine, alanine, phenylalanine, threonine, proline, 4-hydroxyproline or an oligonucleotide or analog that comprises about 4 to about 21 monomers.

When a substituent is an oligonucleotide or a polymer usually only a one of these is bonded to the formula 1 compound. Typically, when $R^1$-$R^2$ and $R^4$-$R^6$ comprise one or more of these substituents (or others described herein), the substituent is present in the β-configuration, while $R^3$ typically comprises a substituent in the β-configuration. In some embodiments, $R^2$ is in the α-configuration.

In some embodiments, one or more of $R^1$-$R^6$, $R^{10}$, $R^{15}$, $R^{17}$ and $R^{18}$ independently comprise a nucleoside, a nucleotide, an oligonucleotide or an analog of any of these moieties. Typically such moieties are linked to the steroid nucleus through a terminal hydroxyl, thiol, acyl moiety or amine at the 5', 3' or 2' positions, when a hydroxyl, thiol, acyl moiety or amine is present at that position. For oligonucleotides and oligonucleotide analogs, the linkage to the steroid occasionally is through a sugar hydroxyl at an internal 2' position.

Analogs of phosphodiester linkages include phosphorothioate linkages and others as described in the cited references. Oligonucleotide coupling groups means any moiety suitable for generating a phosphodiester linkage or phosphodiester analog linkage between adjacent nucleotides or their analogs. Suitable oligonucleotide coupling groups include —OH, H-phosphonate, alkylphosphonamidites or phosphoramidites such as β-cyanoethyl-phosphoramidite, N,N-diisopropylamino-β-cyanoethoxyphosphine and others as described in the cited references. Suitable purine and pyrimidine bases include adenine, guanine, cytosine, thymine, uracil and others as described in the cited references. Suitable nucleosides, nucleotides, oligonucleotides and their analogs have been described, see e.g., U.S. Pat. Nos. 4,725,677, 4,973,679, 4,997,927, 4,415,732, 4,458,066, 5,047,524, 4,959,463, 5,212,295, 5,386,023, 5,489,677, 5,594,121, 5,614,622, 5,624,621; and PCT publication Nos. WO 92/07864, WO 96/29337, WO 97/14706, WO 97/14709, WO 97/31009, WO 98/04585 and WO 98/04575 all of which are incorporated herein by reference. The formula 1 compounds, e.g., those named in any of the compound groups 1 through 42-25-10-6, are suitable for linkage to oligonucleotides modulate the lipophilicity of oligonucleotides or the transport or permeation of an oligonucleotide into cells. Such linkages may be biologically labile to facilitate release of the steroid from the oligonucleotide once the conjugate has entered the cell.

Table 2 shows these and other exemplary moieties that one or more of $R^1$-$R^6$, $R^{10}$, $R^{15}$, $R^{17}$ and $R^{18}$ independently can comprise. Pr means a protecting group. These moieties are often bonded to one or more of the $R^1$, $R^2$ and $R^4$ positions, usually to one or two of those positions. For structures with more than one of a given variable, e.g., X in structure A3 or A5, each is independently selected.
TABLE 2
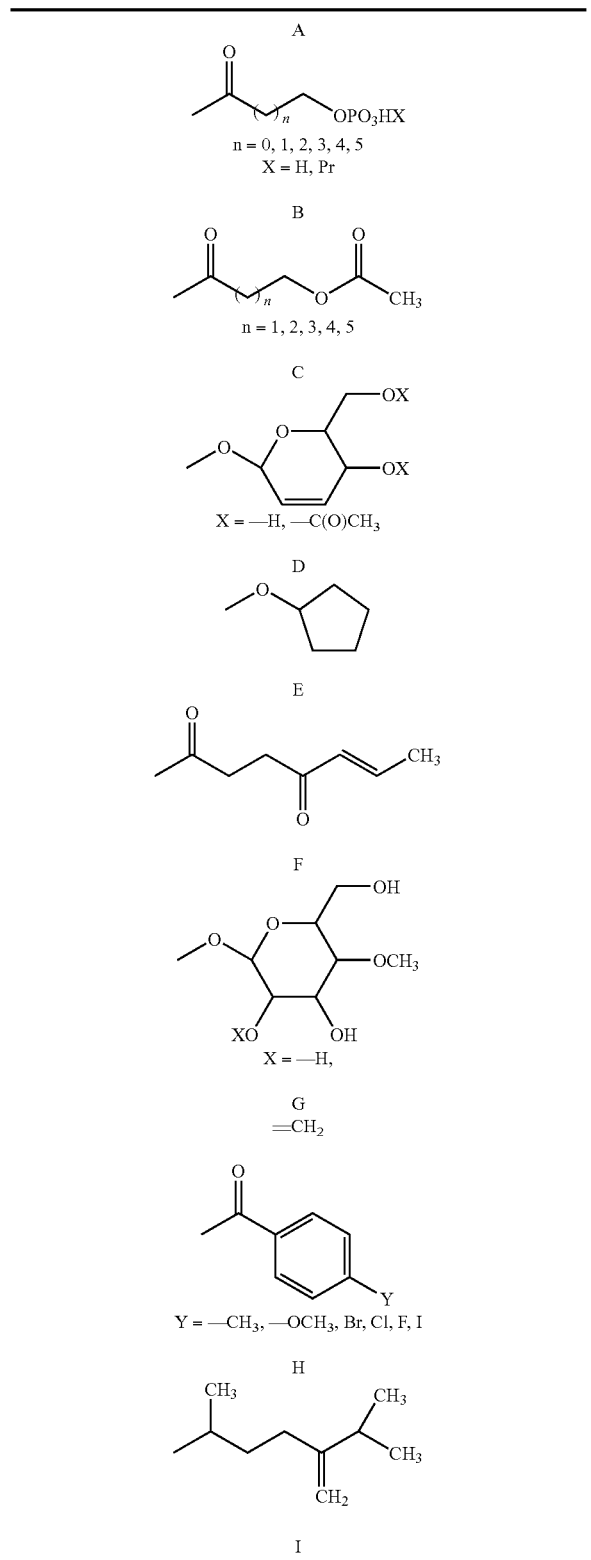
TABLE 2-continued
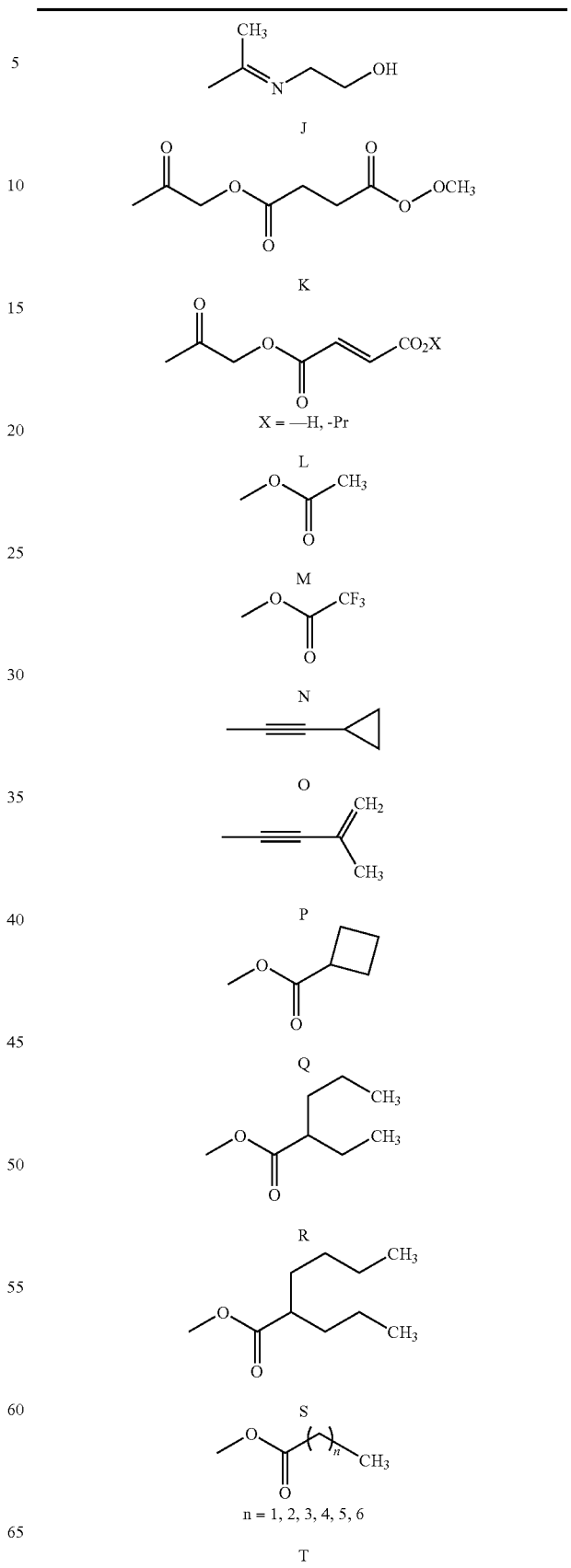

TABLE 2-continued

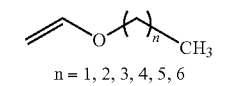
n = 1, 2, 3, 4, 5, 6

U
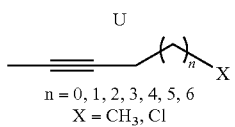
n = 0, 1, 2, 3, 4, 5, 6
X = CH$_3$, Cl

V
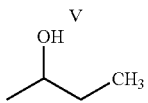

W
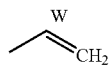

X
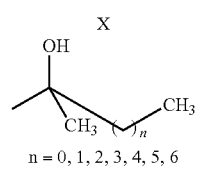
n = 0, 1, 2, 3, 4, 5, 6

Y
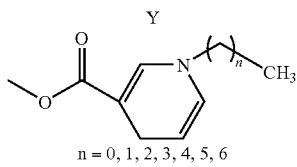
n = 0, 1, 2, 3, 4, 5, 6

Z
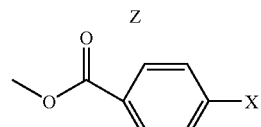
X = F, Cl, Br, NO$_2$, OCH$_3$, OC$_2$H$_5$, CN

A1
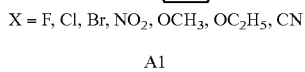
X = H, F, Cl, Br, NO$_2$, OCH$_3$, OC$_2$H$_5$, CN

A2
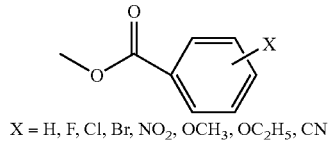
n = 1, 2, 3, 4, 5, 6

A3
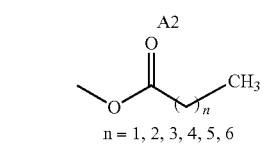
X = H, F, Cl, Br, NO$_2$, OCH$_3$, OC$_2$H$_5$, CN

A4
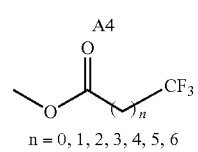
n = 0, 1, 2, 3, 4, 5, 6

A5

TABLE 2-continued

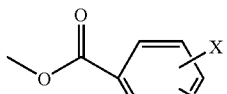
X = H, F, Cl, Br, NO$_2$, OCH$_3$, OC$_2$H$_5$, CN

A6
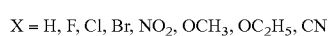
X = H, Pr

Typical containers for storage of the invention compositions and formulations will limit the amount of water that reaches the materials contained therein. Typically, formulations are packaged in hermetically or induction sealed containers. The containers are usually induction sealed. Water permeation characteristics of containers have been described, e.g., Containers—Permeation, chapter, USP 23 <671>, United States Pharmacopeial Convention, Inc., 12601 Twinbrook Parkway, Rockville, Md. 20852, pp. 1787 et seq. (1995).

The use of formula A compounds for treatment of certain diseases, e.g., infections such as malaria, HCV or *Cryptosporidium*, has been described. Formula A compounds have the structure

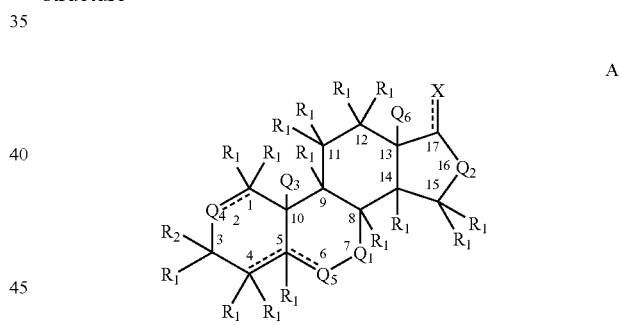

A where $Q_1$ is —C(R$_1$)$_2$— or —C(O)—; $Q_2$ is —C(R$_1$)$_2$—, —C(R$_1$)(Y)—, —C(Y)— or —CH$_2$—CH$_2$—; $Q_3$ is —H or —C(R$_1$)$_3$—; $Q_4$ is —C(R$_1$)$_2$—, —C(O)—, hydroxyvinylidine (—CH(CH=CHOH)—) or methyl methylene (—CH(CH)$_3$—); $Q_5$ is —C(R$_1$)$_2$— or —C(O)—; X and Y independently are —OH, —H, lower alkyl (e.g., C$_{1-6}$ alkyl), —O—C(O)—R$_5$, —C(O)—OR$_5$, halogen (i.e., —F, —Cl, —Br or —I) or =O; each R$_1$ independently is —H, —F, —Cl, —Br, —I, —OH, C$_{1-6}$ alkoxy, or C$_{1-6}$ alkyl; R$_2$ is —H, —OH, —F, —Cl, —Br, —I, C$_{1-6}$ alkyl, C$_{1-6}$ alkoxy, —OR$_3$, an ester (e.g., —O—C(O)—R$_4$ or —C(O)—O—R$_4$), a thioester (e.g., —O—C(S)—R$_4$ or —C(S)—O—R$_4$), a thioacetal (e.g., —S—C(O)—R$_4$, or —C(O)—S—R$_4$), a sulfate ester (e.g., —O—S(O)(O)—O—R$_4$), a sulfonate ester (e.g., —O—S(O)—O—R$_4$) or a carbamate (e.g., —O—C(O)—NH—R$_4$ or —NH—C(O)—O—R$_4$) or R$_2$, together with the R$_1$ that is bonded to the same carbon atom is =O; R$_3$ is —S(O)(O)—OM, —S(O)(O)—O—CH$_2$—CH(O—C(O)—R$_6$)—CH$_2$—

O—C(O)—R$_6$, —P(O)(O)—O—CH$_2$—CH(O—C(O)—R$_7$)—CH$_2$—O—C(O)—R$_7$, a glucuronide group of structure (B)

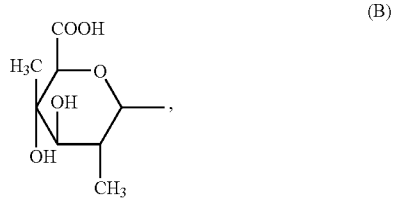

(B)

or R$_3$ is C$_{1-18}$ alkyl, C$_{2-18}$ alkenyl, C$_{2-18}$ alkynyl, a C$_{1-18}$ ester or a C$_{1-18}$ thioester, where any of the foregoing C$_{1-18}$ or C$_{2-18}$ moieties are optionally substituted at one or more hydrogen atoms with one or more independently selected —OR$^{PR}$, (including —OH), —NHR$^{PR}$, (including —NH$_2$) or —SR$^{PR}$, (including —SH) groups, or R$_3$ is a C$_{1-18}$ fatty acid, C$_{2-10}$ alkynyl, (J)$_n$-phenyl-C$_{1-5}$-alkyl, (J)$_n$-phenyl-C$_{2-5}$-alkenyl; R$_4$ is —H, a protecting group, optionally substituted C$_{1-18}$ alkyl, optionally substituted C$_{1-18}$ alkenyl, optionally substituted C$_{1-18}$ alkynyl, optionally substituted aryl, optionally substituted aryl-C$_{1-6}$ alkyl, optionally substituted aryl-C$_{2-6}$ alkenyl, optionally substituted aryl-C$_{2-6}$ alkynyl, optionally substituted heterocycle-C$_{1-6}$ alkyl, optionally substituted C$_{2-6}$ alkenyl-heterocycle, optionally substituted C$_{2-6}$ alkynyl-heterocycle or an optionally substituted heterocycle, where any of the foregoing moieties are optionally substituted at one, two, three, four, five or more carbon or hydrogen atoms with one or more independently selected —O—, —S—, —NR$^{PR}$— (including —NH—), —NH—C(O)—, —OR$^{PR}$ (including —OH), —NHR$^{PR}$ (including —NH$_2$), —SR$^{PR}$ (including —SH), =O, =S, =N—OH, —CN, —NO$_2$, —F, —Cl, —Br or —I groups or atoms; each R$_5$ independently is straight or branched C$_{1-14}$ alkyl; each R$_6$ independently is straight or branched C$_{1-14}$ alkyl; each R$_7$ independently is straight or branched C$_{1-14}$ alkyl or a glucuronide group of structure (B); each R$^{PR}$ independently is —H or an independently selected protecting group; n is 0, 1, 2 or 3; each J independently is —F, —Cl, —Br, —I, C$_{1-4}$ alkyl, C$_{1-4}$ alkenyl, C$_{1-4}$ alkoxy, carboxy, nitro, sulfate, sulfonyl, a C$_{1-6}$ carboxyl ester or a C$_{1-6}$ sulfate ester; M is hydrogen, sodium, —S(O)(O)—O—CH$_2$—CH(O—C(O)—R$_6$)—CH$_2$—O—C(O)—R$_6$, —P(O)(O)—O—CH$_2$—CH(O—C(O)—R$_7$)—CH$_2$—O—C(O)—R$_7$ or a glucuronide group of structure (A); the dotted lines in formula 1 represent an optional double bond, provided that there are not double bonds at both the 4-5 and 5-6 positions and provided that when a double bond is present, zero or 1 R$_1$ group is bonded to carbon atoms at the 1-, 2-, 4-, 5-, 6- or 17 positions so that these carbon atoms are tetravalent; and the salts, stereoisomers, positional isomers, metabolites, analogs or precursors.

The formula A compounds, particularly where both R$_1$ at the 11-position are not hydroxyl, alkoxy or a moiety that can hydrolyze to a hydroxyl, are generally suitable for use in the methods and compositions that are disclosed herein, e.g., their use to enhance a subject's Th1 immune responses. Methods of administration and dosages are essentially as described herein.

Intermittent dosing methods. One can intermittently administer the formula 1 compound(s), e.g., BrEA or a BrEA ester, to a subject without some of the undesired aspects normally associated with discontinuous dosing. Such undesired aspects include development of resistance of a pathogen (virus such as HIV or a parasite such as a Plasmodium parasite) to the therapeutic agent or failure of the patient or subject to adhere to a dosing regimen. Intermittent dosing protocols include administration of a formula 1 compound, e.g., orally, topically or parenterally as follows: (1) dosing for about 3 to about 20 days, (2) no dosing of the formula 1 compound for about 4 to about 20 days, (3) dosing for about 4 to about 20 days and (4) optionally repeating the dosing protocol 1, 2, 3, 4, 5, 6, 10, 15, 20, 30 or more times. Often, the dosing of steps (1) and (3) will be maintained for about 3-15 days, usually about 3-5 days. In general, steps (1)-(3) of the dosing protocol recited above, will be repeated at least one time, typically at least 2, 3, 4, 5 or 6 times. For infections that tend to remain chronic, e.g., HIV, HCV or other chronic virus or parasite infection, the intermittent dosing protocol is typically maintained over a relatively long time period, e.g., for at least about 6 months to about 5 years.

In these intermittent dosing protocols, the formula 1 compound(s) can be administered by any suitable route, e.g., intramuscular (i.m. or I.M.), subcutaneous (s.c. or S.C.), intravenous (i.v. or I.V.), intradermal, other parenteral route, aerosol using about 0.1 to about 10 mg/kg/day, usually about 0.2-4 mg/kg/day. Alternatively, one can administer the formula 1 compound(s) orally using about 4 to about 40 mg/kg/day, usually about 6-20 mg/kg/day. In some embodiments, the intermittent dosing methods exclude dosing protocols that are commonly used to deliver contraceptive steroids to, e.g., human females, such as daily dosing for 21 days, followed by no dosing for 7 days. In general, the non-aqueous formulations described herein that contain formula 1 compound(s) are administered i.m. or s.c., while aqueous formulations that contain formula 1 compound(s) is administered by i.v., i.m., s.c. or other parenteral routes. The daily doses can be administered as a single dose, especially for doses given parenterally, or the dose can be subdivided into two, three or four subdoses, usually two, especially for doses given orally.

Exemplary embodiments are (a) administering a formula 1 compound(s), e.g., BrEA or an ester or carbonate of BrEA, once every other day for 20 days, followed by (b) no dosing for 1, 2, 3, 4, 5, 6, 10, 15, 20, 25, 30, 35, 40, 45, 50, 55, 60 or more days and then (c) administering the formula 1 compound(s) at least once more on one day, e.g., administering the formula 1 compound(s) once every other day for 20 days and (d) optionally repeating (a), (b) and (c) 1, 2, 3, 4, 5 or 6 times or more. A subset of these embodiments are (a) administering a formula 1 compound(s), e.g., BrEA or an ester or carbonate of BrEA, once every other day for 20 days, followed by (b) no dosing for about 10-40 days and then (c) administering the formula 1 compound(s) at least once more on one day, e.g., administering the formula 1 compound(s) once every other day for 20 days and (d) optionally repeating (a), (b) and (c) 1, 2, 3, 4, 5 or 6 times or more. In any of these embodiments, one can administer the formula 1 compound(s) in 2 or 3 subdoses per day.

Other embodiments are (a) administering a formula 1 compound(s), e.g., BrEA or an ester or carbonate of BrEA, once every day for about 8-12 days, followed by (b) no dosing for 1, 2, 3, 4, 5, 6, 10, 15, 20, 25, 30, 35, 40, 45, 50, 55, 60 or more days and then (c) administering the formula 1 compound(s) at least once more on one day, e.g., administering the formula 1 compound(s) once per day for about 8-12 days and (d) optionally repeating (a), (b) and (c) 1, 2, 3, 4, 5 or 6 times or more. A subset of these embodiments are (a) administering a formula 1 compound(s), e.g., BrEA or an ester or carbonate of BrEA, once every day for about 10 days, followed by (b) no dosing for about 10-40 days and then (c) administering the formula 1 compound(s) at least once more on one day, e.g., administering the formula 1 compound(s) once per day for about 10 days and (d) optionally repeating (a), (b) and (c) 1, 2, 3, 4, 5 or 6 times or more. In any of these embodiments, one can administer the formula 1 compound(s) in 2 or 3 subdoses per day.

One aspect of invention intermittent dosing is monitoring the subject's response to dosing. For example, while dosing a subject who has a viral infection (e.g., HCV, HIV, SIV, SHIV), one can measure the subject's or pathogen's response, e.g., amelioration of one or more symptoms or a change in infectious particles or viral RNA in the serum. Once a response is observed dosing can be continued for one, two or three additional days, followed by discontinuing the dosing for at least one day (at least 24 hours), usually for at least 2 or 3 days. Once the subject's response shows signs of remission (e.g., viral serum RNA begins to increase), dosing can be resumed for another course. An aspect of the subject's response to formula 1 compound(s) is that the subject may show a measurable response within a short time, usually about 5-10 days, which allows straightforward tracking of the subject's response, e.g., by monitoring viral titer in peripheral white blood cells ("PBMC") or by measuring viral nucleic acid levels in the blood. One may monitor one or more immune cell subsets, e.g., NK, LAK, dendritic cells or cells that mediate ADCC immune responses, during and after intermittent dosing to monitor the subject's response and to determine when further administration of the formula 1 compound is indicated. These cell subsets are monitored as described herein, e.g., by flow cytometry.

For any of the treatments or methods described herein, prolonged beneficial effects or a sustained immune response by a subject may result from a single administration or a few daily administrations of the formula 1 compound for from intermittent treatment with the formula 1 compound. A single administration means that a formula 1 compound is administered to the subject in one, two, three or more doses within a 24 hour period and no further administration of any formula 1 compound to the subject occurs for at least about 45 days to about 2 months, e.g., for 3, 4, 5, 6 or more months. Prolonged beneficial effects or immune responses may also persist after a short course of treatment has been completed (e.g., daily dosing for 2, 3, 4, 5 or 6 days) and the subject is no longer receiving any formula 1 compound, or, in some cases, any other therapeutic treatment to treat the primary cause of the subject's pathological condition. Such beneficial effects can persist for more than about 5-30 days.

In some cases, beneficial effects from treatment have been observed for more than 3 months (4 or 5 or more months) after a short course of treatment of a subject with a formula 1 compound. Thus, administration of a formula 1 compound provides a method to effectively protect a subject against progression of an infection or against adverse consequences of unwanted immune reactions (e.g., inflammation) or against immunosuppression (from infection, chemotherapy, etc), without any dosing of the compound for at least 3 months after an initial dosing protocol, which could be an intermittent or a continuous dosing protocol over, e.g., 1 day to about 4 months (1-15 days, about 1 month, about 2 months, etc).

SYNTHESIS METHODS

Reagents and reaction conditions that one can use to make the formula 1 compounds have been described, see e.g., the citations above, U.S. Pat. Nos. 5,874,598, 5,874,597, 5,874,594, 5,840,900; PCT publication number WO 9901579. General chemical synthetic methods to link a variety of organic moieties to various reactive groups have been described. For example, in G. T. Hermanson, *Bioconjugate Techniques*, Academic Press, 1996, functional targets such as amino acids, peptides and carbohydrates are described at pages 3-136, while the chemistries of reactive groups in the functional targets, e.g., amine, thiol, carboxyl, hydroxyl, aldehyde, ketone and reactive hydrogen atoms (e.g., —H linked to an electron-donating moiety such as a heteroaryl moiety) are described at pages 137-166. This reference also describes reagents useful to make the derivatives, e.g., zero-length cross-linkers, heterobifunctional cross-linkers, homobifunctional cross-linkers, tags, probes and polymers are described at pages 169-416 and 605-638. This reference also describes synthetic methods to modify oligonucleotides at pages 639-671.

In one aspect, amino acids or peptides are linked to the steroid through the amine group using a coupling reagent such as phosgene (CI—CO—CI) or CI—CS—CI and suitably protected amino acids or peptides and steroids, which are protected as needed. Such linkage generates an intervening —CO—O— or a —CS—O— moiety between the amino acid or peptide and the steroid nucleus.

Exemplary synthesis schemes. By way of exemplification and not limitation, the following methods are used to prepare the one or more of the compounds disclosed herein. Starting materials and straightforward variations of the schemes are found, e.g., in the following references, which are incorporated herein by reference: A. P. Davis, et al., Tetrahedron Lett., 33: 5111-5112, 1992; I. Takashi, et al., Chem. Pharm. Bull., 34: 1929-1933, 1986; I. Weisz, et al., Arch. Pharm., 319: 952-953, 1986; T. Watabe, et al., J. Med. Chem., 13: 311-312, 1970; M. Davis, et al., J. Chem. Soc. C., (11): 1045-1052, 1967; R. C. Cambie, et al., J. Chem. Soc., Perkin Trans. 1, (20): 2250-2257, 1977; L. Minale, et al., J. Chem. Soc., Perkin Trans. 1, (20): 2380-2384, 1974; C. K. Lai, et al., Steroids, 42: 707-711, 1983; S. Irie, et al., Synthesis, (9): 1135-1138, 1996; E. J. Corey, J. Am. Chem. Soc., 118: 8765-8766, 1996; M. E. Annunziato, et al., Bioconjugate Chem., 4: 212-218, 1993; N. J. Cussans, et al., J. Chem. Soc., Perkin Trans. 1, (8): 1650-1653, 1980; D. H. R. Barton, et al., J. Chem. Soc., Chem. Commun., (9): 393-394, 1978; H. Loibner, et al., Helv. Chim. Acta, 59: 2100-2113, 1976; T. R. Kasturi, et al., Proc. Indian Acad. Sci., [Ser.]: Chem. Sci., 90: 281-290, 1981; T. Back, J. Org. Chem., 46: 1442-1446, 1981; A. Canovas, et al., Helv. Chim. Acta, 63: 486-487, 1980; R. J. Chorvat, et al., J. Org. Chem., 43: 966-972, 1978; M. Gumulka, et al., Can. J. Chem., 63: 766-772, 1985; H. Suginome, et al., J. Org. Chem., 55: 2170-2176, 1990; C. R. Engel, et al., Can. Heterocycles, 28: 905-922, 1989; H. Sugimone, et al., Bull. Chem. Soc. Jpn., 62: 193-197, 1989; V. S. Salvi, et al., Can. Steroids, 48: 47-53, 1986; C. R. Engel, et al., Can. Steroids, 47: 381-399, 1986; H. Suginome, et al., Chem. Lett. (5): 783-786, 1987; T. Iwadare, et al., J. Chem. Soc., Chem. Commun., (11): 705-706, 1985; H. Nagano, et al., J. Chem. Soc., Chem. Commun., (10): 656-657, 1985; V. S. Salvi, et al., Steroids, 27: 717-725, 1976; C. H. Engel, et al, Steroids, 25: 781-790, 1975; M. Gobbini, et al., Steroids, 61: 572-582, 1996; A. G. Gonzalez, et al., Tetrahedron, 46: 1923-1930, 1990; S. C. Bobzin, et al., J. Org. Chem., 54: 3902-3907, 1989; B. Solaja, et al., Croat. Chem. Acta, 59: 1-17, 1986; Y. Kashman, et al., Tetrahedron, 27: 3437-3445, 1971; K. Yoshida, et al., Chem. Pharm. Bull. (Tokyo), 15: 1966-1978, 1967; P. B. Sollman, et al., Chem. Commun. (11): 552-554, 1967; H. Suginome, et al., J. Org. Chem., 55: 2170-2176, 1990; H. Suginome, et al., Journal Chem. Lett. (5): 783-786, 1987; G. A. Tolstikov, et al., Zh. Org. Khim., 22: 121-132, 1986; T. Terasawa, et al., J. Chem. Soc., Perkin Trans. 1, (4): 990-1003, 1979; Z. Zhuang, et al., Yougi Huaxue, (4): 281-285, 1986; W. T. Smith, et al., Trans. Ky. Acad. Sci., 45: 76-77, 1984; A. K. Batta, et al., Steroids, 64: 780-784, 1999; B. Ruan, et al., Steroids, 65: 29-39, 2000; L. Garrido, et al., Steroids, 65: 88, 2000; P. Ramesh, et al., Steroids, 64: 785-789, 1999; M. Numazawa, et al., Steroids, 64: 187-196, 1999; P. N. Rao, et al., Steroids, 64: 205-212, 1999; M. Numazawa, et al., Steroids, 64: 320-327, 1999; U.S. Pat. Nos. 3,281,431, 3,301,872, 3,325,535, 3,325,536, 3,952,018, 4,602,008, 5,571,795, 5,627,270, 5,681,964, 5,744,453; international publication numbers WO 9408588, WO 9508558, WO 9508559, WO 9638466, WO 9809450; United Kingdom patent numbers GB 1168227, GB 813529, GB 802618; French patent number 824529; Japan patent number JP 45010134; European patent applications EP 232788, EP 430078; and German patent number DE 19631189.

Scheme 1. For the structures shown in scheme 1, $R^5$-$R^9$ are as defined for formula 1 compounds. Thus, when $R^5$ and $R^6$ are both —$CH_3$ in the β-configuration, $R^7$, $R^3$ and $R^9$ are all —$CH_2$—, H at the 9 and 14 positions are in the α-configuration, acetate at the 3-position is in the β-configuration, and H at the 8 position is in the β-configuration, the first compound in scheme 1 is DHEA acetate. The acetate groups at the 3, 7, 16, 17 or other positions in this scheme and in other schemes disclosed herein may independently be other ester moieties as described herein, e.g., $C_{2-50}$ esters including —C(O)—$(CH_2)_{0-4}$—$(CF_2)_{0-4}$—$CF_3$, including —C(O)—$CF_3$, —C(O)—$C_{2-29}$ optionally substituted alkyl, —C(O)—$CH_2$—$C_{2-28}$ optionally substituted alkenyl, —C(O)—$CH_2$—$C_{2-28}$ optionally substituted alkynyl, —C(O)—$(CH_2)_{0-6}$-optionally substituted phenyl, or —C(O)—$(CH_2)_{0-6}$-optionally substituted heterocycle or other organic moieties as disclosed herein or in the cited references.

Typical substituents for these organic moieties are as described herein, including one, two, three or more independently selected —O—, =O, optionally protected hydroxyl, —S—, optionally protected thiol, —NH—, optionally protected —$NH_2$, optionally protected —C(O)OH, —C(O)—NH—, —C(O)—$NH_2$, —$NH_2$—C(O)—H, —$NH_2$—C(O)—$CO_4H_{1-9}$, —$NH_2$—C(O)—O—$CO_4H_{1-9}$, —CN, —$NO_2$, —$N_3$ or halogen. Reactive groups are protected as needed, e.g., =O would usually be protected in the LiCR reaction that is used to generate compound 1 in scheme 1 below.

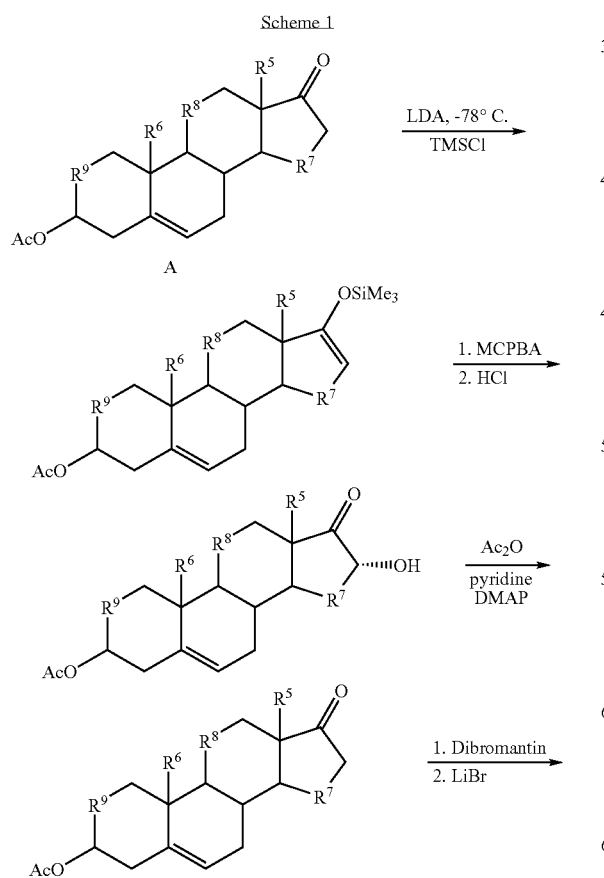

Scheme 1

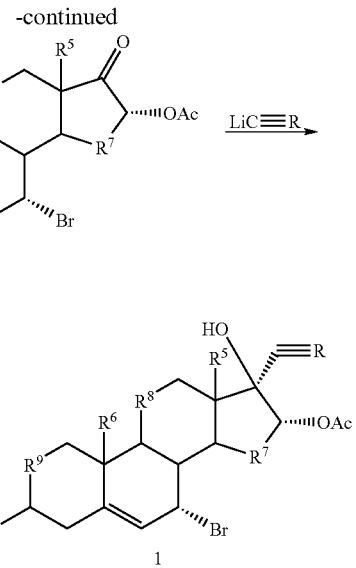

Abbreviations:
LDA = lithium diisopropyl amide; MCPBA = m-chloroperbenzoic acid; TMSCl = trimethychlorosilane; DMAP = 4-dimethylaminopyridine; Dibromantin = 1,3-dibromo-4,4-dimethylhydantoin.
R = $CR^4$; $R^4$ = —H or a C1-C50 organic moiety as described herein, e.g., —H, —$C_{1-20}$ optionally substituted alkyl, —$C_{1-20}$ optionally substituted alkenyl, —$C_{1-20}$ optionally substituted alkynyl, —$(CH_2)_{0-6}$-optionally substituted phenyl or —$(CH_2)_{0-6}$-optionally substituted heterocycle.

Scheme 2. Compounds of formula 2 are prepared from structure A compounds shown in scheme 1 using the last two steps of Scheme 1: (1) dibromantin, (2) LiBr, (3) Li—C—R, where R is $CR^4$ and $R^4$ is —H or —$C_{1-12}$ optionally substituted alkyl. When $R^7$, $R^8$ and $R^9$ are all —$CH_2$—, H at the 9 and 14 positions are in the α-configuration and H at the 8 position is in the β-configuration the first compound in scheme 1 is DHEA acetate. Typical substituents for the $R^4$ alkyl moiety includes one, two or more independently selected —O—, optionally protected =O, optionally protected hydroxyl, —S—, optionally protected thiol, —NH—, optionally protected —$NH_2$, optionally protected —C(O)OH, —C(O)—NH—, —C(O)—$NH_2$, —$NH_2$—C(O)—H, —$NH_2$—C(O)—$C_{0-4}H_{1-9}$, —$NH_2$—C(O)—O—$CO_4H_{1-9}$, —CN, —$NO_2$, —$N_3$ or halogen.

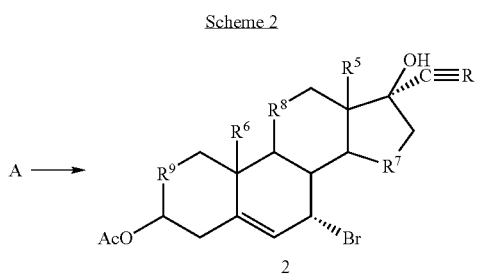

Scheme 2

Scheme 3. The allylic bromination at C-7 is done as in Scheme 1. R and $R^4$ are as defined in Schemes 1 and 2.

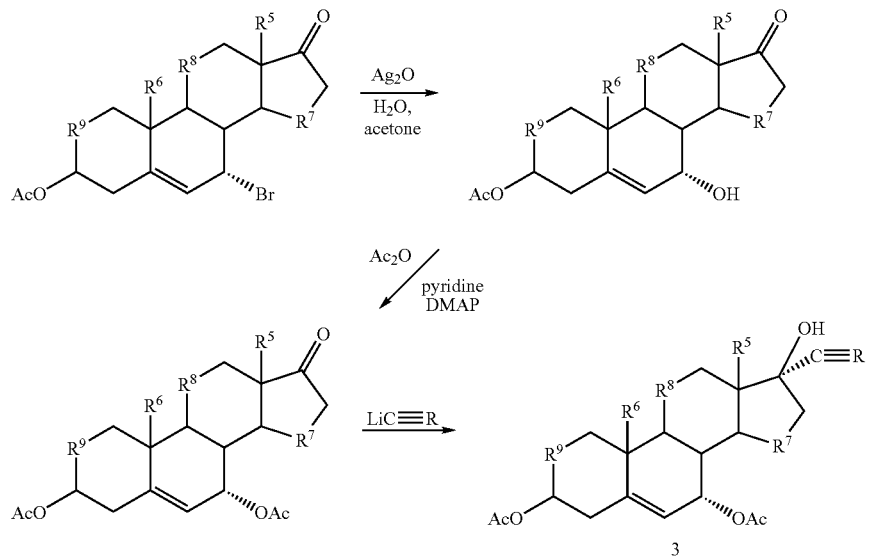

Scheme 4. The addition of lithium reagent (lithium acetylide when R is —CH) to the 17-position >C=O in the presence of the bromide at C-16 results in epoxide formation or in a pinacol rearrangement. Alternatively, compounds without of structure 3 can be dehydrated by mild acid catalysis to form compounds of formula 4 by treatment of the alkene with Br$_2$, H$_2$O. R and R$^4$ are as defined in Schemes 1 and 2.

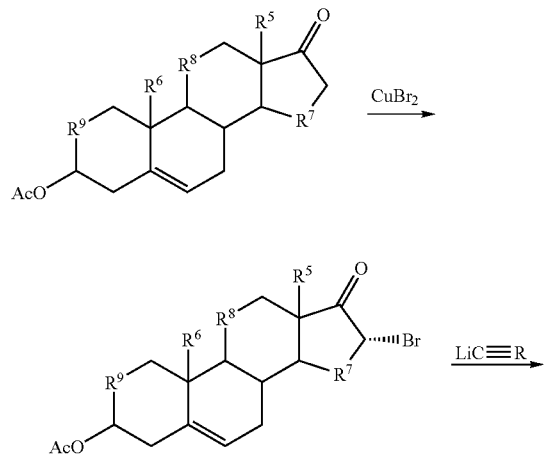

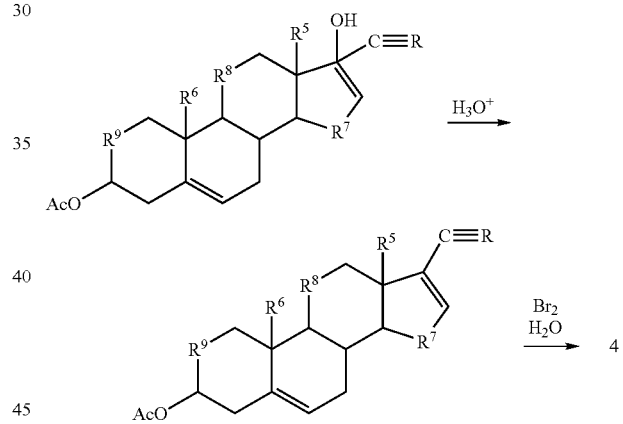

Scheme 5. Sodium borohydride gives a mixture of epimers at C-7, which may be separated by standard methods, e.g., HPLC, TLC or column chromatography. To obtain the pure 7α—OH compound, allylic bromination followed by hydrolysis is accomplished as described in Schemes 1 and 3.

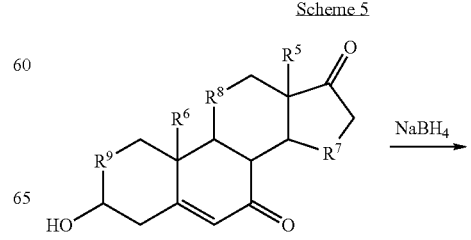

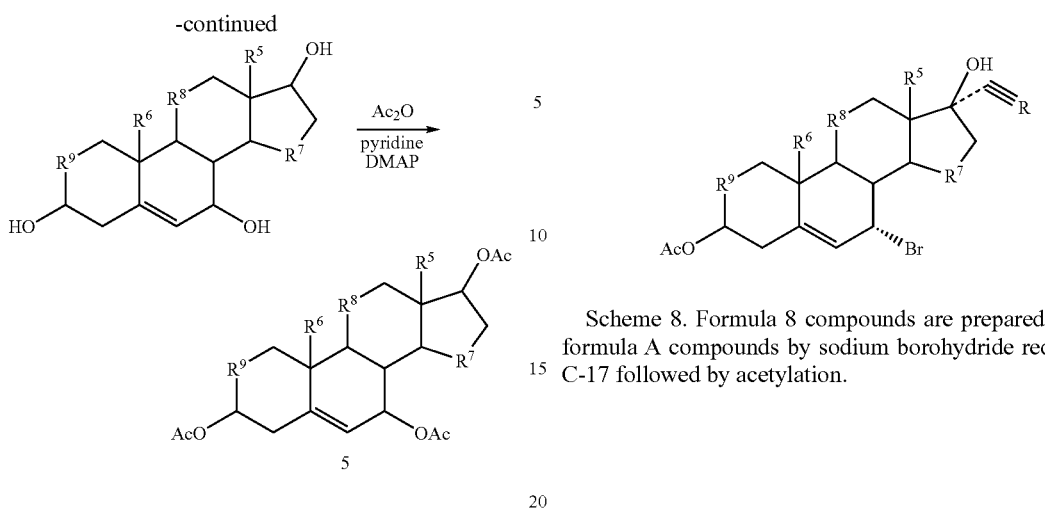

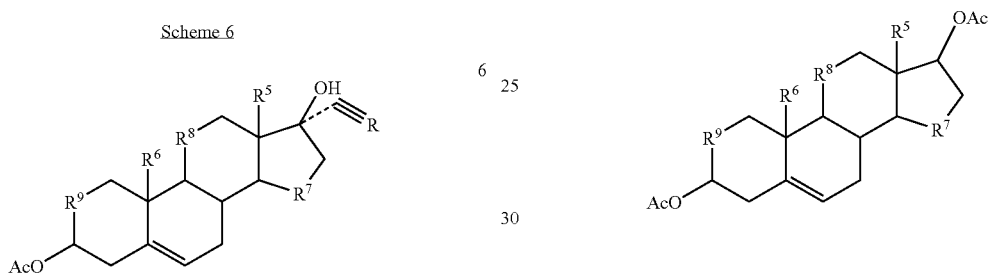

Scheme 6. Formula 6 compounds are prepared by treatment of the acetate with lithium acetylide as in Schemes 1, 2, 3 or 4. R and $R^4$ are as defined in Schemes 1 and 2.

Scheme 7. Formula 7 compounds are prepared from the 3-acetate with reagents described in Schemes 1 and 4. R and $R^4$ are as defined in Schemes 1 and 2.

Scheme 8. Formula 8 compounds are prepared from the formula A compounds by sodium borohydride reduction at C-17 followed by acetylation.

Scheme 9. The starting material is made using reactions described in Schemes 1 and 3.

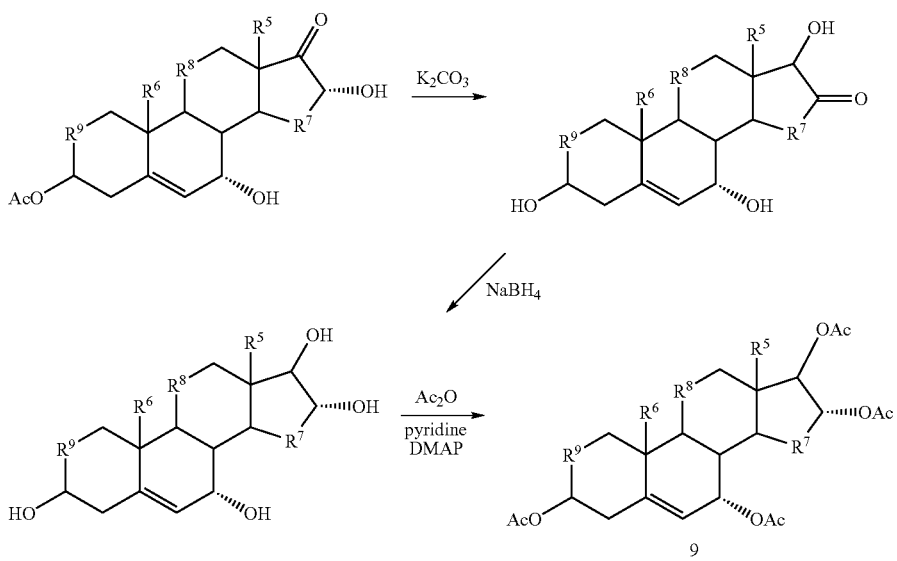

Scheme 10. Reduction and acetylation at C-3 and hydrolysis and oxidation at C-17 will allow formula 10a and 10b compounds to undergo functionalization as shown in Schemes 1-9 at C-3, C-16 and C-17. The 7-oxo acetate can be substituted for the formula A compound 3-acetate and functionalization at C-3, C-16 and C-17 is achieved similarly for 7-oxo compounds using the reactions shown in schemes 1-9.

Treatment of 10a with LDA, followed by alkylation of the enolate allows introduction of side chains such as $R^{10}$, which may be, e.g., C1-C20 alkyl (methyl, ethyl), C1-C20 alkenyl ($CH_2$=CH—($CH_2$)$_{0-6}$—), benzyl, —($CH_2$)$_{1-4}$—O—($CH_2$)$_{0-4}$—$CH_3$.

the presence of $Na_2CO_3$. Alternatively, if the alcohol is treated with phosphoric acid diesters in the presence of triphenylphospine ($PPh_3$) and diethylazodicarboxylate (DEAD) the corresponding triesters are formed with inversion (Mitsunobu reaction).

Phosphothioesters, $R^B$O—P(S$R^{PR}$)(O)—O— are generated by treatment of alcohols with the monothio analog of diethylchlorophosphate as described for phosphoesters yielding the phosphothioesters. Carbonates, $R^B$O—C(O)—O—

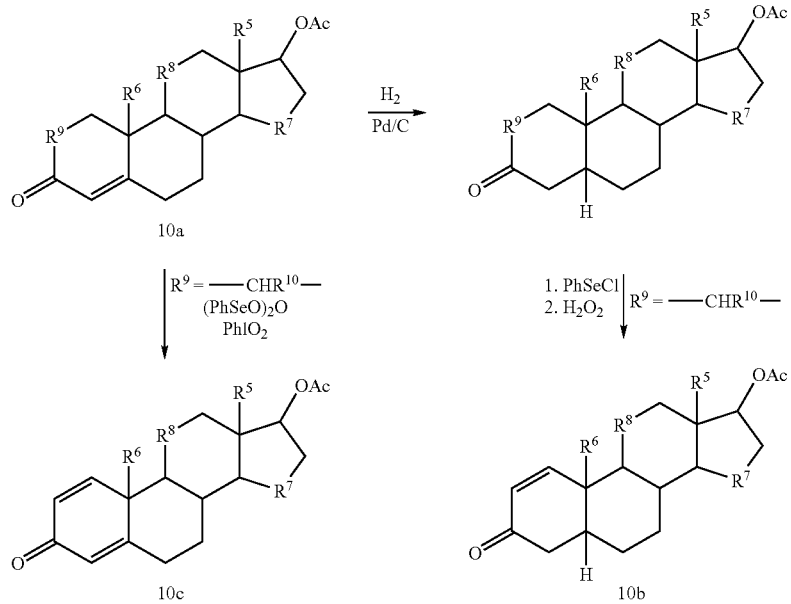

Scheme 10

Schemes 1-9 show the introduction of the hydroxyl function at the positions shown. Methods to convert hydroxyl to other functional groups are accomplished essentially as described, e.g., in the references cited herein. For example, esters, of formula 1-10c compounds, such as —O—C(O)—$R^B$ where $R^B$ is a $C_{1-50}$ organic moiety, are prepared from the steroid alcohol by treatment with the appropriate acid anhydride or acid chloride ($R^B$—C(O)—Cl) to form any desired ester. Ethers, such as —O—$R^B$, are prepared from alcohols by formation of the alkaline metal alkoxide ($Na^+$ or $K^+$) followed by treatment with a primary or secondary iodide ($R^B$—I). Thionoesters, $R^B$—C(S)—O—, are prepared by treating the $R^B$—C(O)—O— ester with Lawesson's reagent.

Sulfates, NaO-S(O)(O)—O—, $R^B$—O— S(O)(O)—O—, e.g., $CH_3(CH_2)_{0-18}$—S(O)(O)—O—, are prepared by treatment of alcohols with chlorosulfonic acid followed by NaOH or alternatively by oxidation of sulfites using $KMnO_4$. If the alkyl (e.g., methyl) ester is desired alkylchloro-sulfonate (methylchloro-sulfonate) can be used. Sulfites HO—S(O)—O— and ammonium salts $NH_4O$—S(O)—O, or $R^B$ O—S(O)—O— esters (e.g., $CH_3O$—S(O)—O—) are prepared by standard methods. The ammonium salts are prepared by treatment of alcohols with ammonia and sulfur dioxide. The esters such as alkyl, alkenyl and alkynyl esters (e.g., methyl ester) are obtained when alcohols are treated with alkylchlorosulfite (e.g., methycholorosulfite), alkenylchlorosulfite or alkynylchlorosulfite in the presence of a suitable base such as triethylamine. Phosphoesters, $R^B$O—P(O$R^{PR}$)(O)—O— are prepared by treating the alcohol with diethylchlorophosphate in are generated from the corresponding steroid alcohol using the chloroformate ($R^B$—C(O)—Cl), e.g., $C_{1-20}$ alkyl, alkenyl or alkynyl chloroformates (e.g. $CH_3(CH_2)_{0-5}$—C(O)Cl). Carbamates, $R^B$—NH—C(O)—O— are made from steroid alcohols by treatment with isocyanates ($R^BN$=C=O) or NaOCN in the presence of trifluororoacetic acid. Aminoacid esters, ZNX—CHY—C(O)—O— are generated by coupling the steroid alcohol with the acid chloride of the N-protected amino acid.

Oxidation of hydroxyl groups that are linked to the steroid nucleus is used to obtain ketones and related functionalities. For example, conversion of alcohols to ketones can be achieved using a variety of oxidizing agents such as $CrO_3$ in AcOH, or pyridinium cholorchromate, pyridinium dichromate or oxalyl chloride with triethylamine (Swern oxidation). Thioketones (=S) are prepared by treating ketones with Lawesson's reagent (2,4-bis(4-methoxyphenyl)-1,3,2,4-dithiadiphosphetane-2,4-disulfide; commercially available from Aldrich). Thioacetals, —C(S$R^B$)(S$R^B$)—, are prepared from ketones (—C(O)—) by treatment with $R^B$—SH thiols under acid catalysis conditions (e.g., HCl). Phosphonoesters, RO—P(O$R^{PR}$)(O)—, are generated by addition of the phosphorus acid diester to ketones in the presence of KF to yield hydroxy phosphonoesters. One may optionally remove the hydroxy group using a dehydration and hydrogenation sequence.

Substitution of hydroxyl groups is used to generate a number of functionalities. For example, thiols, —SH, are prepared from alcohols by conversion of the alcohol with inversion to the bromide using $PBr_3$. Treatment of the bromide with thiourea followed by NaOH gives the thiol. Thioethers, $R^B$—S—, are prepared from thiols by treatment with NaOH and the required halide, e.g., alkyl halide. Alternatively, alcohol derivatives like tosylates or mesylates can be displaced by thiolate anions, $R^B$—S—, to yield the thioether. Thioesters, R—C(O)—S—, are prepared by treating the tosylate (mesylate) of the alcohol with the sodium salt of the thioacid.

Substitution of hydroxyl groups can be used to generate both esters, $R^B$O—C(O)—, and amides, NHR$^B$—C(O)—, linked to the steroid at carbon atoms. For amides and amines, $R^B$ is —H, a protecting group or a $C_{1-50}$ organic moiety. These are synthesized from the steroid bromide with inversion by displacement with NaCN. The cyanide group can be hydrolyzed to the amide or the acid. The acid is esterified or treated by standard peptide coupling reactions with an O-protected amino acid in the presence of a suitable carboxyl activating agents such as dicyclohexylcarbodiimide (DCC) to form steroid —C(O)—NH—CHY—C(O)—OR, where Y is the side chain of an amino acid or a $C_1$-$C_{10}$ organic moiety and R is a protecting group (or hydrogen when deprotected).

Amines and derivatives of amines, e.g., $R^B$NH—, $R^B$—C(O)NH—, $R^B$OC(O)—NH— or $R^B$O—C(O)—CHR$^B$—NH— linked to steroid carbon atoms, are typically prepared by standard methods. For example, amines ($NH_2$-steroid) are generally prepared using the Hoffmann rearrangement ($Br_2$, NaOH) from the amide ($NH_2$—C(O)-steroid) or the Curtius rearrangement ($NaN_3$) from the acid chloride of the steroid. The $R^B$ substituent can subsequently be introduced by alkylation. Steroid alcohols can be used as starting materials under standard Mitsunobu conditions ($PPh_3$, DEAD) to yield N-Boc sulfonamides using N-(t-butoxycarbonyl)-p-toluenesulfonamide. One can selectively remove either protecting group. Treatment with trifluoroacetic acid affords the sulfonamide ($R^B$—S(O)(O)—NH-steroid). Alternatively, sodium napthalenide deprotects to give the N-Boc compound. Amines ($NH_2$-steroid) can be converted to amides ($R^B$NH—C(O)-steroid) using acyl chlorides ($R^B$—C(O)_Cl). Treatment with ethyl chloroformate gives the N-carbamate ($R^B$O—C(O)—NH-steroid). The amine ($NH_2$-steroid) can be alkylated with an α-bromoester ($R^B$—C(O)—CHY—$NH_2$) to yield the amino acid substituted steroid ($R^B$—O—C(O)—CHY—NH-steroid).

Where reactions such as substitutions give a product mixture, the desired intermediate is optionally separated from other products or at least partially enriched (e.g., enriched at least about 10-fold, usually at least about 50-100-fold) from other products before subsequent reactions are conducted. Substitution at steroid carbon atoms will generally proceed with greatest efficiency at the 3-position, which is relatively sterically unhindered and C-17 is generally somewhat less accessible than the C-3 position. The relative reactivities of the C-3, C-7, C-17 and C-16 positions allows one to use their reactivities to control the sequential introduction of different functional groups into the same steroid molecule. Also, groups such as hydroxyl at more reactive positions, C-3 or C-17, may be sequentially protected or deprotected to allow introduction of functional groups at other positions, such as C-7 or C-16.

Polymers such as PEG are linked to the compounds essentially as described above. For example, PEG200 or PEG300 is linked to the steroid at the 3, 7, 16, 17 or other positions by an ether linkage (PEG-O-steroid) using a PEG alkoxide (PEG-ONa), to displace the steroid bromide. Alternatively, PEG—Br can be treated with the steroid alkoxide. Polyethylene glycol esters such as those described in U.S. Pat. No. 5,681,964 can also be prepared using a suitable formula 1 compound and the methods described therein. Monosaccharides or polysaccharides and oligonucleotides are linked to steroid hydroxyl groups using known methods, see e.g., U.S. Pat. No. 5,627,270.

Formula 1 steroid analogs that comprise one or more ring heteroatoms are synthesized according to the following methods.

Scheme 11. Formula 1 compounds that comprise two or three ring heteroatoms are prepared as shown in the schemes. In the scheme, X is —$CH_2$—, —NH—, —O—, or —S—; $R^{40}$ is —H or —Br; $R^{41}$ is an organic moiety having about 12 carbon atoms or less, typically $C_1$-$C_8$ optionally substituted alkyl (e.g., methyl, hydroxymethyl, ethyl, propyl) or $C_2$-$C_8$ optionally substituted alkenyl having a single double bond (e.g., vinyl) with 1, 2, 3 or more independently selected substituents (e.g., —OH, —COOH, —O—) and with any substituents that comprise a functional group generally being protected. Preparation of compound 20 from 19 is accomplished using a glycol such as $HOC(CH_3)_2C(CH_3)_2OH$ in acid ($H^+$) (B. H. Lipshutz et al., Synth. Commun. 12: 267, 1982). The use of a bulky protecting group facilitates generation of a double bond at the 5-6 position over the 4-5 position.

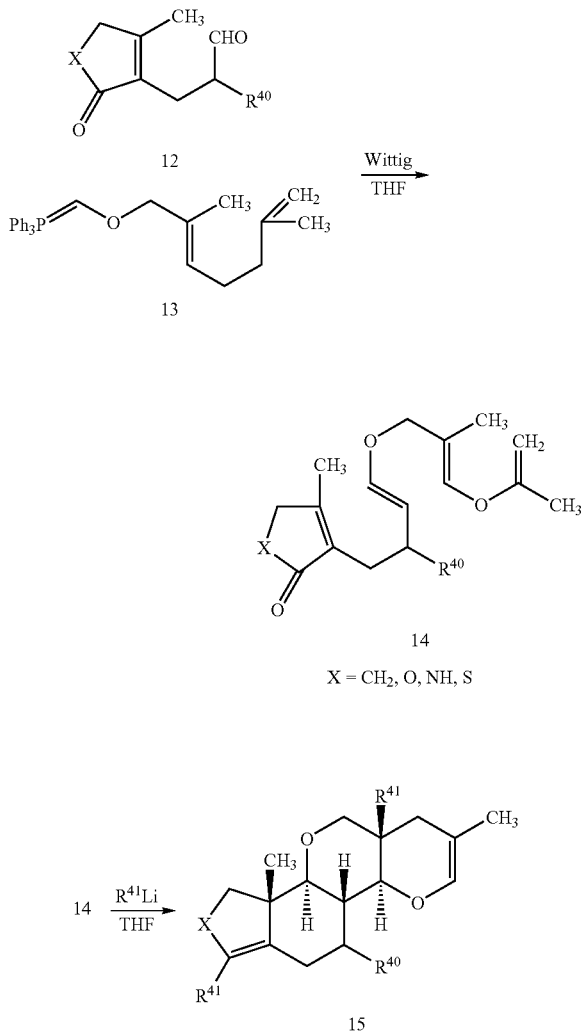

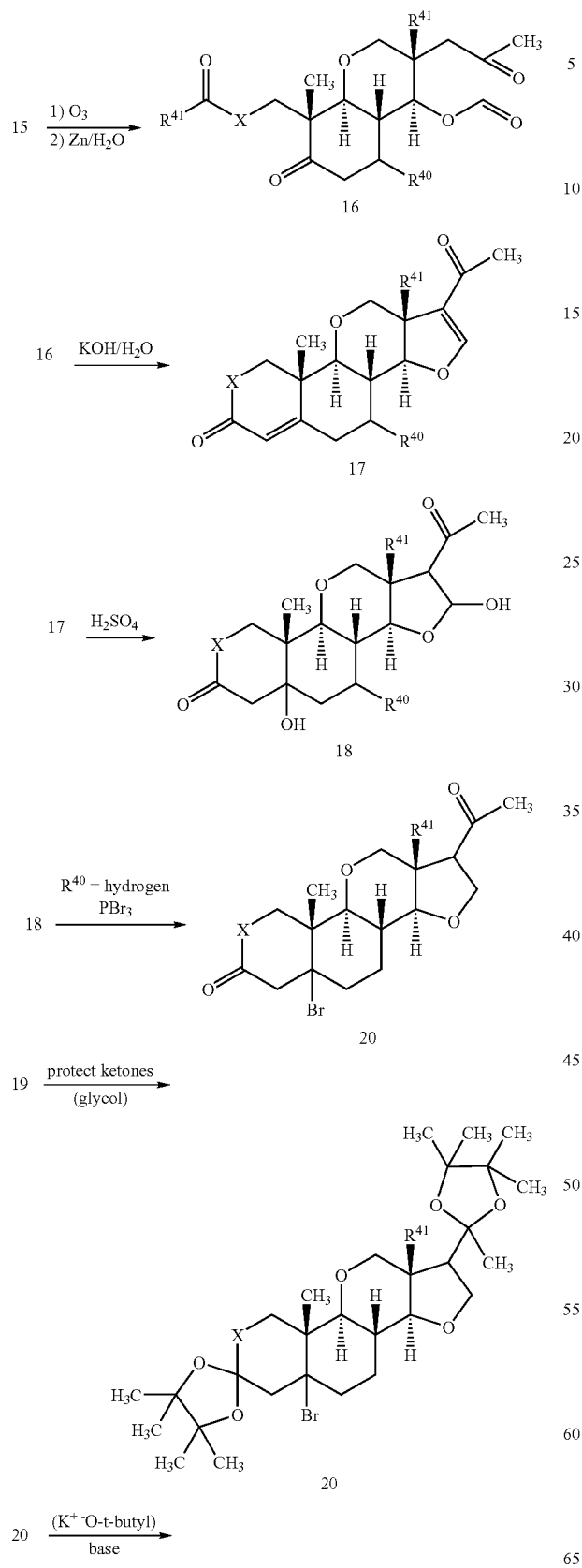
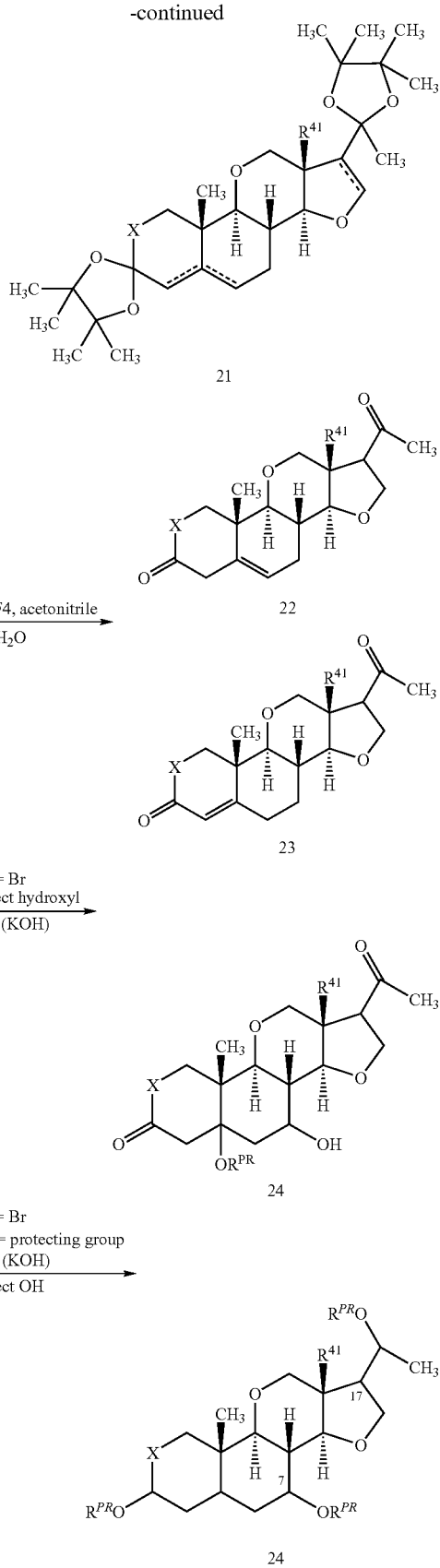

Schemes 12A-12D. Compounds of structure 12 are generated as shown in the schemes below. Most of the reactions are conducted essentially as described. See e.g., W. D. Langley, *Org. Syn. I*, 122, 1932 (compound 30); R. Ratcliffe et al., *J. Org. Chem.* 35: 4000, 1970 (compound 32); A. I. Meyers et al., *J. Org. Chem.* 39: 2787, 1974 (compound 33, 41); J. L. Isidor et al., *J. Org. Chem.* 38: 544, 1973 (compound 35); G. Wittig et al., Chem. Ber. 87: 1318, 1954 (compound 36); P. M. Pojer et al., *Tet. Lett.* 3067, 1976 (compound 38); A. Maercker, *Org. React.* 14: 270, 1965 (compound 37); E. J. Corey et al., *Tet. Lett.* 3269 1975 (compound 37); R. S. Tipson, *J. Org. Chem.* 9: 235, 1944 (compound 39); G. W. Kabalka, *J. Org. Chem.* 51: 2386, 1986; B. B. Carson et al., *Org. Synth.* 1: 179, 1941 (compound 43); H. J. Bestman et al., *Justus Liebigs Ann. Chem.* 693: 132 1966 (compound 39); M. Miyano et al., *J. Org. Chem.* 37: 268, 1972 (compound 51); W. H. Glaze et al., *J. Org. Chem.* 33: 1987, 1968 (compound 52).

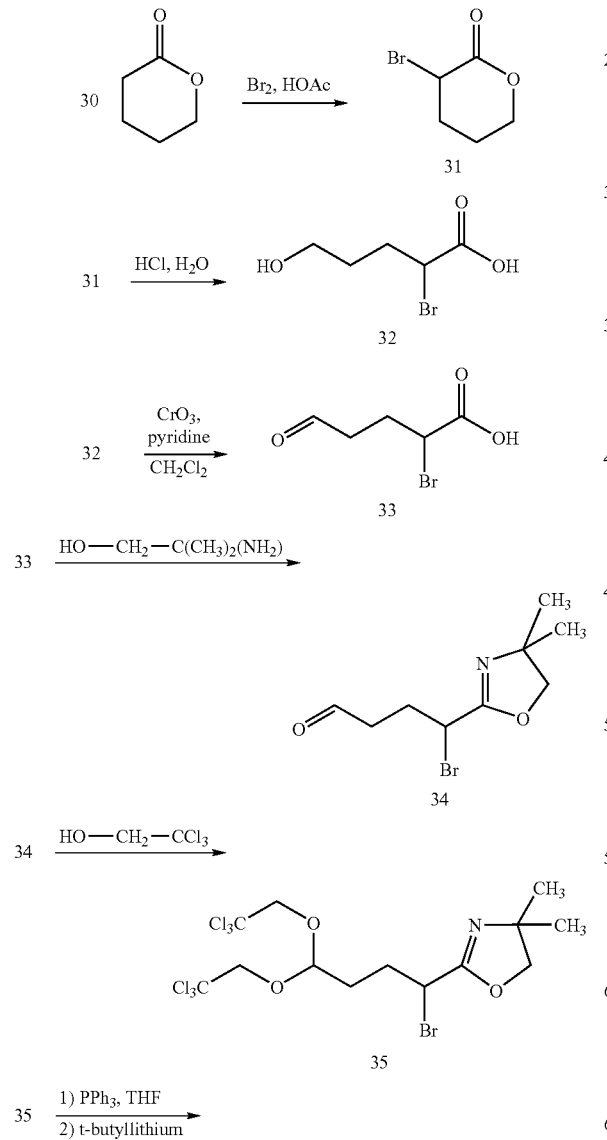

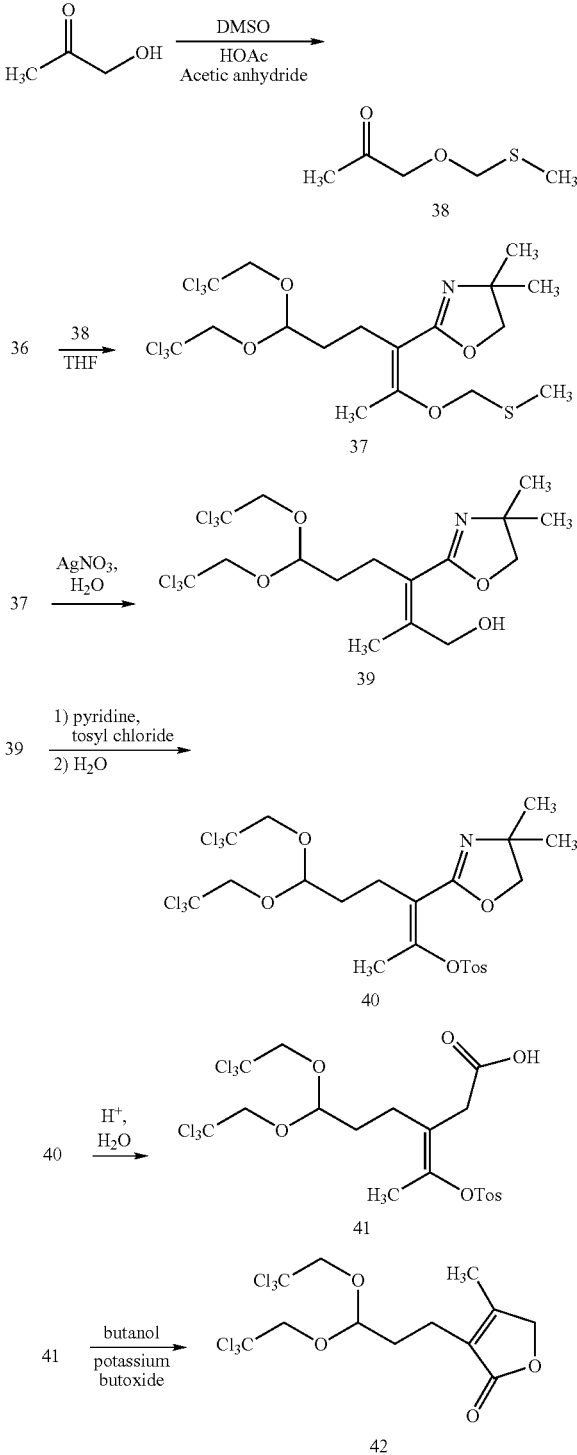

-continued
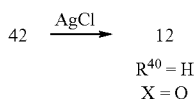
R⁴⁰ = H
X = O
Compounds of structure 12 where X is NH, S and CH₂ are prepared as shown in schemes 12B, 12C and 12D respectively.
Scheme 12B
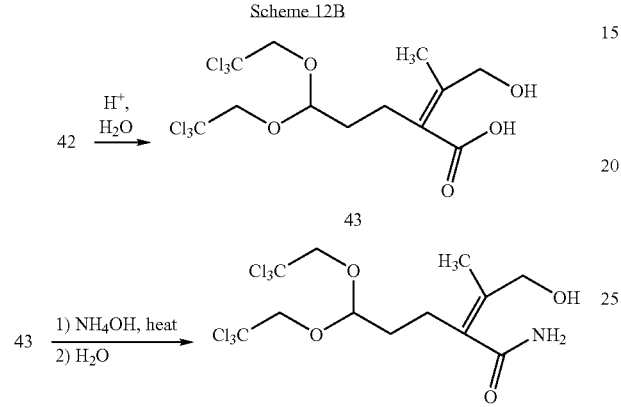
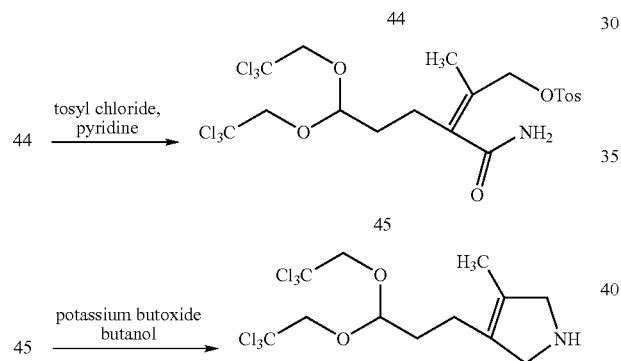
Scheme 12C
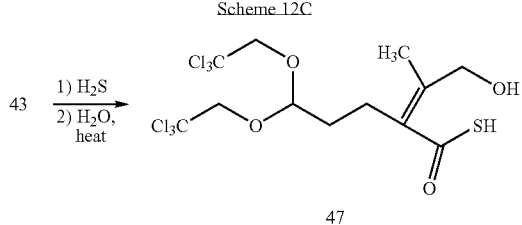
-continued
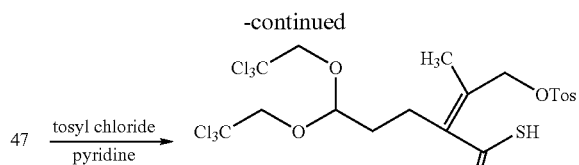
Scheme 12D
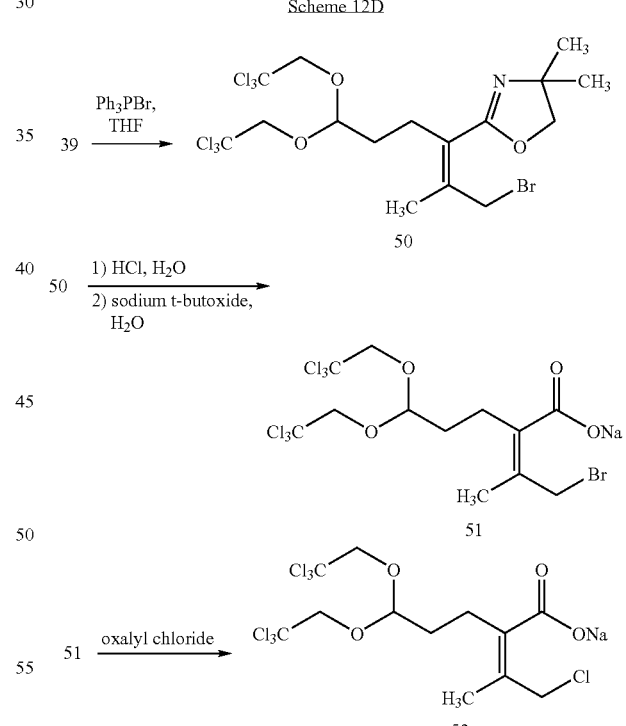
$12$
$X = S$
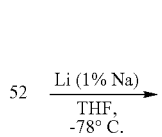 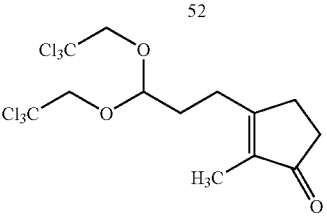

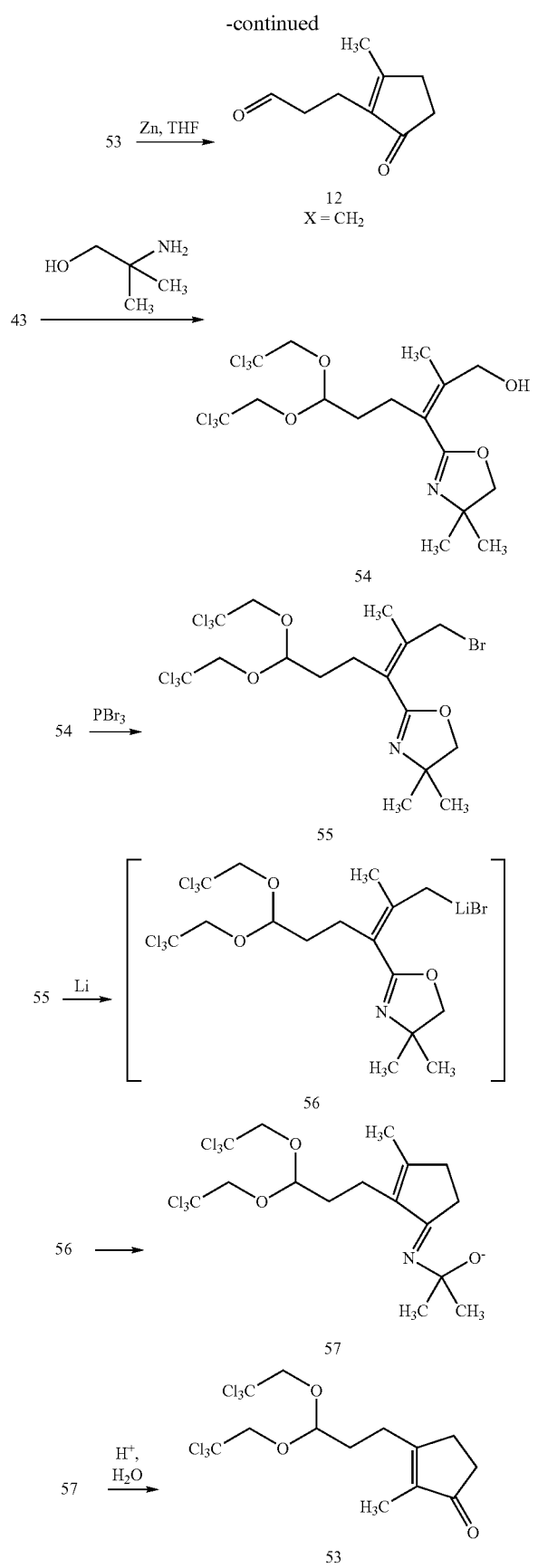
Scheme 13. The scheme and reactions shown below are used to prepare the compound of structure 13 and related compounds that are used to introduce oxygen, carbon, nitrogen or sulfur into the $R^7$ and $R^8$ positions of formula 1 compounds. The reactant in the preparation of compound 63, 3-chloro-2-methylpropene (reg. No. 563-47-3), is available commercially (e.g., Aldrich, Fluka).
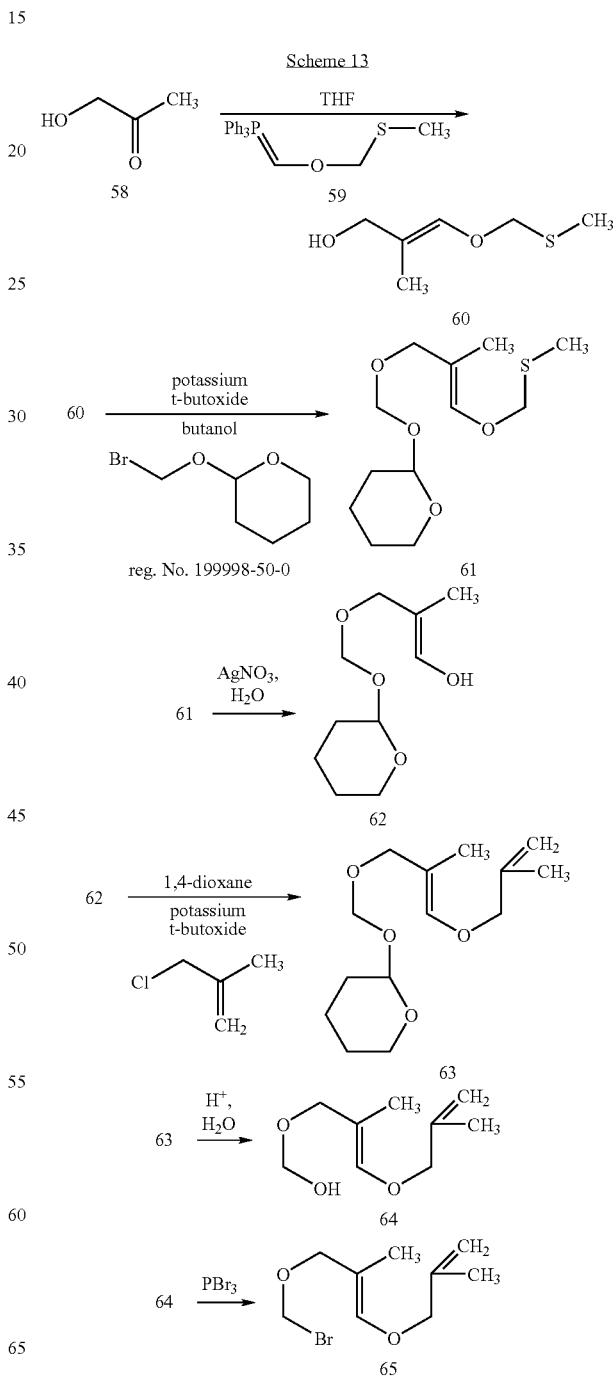

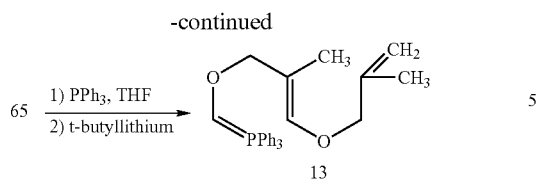
Compound 59 and analogs of compound 59 where CH$_2$, S or NH CH$_2$ replaces oxygen are prepared as shown in the following reactions. Conditions suitable for conversion of compound 106 to 107 have been described (T. Hamada et al., *Heterocycles* 12: 647, 1979; T. Hamada et al., *J. Am. Chem. Soc.* 108: 140, 1986).
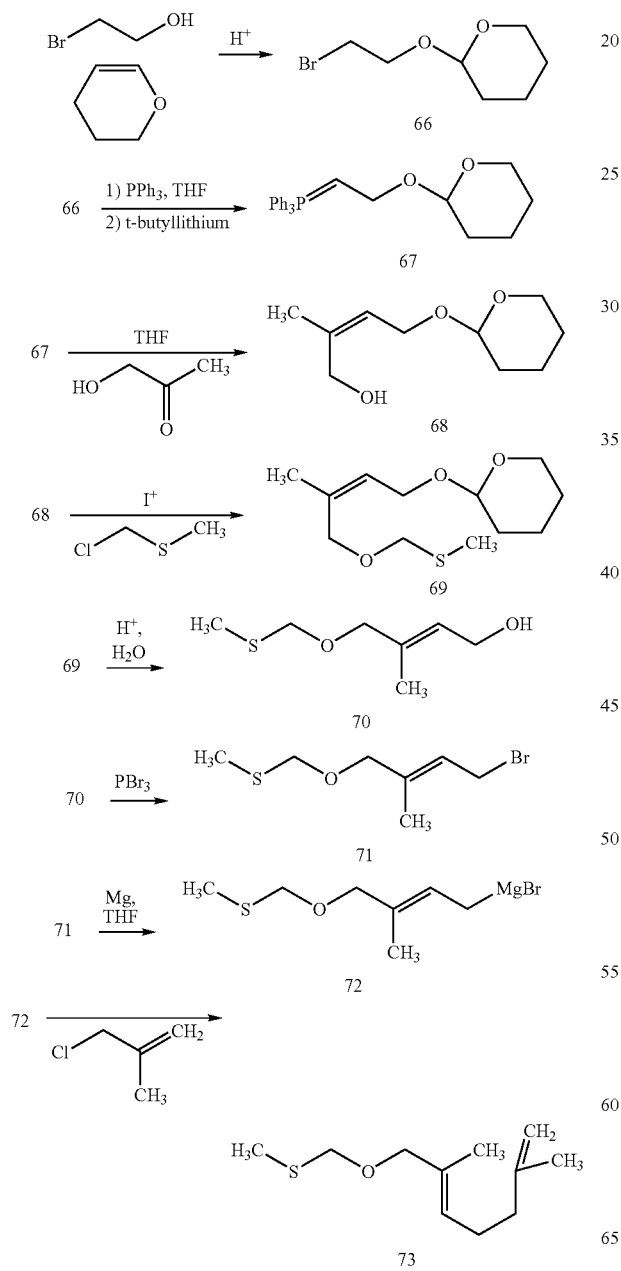
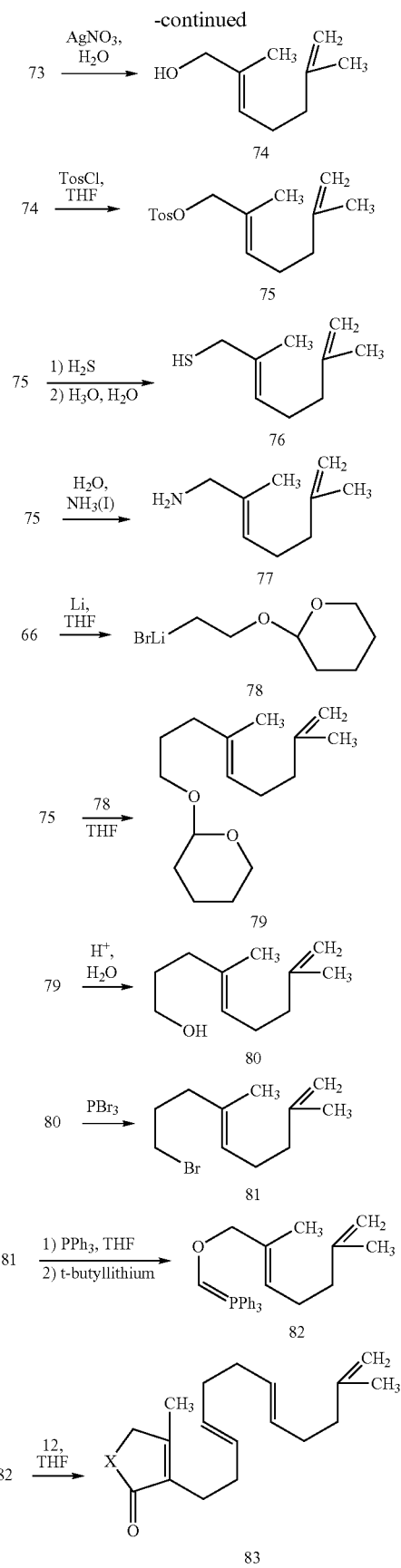

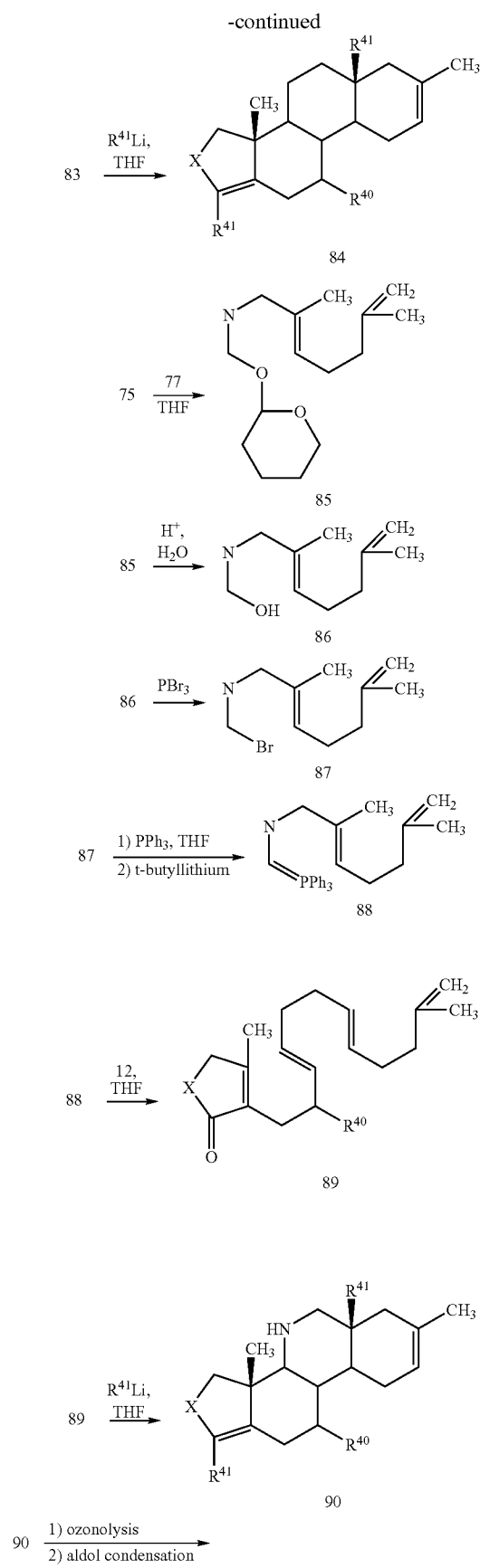
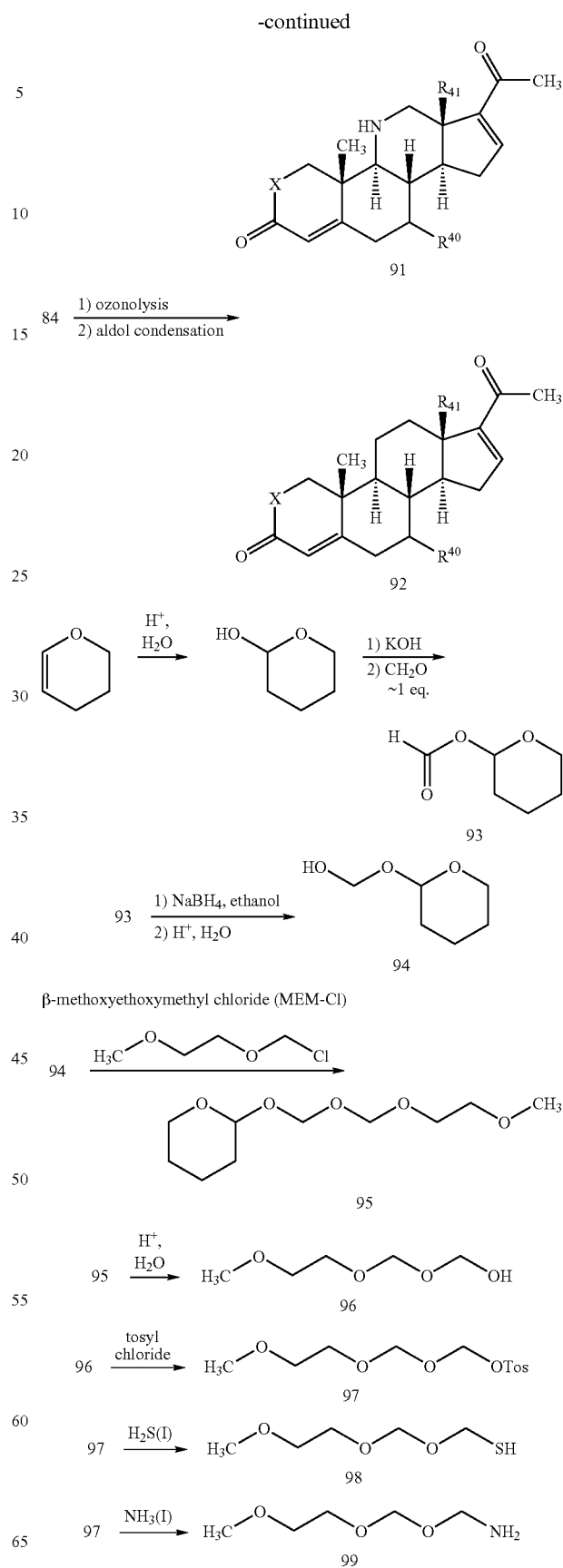

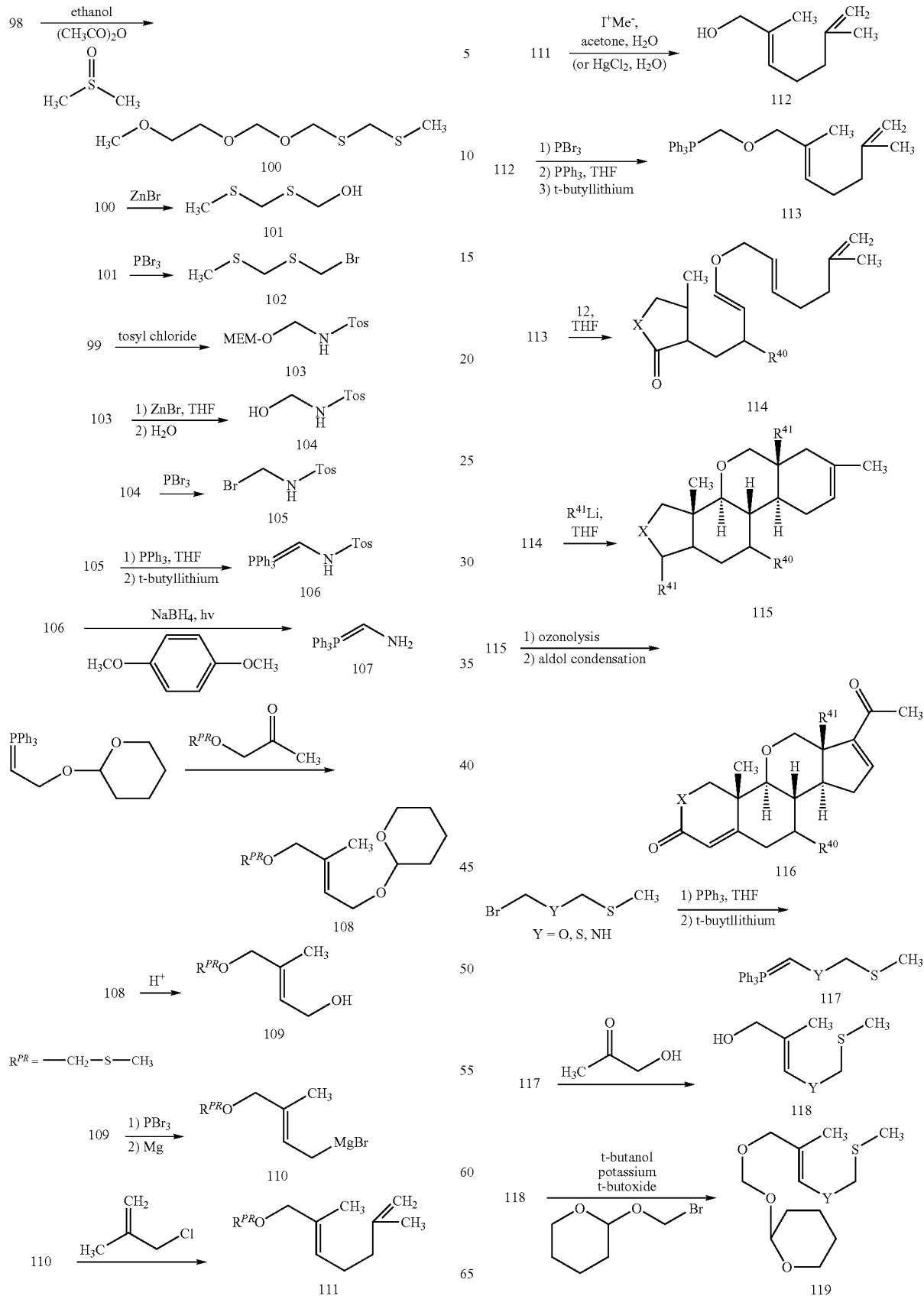

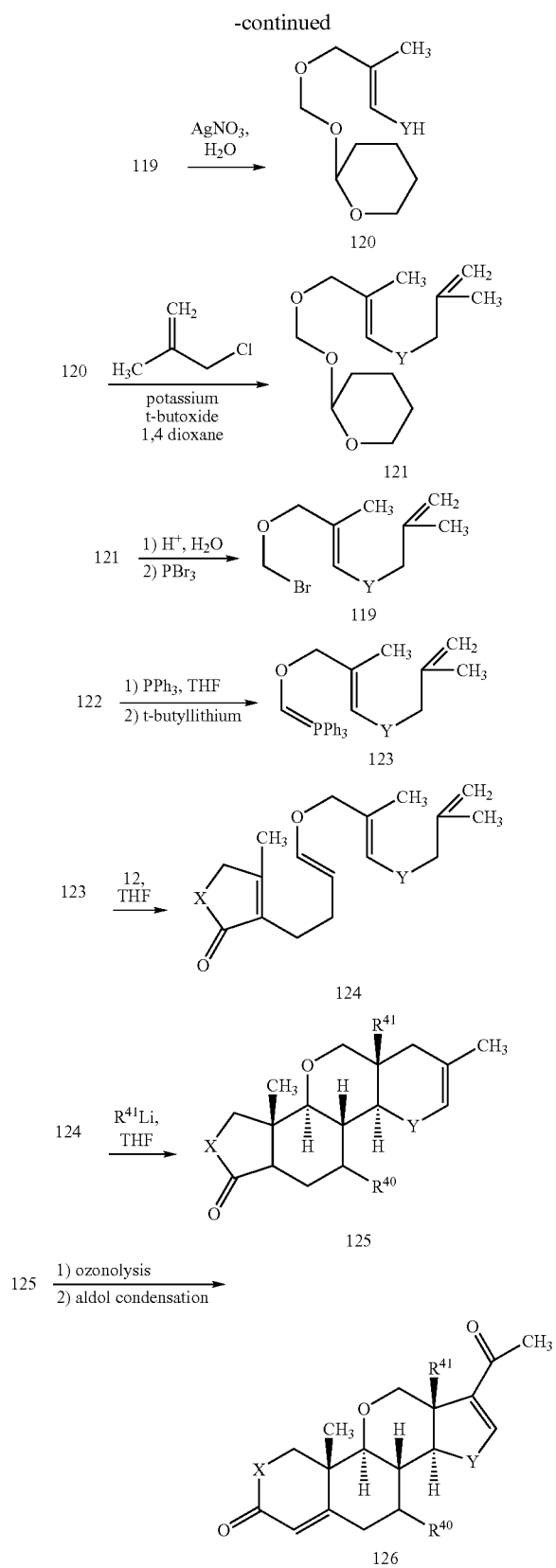

Conversion of the methyl ketone (—C(O)—CH₃) moiety in compounds having the structure

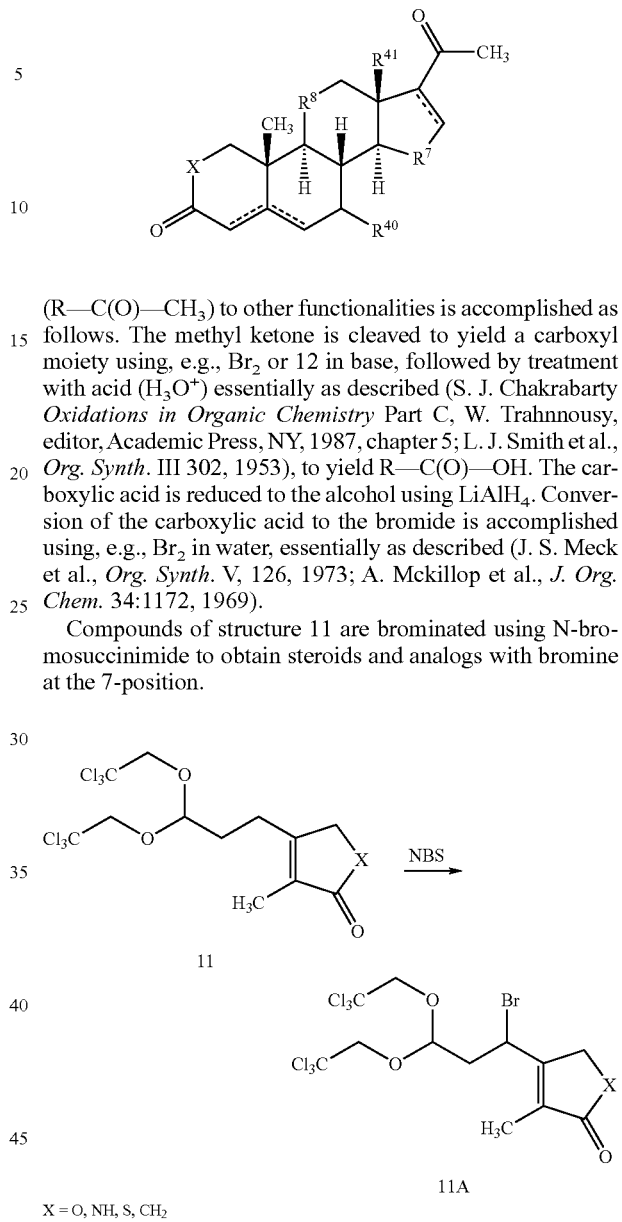

(R—C(O)—CH₃) to other functionalities is accomplished as follows. The methyl ketone is cleaved to yield a carboxyl moiety using, e.g., Br₂ or 12 in base, followed by treatment with acid (H₃O⁺) essentially as described (S. J. Chakrabarty *Oxidations in Organic Chemistry* Part C, W. Trahnnousy, editor, Academic Press, NY, 1987, chapter 5; L. J. Smith et al., *Org. Synth*. III 302, 1953), to yield R—C(O)—OH. The carboxylic acid is reduced to the alcohol using LiAlH₄. Conversion of the carboxylic acid to the bromide is accomplished using, e.g., Br₂ in water, essentially as described (J. S. Meck et al., *Org. Synth*. V, 126, 1973; A. Mckillop et al., *J. Org. Chem*. 34:1172, 1969).

Compounds of structure 11 are brominated using N-bromosuccinimide to obtain steroids and analogs with bromine at the 7-position.

The 11A compounds are deprotected to yield the aldehyde compounds 12. As shown in scheme 11, the bromine atom is ultimately found at the 7-position. The bromine may be converted to a hydroxyl by reaction of the steroid with base (e.g., aqueous KOH), and the hydroxyl may in turn be protected using known methods, e.g., using C₆H₅—CH₂—Br and base (KOH). The alcohol is protected and deprotected essentially using described methods, see, e.g., W. H. Hartung et al., *Org. React*. 7: 263, 1953; E. J. Rerst et al., *J. Org. Chem*. 29: 3725, 1968; A. M. Felix et al., *J. Org. Chem*. 43: 4194, 1978; D. A. Evans et al., *J. Am. Chem. Soc*. 101: 6789, 1979; international publication number WO 98/02450. Similar reactions are used to convert a bromine at other positions to a hydroxyl. Other substituents are linked to the steroids as described in schemes 1-10.

Alternative routes to introduce a functional group into the 7-position are also suitable. For example, formula 1 compounds that have a double bond at the 5-6 position and are unsubstituted at the 7-position are optionally protected, e.g., hydroxyl groups are protected with acetate, and a ketone is introduced into the 7-position by oxidation with chromic acid essentially as described (U.S. Pat. No. 2,170,124). The carbonyl (=O) at 7 is reduced to a hydroxyl using mild conditions, e.g., Al(Oi-Pr)$_3$, to avoid reducing the 5-6 double bond. The use of stronger reducing conditions, e.g., reduction with LiBH$_4$ in THF, leads to conversion of the 7-carbonyl to hydroxyl and to reduction of the 5-6 double bond and other double bonds that may be present in the molecule.

Selective hydrogenation of a double bond at the 16-17 position without reduction of a double bond at 5-6 is accomplished using H$_2$ and Pd. In general, ketones (=O) can be protected using a glycol, e.g., reaction with ethylene glycol in p-toluenesulfonic acid and benzene, before subsequent oxidation or reduction reactions are conducted.

Various groups that may comprise the formula 1 compounds described herein, e.g., hydroxyl groups or ketones bonded to the steroid nucleus, or substituted alkyl groups, substituted heterocycles, amino acids and peptides, can contain one or more reactive moieties such as hydroxyl, carboxyl, amino or thiol. Intermediates used to make formula 1 compounds may be protected as is apparent in the art. Noncyclic and cyclic protecting groups and corresponding cleavage reactions are described in "Protective Groups in Organic Chemistry", Theodora W. Greene (John Wiley & Sons, Inc., New York, 1991, ISBN 0-471-62301-6) (hereafter "Greene") and will not be detailed here. In the context of the present invention, these protecting groups are groups that can be removed from the molecule of the invention without irreversibly changing the covalent bond structure or oxidation/reduction state of the remainder of the molecule. For example, the protecting group, —R$^{PR}$, that is bonded to an —O— or —NH— group can be removed to form —OH or —NH$_2$, respectively, without affecting other covalent bonds in the molecule. At times, when desired, more than one protecting group can be removed at a time, or they can be removed sequentially. In compounds of the invention containing more than one protecting group, the protecting groups are the same or different.

Protecting groups are removed by known procedures, although it will be understood that the protected intermediates fall within the scope of this invention. The removal of the protecting group may be arduous or straightforward, depending upon the economics and nature of the conversions involved. In general, one will use a protecting group with exocyclic amines or with carboxyl groups during synthesis of a formula 1 compound. For most therapeutic applications amine groups should be deprotected. Protecting groups commonly are employed to protect against covalent modification of a sensitive group in reactions such as alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the invention compounds. Suitable protecting groups and criteria for their selection are described in T. W. Greene and P. G. M. Wuts, Eds. "Protective Groups in Organic Synthesis" 2nd edition, Wiley Press, at pps. 10-142, 143-174, 175-223, 224-276, 277-308, 309-405 and 406-454.

Determination of whether a group is a protecting group is made in the conventional manner, e.g., as illustrated by Kocienski, Philip J.; "*Protecting Groups*" (Georg Thieme Verlag Stuttgart, New York, 1994) (hereafter "Kocienski"), Section 1.1, page 2, and Greene Chapter 1, pages 1-9. In particular, a group is a protecting group if when, based on mole ratio, 90% of that protecting group has been removed by a deprotection reaction, no more than 50%, typically 25%, more typically 10%, of the deprotected product molecules of the invention have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment of the invention, a group is a protecting group if when, based on mole ratio determined by conventional techniques, 90% of that protecting group has been removed by a conventional deprotection reaction, no more than 50%, typically 25%, more typically 10%, of the deprotected product molecules of the invention have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected molecule of the invention.

Protecting groups are also described in detail together with general concepts and specific strategies for their use in Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184, Chapter 6, Amino Protecting Groups, pages 185-243, Chapter 7, Epilog, pages 244-252, and Index, pages 253-260, are incorporated with specificity in the context of their contents. More particularly, Sections 2.3 Silyl Ethers, 2.4 Alkyl Ethers, 2.5 Alkoxyalkyl Ethers (Acetals), 2.6 Reviews (hydroxy and thiol protecting groups), 3.2 Acetals, 3.3 Silylene Derivatives, 3.4 1,1,3,3-Tetraisopropyldisiloxanylidene Derivatives, 3.5 Reviews (diol protecting groups), 4.2 Esters, 4.3 2,6,7-Trioxabicyclo[2.2.2]octanes [OBO] and Other Ortho Esters, 4.4 Oxazolines, 4.5 Reviews (carboxyl protecting groups), 5.2 O,O-Acetals, 5.3 S,S-Acetals, 5.4 O,S-Acetals, 5.5 Reviews (carbonyl protecting groups), 6.2 N-Acyl Derivatives, 6.3 N-Sulfonyl Derivatives, 6.4 N-Sulfenyl Derivatives, 6.5 N-Alkyl Derivatives, 6.6 N-Silyl Derivatives, 6.7 Imine Derivatives, and 6.8 Reviews (amino protecting groups), are each incorporated with specificity where protection/deprotection of the requisite functionalities is discussed. Further still, the tables "Index to the Principal Protecting Groups" appearing on the inside front cover and facing page, "Abbreviations" at page xiv, and "reagents and Solvents" at page xv are each incorporated in their entirety herein at this location.

Typical hydroxy protecting groups are described in Greene at pages 14-118 and include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy) methyl, 2-(Trimethylsilyl)ethoxymethyl, Tetrahydropyranyl, 3-Bromotetrahydropyranyl, Tetrahydrothiopyranyl, 1-Methoxycyclohexyl, 4-methoxytetrahydropyranyl, 4-Methoxytetrahydrothiopyranyl, 4-Methoxytetrahydrothiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p—Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p, p'-Dinitrobenzhydryl, 5-Dibenzosuberyl, Triphenylmethyl, alpha-Naphthyldiphenylmethyl, p-methoxyphenyldiphenylmethyl, Di(p-methoxyphenyl)phenylmethyl, Tri(p-methoxyphenyl)methyl, 4-(4'—Bromophenacyloxy)phenyldiphenylmethyl, 4,4',4"-Tris(4,5-dichlorophthalimidophenyl)methyl, 4,4', 4"-Tris(levulinoyloxyphenyl)methyl, 4,4', 4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl, S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenyl-methoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3-tetramethyl-butyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitro-phenylsulfenate); and Sulfonates (Sulfate, Methanesulfonate (Mesylate), Benzylsulfonate, Tosylate (Tos)).

More typically hydroxy protecting groups include subtituted methyl ethers, substituted benzyl ethers, silyl ethers, and esters including sulfonic acid esters, still more typically, trialkylsilyl ethers, tosylates and acetates.

Typical 1,2- and 1,3-diol protecting groups are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, alpha-Methoxybenzylidene, 1-(N,N-Dimethylamino)ethylidene Derivative, alpha-(N,N-Dimethylamino)benzylidene Derivative, 2-Oxacyclopentylidene); and Silyl Derivatives (Di-t-butylsilylene Group, 1,3-(1,1,3,3-Tetraiso-propyldisiloxanylidene) Derivative, Tetra-t-butoxydisiloxane-1,3-diylidene Derivative, Cyclic Carbonates, Cyclic Boronates, Ethyl Boronate, Phenyl Boronate).

More typically, 1,2- and 1,3-diol protecting groups include epoxides and acetonides.

Typical amino protecting groups are described in Greene at pages 315-385 and include Carbamates (Methyl and Ethyl, 9-Fluorenylmethyl, 9(2-Sulfo)fluoroenylmethyl, 9-(2,7-Dibromo)fluorenylmethyl, 2,7-Di-t-buthyl-[9-(10,10-dioxo-10,10,10,10-tetrahydrothioxanthyl)]-methyl, 4-Methoxyphenacyl); Substituted Ethyl (2,2,2-Trichoroethyl, 2-Trimethylsilylethyl, 2-Phenylethyl, 1-(1-Adamantyl)-1-methylethyl, 1,1-Dimethyl-2-haloethyl, 1,1-Dimethyl-2,2-dibromoethyl, 1,1-Dimethyl-2,2,2-trichloroethyl, 1-Methyl-1-(4-biphenylyl)ethyl, 1-(3,5-Di-t-butylphenyl)-1-methylethyl, 2-(2'- and 4'-Pyridyl)ethyl, 2-(N,N-Dicyclohexylcarboxamido)ethyl, t-Butyl, 1-Adamantyl, Vinyl, Allyl, 1-Isopropylallyl, Cinnamyl, 4-Nitrocinnamyl, 8-Quinolyl, N—Hydroxypiperidinyl, Alkyldithio, Benzyl, p-Methoxybenzyl, p-Nitrobenzyl, p—Bromobenzyl, p-Chorobenzyl, 2,4-Dichlorobenzyl, 4-Methylsulfinylbenzyl, 9-Anthrylmethyl, Diphenylmethyl); Groups With Assisted Cleavage (2-Methylthioethyl, 2-Methylsulfonylethyl, 2-(p-Toluenesulfonyl)ethyl, [2-(1,3-Dithianyl)]methyl, 4-Methylthiophenyl, 2,4-Dimethylthiophenyl, 2-Phosphonioethyl, 2-Triphenylphosphonioisopropyl, 1,1-Dimethyl-2-cyanoethyl, m-Choro-p-acyloxybenzyl, p-(Dihydroxyboryl)benzyl, 5-Benzisoxazolylmethyl, 2-(Trifluoromethyl)-6-chromonyl methyl); Groups Capable of Photolytic Cleavage (m-Nitrophenyl, 3,5-Dimethoxybenzyl, o-Nitrobenzyl, 3,4-Dimethoxy-6-nitrobenzyl, Phenyl(o-nitrophenyl)methyl); Urea-Type Derivatives (Phenothiazinyl-(10)-carbonyl Derivative, N'-p-Toluenesulfonylaminocarbonyl, N'-Phenylaminothiocarbonyl); Miscellaneous Carbamates (t-Amyl, S-Benzyl Thiocarbamate, p-Cyanobenzyl, Cyclobutyl, Cyclohexyl, Cyclopentyl, Cyclopropylmethyl, p-Decyloxybenzyl, Diisopropylmethyl, 2,2-Dimethoxycarbonylvinyl, o-(N,N-Dimethyl-carboxamido)benzyl, 1,1-Dimethyl-3-(N,N-dimethylcarboxamido)propyl, 1,1-Dimethylpropynyl, Di(2-pyridyl)methyl, 2-Furanylmethyl, 2-Iodoethyl, Isobornyl, Isobutyl, Isonicotinyl, p-(p'-Methoxyphenylazo)benzyl, 1-Methylcyclobutyl, 1-Methylcyclohexyl, 1-Methyl-1-cyclopropylmethyl, 1-Methyl-1-(3,5-dimethoxyphenyl)ethyl, 1-Methyl-1-(p-phenylazophenyl)ethyl, 1-Methyl-1-phenylethyl, 1-Methyl-1-(4-pyridyl)ethyl, Phenyl, p-(Phenylazo)-benzyl, 2,4,6-Tri-t-butylphenyl, 4-(Trimethylammonium)benzyl, 2,4,6-Trimethylbenzyl); Amides (N—Formyl, N-Acetyl, N-Choroacetyl, N-Trichoroacetyl, N-Trifluoroacetyl, N-Phenylacetyl, N-3-Phenylpropionyl, N-Picolinoyl, N-3-Pyridylcarboxamide, N-Benzoylphenylalanyl Derivative, N-Benzoyl, N-p-Phenylbenzoyl); Amides With Assisted Cleavage (N-o-Nitrophenylacetyl, N-o-Nitrophenoxyacetyl, N-Acetoacetyl, (N'-Dithiobenzyloxycarbonylamino)acetyl, N-3-(p—Hydroxyphenyl)propionyl, N-3-(o-Nitrophenyl)propionyl, N2-Methyl-2-(o-nitrophenoxy)propionyl, N2-Methyl-2-(o-phenylazophenoxy)propionyl, N-4-Chlorobutyryl, N-3-Methyl-3-nitrobutyryl, N-o-Nitrocinnamoyl, N-Acetylmethionine Derivative, N-o-Nitrobenzoyl, N-o-(Benzoyloxymethyl) benzoyl, 4,5-Diphenyl-3-oxazolin-2-one); Cyclic Imide Derivatives (N-Phthalimide, N-Dithiasuccinoyl, N-2,3-Diphenylmaleoyl, N-2,5-Dimethylpyrrolyl, N-1,1,4,4-Tetramethyl-disilylazacyclopentane Adduct, 5-Substituted 1,3-Dimethyl-1,3,5-triazacyclohexan-2-one, 5-Substituted 1,3-Dibenzyl-1,3,5-triazacyclohexan-2-one, 1-Substituted 3,5-Dinitro-4-pyridonyl); N-Alkyl and N-Aryl Amines (N-Methyl, N-Allyl, N-[2-(Trimethylsilyl)ethoxy]methyl, N-3-Acetoxypropyl, N-(1-Isopropyl-4-nitro-2-oxo-3-pyrrolin-3-yl), Quaternary Ammonium Salts, N-Benzyl, N-Di(4-methoxyphenyl)methyl, N-5-Dibenzosuberyl, N-Triphenylmethyl, N-(4-Methoxyphenyl)diphenylmethyl, N-9-Phenylfluorenyl, N-2,7-Dichloro-9-fluorenylmethylene, N—Ferrocenylmethyl, N-2-Picolylamine N'-Oxide); Imine Derivatives (N-1,1-Dimethylthiomethylene, N-Benzylidene, N-p-methoxybenzylidene, N-Diphenylmethylene, N-[(2-Pyridyl)mesityl]methylene, N,(N',N'-Dimethylaminomethylene, N,N'-Isopropylidene, N-p-Nitrobenzylidene, N-Salicylidene, N-5-Chlorosalicylidene, N-(5-Chloro-2-hydroxyphenyl)phenylmethylene, N-Cyclohexylidene); Enamine Derivative (N-(5,5-Dimethyl-3-oxo-1-cyclohexenyl)); N-Metal Derivatives (N-Borane Derivatives, N-Diphenylborinic Acid Derivative, N—[Phenyl(pentacarbonylchromium- or -tungsten)]carbenzyl, N-Copper or N-Zinc Chelate); N—N Derivatives (N-Nitro, N-Nitroso, N-Oxide); N—P Derivatives (N-Diphenylphosphinyl, N-Dimethylthiophosphinyl, N-Diphenylthiophosphinyl, N-Dialkyl Phosphoryl, N-Dibenzyl Phosphoryl, N-Diphenyl Phosphoryl); N—Si Derivatives; N—S Derivatives; N-Sulfenyl Derivatives (N-Benzenesulfenyl, N-o-Nitrobenzenesulfenyl, N-2,4-Dinitrobenzenesulfenyl, N-Pentachlorobenzenesulfenyl, N-2-nitro-4-methoxybenzenesulfenyl, N-Triphenylmethylsulfenyl, N-3-Nitropyridinesulfenyl); and N-Sulfonyl Derivatives (N-p-Toluenesulfonyl, N-Benzenesulfonyl, N-2,3,6-Trimethyl-4-methoxybenzenesulfonyl, N-2,4,6-Trimethoxybenzenesulfonyl, N-2,6-Dimethyl-4-methoxybenzenesulfonyl, N-Pentamethylbenzenesulfonyl, N-2,3,5,6-Tetramethyl-4-methoxybenzenesulfonyl, N-4-methoxybenzenesulfonyl, N-2,4,6-Trimethylbenzenesulfonyl, N-2,6-Dimethoxy-4-methylbenzenesulfonyl, N-2,2,5,7,8-Pentamethylchroman-6-sulfonyl, N-Methanesulfonyl, N-.beta.-Trimethylsilyethanesulfonyl, N-9-Anthracenesulfonyl, N-4-(4',8'-Dimethoxynaphthylmethyl)benzenesulfonyl, N-Benzylsulfonyl, N-Trifluoromethylsulfonyl, N-Phenacylsulfonyl).

More typically, amino protecting groups include carbamates and amides, still more typically, N-acetyl groups.

Groups capable of biological cleavage typically include prodrugs. A large number of such groups are described in "Design of Prodrugs", Hans Bundgaard (Elsevier, N.Y., 1985, ISBN 0-444-80675-X) (Bundgaard) and will not be detailed here. In particular, Bundgaard, at pages 1-92, describes prodrugs and their biological cleavage reactions for a number of functional group types. Prodrugs for carboxyl and hydroxyl groups are detailed in Bundgaard at pages 3 to 10, for amides, imides and other NH-acidic compounds at pages 10 to 27, amines at pages 27 to 43, and cyclic prodrugs at pages 62 to 70. These moieties are optionally bonded to the steroid at one two or more of $R^1$-$R^6$, $R^{10}$, $R^{15}$, $R^{17}$ and $R^{18}$.

Metabolites. Also falling within the scope of this invention are the in vivo metabolites of the compounds described herein, to the extent such products are novel and unobvious over the prior art. Such products may result for example from the oxidation, reduction, hydrolysis, amidation, esterification and the like of the administered formula 1 compound, due to enzymatic or chemical processes. Accordingly, the invention includes novel and unobvious compounds produced by a process comprising contacting a compound of this invention with a subject, e.g., a human, rodent or a primate, for a period of time sufficient to yield a metabolic product thereof. Such products typically are identified by preparing a radiolabeled (e.g. $^{14}C$, $^{3}H$, $^{131}I$, $^{32}P$, $^{35}S$ or $^{99}Tc$) compound of the invention, administering it parenterally in a detectable dose (e.g. greater than about 0.5 mg/kg) to an animal such as rat, mouse, guinea pig, primate, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, HPLC or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no therapeutic activity of their own.

Formulations and compositions for preparing formulations. While it is possible for the active ingredient(s) to be administered alone it is usual to present them as pharmaceutical formulations. The formulations, both for veterinary and for human use, of the invention comprise at least one active ingredient, i.e., a formula 1 compound, together with one or more acceptable excipients therefor and optionally other therapeutic ingredients.

Another aspect of the invention relates to compositions comprising one or more pharmaceutically acceptable excipients or carriers. One or more formula 1 compound(s) (also referred to as the "active ingredient(s)") are administered by any route appropriate to the condition to be treated. Suitable routes for the non-aqueous liquid formulations and other formula 1 compound formulations include oral, rectal, nasal, topical (including buccal and sublingual), vaginal and parenteral (including subcutaneous, intramuscular, intravenous, intradermal, intrathecal and epidural). In general, the non-aqueous liquid formulations are delivered by a parenteral route. In other embodiments, such as the invention intermittent dosing methods, the formula 1 compound(s) may be present as a non-aqueous liquid formulation, a dry solid formulation that is an oral, topical, parenteral formulation, or as an aqueous liquid formulation that is used parenterally, orally or topically. It will be appreciated that the preferred route may vary with, for example, the subject's pathological condition or weight or the subject's response to therapy with a formula 1 compound or other therapy appropriate to the circumstances.

The formulations include those suitable for the foregoing administration routes. The formulations may conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17$^{th}$ edition, Nema et al., *PDA J. Pharm. Sci. Tech.* 1997 51:166-171. Methods to make invention formulations include the step of bringing into association an active ingredient(s) with the excipient(s). In general the formulations are prepared by uniformly and intimately bringing into association the active ingredient with liquid excipients or finely divided solid excipients or both, and then, if appropriate, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient(s) may also be presented as a bolus, electuary or paste.

A tablet is made by compression or molding, optionally with one or more accessory ingredients. Compressed tablets may be prepared by compressing in a suitable machine the active ingredient(s) in a free-flowing form such as a powder or granules, optionally mixed with a binder, lubricant, inert diluent, preservative, surface active or dispersing agent. Molded tablets may be made by molding in a suitable machine a mixture of the powdered active ingredient(s) moistened with an inert liquid diluent. The tablets may optionally be coated or scored and optionally are formulated so as to provide slow or controlled release of the active ingredient(s) therefrom.

For infections of the eye or other external tissues e.g. mouth and skin, the formulations are typically applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), often 0.2 to 15% w/w and most often 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound that enhances absorption or penetration of the active ingredient(s) through the skin or other affected areas. Examples of such dermal penetration enhancers include dimethyl sulphoxide and related analogs.

The oily phase of the emulsions of this invention may be constituted from known excipients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier, which acts as a stabilizer. Some embodiments include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween60™, Span80™, cetostearyl alcohol, benzyl alcohol, myristyl alcohol, glyceryl mono-stearate and sodium lauryl sulfate.

The choice of suitable oils or fats for the formulation is based on achieving the desired cosmetic properties. Creams are generally a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient(s) is dissolved or suspended in a suitable excipient(s), especially an aqueous solvent for active ingredient(s) that comprise one or more charges at pH values near neutrality, e.g., about pH 6-8. The active ingredient(s) is typically present in such formulations in a concentration of about 0.5-20% w/w, typically about 1-10% w/w, often about 2-5% w/w.

Formulations suitable for topical administration in the mouth include lozenges comprising the active ingredient in a flavored basis, usually sucrose and acacia or tragacanth; pastilles comprising the active ingredient(s) in an inert basis such as gelatin and glycerin, or sucrose and acacia; and mouthwashes comprising the active ingredient in a suitable liquid excipient(s).

Formulations for rectal administration may be presented as a suppository with a suitable base comprising for example cocoa butter or a salicylate.

Formulations suitable for intrapulmonary or nasal administration have a particle size for example in the range of 0.01 to 500 microns (including average particle sizes in a range between 0.01 and 500 microns in 0.1 micron or other increments, e.g., 0.05, 0.1, 0.5, 1, 1.5, 2.0, 2.5, 3.0, 3.5, 4.0, 4.5, 5.0, 6, 7, 8, 9, 10, 20, 25, 30, 35, 50, 75, 100, etc. microns), which is administered by rapid inhalation through the nasal passage or by inhalation through the mouth so as to reach the alveolar sacs. Suitable micronized formulations include aqueous or oily solutions or suspensions of the active ingredient(s). Formulations suitable for aerosol, dry powder or tablet administration may be prepared according to conventional methods and may be delivered with other therapeutic agents such as compounds heretofore used in the treatment or prophylaxis of viral or other infections as described herein. Such formulation may be administered, e.g., orally, parenterally (i.v., i.m., s.c.), topically or by a buccal route.

Formulations suitable for vaginal administration may be presented as pessaries, tampons, creams, gels, pastes, foams or spray formulations containing in addition to the active ingredient(s) such excipients as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampules and vials, and may be stored in a freeze-dried (lyophilized) condition requiring only the addition of the sterile liquid excipient, for example water for injection, immediately prior to use. Extemporaneous injection solutions and suspensions are prepared from sterile powders, granules and tablets of the kind previously described. Unit dosage formulations are those containing a daily dose or unit daily sub-dose, as recited herein, or an appropriate fraction thereof, of the active ingredient(s).

It should be understood that in addition to the ingredients particularly mentioned above the formulations of this invention may include other agents or excipients conventional in the art having regard to the type of formulation in question, for example those suitable for oral administration may include flavoring agents.

The invention further provides veterinary compositions comprising at least one active ingredient as above defined together with a veterinary excipient(s) therefor. Veterinary excipients are materials useful for the purpose of administering the composition and may be solid, liquid or gaseous materials that are otherwise inert or acceptable in the veterinary art and are compatible with the active ingredient(s). These veterinary compositions may be administered orally, parenterally or by any other desired route.

Invention formulations include controlled release pharmaceutical formulations containing an active ingredient(s) ("controlled release formulations") in which the release of the active ingredient(s) is controlled and regulated to allow less frequency dosing or to improve the pharmacokinetic or toxicity profile of a given active ingredient(s).

An effective dose of active ingredient(s) depends at least on the nature of the condition being treated, toxicity, whether the compound(s) is being used prophylactically (lower doses) or against an active infection or condition, the method of delivery, and the pharmaceutical formulation, and will be determined by the clinician using conventional dose escalation studies. It can be expected to be from about 0.05 to about 30 mg/kg body weight per day. For example, for topical delivery the daily candidate dose for an adult human of approximately 70 kg body weight will range from about 1 mg to about 500 mg, generally between about 5 mg and about 40 mg, and may take the form of single or multiple doses or administration sites.

Embodiments include formulations that comprise a liposome or lipid complex that comprises a formula 1 compound (s), e.g., BrEA or an ester, carbamate, carbonate, amino acid or peptide thereof. Such formulations are prepared according to known methods, e.g., U.S. Pat. Nos. 4,427,649, 5,043,165, 5,714,163, 5,744,158, 5,783,211, 5,795,589, 5,795,987, 5,798,348, 5,811,118, 5,820,848, 5,834,016 and 5,882,678. The liposomes optionally contain an additional therapeutic agent(s), e.g., amphotericin B, cis-platin, adriamycin, a protease inhibitor, a nucleoside or a nucleotide analog, such as one of those mentioned herein. Formulations that comprise liposomes can be delivered to a subject by any standard route, e.g., oral, aerosol or parenteral (e.g., s.c., i.v. or i.m.).

Therapeutic applications. The formula 1 compounds, or the biologically active substances produced from these compounds by hydrolysis or metabolism in vivo, have a number of clinical and non-clinical applications. The compounds are generally useful to enhance Th1 immune responses or to reduce Th2 immune responses. As used herein, reference to Th1 or Th2 immune responses means such responses as observed in mammals generally and not as observed in the murine system, from which the Th1 and Th2 terminology originated. Thus, in humans, Th1 cells preferentially display chemokine receptors CXCR3 and CCR5, while Th2 cells preferentially express the CCR4 molecule and a smaller amount of the CCR3 molecule.

Aspects of the invention include compositions that comprise an amount of at least one formula 1 compound effective to enhance the relative proportion of a desired immune cell subset, e.g., $CD4^+$ T cells, NK cells or dendritic cells, or to modulate one or more functions of immune cell subsets and a pharmaceutically acceptable carrier. Typical immune modulation centers on modulating expression of gene(s) that enhance of Th1 immune responses or reduces of Th2 immune responses. Functions that the formula 1 compounds affected include expression of CD molecules or alteration of the proportion of cell subsets, e.g., $CD4^+$ or $CD8^+$ T cells, or their relative numbers in a subject's blood or tissues. CD molecules participate in the function of various immune cell subsets and can be useful as markers for immune function in vivo. In some aspects, the formula 1 compounds activate immune cells which generally alters (increases or decreases) expression of, or changes the numbers of cells that express combinations of, CD4, CD6, CD8, CD25, CD27, CD28, CD30, CD38, CD39, CD43, CD45RA, CD45RO, CD62L, CD69, CD71, CD90 or HLA-DR molecules. Often, the numbers of cells that express these molecules are increased, e.g., CD25, CD16 or CD69. Typically such increases are observed as an increased proportion of circulating white blood cells that express one or more of these molecules. In some cases the number of such molecules per cell is detectably altered.

Expression of one or more adhesion molecules CD2, CD5, CD8, CD11a, CD11b, CD11c, CD18, CD29, CD31, CD44, CD49a, CD49b, CD49c, CD49d, CD49e, CD49f, CD50, CD54, CD58, CD103 or CD104 are also detectably affected after administration of the formula 1 compounds to a subject. Often, the numbers of cells that express these molecules are increased, e.g., CD5 or CD56. The adhesion molecules function in various aspects of immune responses, such as binding to class I MHC molecules, transducing signals between cells or binding to molecules in the extracellular matrix associated with endothelial or other cell types. Administration of the formula 1 compounds to a subject also affects the numbers of certain immune cell subsets, e.g., NK cells (e.g., $CD8^-$, $CD56^+$ or $CD8^+$, $CD56^+$) or lymphokine activated killer cells (LAK). Increased circulating NK or LAK cells are typically observed, which is reflected in increased numbers of cells that express one or more of CD16, CD38, CD56, CD57 or CD94. Also, increased numbers of circulating dendritic cell precursors are observed, as shown by increases in cells that express one or more of CD11c, CD80, CD83, CD106 or CD123. Although one can observe an increased proportion of circulating white blood cells that express one or more of these molecules, in some instances the number of such molecules per cell is detectably altered. Both the cell numbers and the density of CD molecule per cell can also be detectably modulated. Modulation of immune cell subsets typically occurs on intermittent dosing of a formula 1 compound.

Expression of one or more homing receptors such as CD62L is may also be detectably affected after administration of the formula 1 compounds to a subject. Often, the numbers of cells that express these molecules are increased, e.g., CD62L.

Other CD molecules that are modulated by the presence of the formula 1 compounds in a subject include cytokine receptor molecules such as CD115, CDW116, CD117, CD118, CDW119, CD120a, CD120b, CD121a, CD121b, CD122, CD123, CD124, CD125 CD126, CDW127, CDW128 or CDW130. Often, the numbers of receptor molecules per cell will be modulated. For example, receptors for cytokines that mediate Th1 immune responses (e.g., IL-2, $\gamma$IFN) will typically increase in or on cells that mediate Th1 immune responses. Modulation of these molecules may be by direct interactions with a receptor(s) in the cell that expresses the cytokine receptor or indirectly by modulation of cytokine synthesis in the affected cells or in other cells, typically immune cells, that may interact with the cells whose receptor synthesis is being modulated.

Treatment of a subject with a formula 1 compound can result in a change of at least 25-50% above or below (e.g., at least 30% or at least 40% above or below) the control or basal level of some immune cell subsets. For example, increases of more than about 30% in the total numbers of activated $CD8^+$ T cells, e.g., $CD8^+$, $CD69^+$, $CD25^+$ T cells, $CD8^+$, $CD69^+$, $CD25^-$ T cells or $CD8^+$, $CD69^-$, $CD25^+$ T cells, usually occurs by 7 days after a single dose of a formula 1 compound to a subject. Such increases may be greater than 50%, 60% or 100% in the total numbers of activated $CD8^+$ T cells or subsets of activated $CD8^+$ T cells in individual subjects. Typically such increases are about in the total numbers of activated $CD8^+$ T cells or subsets of activated $CD8^+$ T cells averages about 30-40%, with individual subjects experiencing increases over 100% in the numbers of activated $CD8^+$ T cells per unit blood volume compared to the basal level.

Administration of the formula 1 compounds can affect other immune cell subsets. For example, the concentration of circulating $CD4^+$, $CD69^+$, $CD25^-$ (Th1 helper cells) and $CD8^+$, $CD16^+$, $CD38^+$ LAK cells or $CD8^-$, $CD16^+$, $CD38^+$ LAK cells typically increases during or after the course of dosing a subject with a formula 1 compound. Also, $CD8^-$, $CD16^+$, $CD38^+$ and $CD8^+$, $CD16^+$, $CD38^+$ (ADCC effector cells) and low side scatter $Lin^-$, $DR^+$, $CD123^+$ (dendritic precursors) or low side scatter $Lin^-$, $DR^+$, $CD11c^+$ (dendritic cells or precursors) may show modest to significant increases.

In subjects that are immunosuppressed, e.g., from infection (e.g., viral (HIV, HCV), bacterial infection or parasite infection) or from chemotherapy (e.g., an antiviral therapy, a cancer chemotherapy or a radiation therapy), administration of the formula 1 compounds to the subject results in a favorable shift in the balance of Th1 or Th2 responses the subject can mount in the face of immunosuppression. When Th1 responses are suboptimal or insufficient, treatment with a formula 1 compound results in enhancement of Th1 responses or a reduction in Th2 responses. Conversely, when Th2 responses are suboptimal or insufficient, treatment with a formula 1 compound results in enhancement of Th2 responses or a reduction in Th1 responses. The formula 1 compounds can thus be used to shift the nature of a subject's immune response to result in a more balanced immune response from immunosuppression. Alternatively, the compounds can selectively suppress inappropriate or unwanted immune responses. Enhanced Th1 responses appears to be at least partly due to one or more of (i) a reduction in biological restraints, e.g., high levels of IL-4 or IL-10, on Th1 functions by preexisting primed Th1 effector cells, (ii) enhanced differentiation of Th0 cells to Th1 cells or enhanced responses mediated by Th1 cells, (iii) enhanced function of accessory cell function, e.g., antigen presentation by dendritic precursor cells or by macrophages, (iv) enhanced proliferation and differentiation of Th1 precursor or progenitor cells, (v) enhanced IL-12 expression in dendritic cells or their precursors, which results in enhanced differentiation of Th1 cells from Th0 precursors, (vi) enhanced expression or activity of factors associated with Th1 functions, e.g., IL-2, gamma interferon ($\gamma$IFN) or lymphotoxin.

An aspect of the invention methods is an alteration in the expression of IL-4 or IL-10 that occurs after administration of a formula 1 compound, e.g., BrEA, to a subject. A consistent observation is that extracellular IL-4 or IL-10 levels rapidly decrease to levels that are undetectable by ELISA. Intracellular IL-10 levels are reduced to levels that are near or below the limits of detection by flow cytometry. The administration of a formula 1 compound to a subject thus provides a means to inhibit either or both of these interleukins. Such inhibition may be associated with enhancement of Th1 immune responses relative to Th2 or Th0 responses, e.g., in subjects where Th1 responses are suppressed (e.g., from viral, bacterial or parasite infection (HIV, HCV, etc) or chemotherapy) or are otherwise suboptimal. In many subjects, levels of either IL-4 or IL-10, usually IL-10, before dosing with a formula 1 compound is low or undetectable. In these subjects, dosing with the formula 1 compound results in a rapid drop in the interleukin that is detectable, usually IL-4.

In some embodiments, the formula 1 compound(s) is administered to a subject who has a pathogen infection, such as a viral, bacterial or parasite infection. The formula 1 compounds can be considered for use in a broad scope of infections (see, e.g., J. B. Peter, editor, *Use and Interpretation of Laboratory Tests in Infectious Disease*, 5$^{th}$ edition, Specialty Laboratories, Santa Monica, Calif. 90404, 1998, pages 1-271), since the compounds generally enhance Th1 immune responses and/or reduce Th2 immune responses. Difficulty in treating some infections, e.g., progressive toxoplasmic encephalitis, malaria, tuberculosis, leishmaniasis and schistosomiasis, often appear to be associated with unwanted Th2 immune responses. Typically unwanted Th2 immune responses are associated with, or caused by, increased expression of one or more cytokines or interleukins such as IL-4 and IL-10. Administration of a formula 1 compound, or other compounds disclosed herein, will generally reduce the expression of one or more of the Th2-associated cytokines or interleukins. At the same time, the compounds enhance the expression of one or more cytokines or interleukins associated with Th1 immune responses. Because of their capacity to modulate Th1 and Th2 immune responses, the compounds are useful for a variety of clinical conditions, e.g., infection, immunosuppression or cancer, where an enhanced Th1 immune response is desired. For example, in disseminated or diffuse tuberculosis, a reduced Th2 response would be desirable to allow a patient to slow progression of the disease or to clear infected cells more efficiently.

An aspect of the invention provides embodiments where a formula 1 compound and a glutathione reductase inhibitor such as buthathione sulfoximine [$CH_3$—$(CH_2)_3$—$S(=O)$ $(=NH)$—$(CH_2)_2$—$CHNH_2$—$C(O)$—$OH$] are administered to a subject to treat infections, e.g., a parasite infection such as malaria, *Toxoplasma*, *Cryptosporidium*, or to treat a cancer or malignancy. The decreased supply of reduced glutathione may enhance phagocytosis by macrophage, possibly due to enhanced oxidative damage in infected cells or in replicating malignant cells. Alternatively, the use of a glutathione reductase inhibitor may result in improved recognition of infected or malignant cells by the immune system. A formula 1 compound, such as BrEA, and buthathione sulfoximine are used, e.g., to enhance clearance of ring stage malaria from infected cells or to enhance immune system recognition of malignant cells compared to the use of the formula 1 compound alone. The infections and malignancies where these embodiments apply are as described herein.

Another aspect of the invention provides for the use of a formula 1 compound and a flavonoid, e.g., a naragin flavonoid, to enhance the bioavailability of the formula 1 compound. In these embodiments, the an effective amount of a flavonoid is administered to a subject who is receiving a formula 1 compound. Typically about 1-10 mg of flavonoid per kg of body weight is administered to the subject a flavonoid such as bavachinin A, didymin (isosakuranetin-7-rutinoside or neoponcirin), flavanomarein (isookanine-7-glucoside), flavanone azine, flavanone, diacetylhydrazone, flavanone hydrazone, silybin, silychristin, isosilybin or silandrin. The flavonoid compound is typically administered with the formula 1 compound or a few hours, e.g., about 1, 2 or 3 hours, before the formula 1 compound is administered to the subject.

Liposome formulations can be used to enhance delivery of the formula 1 compound(s) to certain cell types such as tumor cells (see e.g., U.S. Pat. No. 5,714,163) or to cells of the reticuloendothelial system ("RES"). The RES includes macrophages, mononuclear phagocytic cells, cells lining the sinusoids of the spleen, lymph nodes, and bone marrow, and the fibroblastic reticular cells of hematopoietic tissues. In general, RES cells are phagocytic and they are targets for targeted delivery of a formula 1 compound(s) in vitro or in vivo using liposomes, or other compositions or formulations. Thus, one can deliver formula 1 compound to a neoplasm that is derived from reticuloendothelial tissue (reticuloendothelioma). The liposomes may also optionally comprise a peptide from an infectious agent such as a malaria parasite. The peptides may facilitate the generation of a MHC class II and B cell response.

Vaccine adjuvants. The compounds disclosed herein may also be used as vaccine adjuvants with immunogens or components of immunogenic compositions to prepare antibodies capable of binding specifically to the formula 1 compounds, their metabolic products which retain immunologically recognized epitopes (sites of antibody binding) or to standard antigens that are used for vaccination against, e.g., infectious agents or malignant cells. The immunogenic compositions therefore are useful as intermediates in the preparation of antibodies that bind to formula 1 compounds for use, e.g., in diagnostic, quality control, or the like, methods or in assays for the compounds or their novel metabolic products. In addition, the compounds are useful for raising antibodies against otherwise non-immunogenic polypeptides, in that the compounds may serve as haptenic sites stimulating an immune response.

The hydrolysis products of interest include products of the hydrolysis of the protected acidic and basic groups discussed above. In some embodiments the acidic or basic amides comprising immunogenic polypeptides such as albumin, keyhole limpet hemocyamin and others described below generally are useful as immunogens. The metabolic products described above may retain a substantial degree of immunological cross reactivity with the compounds of the invention. Thus, the antibodies of this invention will be capable of binding to the unprotected compounds of the invention without binding to the protected compounds; alternatively the metabolic products, will be capable of binding to the protected compounds and/or the metabolic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se. Any of the methods used heretofore for conjugating haptens to immunogenic polypeptides or the like are suitably used here, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or $C_{2-8}$ alkyl-N=C=N—$C_{2-8}$ alkyl are useful in preparing the conjugates of this invention. The conjugates comprise a compound of the invention attached by a bond or a linking group of 1-100, typically, 1-25, more typically about 1-10 carbon atoms to the immunogenic substance. The conjugates are separated from starting materials and by products using chromatography or the like, and then are sterile filtered and vialed for storage. Synthetic methods to prepare hapten-carrier immunogens have been described, see e.g., G. T. Hermanson, *Bioconjugate Techniques* Academic Press, 1996, pages 419-493.

The compounds of this invention are cross-linked for example through any one or more of the following groups: a hydroxyl group, a carboxyl group, a carbon atom, or an amine group. Included within such compounds are amides of polypeptides where the polypeptide serves as an above-described protecting group.

Animals are typically immunized against the immunogenic conjugates or derivatives and antisera or monoclonal antibodies prepared in conventional fashion.

In embodiments where the formula 1 compounds are used as adjuvants to enhance a subject's immune response to antigens such as proteins, peptides or virus or cell preparations, the formula 1 compound is administered at about the same time that the antigen is delivered to the subject, e.g., within about 7 days of when the antigen is administered to the subject. In some embodiments, the formula 1 compound is administered 1, 2, 3 or 4 days before the antigen is administered to the subject. In other embodiments, the formula 1 compound is administered on the same day that the antigen is administered to the subject. In additional embodiments, the formula 1 compound is administered 1, 2 or 3 days after the antigen is administered. The formula 1 compound can be administered to the subject using any of the formulations or delivery methods described herein or in the references cited herein. Aspects of the invention include compositions or formulations that comprise a formula 1 compound, one or more excipients and an antigen or antigen preparation such as disrupted cells or viruses or such as attenuated viruses or a DNA vaccine.

Related embodiments include a method comprising administering to a subject (e.g., a mammal such as a human or a primate), or delivering to the subject's tissues, an effective amount of a formula 1 compound and a specific antigen. These methods are useful to enhance the subject's immune response to the antigen. Immune responses that are enhanced include a mucosal immune response to an antigen such as a protein, peptide, polysaccharide, microorganism, tumor cell extract or lethally radiated tumor or pathogen cells (e.g., antigens or cells from melanoma, renal cell carcinoma, breast cancer, prostate cancer, benign prostatic hyperplasia, virus or bacteria, or other tumor or pathogen as disclosed herein). Aspects of these embodiments include enhancement of the subject's immune response when an antigen or immunogen is administered intranasally or orally. In these aspects, the formula 1 compound is administered about simultaneously with the antigen or within about 3-72 hours of antigen administration. The use of immune modulating agents to enhance immune responses to a vaccine has been described, e.g., U.S. Pat. No. 5,518,725.

Other uses for the formula 1 compound(s) include administering the compound(s) to a subject who suffers from a pathological condition(s). The treatment may treat or ameliorate the source of the condition(s) and/or symptoms associated with the pathological condition(s) such as infection with a pathogen(s) (viruses, bacteria, fungi), a malignancy, unwanted immune response, i.e., an immune response that causes pathology and/or symptoms, e.g., autoimmune conditions or allergy or conditions such as hypoproliferation conditions, e.g., normal or impaired tissue growth, or wound healing or burn healing, or in immunosuppression conditions, e.g., conditions characterized by an absence of a desired response and/or an inadequate degree of a desired response.

Many cancers or malignancies are associated with an unwanted Th2 immune response or a deficient Th1 response. An insufficient Th1 immune response may play a role in the capacity of malignant cells to escape immune surveillance. These conditions include non-small cell lung cancer, bronchogenic carcinoma, renal cell cancer or carcinoma, lymphoma, glioma, melanoma, pancreatic or gastric adenocarcinoma, human pappilomavirus associated cervical intraepithelial neoplasia, cervical carcinoma, hepatoma and cutaneous T-cell lymphoma (mycosis fungoides, Sezary syndrome).

In some of these embodiments, the subject's hyperproliferation or malignant condition may be associated with one or more pathogens. For example hepatocellular carcinoma associated with HCV or HBV, Kaposi's sarcoma associated with HIV-1 or HIV-2, T cell leukemia associated with HTLV I, Burkitt's lymphoma associated with Epstein-Barr virus or papillomas or carcinoma associated with papilloma viruses (HPV 6, HPV 11, HPV 16, HPV 18, HPV 31, HPV 45) or gastric adenocarcinoma or gastric MALT lymphoma associated with *Helicobacter pylori* infection. In other embodiments, the formula 1 compound(s) is administered to a subject who has a hyperproliferation condition that appears to not be associated with a pathogen, e.g., melanoma, or a cancer or precancer arising in the throat, esophagus, stomach, intestine, colon, ovary, lung, breast or central nervous system.

In an exemplary embodiment, human patients suffering from melanoma or melanoma precursor lesions are treated with a topical cream formulation containing 2-20% BrEA (w/w). The cream is applied to primary nevi (dysplastic nevi or common acquired nevi), primary cutaneous melanomas, secondary cutaneous melanomas and the skin surrounding the nevi or melanomas. The areas to be treated are washed with soap or swabbed with an alcohol (e.g., ethanol or isopropanol) prior to administering the cream, when this is practical. About 0.1-0.4 g of cream, depending on the size of the treated area, is applied once or twice per day per treated region or lesion for about 10-20 days. The cream is left undisturbed at the administration site for about 15-30 minutes before the patient resumes normal activity. Progression of the nevi and melanomas is retarded in the majority of patients and significant regression is observed for some lesions. Following initial treatment, the formulation is administered every other day for at least 1 to 4 months using the same dosing described for the initial round of treatment. For these patients, standard therapy to treat precursor lesion or melanoma, e.g., dimethyl triazeno imidazole carboxamide or nitrosoureas (e.g., BCNU, CCNU), is optionally started or continued according to the recommendations of the patient's doctor and with the patient's informed approval. In cases where a tumor or precursor lesion is surgically removed and the site has sufficiently healed, the patient optionally continues using the topical formulation at the site and the adjacent surrounding area every other day for at least 1 to 4 months. In some of these embodiments, a formula 1 compound(s) is administered daily continuously as an oral composition or formulation, e.g., for a formula 1 compound(s) that is a new compound per se. BrEA is optionally also administered systemically using, e.g., a formulation described in the examples below to deliver 1-5 mg/kg/day every other day for about 1 week to about to 4 months, e.g., in the case of malignant melanoma.

Insufficient Th1 immune responses are often associated with viral infection. Viral infections may arise from DNA or RNA viruses, e.g., herpesviruses, hepadnaviruses, adenoviruses, retroviruses, togaviruses, alphaviruses, arboviruses, flaviviruses, rhinoviruses, papillomaviruses and/or pestiviruses. Exemplary viruses have been described. See, for example B. N. Fields, et al., editors, *Fundamental Virology*, $3^{rd}$ edition, 1996, Lippencott-Raven Publishers, see chapter 2 at pages 23-57, including table 4 at pages 26-27, table 5 at pages 28-29, chapter 17 at pages 523-539, chapters 26-27 at pages 763-916, chapter 32 at pages 1043-1108 and chapter 35 at pages 1199-1233. As used herein, retroviruses include human and animal viruses, e.g., HIV-1, HIV-2, LAV, human T-cell leukemia virus I ("HTLV I"), HTLV II, HTLV III, SIV, SHIV, FIV, FeLV. Additional viruses, including their genogroups, clades, isolates, strains and so forth, that may establish a virus infection include human hepatitis C virus ("HCV"), human hepatitis B virus ("HBV"), human hepatitis A virus ("HAV"), duck hepatitis virus, woodchuck hepatitis virus, human ("HPV", e.g., HPV 6, HPV 11, HPV 16, HPV 18, HPV 31, HPV 45) or animal papilloma viruses, Poliovirus, Herpes simplex virus 1 ("HSV-1"), Herpes simplex virus 2 ("HSV-2"), human Herpesvirus 6 ("HHV-6"), human Herpesvirus 8 ("HHV-8"), Dengue virus (types 1-4), Western Equine Encephalitis Virus, Japanese Encephalitis Virus, Yellow Fever Virus and Bovine Viral Diarrhea Virus.

Other conditions where an immune imbalance or an excessive Th2 immune response is involved include autoimmune diseases such as SLE (systemic lupus erythematosus), osteoporosis, multiple sclerosis, myasthenia gravis, Graves disease, mite-associated ulcerative dermatitis, rheumatoid arthritis and osteoarthritis. Excessive Th2 immune responses are also associated with an unwanted symptom or pathology, e.g., fatigue, pain, fever or an increased incidence of infection, that is associated with aging, allergy and inflammation conditions such as allergic bronchopulmonary aspergillosis in cystic fibrosis patients, atopic asthma, allergic respiratory disease, allergic rhinitis, atopic dermatitis, subepithelial fibrosis in airway hyperresponsiveness, chronic sinusitis, perennial allergic rhinitis, Crohn's disease (regional enteritis), ulcerative colitis, inflammatory bowel disease, fibrosing alveolitis (lung fibrosis).

Other clinical indications that have an association with or have a symptom(s) that is consistent with an excessive Th2 immune response, e.g., fatigue, pain, fever or an increased incidence of infection, are schizophrenia, acute myelitis, sarcoidosis, burns, trauma (e.g., bone fracture, hemorrhage, surgery) and immune responses to xenotransplantation. This common underlying immune component in at least part of the pathology of all of these conditions allows a single agent to be effectively used to treat the condition or to treat one or more symptoms that are associated with insufficient Th1 responses or with excessive Th2 responses. In all of the conditions where an insufficient Th1 response or an unwanted Th2 response is present, amelioration of one or more symptoms associated with the condition is accomplished by administering an effective amount of a formula 1 compound according to the methods described herein. Thus, one may intermittently administer a formula 1 compound using a formulation and a route of administration as described herein.

In some applications, the formula 1 compound(s) may directly and/or indirectly interfere with replication, development or cell to cell transmission of a pathogen such as a virus or a parasite (malaria). Improvement in a subject's clinical condition may arise from a direct effect on an infectious agent or on a malignant cell. Interference with cellular replication can arise from inhibition of one or more enzymes that a parasite or an infected cell uses for normal replication or metabolism, e.g., glucose-6-phosphate dehydrogenase, which affects cellular generation of NADPH (see, e.g., Raineri et al., *Biochemistry* 1970 9: 2233-2243). This effect may contribute to cytostatic effects that some formula 1 compounds can have. Modulation of cellular enzymes expression or activity may also interfere with replication or development of a pathogen, e.g., HIV or malaria parasites or with replication or development of neoplastic cells, e.g., inhibition of angiogenesis. Clinical improvement will also generally result from an enhanced Th1 immune response.

In other applications, embodiments are a method comprising contacting a formula 1 compound(s) with a cell(s), whereby the formula 1 compound(s) forms a complex with a steroid hormone receptor or results in the modulation of a biological activity. The steroid hormone receptor may be an orphan nuclear hormone receptor that displays a moderate or high binding affinity for the formula 1 compound(s). In some embodiments, the steroid receptor is a known steroid receptor. Biological effects from interaction of a formula 1 compound and a receptor can lead to interference with the replication or development of a pathogen or the cell(s) itself. For example, expression of HIV transcripts in HIV-infected cells may be altered. The receptor-formula 1 compound complex may directly interfere with LTR-dependent transcription of HIV genes, leading to reduced viral replication.

Invention embodiments include compositions comprising a partially purified or a purified complex comprising a formula 1 compound and a steroid receptor. Such a steroid receptor(s) may be an orphan steroid receptor or a characterized steroid receptor, where either type binds the formula 1 compound with a moderate or high binding affinity, e.g., less than about $0.5\text{-}10\times10^{-6}$ M, usually less than about $1\times10^{-7}$ M, or, for higher affinity interactions, less than about $0.01\text{-}10\times10^{-9}$ M. The formula 1 compound(s) may also enhance immune responses such that both immune responses and altered intracellular conditions simultaneously exist to ameliorate one or more of the pathological conditions described herein.

The formula 1 compounds may be used to identify receptors that modulate biological responses, e.g., receptors that participate in effecting enhanced Th1 cytokine synthesis. Invention embodiments include a method, "Method 1", which permits the determination of one or more effects of a test compound on a steroid receptor in various biological systems. Generally, the test compound is a formula 1 compound. Such systems include cells containing a DNA construct that constitutively or inducibly expresses a steroid receptor(s) of interest, e.g., SXR, CARβ, RXR, PXR, PPARα or mixtures or dimers thereof, e.g., SXR/RXR. In other biological systems, the steroid receptor can be under the transcriptional control of a regulatable promoter. Alternatively, the expression another gene such as a steroid-inducible gene, e.g., a steroid-inducible cytochrome P-450. For this method, a source of steroid receptors is generally combined with a means of monitoring them, e.g., by measuring the transcription of a gene regulated by the receptor. Cells that comprise the steroid receptor and optional monitoring means are sometimes referred to herein as the "biological system." Sources of steroid receptors include cell lines and cell populations that normally express the steroid receptor of interest and extracts obtained from such cells. Another source for a useful biological system for purposes of this method is tissues from experimental animals that express the receptor.

In one aspect, method 1 allows one to determine one or more effects of a formula 1 compound on a steroid receptor using a method that comprises (a) providing a biological system, e.g., a cell extract, cells or tissue, comprising cells having a plurality of steroid receptors that comprise monomers, homodimers or heterodimers that comprise a steroid receptor, e.g., SXR, CAR-β, RXR, PPARα, PXR or dimers that comprise one or more of these; (b) activating or inhibiting the plurality of monomers, homodimers or heterodimers that comprise the steroid receptor by contacting the cells with a steroid receptor (e.g., SXR, CAR-β, RXR, PPARα or PXR) agonist or antagonist; (c) removing substantially all of the steroid receptor agonist or antagonist from the cells; (d) determining an activity of the plurality of monomers, homodimers or heterodimers that comprise the steroid receptor while in an activated state in the absence of agonist or antagonist; (e) exposing the cells to the test compound; (f) determining at least one effect of the test compound on the activity of the plurality of monomers, homodimers or heterodimers that comprise one or more of the steroid receptors while they remain substantially free of agonist or antagonist; and (g) optionally classifying the test compound as an agonist or an antagonist of the steroid receptor, or a neutral compound having little or no detectable effect.

The effects that method 1 can measure include determining or measuring an effect on a gene whose expression is affected by the steroid receptor. The gene could be a gene associated with a pathological condition such as an infectious agent, an immune disorder or a hyperproliferation condition.

Thus, another aspect of method 1, "method 1A", is determining if a chemical not previously known to be a modulator of protein biosynthesis can transcriptionally modulating the expression of a gene that encodes a protein associated with the maintenance or treatment of one or more symptoms of a pathological condition. This method comprises: (a) contacting a sample which comprises eucaryotic cells with a formula 1 compound, wherein the eucaryotic cells comprise a plurality of steroid receptor proteins and a DNA construct containing in 5' to 3' order (i) a modulatable transcriptional regulatory sequence of the gene encoding the protein of interest, (ii) a promoter of the gene encoding the protein of interest, and (iii) a reporter gene which expresses a polypeptide capable of producing a detectable signal, coupled to, and under the control of, the promoter, under conditions such that the chemical, if capable of acting as a transcriptional modulator of the gene encoding the protein of interest, causes a measurable or detectable signal to be produced by the polypeptide expressed by the reporter gene; (b) quantitatively determining the amount of the signal so produced; and (c) optionally comparing the amount so determined with the amount of produced signal detected in the absence of any chemical being tested or upon contacting the sample with other chemicals so as to identify the chemical as one that causes a change in the detectable signal produced by the polypeptide, and determining whether the chemical specifically transcriptionally modulates expression of the gene associated with the maintenance or treatment of one or more symptoms of the pathological condition.

In conducting method 1A, one typically contacts a sample that contains a predefined number of identical or essentially identical eucaryotic cells with a predetermined concentration of a compound of formula 1. The eucaryotic cells comprise a DNA construct that is made using conventional molecular biology methods and protocols. Generally the DNA construct contains in 5' to 3' order (i) a transcriptional regulatory sequence that participates in modulating expression of the gene that is associated with maintaining or treating the pathological condition, (ii) the gene's promoter, and (iii) a reporter gene which expresses a polypeptide capable of producing a detectable signal, coupled to, and under the control of, the promoter. The construct is maintained under conditions such that the formula 1 compound, if capable of acting as a transcriptional modulator of the gene encoding the protein of interest, causes a measurable or detectable signal to be produced by the polypeptide expressed by the reporter gene. Once sufficient time for generation of a detectable response or signal has passed, one can determine the amount of the signal produced. Typically the response or signal is measured quantitatively, but a qualitative measurement can be useful for rapid screening purposes.

For method 1A, one can also optionally compare the detectable signal with the amount of produced signal that (i) one detects in the absence of any formula 1 compound or (ii) when contacting the sample with other chemicals, which identifies the formula 1 compound as a chemical that causes a change in the detectable signal the polypeptide produces. One then typically determines whether the formula 1 compound specifically transcriptionally modulates expression of the gene associated with the maintenance or treatment of one or more symptoms of the pathological condition.

Other aspects of the method 1 and 1A include a screening method comprising separately contacting each of a plurality of identical, essentially identical or different samples, each sample containing a predefined number of such cells with a with a predetermined concentration of each different formula 1 compound to be tested, e.g., wherein the plurality of samples comprises more than about $1 \times 10^3$ or more than about $1 \times 10^4$ samples or about $0.5-5 \times 10^5$ samples. In other aspects one determines the amount of RNA by quantitative polymerase chain reaction. In any of methods 1 or 1A, a formula 1 compound such as any one of those described or named herein may be utilized.

Aspects of the invention include another method, "method 2", which centers on identifying a gene whose expression is modulated by a candidate binding partner for infectious disease therapeutic agents. Typically the binding partner is a steroid receptor, e.g., a monomer, homodimer or heterodimer that comprises SXR, CAR-β, PXR, PPARα or RXR or a homolog or isoform thereof. The steroid receptor is typically present as a complex that comprises, e.g., the formula 1 compound and the regulated gene's DNARS, which the steroid receptor, or a complex that comprises the steroid receptor, recognizes and specifically binds to. Such complexes can also comprise a transcription factor that binds to the steroid receptor or to nucleic acid sequences adjacent to or near the DNARS. Exemplary transcription factors that may be present include one or more of ARA54, ARA55, ARA70, SRC-1, NF-κB, NFAT, AP1, Ets, p300, CBP, p300/CBP, p300/CPB-associated factor, SWI/SNF and human homologs of SWI/SNF, CBP, SF-1, RIP140, GRIP1 and Vpr. In general, one provides a first and a second group of cells in vitro or in vivo and contacts the first group of cells with the infectious disease therapeutic agent, but does not contact the second group of cells in vitro or in vivo with the infectious disease therapeutic agent. Recovering RNA from the cells, or generating cDNA derived from the RNA, is accomplished by conventional protocols. Analysis of the RNA, or cDNA derived from the RNA, from the first and the second group of cells identifies differences between them, which one can use to identify a gene whose regulation is modulated by the candidate binding partner for the infectious disease therapeutic agent or any DNARS associated with that gene.

An aspect of method 2 is determining the capacity of a formula 1 compound to modulate, or participate in the modulation of, the transcription of a gene associated with the maintenance or treatment of one or more symptoms of a pathological condition. It is expected that in general, the formula 1 compounds will cause an increase in the transcription of such genes. The pathological condition is typically one associated with an infectious agent, e.g., virus, parasite or bacterium, but can also include an immune condition, e.g., an autoimmune condition or an immune deficiency. The pathological condition may also be an insufficient immune response to an infection or an insufficient response to a hyperproliferation condition or malignancy. Other pathological conditions that one can apply the method to are inflammation conditions.

In some aspects, the formula 1 compounds used in method 2 will be labeled. Such compounds are prepared by conventional methods using standard labels, such as radiolabels, fluorescent labels or other labels as described herein and in the cited references.

An embodiment of method 2 involves analyzing the RNA, or cDNA derived from it, by subtraction hybridization. In this embodiment, the RNA or cDNA obtained from the first and second groups of cells is hybridized and the resulting duplexes are removed. This allows recovery of nucleic acids that encode genes whose transcription is modulated by the candidate binding partner, which is usually a steroid receptor. One can use conventional methods to amplify and obtain nucleic acid and protein sequence information from the nucleic acids recovered by this method. The nucleic acid sequences that are transcriptionally induced or repressed by the formula 1 compound are candidate binding partners.

A transcriptionally induced gene(s) will be enriched in the group 1 cells treated with the formula 1 compound, while any repressed gene(s) will be depleted or absent. In these embodiments, the RNA recovered after removal of duplexes is typically amplified by standard RT-PCR or PCR protocols. These protocols typically use specific sets of random primer pairs, followed by analysis of the amplified nucleic acids by gel electrophoresis. Nucleic acids that are induced by the formula 1 compound will appear as a band(s), usually duplex DNA, that is not present in the control or second set of cells. Nucleic acids that are transcriptionally repressed by the formula 1 compound's binding partner will be depleted or absent in the first group of cells. Once such gene candidates are identified, they can be cloned and expressed and the capacity of the DNARS associated with the gene to form a complex that comprises a candidate binding partner and an optionally labeled formula 1 compound is analyzed by conventional methods, e.g., equilibrium dialysis, affinity chromatography using, e.g., the DNARS immobilized on a column, or coprecipitation of complexes that comprise an optionally labeled DNARS and candidate binding partner using anti-binding partner antibodies. Nucleic acid sequence analysis is usually used to identify regions adjacent to the coding regions of the regulated gene to identify any DNARS associated with the gene. The identity of a DNARS can be established by the binding to the DNARS of complexes that comprise a candidate binding partner, e.g., a steroid receptor, and optionally also comprise a formula 1 compound. The location and identity of the DNARS can be accomplished by DNA footprinting or other methods for detecting binding interactions. The DNARS, the receiver or the formula 1 compound can be labeled in these variations of method 2.

In general, the second group of cells will be identical or essentially identical to the first group of cells. In embodiments (for both methods 1 and 2) where the cells are "essentially identical", the first or the second group of cells may differ from each other by the presence or absence of a DNA construct(s) that expresses (i) a steroid receptor and/or (ii) an easily detected protein, e.g., a β-galactosidase, a peroxidase, a phosphatase, or a chloramphenicol acetyltransferase, whose transcriptional regulation is usually modulated by a steroid receptor. In these embodiments, the difference between the first and the second group of cells is used to facilitate the analysis of the biological effects of the formula 1 compound and the steroid receptor binding partner. Groups of cells are considered "identical" if they do not display known or obvious morphological or genetic differences.

Usually, the second group of cells will serve as a control, and they will thus not be exposed to any formula 1 compound before obtaining the RNA or cDNA. But, for some embodiments, one can expose the second group of cells to a known agonist or antagonist of the steroid receptor binding partner. This allows one to compare the potency of the formula 1 compound with the potency of the agonist or antagonist.

In other embodiments, one can modify method 2 by providing a third group of cells, which is optionally used as an untreated control when the second group of cells is treated with a steroid receptor agonist or antagonist. In these embodiments, one will typically compare the effect of the formula 1 compound and the agonist or the antagonist of the expression of a gene or DNA construct. The DNA construct would comprise a promoter or other regulatory sequences that are subject to transcriptional modulation, usually increase transcription, by the formula 1 compound in concert with its binding partner.

Exemplary mammalian and other steroid receptors, including orphan steroid receptors, their homologs, isoforms and co-factors (e.g., co-repressors, transcription factors, gene promoter regions or sequences) that these complexes can comprise are steroidogenic factor-1 (SF-1), chicken ovalbumin upstream promoter-transcription factor (COUP-TFI) and its mammalian homologs, silencing mediator for retinoid and thyroid hormone receptor (SMRT) and its mammalian homologs, NF-E3, COUP-TFII and its mammalian homologs, testicular orphan receptor TR2, thyroid hormone α1 (TR α1), retinoid X receptor α, TR α1/RXR α heterodimer, direct repeat-4 thyroid hormone response element (DR4-TRE), estrogen receptor (ER), estrogen receptor related α (ERRα), estrogen receptor related β (ERRβ), steroid xenobiotic receptor (SXR), hepatocyte nuclear factor 4 (HNF-4), hepatocyte nuclear factor 3 (HNF-3), liver X receptors (LXRs), LXRα, estrogen receptor α (ERα), constitutive androstane receptor-β, (CAR-β), RXR/CAR-β heterodimer, short heterodimer partner (SHP), SHP/ERα heterodimer, estrogen receptor β, SHP/ERβ heterodimer, testicular orphan receptor TR4, TR2/TR4 heterodimer, pregnane X receptor (PXR) and isoforms, cytochrome P-450 monooxygenase 3A4 gene promoter region and isoforms, HNF-4/cytochrome P-450 monooxygenase 3A4 gene promoter region and isoforms complex, HIV-1 long terminal repeat (LTR), HIV-2 LTR, TR2/HIV-1 LTR complex, TR4/HIV-1 LTR complex, TR4/HIV-1 LTR complex, TR α1/TR4/HIV-1 LTR complex, TR2 isoforms (TR2-5, TR7, TR9, TR11), DAX-1, DAX-1/steroidogenic acute regulatory protein gene promoter region, RevErb, Rev-erbA α, Rev-erb β, steroid receptor coactivator amplified in breast cancer (AIB 1), p300/CREB binding protein-interacting protein (p/CIP), thyroid hormone receptor (TR, T3R), thyroid hormone response elements (T3REs), constitutive androstane receptor (CAR), *Xenopus* xSRC-3 and mammalian (human) homologs, TAK1, TAK1/peroxisome proliferator-activated receptor α (PPARα) complex, PPARα/RXRα complex, TAK-1/RIP-140 complex, retinoic acid receptor (RAR), RARβ, TR4/RXRE complex, SF-1/steroid hydroxylase gene promoter region, SF-1/oxytocin gene promoter region, SF-1/ACTH receptor gene promoter region, rat Ear-2 and mammalian homologs, human TR3 orphan receptor (TR3), RLD-1, OR-1, androgen receptor, glucocorticoid receptor, estrogen receptor, progesterone receptor, mineralcorticoid receptor, OR1, OR1/RXRα complex, TIF-1, CBP/P300 complex, TRIP1/SUG-1 complex, RIP-140, SRC1α/P160 complex and TIF-2/GRIP-1 complex, RAR/N-CoR/RIP13 complex, RAR/SMRT/TRAC-2 complex, and the DNARS 5' AGGTCANAGGTCA 3' or 5' TGCACGTCA 3'. One of these complexes can be included in invention methods when, e.g., they are performed in cell-free assays. Formation of these complexes in cells is facilitated by inserting into the cells a DNA construct(s) that expresses one or more of these proteins, e.g., mammalian or yeast cells containing a stable DNA construct or a construct used for transient transfection assays. Methods to perform assays or to induce biological responses in vitro or in vivo using the formula 1 compounds as agonists, antagonists or as reference standards are essentially as described, see, e.g., U.S. Pat. Nos. 5,080,139, 5,696,133, 5,932,431, 5,932,555, 5,935,968, 5,945,279, 5,945,404, 5,945,410, 5,945,412, 5,945,448, 5,952,319, 5,952,371, 5,955,632, 5,958,710, 5,958,892, 5,962,443; International Publication Numbers WO 96/19458, WO 99/41257, WO 99/45930. The complexes or assay systems, that comprise a formula 1 compound and that are employed in the practice of these methods are included as aspects of the invention.

The formula 1 compounds typically interact with one or more biological ligands to effect a biological response. To facilitate the identification of candidate binding partners for the formula 1 compounds, one can use a radiolabeled formula 1 compound that is linked to a support, usually a solid support, as a means to recover the candidate binding partners. The formula 1 compound can be linked to the support through, e.g., the 3-, 7-, 16- or 17-position of the steroid nucleus. Linking agents are known for such uses and include homobifunctional and heterobifunctional agents, many of which are commercially available. The linker one uses will typically comprise about 2-20 linked atoms. The linked atoms usually comprise mostly carbon, with one, two or three oxygen, sulfur or nitrogen atoms that replace one or more carbon atoms. One can use a cDNA expression library that one has made from suitable cells or tissues as a source of candidate binding partners. The cells or tissues can be obtained from a mammalian or a vertebrate host, e.g., human, mouse, bird, primate, or from other sources, e.g., insects (e.g., *Drosophila*), other invertebrates (e.g., yeast, bacteria, *Mycoplasma* sp., *Plasmodium* sp., *Tetrahymena* sp., *C. elegans*) or other organism groups or species listed herein or in the cited references. Suitable tissues include skin, liver tissue or cells, including hepatocytes and Kupfer cells, fibrocytes, monocytes, dendritic cells, kidney cells and tissues, brain or other central nervous system cells or tissues, including neurons, astrocytes and glial cells, peripheral nervous system tissues, lung, intestine, placenta, breast, ovary, testes, muscle, including heart or myocyte tissue or cells, white blood cells, including T cells, B cells, bone marrow cells and tissues, lymph tissues or fluids and chondrocytes.

Typically a candidate binding partner that one isolates from a non-human source will have a human homolog that has similar binding properties for the formula 1 compound. Non-human candidate binding partners can thus be used to facilitate recovery of the human homologs, e.g., by preparing antiserum for precipitating the human homolog from a solution that comprises the human homolog or by comparing the sequence of the non-human candidate binding partner with known human gene sequences. Once a source of the candidate binding partner is obtained, it can be contacted with labeled formula 1 compound, usually radiolabeled with, e.g., $^{14}C$ or $^{3}H$, and complexes that comprise the labeled formula 1 compound and the candidate binding partner is recovered using, e.g., affinity chromatography or antibody precipitation methods. The recovery of the complex provides a source of at least partially purified candidate binding partner, i.e., the candidate binding partner is enriched, e.g., at least 10-fold enriched, or at least 100-fold enriched, or at least 500-fold enriched, compared to its abundance in the original candidate binding partner source material.

Aspects of the invention include a composition comprising a partially purified (purified at least about 2-fold to about 10-fold relative to natural sources, e.g., cells or a cell lysate) compiles or a purified (purified at least about 20-fold to about 5000-fold relative to natural sources, e.g., cells or a cell lysate) complex (where the partially purified or purified complex is optionally isolated) comprising a formula 1 compound and a steroid receptor, a serum steroid-binding protein (e.g., human serum albumin, α1-acid glycoprotein, sex hormone-binding globulin, testosterone-binding globulin, corticosteroid-binding globulin, androgen binding protein (rat)) or another binding partner, e.g., transcription factor or DNARS. An aspect of these compositions includes a product produced by the process of contacting the partially purified or the purified composition with one or more cells, one or more tissues, plasma or blood.

Other aspects include a method to determine a biological activity of a formula 1 compound comprising: (a) contacting the formula 1 compound(s) with a cell or cell population; (b) measuring one or more of (i) a complex between a binding partner and the formula 1 compound, (ii) proliferation of the cell or cell population, (iii) differentiation of the cell or cell population (iv) an activity of a protein kinase C, (v) a level of phosphorylation of a protein kinase C substrate, (vi) transcription of one or more target genes, (vii) inhibition of the cellular response to steroids, e.g., glucocorticoids, (viii) inhibition of steroid-induced transcription, e.g., glucocorticoids, sex steroids or (ix) inhibition of HIV LTR-driven transcription; and (c) optionally comparing the result obtained in step (b) with an appropriate control. Aspects of this embodiment include (i) the method wherein the binding partner is a steroid receptor, a transcription factor or a DNARS, (ii) the method wherein the biological activity determined is a modulating activity of the formula 1 compound for replication or cytopathic effects associated with a retrovirus, a hepatitis virus or a protozoan parasite, (iii) the method wherein the biological activity determined is a modulating activity of the formula 1 compound for replication, cytopathic effects associated with the retrovirus, the hepatitis virus or the protozoan parasite or the biological activity determined is metabolism (assay by $^{3}H$-thymidine uptake or other assay as referenced or described herein) of a cell or cell population comprising NK cells, phagocytes, monocytes, macrophages, basophils, eosinophils, dendritic cells, synoviocytes, microglial cells, fibrocytes, transformed (neoplastic) cells, virus-infected cells, bacteria-infected cells or parasite-infected cells, and (iv) the method wherein the target gene is a virus gene, a bacterial gene, a parasite gene, a gene associated with cancer, e.g., wherein the virus gene is a DNA or an RNA polymerase gene, a reverse transcriptase gene, an envelope gene, a protease gene or a gene associated with viral nucleic acid replication or a viral structural gene.

An embodiment is a method comprising contacting a complex that comprises a steroid receptor and a formula 1 compound with a transactivator protein, whereby a complex comprising the steroid receptor protein, the formula 1 compound and the transactivator protein forms, wherein the transactivator protein is in (1) a cell or tissue extract (e.g., nuclei, lysate containing nuclei or lysate without nuclei from a cell(s) or tissue(s)), (2) a partially purified or purified cell or tissue extract, (3) a cell(s) in tissue culture or (4) a cell(s) in a subject, where any of (1)-(4) optionally comprises a target gene (native gene or introduced by standard gene manipulation techniques) whose level of expression is optionally assayed after the complex forms. In some of these embodiments, the transactivator protein is partially purified or purified and is in the cell or tissue extract or the partially purified or purified cell or tissue extract. The transactivator protein may be TIF-1, CBP/P300, TRIP1/SUG-1, RIP-140, SRC1α/P160, or TIF-2/GRIP-1. In any of these embodiments the complex comprising the steroid receptor protein, the formula 1 compound and the transactivator protein may increase or decrease transcription of the target gene compared to a suitable control (e.g., control under same conditions, but lacking any added compound that corresponds to the formula 1 compound, or where another compound (e.g., a steroid that is known to bind to the steroid receptor) is used as a benchmark or reference standard against which altered target gene expression is measured). In these methods, the target gene may be a pathogen gene (e.g., virus, bacterium, parasite, fungus, yeast) or a gene associated with a pathological condition (autoimmunity, inflammation, hyperproliferation).

The formula 1 compounds are suitable for use in certain described methods that use steroids to modulate biological activities in cells or tissues. For example, a formula 1 compound(s) can be used to selectively interact with specific steroid receptors or steroid orphan receptor, or their subtypes, that are associated with a pathological condition(s) in a subject, essentially as described in U.S. Pat. No. 5,668,175. In these applications, the formula 1 compound may act as a ligand for the receptor to modulate abnormal expression of a gene product(s) that correlates with the pathological condition (a steroid hormone responsive disease state). Such genes are normally regulated by steroid hormones. In other applications, one can use the formula 1 compounds to screen for ligands that bind to a steroid receptor or steroid orphan receptor and one or more transcription factors (or cofactors) such as AP-1 and/or with a DNA sequence(s), essentially as described in U.S. Pat. No. 5,643,720. Similarly, the formula 1 compounds can be used essentially as described in U.S. Pat. Nos. 5,597,693, 5,639,598, 5,780,220, 5,863,733 and 5,869,337. In some of these embodiments, the formula 1 compound(s) is labeled to facilitate its use. Suitable labels are known in the art and include radiolabels (e.g., $^{3}H$, $^{14}C$, $^{32}P$, $^{35}S$, $^{131}I$, $^{99}Tc$ and other halogen isotopes), fluorescent moieties (e.g., fluorescein, resorufin, Texas Red, rhodamine, BODIPY, arylsulfonate cyanines), chemiluminescent moieties (e.g., acridinium esters), metal chelators, biotin, avadin, peptide tags (e.g., histidine hexamer, a peptide recognized by monoclonal or polyclonal antibodies), covalent crosslinking moieties. One prepares the labeled compounds according to known methods.

Methods suitable to measure the biological effects of various compounds, e.g., activation, on immune system cells (e.g., NK cells, phagocytes, monocytes, macrophage, neutrophils, eosinophils, dendritic cells, synoviocytes, microglial cells, fibrocytes) have been described, e.g., Jakob et al., *J. Immunol.* 1998 161:3042-3049, Pierson et al., *Blood* 1996 87:180-189, Cash et al., *Clin. Exp. Immunol.* 1994 98:313-318, Monick et al., *J. Immunol.* 1999 162:3005-3012, Rosen et al., *Infect. Immun.* 1999 67:1180-1186, Grunfeld et al., *J. Lipid Res.* 1999 40:245-252, Singh et al., *Immunol. Cell Biol.* 1998 76:513-519, Chesney et al., *Proc. Natl. Acad. Sci. USA* 1997 94:6307-6312, Verhasselt et al., *J. Immunol.* 1999 162: 2569-2574, Avice et al., *J. Immunol.* 1999 162:2748-2753, Cella et al., *J. Exp. Med.* 1999 189:821-829, Rutalt et al., *Free Radical Biol. Med.* 1999 26:232-238, Akbari et al., *J. Exp. Med.* 1999 189:169-178, Hryhorenko et al., *Immunopharmacology* 1998 40:231-240, Fernvik et al., *Inflamm. Res.* 1999 48:28-35, Cooper et al., *J. Infect. Dis.* 1999 179:738-742, Betsuyaku et al., *J. Clin. Invest.* 1999 103:825-832, Brown et al., *Toxicol. Sci.* 1998 46:308-316, Sibelius et al., *Infect. Immunol.* 1999 67:1125-1130. The use of formula 1 compounds in such methods are aspects of the invention and they permit, e.g., measurement of the biological effects of formula 1 compounds on genes whose expression is regulated by the formula 1 compound and the steroid receptor.

Embodiments include any of the methods described above, e.g., method 1, wherein the cells or biological system comprises NK cells, phagocytes, monocytes, macrophage, neutrophils, eosinophils, dendritic cells, synoviocytes, microglial cells, glial cells, fibrocytes or hepatocytes, that optionally comprise a DNA construct that expresses one or two cloned steroid receptors. The method optionally analyzes the effect of a formula 1 compound on the cells compared to controls. Controls include the use of a known agonist or antagonist for the steroid receptor or the comparison of cells exposed to a formula 1 compound with control cells (usually the same cell type as the treated cells) that are not exposed to the formula 1 compound. A response, e.g., activation of the steroid receptor can be measured by known assays compared to controls.

The formula 1 compound will, in some cases modulate (increase or decrease) transcription of one or more genes in the cells. In other cases, the formula 1 compound will enhance lysosome movement in one or more of the subject's NK cells, phagocytes, monocytes, macrophages, neutrophils, eosinophils, dendritic cells synoviocytes, microglial cells or fibrocytes. Such effects will typically be mediated directly or indirectly through steroid receptors that act to modulate gene transcription, e.g., cause enhances protein kinase C (PKC) activity in the cells used in the assay, e.g., PKCα, PKCβ, PKCγ or PKCζ.

Other related embodiments are a composition comprising a partially purified or a purified complex comprising a formula 1 compound and a steroid receptor, a serum steroid-binding protein (e.g., human serum albumin, α1-acid glycoprotein, sex hormone-binding globulin, testosterone-binding globulin, corticosteroid-binding globulin, androgen binding protein (rat)) or another binding partner, e.g., transcription factor or DNARS. An aspect of these compositions includes a product produced by the process of contacting the partially purified or the purified composition with one or more cells, one or more tissues, plasma or blood.

Another embodiment comprises a method to determine a biological activity of a formula 1 compound comprising: (a) contacting the formula 1 compound(s) with a cell or cell population; (b) measuring one or more of (i) a complex between a binding partner and the formula 1 compound, (ii) proliferation of the cell or cell population, (iii) differentiation of the cell or cell population (iv) an activity of a protein kinase C, (v) a level of phosphorylation of a protein kinase C substrate, (vi) transcription of one or more target genes, (vii) inhibition of the cellular response to steroids, e.g., glucocorticoids, (viii) inhibition of steroid-induced transcription, e.g., glucocorticoids, sex steroids or (ix) inhibition of HIV LTR-driven transcription; and (c) optionally comparing the result obtained in step (b) with an appropriate control. Aspects of this embodiment include (i) the method wherein the binding partner is a steroid receptor, a transcription factor or a DNARS, (ii) the method wherein the biological activity determined is a modulating activity of the formula 1 compound for replication or cytopathic effects associated with a retrovirus, a hepatitis virus or a protozoan parasite, (iii) the method wherein the biological activity determined is a modulating activity of the formula 1 compound for replication, cytopathic effects associated with the retrovirus, the hepatitis virus or the protozoan parasite or the biological activity determined is metabolism (assay by $^3$H-thymidine uptake or other assay as referenced or described herein) of a cell or cell population comprising NK cells, phagocytes, monocytes, macrophages, basophils, eosinophils, dendritic cells, synoviocytes, microglial cells, fibrocytes, transformed (neoplastic) cells, virus-infected cells, bacteria-infected cells or parasite-infected cells, and (iv) the method wherein the target gene is a virus gene, a bacterial gene, a parasite gene, a gene associated with cancer, e.g., wherein the virus gene is a DNA or an RNA polymerase gene, a reverse transcriptase gene, an envelope gene, a protease gene or a gene associated with viral nucleic acid replication or a viral structural gene.

Another embodiment is a method comprising contacting a complex that comprises a steroid receptor and a formula 1 compound with a transactivator protein, whereby a complex comprising the steroid receptor protein, the formula 1 compound and the transactivator protein forms, wherein the transactivator protein is in (1) a cell or tissue extract (e.g., nuclei, lysate containing nuclei or lysate without nuclei from a cell(s) or tissue(s)), (2) a partially purified or purified cell or tissue extract, (3) a cell(s) in tissue culture or (4) a cell(s) in a subject, where any of (1)-(4) optionally comprises a target gene (native gene or introduced by standard gene manipulation techniques) whose level of expression is optionally assayed after the complex forms. In some of these embodiments, the transactivator protein is partially purified or purified and is in the cell or tissue extract or the partially purified or purified cell or tissue extract. The transactivator protein may be TIF-1, CBP/P300, TRIP1/SUG-1, RIP-140, SRC1α/P160, or TIF-2/GRIP-1. In any of these embodiments the complex comprising the steroid receptor protein, the formula 1 compound and the transactivator protein may increase or decrease transcription of the target gene compared to a suitable control (e.g., control under same conditions, but lacking any added compound that corresponds to the formula 1 compound, or where another compound (e.g., a steroid that is known to bind to the steroid receptor) is used as a benchmark against which altered target gene expression is measured). In these methods, the target gene may be a pathogen gene (e.g., virus, bacterium, parasite, fungus, yeast) or a gene associated with a pathological condition (autoimmunity, inflammation, hyperproliferation).

The biological effects observed while performing the methods described herein are expected to usually involve the formation of complexes that contain two or more components. These components can include one or more transcription factors or co-regulators or co-repressors of transcription and their homologs and isoforms. These factors and complexes containing them include members of the steroid receptor coactivator-1 family (SRC-1, SRC-1/serum response factor), NF-κB, NFAT, p300, CBP, p300/CBP, p300/CPB-associated factor, SWI/SNF and human and other homologs, BRG-1, OCT-1/OAF, AP1, Ets, androgen receptor associated protein 54 (ARA54), androgen receptor associated protein 55 (ARA55), androgen receptor associated protein 70 (ARA70), RAC3/ACTR, CREB-binding protein (CPB), SRC-1α, receptor interacting protein-140 (RIP-140), transcription factor activator protein-1, activation function-2, glucocorticoid receptor-interacting protein-1 (GRIP-1), receptor interacting protein-160 (RIP-160), suppressor of gal4D lesions (SUG-1), transcription intermediary factor-1 (TIF-1), transcription intermediary factor-2 (TIF-2), SMRT, N-CoR, N-CoA-1, p/CIP, stroidogenic factor-1 (SF-1), p65 (RelA), and Vpr encoded by the human immunodeficiency virus and its isoforms and homologs. One or more of these factors can be present in complexes that comprise a formula 1 compound and a steroid receptor, such as SXR, PPARα, CAR-β, RXR and/or PXR.

In a related embodiment, a formula 1 compound is used to exert a cytostatic effect on mammalian cells in vitro. Typically such cells are lymphoid cells, e.g., T cell populations from, e.g., blood or organs that are rich in lymphoid cells (e.g., spleen, lymph tissue or nodes), or transformed T cell lines. Such activity provides an estimate of the potency of formula 1 compounds to mediate immunological effects, such as enhancing Th1 immune responses or suppressing expression of one or more Th2-associated cytokines. Thus, an invention method comprises (a) contacting a formula 1 compound and lymphoid cells in vitro, (b) determining the degree of cytostasis that the compound exerts to identify a cytostatic compound and (c) optionally administering the cytostatic compound to an immune suppressed subject to determine the effect of the compound on one or more of the subject's immune responses as described herein, e.g., enhanced Th1 cytokine or cell response or decreased Th2-associated cytokine expression. Typically, such methods are conducted using a range of formula 1 compound concentrations and suitable controls, such as a known cytostatic agent or a blank that contains solvent that lacks the formula 1 compound. Inhibition of cell proliferation is measured by standard methods. Methods to measure the cytostatic effects of the compounds includes measuring viable cell numbers in treated and untreated cultures or by measuring DNA synthesis using e.g., $^3$H-thymidine incorporation into DNA in treated and untreated cultures. Typical ranges of formula 1 concentrations in the cell growth medium are about 0.1 µM to about 100 µM, using about 4-6 different concentrations of compounds with a fixed number of cells (e.g., about $0.4 \times 10^5$ to about $5 \times 10^5$). The formula 1 compound is left in contact with the cells in tissue culture for a sufficient time to observe cytostasis, e.g., about 16 hours to about 6 days, typically about 24-72 hours. In these embodiments, one may optionally screen for modulation of a biological activity of a steroid receptor, e.g., activation of PPARα, which may be associated with the cytostasis the compound induced.

In some applications, the formula 1 compound(s) appears to bring about an improvement of one or more of the symptoms associated with an infection or a condition. For example, treatment of subjects who are immune suppressed, e.g., from a retrovirus infection, cancer chemotherapy or other cause, generally show improvement of one or more associated symptoms, such as weight loss, fever, anemia, fatigue or reduced infection symptoms that are associated with a secondary infection(s), e.g., HSV-1, HSV-2, papilloma, human cytomegalovirus ("CMV"), Pneumocystis (e.g., P. carinii) or Candida (C. albicans, C. krusei, C. tropicalis) infections. The formula 1 compounds are also useful to facilitate immune system recovery in autologous bone marrow transplant or stem cell transplant situations. In some embodiments, the formula 1 compound(s) is administered as a nonaqueous liquid formulation as described herein or the formula 1 compound(s) is administered according to any of the intermittent dosing protocols described herein using a solid or liquid formulation(s). In the case of a subject who has a retroviral infection with symptoms that include one or more of, a relatively low CD4 count (e.g., about 10-200, usually about 20-100), one or more additional pathogen infections (HSV-1, HSV-2, HHV-6, HHV-8, CMV, HCV, a HPV, P. carinii or Candida infection) and one or more of anemia, fatigue, Kaposi's sarcoma, fever or involuntary weight loss (at least about 5% of body weight), administration of about 0.1 to about 10 mg/kg/day (usually about 0.4 to about 5 mg/kg/day) of a formula 1 compound(s) to the subject typically results in noticeable improvement of one or more of the symptoms within about 1-4 weeks. In other embodiments, the formula 1 compound(s) is administered to a subject who has a condition that appears to be associated with a viral infection, e.g., pneumonia or retinitis associated with CMV, nasopharyngeal carcinoma or oral hairy leukoplakia associated with Epstein-Barr virus, progressive pancephalitis or diabetes associated with Rubella virus or aplastic crisis in hemolytic anemia associated with Parvovirus 19.

In an exemplary embodiment, human patients infected with HCV are dosed with an aqueous isotonic α-cyclodextrin or β-cyclodextrin formulation containing about 20 mg/mL BrEA. The formulation is delivered intravenously in a single daily dose or two subdoses per day. The patients are dosed with 1 to 10 mg/kg/day for 4 to 10 days, followed by no dosing for 5 to 30 days, followed by dosing again with the cyclodextrin formulation for 4 to 10 days. The dosing regimen is repeated one, two or more times. Clinical markers for HCV infection are followed during treatment, e.g., viral nucleic acid in the blood or plasma, liver enzyme levels in the blood or plasma (e.g., AST/SGOT, ALT/SGPT, alkaline phosphatase). For these patients, a standard anti-HCV treatment(s), e.g., interferon and/or ribavirin, is optionally started or continued according to the recommendations of the patient's doctor and with the patient's informed approval. In some of these embodiments, a formula 1 compound(s) is administered daily continuously as a component in an oral or parenteral composition or formulation, e.g., for a formula 1 compound(s) that is a new compound per se. BrEA is optionally also administered systemically using, e.g., the formulation of example 1 to deliver 1-5 mg/kg/day every other day for about 1 to 4 months, or an oral formulation to deliver about 5-40 mg/kg/day every other day for about 1 to 4 months.

In any of the embodiments disclosed herein, one can optionally administer an additional therapeutic treatment in conjunction with, i.e., before, during or after, administration of a formula 1 compound(s) to a subject(s). For example, in subjects who have a viral or parasite infection and are in the course of administration of a formula 1 compound, other treatments can also be administered to the subject, e.g., nucleoside analogs for viral infections or chloroquine for malaria. Such additional treatments will typically include standard therapies for the subject's pathological condition(s), but they can also include experimental or other treatments. For example, one can coadminister vitamins (multivitamins, individual vitamins), antioxidants or other agents (vitamin E, allopurinol), nutritional supplements (liquid protein or carbohydrate preparations) or other therapies as the patient's medical condition warrants and the patient's doctor recommends. Any of these additional treatments can be coupled with the administration of any of the formula 1 compounds, e.g., BrEA, an ester, carbamate, carbonate or amino acid or peptide conjugate thereof, in any of the embodiments described herein.

Such additional treatments are apparent to the skilled artisan. Such treatments are selected based on the condition(s) to be treated, cross-reactivities of ingredients and pharmacoproperties of the combination. For example, when treating retroviral infections in a human or other subject, the formula 1 compounds are combined with one or more reverse transcriptase inhibitors, protease inhibitors, antibiotics or analgesics. Suitable formula 1 compounds include those described, e.g., in compound groups 1 through 42-25-20-6 and elsewhere herein. Exemplary reverse transcriptase inhibitors are AZT, 3TC, D4T, ddI, ddC, adefovir dipivoxil, 9-[2-(R)-[[bis[[(isopropoxycarbonyl)oxy]methoxy]-phosphinoyl]methoxy]propyl]adenine, (R)-9-[2-(phosphonomethoxy)propyl]-adenine and adefovir. Exemplary protease inhibitors are indinavir, nelfinavir, ritonavir, crixivan and sequanavir. Fusion inhibitors may also be used, e.g., HIV fusion inhibitors. When treating viral infections of the respiratory system or other systems, e.g., hepatitis C virus ("HCV") or influenza virus infection (e.g., influenza A or B), the compositions of the invention are optionally used in conjunction with antivirals (such as γ-interferon, amantidine, rimantadine, ribavirin or compounds disclosed in U.S. Pat. Nos. 5,763,483 (especially compounds recited in claims 1 and 2) and 5,866,601), mucolytics, expectorants, bronchodilators, antibiotics, antipyretics, or analgesics.

In some embodiments, formula 1 compound(s) are administered to subjects who have a parasite or bacterial infection, to slow the progression of infection, interfere with replication or development of the infectious agent or to ameliorate one or more of the associated symptoms, e.g., weight loss, anemia or secondary infections. Parasites are malaria parasites, sleeping sickness parasites and parasites associated with gastrointestinal infections. Parasites and bacteria include species, groups, genotypes, strains or isolates of gastrointestinal helminths, microsporidia, isospora, cryptosporidia (*Cryptosporidium parvum*), *Mycobacterium* (*M. avium, M. bovis, M. leprae, M. tuberculosis, M. pneumoniae. M. penetrans*), *Mycoplasma* (*M. fermentans, M. penetrans, M. pneumoniae*), *Trypanosoma* (*T. brucei, T. gambiense, T. cruzi, T. evansi*), *Leishmania* (*L. donovani, L. major, L. braziliensis*), *Plasmodium* (*P. falciparum, P. knowlesi, P. vivax, P. berghei*), *Ehrlichia* (*E. canis, E. chaffeensis, E. phagocytophila, E. equi, E. sennetsu*), *Babesia microti, Haemophilus* (*H. somnus, H. influenzae*), *Brucella* (*B. militensis, B. abortus*), *Bartonella* (*B. henselae*), *Bordetella* (*B. bronchiseptica, B. pertussis*), *Escherichia* (*E. coli*), *Salmonella* (*S. typhimurium*), *Shigella* (*S. flexneri*), *Pseudomonas* (*P. aeruginosa*), *Neisseria* (*N. gonorrhoeae, N. meningitidis*), *Streptococcus*, *Staphylococcus* (*S. aureus*), *Rickettsia* (*R. rickettsii*), *Yersinia* (*Y. enterocolitica*), *Legionella pneumonia* and *Listeria* (*L. monocytogenes*).

One or more of the invention intermittent dosing protocols or one or more of the liquid non-aqueous formulations described herein can be applied by routine experimentation to any of the uses or applications described herein. For a formula 1 compound(s) that is a new compound per se, the compound(s) can be administered to a subject according to an invention intermittent dosing protocol(s) or by other protocols, e.g., continuous daily dosing of a single dose or two or more subdoses per day. In addition any of the formula 1 compounds, e.g., one or more formula 1 compounds that are new per se, can be present in any solid or liquid formulation described herein. These formulations and dosing protocols can be applied by routine experimentation to any of the uses or applications described herein.

Numbered embodiments. Several aspects of the invention and related subject matter include the following numbered embodiments.

In some aspects, the invention relates to non-aqueous liquid formulations that comprise a formula 1 compound. Exemplary embodiments are as follows.

1. A composition comprising one or more compounds of formula 1 or formula 2 and one or more nonaqueous liquid excipients, wherein the composition comprises less than about 3% v/v water.

2. The composition of embodiment 1 wherein the one or more formula 1 compounds has the structure

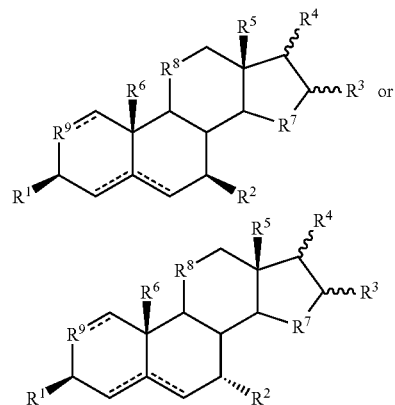

wherein $R^7$ and $R^9$ independently are —$CHR^{10}$—, —$CH_2$—, —CH=, —O—, —S— or —NH—, wherein $R^{10}$ is —OH, —SH, $C_{1-10}$ optionally substituted alkyl, $C_{1-10}$ optionally substituted alkoxy, $C_{1-10}$ optionally substituted alkenyl or $C_{1-10}$ optionally substituted alkynyl; and $R^8$ is —$CH_2$—, —O—, —S— or —NH—, wherein hydrogen atoms at the 5 (if present), 8, 9 and 14 positions respectively are α.α.α.α (i.e., 5α, 8α,9α, 14α), α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, typically α.α.β.α or β.α.β.α.

3. The composition of embodiment 2 wherein the one or more formula 1 compounds has the structure

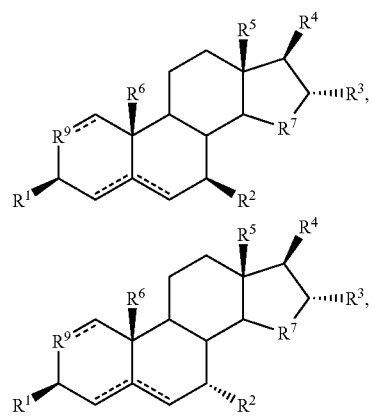

-continued

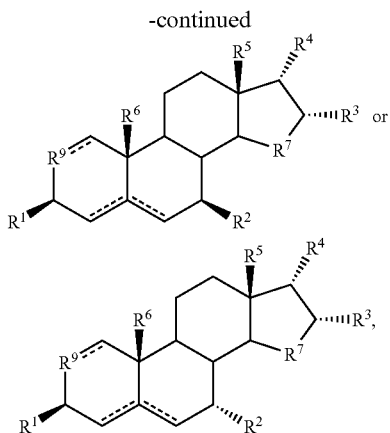

wherein hydrogen atoms at the 5 (if present), 8, 9 and 14 positions respectively are α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α, or β.β.β.β, typically α.α.β.α, or β.α.β.α, 4. The composition of embodiments 1, 2 or 3 wherein one, two, three or four formula 1 compounds are present.

5. The composition of embodiments 1, 2, 3 or 4 wherein the composition comprises less than about 0.3% v/v water.

6. The composition of embodiments 1, 2, 3, 4 or 5 wherein the one or more nonaqueous liquid excipients is one, two or more of an alcohol, a polyethylene glycol, propylene glycol or benzyl benzoate.

7. The composition of any of embodiments 1-6 (embodiment 1, 2, 3, 4, 5 or 6) wherein the formula 1 compound is 16α-bromo-3β-hydroxy-5α-androstan-17-one, 16α-bromo-3β,7β-dihydroxy-5-androstan-17-one, 16α-bromo-3β,7β,17β-trihydroxy-5α-androstene, 16α-bromo-3β,7α-dihydroxy-5α-androstan-17-one, 16α-bromo-3β,7α,17β-trihydroxy-5-androstene, 16α-bromo-3β,7β-dihydroxy-5α-androstane, 16α-bromo-3β,7β-dihydroxy-5-androstene, 16α-bromo-3β,7β,17β-trihydroxy-5α-androstane, 16β-bromo-3β, 17β-dihydroxy-5α-androstane, 16β-bromo-3β, 17β-dihydroxy-5-androstene, 16β-bromo-3β,7β, 17β-trihydroxy-5α-androstane, 16β-bromo-3β-hydroxy-5α-androstan-17-one, 16β-bromo-3β-hydroxy-5α-androsten-17-one, 16β-bromo-3β,7β-dihydroxy-5α-androstan-17-one, 16β-bromo-3β,7β-dihydroxy-5α-androsten-17-one, 3β,7α,-dihydroxyepiandrosterone, 3β,7β,-dihydroxyepiandrosterone, 3β,-hydroxy-7-oxoepiandrosterone.

8. The composition of embodiment 7 wherein the formula 1 compound is 16α-bromo-3β-hydroxy-5α-androstan-17-one.

9. The composition of any of embodiments 1-8 wherein the composition comprises two, three, four or five nonaqueous liquid excipients.

10. The composition of embodiment 9 wherein the composition comprises three or more nonaqueous liquid excipients.

11. The composition of any of embodiments 1-10 wherein the formula 1 compound comprises about 0.0001-99% w/v of the composition.

12. The composition of any of embodiments 1-11 wherein the composition comprises a unit dose.

13. The composition of embodiment 12 wherein the unit dose comprises about 0.5-100 mg/mL of the formula 1 compound.

14. The composition of embodiment 10 wherein the composition comprises about 1.0-60 mg/mL of the formula 1 compound.

15. The composition of embodiment 14 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3α,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

16. The composition of embodiment 1 wherein the one or more nonaqueous liquid excipients comprise a polyethylene glycol, propylene glycol and benzyl benzoate.

17. The composition of embodiment 16 wherein the composition comprises less than about 0.3% v/v water.

18. The composition of embodiment 17 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β, 17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

19. The composition of embodiment 18 wherein the formula 1 compound is 16α-bromo-3β-hydroxy-5α-androstan-17-one.

20. The composition of embodiment 16 that further comprises an alcohol.

21. The composition of embodiment 20 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

22. The composition of embodiment 1 wherein the one or more nonaqueous liquid excipients comprise benzyl benzoate, a polyethylene glycol, an alcohol and optionally an additional nonaqueous liquid excipient.

23. The composition of embodiment 22 wherein the composition comprises less than about 0.3% v/v water.

24. The composition of embodiment 22 or 23 wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstane, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

25. The composition of embodiment 24 wherein the formula 1 compound is 16α-bromo-3β-hydroxy-5α-androstan-17-one.

26. The composition of embodiment 22, 23, 24 or 25 wherein the polyethylene glycol is polyethylene glycol 300 and/or polyethylene glycol 200.

27. The composition of embodiment 26 wherein the alcohol is polyethylene glycol is polyethylene glycol 300.

28. The composition of embodiments 22 or 23 that comprises about 2.5-25% v/v ethanol, about 1-10% v/v benzyl benzoate, about 10-35% v/v polyethylene glycol 300, about 40-65% v/v propylene glycol and about 2-60 mg/mL 16α-bromo-3β-hydroxy-5α-androstan-17-one.

28A. The composition of embodiments 22, 23, 24, 25 or 26 that comprises about 0.1-10% v/v benzyl benzoate, about 0.1-10% v/v benzyl alcohol, about 1-95% v/v polyethylene glycol 200, about 1-95% v/v propylene glycol and about 2-60 mg/mL 16α-bromo-30-hydroxy-5α-androstan-17-one. The embodiment 28A composition may comprise about 2% v/v benzyl benzoate, about 2% v/v benzyl alcohol, about 40% v/v polyethylene glycol 200, about 51% v/v propylene glycol (qs) and about 50 mg/mL 16α-bromo-3β-hydroxy-5α-androstan-17-one.

29. The composition of embodiment 28 that comprises about 12.5% v/v ethanol, about 5% v/v benzyl benzoate, about 25% v/v polyethylene glycol 300, about 57.5% v/v propylene glycol and about 50 mg/mL 16α-bromo-3β-hydroxy-5α-androstan-17-one.

30. The composition of any of embodiments 1-29 that further comprises a local anesthetic.

31. The composition of embodiment 30 wherein the local anesthetic is procaine, benzocaine or lidocaine.

32. The composition of any of embodiments 1-31 wherein the composition comprises a solvate, a suspension, a colloid, a gel or a combination of any of the foregoing.

33. A product produced by the process of contacting a composition comprising one or more compounds of formula 1 and a first nonaqueous liquid excipient with a second nonaqueous liquid excipient wherein the product comprises less than about 3% water and the salts, analogs, configurational isomers and tautomers thereof.

34. The product of embodiment 33 wherein the product comprises less than about 0.3% water.

35. The product of embodiments 33 or 34 wherein the first nonaqueous liquid excipient is a polyethylene glycol (e.g., PEG300 or PEG 200) or propylene glycol.

36. The product of embodiments 33, 34 or 35 wherein the second nonaqueous liquid excipient is a polyethylene glycol (e.g., PEG300 or PEG 200) or propylene glycol.

38. A product produced by the process of contacting a composition comprising one or more compounds of formula 1 and two nonaqueous liquid excipients with a third nonaqueous liquid excipient wherein the product comprises less than about 3% water and the salts, analogs, configurational isomers and tautomers thereof.

39. The product of embodiment 38 wherein the product comprises less than about 0.3% water.

40. The product of embodiments 38 or 39 wherein the two nonaqueous liquid excipients are selected from a polyethylene glycol (e.g., PEG300 or PEG 200), propylene glycol, benzyl benzoate and an alcohol (e.g., ethanol).

41. The product of embodiments 38, 39 or 40 wherein the third nonaqueous liquid excipient is a polyethylene glycol (e.g., PEG300 or PEG 200), propylene glycol, benzyl benzoate or an alcohol (e.g., ethanol).

42. A product produced by the process of contacting a composition comprising one or more compounds of formula 1 and three nonaqueous liquid excipients with a fourth nonaqueous liquid excipient wherein the product comprises less than about 3% water and the salts, analogs, configurational isomers and tautomers thereof.

43. The product of embodiment 42 wherein the product comprises less than about 0.3% water.

44. The product of embodiments 42 or 43 wherein the three nonaqueous liquid excipients are selected from a polyethylene glycol (e.g., PEG300 or PEG 200), propylene glycol, benzyl benzoate and an alcohol (e.g., ethanol).

45. The product of embodiments 42, 43 or 44 wherein the fourth nonaqueous liquid excipient is a polyethylene glycol (e.g., PEG300 or PEG 200), propylene glycol, benzyl benzoate or an alcohol (e.g., ethanol).

46. The product of any of embodiments 33-45 wherein the product has been stored at reduced temperature (about 4° C. to about 8° C.) or at ambient temperature for about 30 minutes to about 2 years.

47. The product of any of embodiments 33-46 wherein the one or more compounds of formula 1 comprise 1, 2, 3 or 4 formula 1 compounds.

48. The product of any of embodiments 33-46 wherein the one or more compounds of formula 1 comprises one formula 1 compound.

49. The product of any of embodiments 33-48 wherein the one or more formula 1 compound is selected from 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β, 17β-dihydroxy-5α-androstene, 16β-bromo-3β,7β, 17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one and 16β-bromo-3β,7β,-dihydroxy-5α-androsten-17-one.

50. The product of embodiment 49 wherein the formula 1 compound is 16α-bromo-3β-hydroxy-5α-androstan-17-one.

51. The product of embodiment 49 that comprises about 2.5-25% v/v ethanol, about 1-10% v/v benzyl benzoate, about 10-35% v/v polyethylene glycol 300, about 40-65% v/v propylene glycol and about 2-60 mg/mL 16α-bromo-3β-hydroxy-5α-androstan-17-one.

52. The product of embodiment 51 that comprises about 12.5% v/v ethanol, about 5% v/v benzyl benzoate, about 25% v/v polyethylene glycol 300, about 57.5% v/v propylene glycol and about 50 mg/mL 16α-bromo-3β-hydroxy-5α-androstan-17-one.

53. The product of any of embodiments 33-52 that further comprises a local anesthetic.

54. The composition of 52 wherein the local anesthetic is procaine, benzocaine or lidocaine.

55. A product produced by the process of contacting a composition comprising a compound of formula 1 with a nonaqueous liquid excipient wherein the product comprises less than about 3% v/v water and the salts, analogs, configurational isomers and tautomers thereof.

56. The product of embodiment 55 wherein the product comprises less than about 0.3% v/v water.

57. The product of embodiment 53 wherein the product has been stored at reduced temperature (about 4° C. to about 8° C.) or at ambient temperature for about 1 hour to about 2 years.

58. The product of embodiment 53 wherein the first non-aqueous liquid excipient is a polyethylene glycol, an alcohol, propylene glycol or benzyl benzoate.

59. The product of any of embodiments 33-58 wherein the formula 1 compound comprises about 0.01% to about 99% w/v of the product.

60. The product of any of embodiments 33-59 wherein the product is a unit dose.

61. The unit dose of embodiment 60 comprising a solution containing about 0.5-70 mg/mL of the one or more formula 1 compound.

62. The product of any of embodiments 55-61 wherein the one or more formula 1 compound is selected from 16α-bromo-3β-hydroxy-5α-androstan-17-one, 16α-bromo-3β, 7β-dihydroxy-5α-androstan-17-one, 16α-bromo-3β,7β, 17β-trihydroxy-5α-androstene, 16α-bromo-3β,7β-dihydroxy-5α-androstane, 16α-bromo-3β,7β-dihydroxy-5α-androstene, 16α-bromo-3β,7β,17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one and 16β-bromo-3β,7β,-dihydroxy-5α-androsten-17-one.

63. The product of embodiment 62 wherein the formula 1 compound is 16α-bromo-3β-hydroxy-5α-androstan-17-one.

64. The product of any of embodiments 33-61 wherein the one or more formula 1 compound is selected from the compounds or one or more of the species of compounds within the genera named in compound groups 1 through 21-10-6.

65. A method comprising administering the composition or product of any of embodiments 1-64 to a subject suffering from a pathogen infection or a malignancy or an immune suppression or disregulation condition, e.g., a suppressed Th1 immune response or an unwanted Th2 immune response.

66. The method of embodiment 65 wherein the pathogen infection is a DNA virus infection or an RNA virus infection.

67. The method of embodiment 66 wherein the RNA virus infection is a retrovirus infection or a hepatitis virus infection.

68. The method of embodiment 67 wherein the retrovirus infection or hepatitis virus infection is an HIV, FIV, SIV, SHIV or hepatitis C virus infection.

69. The method of embodiment 65 wherein the pathogen infection is an intracellular parasite infection.

70. The method of embodiment 69 wherein the intracellular parasite infection is a malaria infection.

71. The method of embodiment 65 wherein the formula 1 compound has the structure

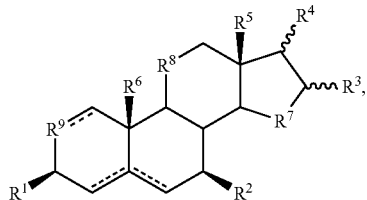

-continued

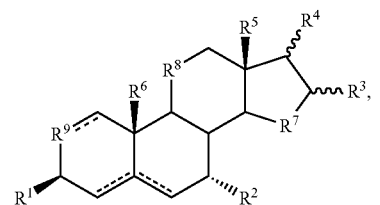

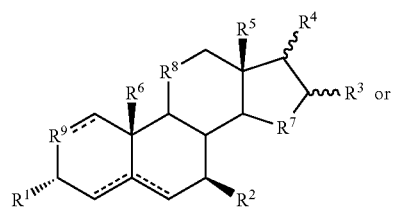

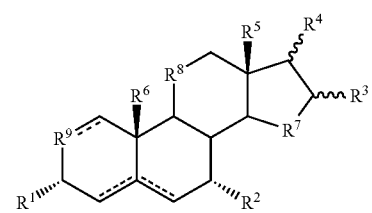

wherein one, two or three of $R^7$, $R^8$ and $R^9$ are —$CH_2$— or —CH= and wherein the configuration of hydrogen atoms at the 5 (if present), 8, 9 and 14 positions respectively are α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, typically α.α.β.α or β.α.β.α.

72. The method of embodiment 71 wherein the formula 1 compound has the structure

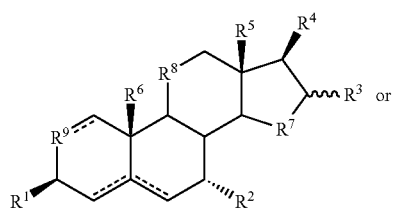

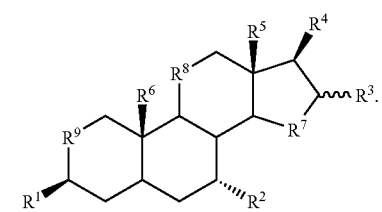

73. The method of embodiment 72 wherein $R^1$, $R^2$ and $R^4$ independently are —OH, aC2-C20 ester or C1-C20 alkoxy, $R^3$ is —H and two or three of $R^7$, $R^8$ and $R^9$ are —$CH_2$—.

74. The method of embodiment 72 or 73 wherein the formula 1 compound has the structure

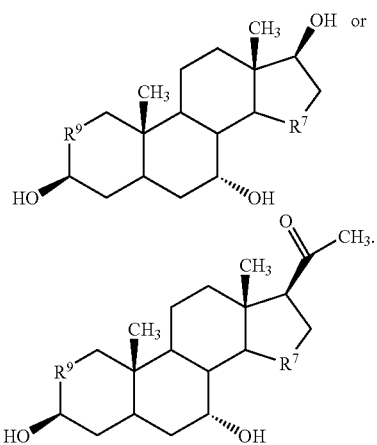

75. The method of any of embodiments 71-74 wherein the configuration of hydrogen atoms at the 5 (if present), 8, 9 and 14 positions respectively are α.α.β.α or β.α.β.α.

In other embodiments, the formula 1 compounds include new compounds, some of which are described in the following numbered embodiments.

1A. A compound of formula 1 having the structure

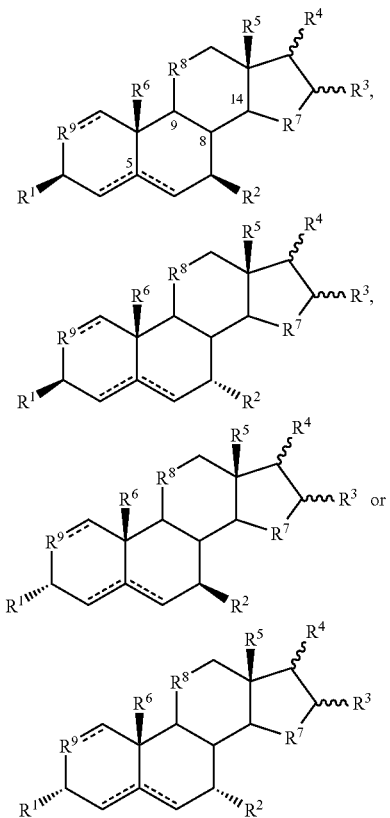

wherein $R^7$, $R^8$ and $R^9$ are independently selected and wherein one, two or three of $R^7$, $R^8$ and $R^9$ are not —$CH_2$— or —CH= and wherein hydrogen atoms at the 5 (if present), 8, 9 and 14 positions respectively are in the α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, configurations, typically α.α.β.α or β.α.β.α.

2A. The compound of embodiment 1A wherein $R^8$ is —$CH_2$—, —O—, —S— or —NH—.

3A. The compound of embodiment 1A or 2A wherein $R^7$ is —$CH_2$—$CHR^{10}$—, —O—$CHR^{10}$— or —O—C(O)—.

4A. The compound of embodiment 1A, 2A or 3A wherein $R^8$ or $R^9$ is absent.

5A. The compound of embodiment 1A or 2A wherein $R^7$ and $R^9$ independently are —$CHR^{10}$—, —$CH_2$—, —CH=, —O—, —S— or —NH—, wherein $R^{10}$ is —OH, —SH, a $C_{1-30}$ organic moiety, a $C_{1-30}$ ester, $C_{1-10}$ optionally substituted alkyl, $C_{1-10}$ optionally substituted alkoxy, $C_{1-10}$ optionally substituted alkenyl or $C_{1-10}$ optionally substituted alkynyl.

6A. The compound of embodiment 1A, 2A, 3A, 4A or 5A wherein the formula 1 compound has the structure

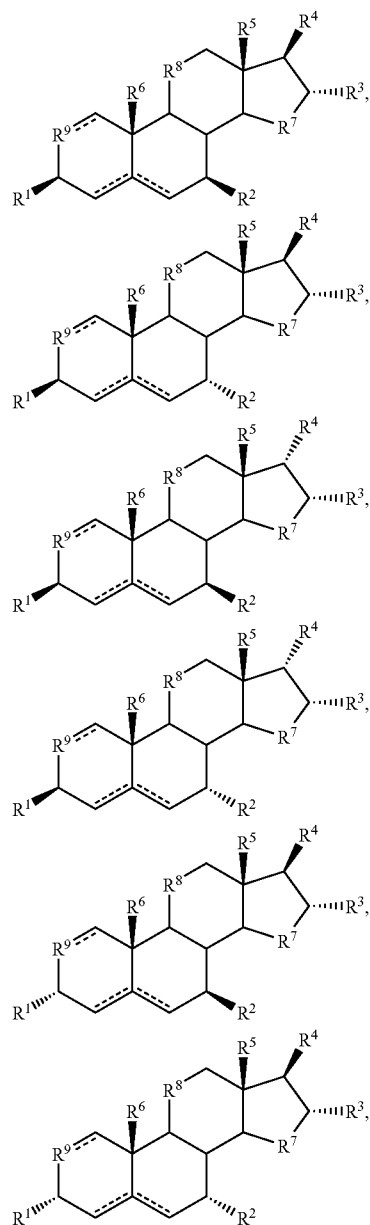

-continued

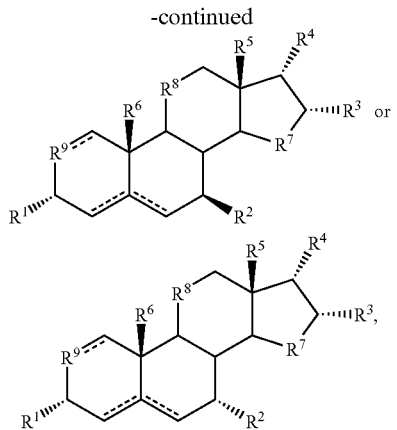

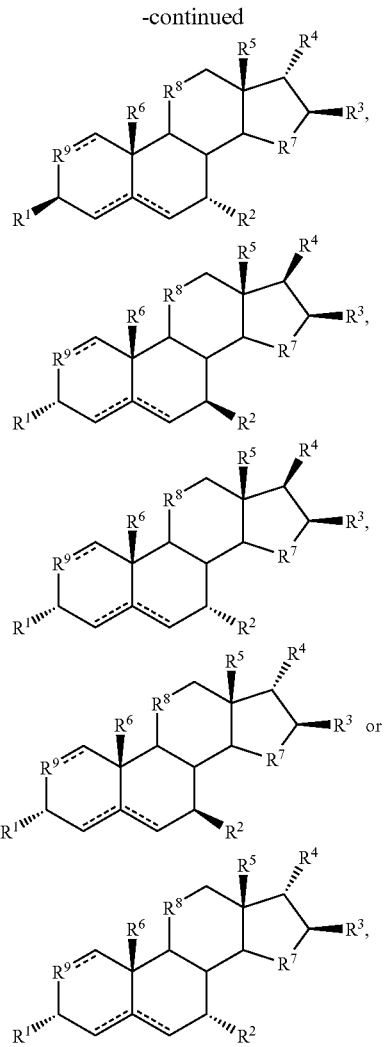

wherein hydrogen atoms at the 5 (if present), 8, 9 and 14 positions respectively are in the α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β configurations, typically α.α.β.α or β.α.β.α, 7A. The compound of embodiment 6A wherein $R^4$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —$OR^{PR}$, —$SR^{PR}$ or —$NHR^{PR}$.

8A. The compound of embodiment 6A or 7A wherein $R^1$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —$OR^{PR}$, —$SR^{PR}$ or —$NHR^{PR}$.

9A. The compound of embodiment 1A, 2A or 3A wherein the formula 1 compound has the structure

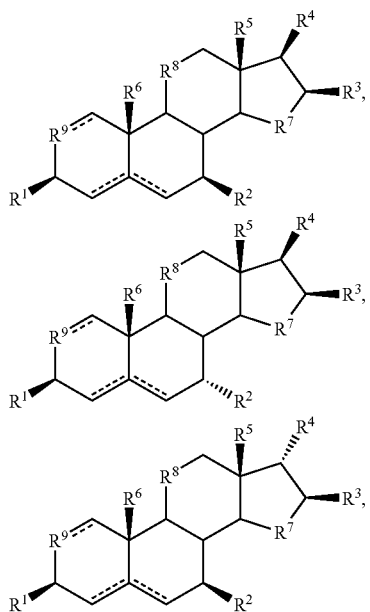

wherein hydrogen atoms at the 5 (if present), 8, 9 and 14 positions respectively are α.α.α.α, α.α.α.β, α.α.β.α, α.β.α.α, β.α.α.α, α.α.β.β, α.β.α.β, β.α.α.β, β.α.β.α, β.β.α.α, α.β.β.α, α.β.β.β, β.α.β.β, β.β.α.β, β.β.β.α or β.β.β.β, typically α.α.β.α or β.α.β.α, 10A. The compound of embodiment 9A wherein $R^4$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —$OR^{PR}$, —$SR^{PR}$ or —$NHR^{PR}$.

11A. The compound of embodiment 9A or 10A wherein $R^1$ is —OH, =O, —SH, a $C_{1-30}$ ester or $C_{1-30}$ alkoxy, wherein the ester or alkoxy moiety is optionally substituted with one, two or more independently selected substituents, which are optionally selected from —F, —Cl, —Br, —I, —O—, =O, —S—, —NH—, —$OR^{PR}$, —$SR^{PR}$ or —$NHR^{PR}$.

12A. A composition comprising a compound of any of embodiments 1A-11A and an excipient suitable for human pharmaceutical use or for veterinary use, e.g., an excipient disclosed herein or in the cited references.

13A. A product produced by the process of contacting a compound of any of embodiments 1A-11A and an excipient suitable for human pharmaceutical use or for veterinary use, e.g., an excipient disclosed herein or in the cited references.

14A. The use of a compound, composition or product of any of embodiments embodiments 1A-13A to prepare a medicament for use to prevent or to treat, or to ameliorate one or more symptoms associated, with an infection, an immunosuppression condition, a malignancy, a pre-malignant condition or to modulate a mammal's immune response, such as enhancing a Th1 response or decreasing a Th2 response, e.g., an infection, malignancy or immune dysregulation as described herein or in the cited references.

15A. The use of embodiment 14A, wherein the infection is a viral infection (e.g., HIV, HCV, a Herpesvirus, a togavirus, a human papilloma virus infection or other virus described herein or in the cited references), a bacterial infection (e.g., *Borrelia* sp., *Legionella* sp. or other bacterium described herein or in the cited references), a fungal or a yeast infection (e.g., *Candida* sp., *Aspergillus* sp. or other yeast described herein or in the cited references) or a parasite infection (e.g., a malaria parasite, a gastrointestinal nematode, a helminth, *Leishmania* sp., *Cryptosporidium* sp., *Toxoplasma gondii*, *Pneumocystis carinii*, *Schistosoma* sp., *Strongyloides stercoralis* or other parasite described herein or in the cited references).

16A. The compound, composition, product or use of any of embodiments 1A-15A, wherein the formula 1 compound is a compound named in any of compound groups 1 through 42-25-10-6, or the formula 1 compound is a species in any genus described in any of compound groups 1 through 42-25-10-6.

In other aspects, the invention provides dosing methods suitable to treat the conditions described herein. The following embodiments describe some of these methods.

1B. A method comprising intermittently administering one or more compounds of formula 1 (or a composition comprising a formula 1 compound) to a subject or delivering to the subject's tissues a formula 1 compound(s) (or a composition comprising a formula 1 compound), e.g., any formula 1 compound named or described herein, including the compounds described in embodiments 1-64 and 1A-11A above.

2B. The method of embodiment 1B wherein the subject has an infection, a hyperproliferation disorder, a hypoproliferation condition, an immunosuppression condition, an unwanted immune response or wherein the subject has recently experienced or will shortly experience trauma, surgery or a therapeutic treatment wherein the therapeutic treatment is one other than the method of embodiment 1B.

3B. The method of embodiment 2B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation, or any combination of the foregoing.

4B. The method of embodiment 3B wherein the subject's immunosuppression condition is ameliorated or the unwanted immune response (e.g., a Th2 response) is reduced or wherein the subject's Th1 immune response is enhanced.

5B. The method of embodiment 3B wherein the subject's innate immunity, specific immunity or both is enhanced.

6B. The method of embodiment 5B wherein the subject's innate immunity is enhanced.

7B. The method of embodiment 6B wherein the subject's specific immunity is enhanced, e.g., wherein the subject's Th2 immune response is reduced or wherein the subject's Th1 immune response is enhanced.

8B. The method of embodiment 2B wherein the one or more compounds of formula 1 is or are administered according to the a dosing regimen comprising the steps, (a) administering the one or more compounds of formula 1 to the subject at least once per day for at least 2 days;

(b) not administering the one or more formula 1 compounds to the subject for at least 1 day;

(c) administering the one or more formula 1 compounds to the subject at least once per day for at least 2 days; and (d) optionally repeating steps (a), (b) and (c) at least once or variations of steps (a), (b) and (c) at least once.

9B. The method of embodiment 8B wherein step (c) comprises the same dosing regimen as step (a).

10B. The method of embodiment 9B wherein step (a) of the dosing regimen comprises administering the one or more formula 1 compounds once per day, twice per day, three times per day or four times per day.

11B. The method of embodiment 10B wherein step (a) of the dosing regimen comprises administering the one or more formula 1 compounds once per day or twice per day.

12B. The method of embodiment 10B wherein step (a) comprises administering the one or more formula 1 compounds for about 3 to about 24 days.

13B. The method of embodiment 12B wherein step (a) comprises administering the one or more formula 1 compounds for about 4 to about 12 days.

14B. The method of embodiment 13B wherein step (a) comprises administering the one or more formula 1 compounds for about 4 to about 8 days.

15B. The method of embodiment 14B wherein step (b) comprises not administering the one or more formula 1 compounds for about 3 to about 120 days.

16B. The method of embodiment 15B wherein step (b) comprises not administering the one or more formula 1 compounds for about 4 to about 60 days.

17B. The method of embodiment 16B wherein step (b) comprises not administering the one or more formula 1 compounds for about 5 to about 30 days.

18B. The method of embodiment 16B wherein step (b) comprises not administering the one or more formula 1 compounds for about 8 to about 60 days.

19B. The method of embodiment 15B wherein steps (a), (b), and (c) are repeated at least about 4 times.

20B. The method of embodiment 15B wherein steps (a), (b), and (c) are repeated about 5 times to about 25 times.

21B. The method of embodiment 15B wherein steps (a), (b), and (c) and repetitions of steps (a), (b), and (c) occur over a time period of at least about 2 months.

22B. The method of embodiment 15B wherein steps (a), (b), and (c) and repetitions of steps (a), (b), and (c) occur over a time period of at least about 12 months.

23B. The method of embodiment 8B wherein step (b) comprises not administering the one or more formula 1 compounds for about 3 to about 120 days.

24B. The method of embodiment 23B wherein step (b) comprises not administering the one or more formula 1 compounds for about 4 to about 60 days.

25B. The method of embodiment 24B wherein step (b) comprises not administering the one or more formula 1 compounds for about 5 to about 30 days.

26B. The method of embodiment 23B wherein step (b) comprises not administering the one or more formula 1 compounds for about 8 to about 60 days.

27B. The method of embodiment 8B wherein step (d) comprises repeating steps (a), (b), and (c) at least once.

28B. The method of embodiment 27B wherein step (d) comprises repeating steps (a), (b), and (c) about 3 times to about 25 times.

29B. The method of embodiment 1B wherein steps (a), (b), and (c) and repetitions of steps (a), (b), and (c) occur over a time period of at least about 2 months.

30B. The method of embodiment 29B wherein steps (a), (b), and (c) and repetitions of steps (a), (b), and (c) occur over a time period of at least about 12 months.

31B. The method of any of embodiments 8B-30B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or any combination of the foregoing.

32B. The method of embodiment 31B wherein the subject's immunosuppression condition is ameliorated or the unwanted immune response is reduced.

33B. The method of embodiment 32B wherein the subject's innate immunity, specific immunity or both is enhanced.

34B. The method of embodiment 33B wherein the subject's innate immunity is enhanced.

35B. The method of embodiment 34B wherein the subject's specific immunity is enhanced.

36B. The method of embodiment 8B wherein step (c) comprises the a shorter dosing regimen than step (a).

37B. The method of embodiment 36B wherein step (a) comprises administering the formula 1 compound for 7 to about 24 days.

38B. The method of embodiment 37B wherein step (c) comprises administering the formula 1 compound for 4 to about 12 days.

39B. The method of embodiment 38B wherein step (b) comprises not administering the formula 1 compound for about 3 to about 120 days.

40B. The method of embodiment 39B wherein step (b) comprises not administering the formula 1 compound for about 4 to about 60 days.

41B. The method of embodiment 40B wherein step (b) comprises not administering the formula 1 compound for about 5 to about 30 days.

42B. The method of embodiment 36B wherein step (d) comprises repeating steps (a), (b), and (c) at least once.

43B. The method of embodiment 42B wherein step (d) comprises repeating steps (a), (b), and (c) about 3 times to about 25 times.

44B. The method of embodiment 36B wherein steps (a), (b), and (c) and repetitions of steps (a), (b), and (c) occur over a time period of at least about 2 months.

45B. The method of embodiment 44B wherein steps (a), (b), and (c) and repetitions of steps (a), (b), and (c) occur over a time period of at least about 12 months.

46B. The method of any of embodiments 36B-45B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or any combination of the foregoing.

47B. The method of embodiment 46B wherein the subject's immunosuppression condition is ameliorated or the unwanted immune response is reduced.

48B. The method of embodiment 47B wherein the subject's innate immunity, specific immunity or both is enhanced.

49B. The method of embodiment 48B wherein the subject's innate immunity is enhanced.

50B. The method of embodiment 48B wherein the subject's specific immunity is enhanced.

51B. The method of embodiment 8B wherein step (c) comprises a longer dosing period than step (a).

52B. The method of embodiment 51B wherein step (a) comprises administering the formula 1 compound for 7 to about 24 days.

53B. The method of embodiment 52B wherein step (c) comprises administering the formula 1 compound for 4 to about 12 days.

54B. The method of embodiment 53B wherein step (b) comprises not administering the formula 1 compound for about 3 to about 120 days.

55B. The method of embodiment 54B wherein step (b) comprises not administering the formula 1 compound for about 4 to about 60 days.

56B. The method of embodiment 55B wherein step (b) comprises not administering the formula 1 compound for about 5 to about 30 days.

57B. The method of embodiment 51B wherein step (d) comprises repeating steps (a), (b), and (c) at least once.

58B. The method of embodiment 57B wherein step (d) comprises repeating steps (a), (b), and (c) about 3 times to about 25 times.

59B. The method of embodiment 51B wherein steps (a), (b), and (c) and repetitions of steps (a), (b), and (c) occur over a time period of at least about 2 months.

60B. The method of embodiment 59B wherein steps (a), (b), and (c) and repetitions of steps (a), (b), and (c) occur over a time period of at least about 12 months.

61B. The method of any of embodiments 51B-60B wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation or any combination of the foregoing.

62B. The method of embodiment 61B wherein the subject's immunosuppression condition is ameliorated or the unwanted immune response is reduced.

63B. The method of embodiment 62B wherein the subject's innate immunity, specific immunity or both is enhanced or wherein the subject's Th1 immune response is enhanced or the subject's Th2 immune response is decreased.

64B. The method of embodiment 8B wherein the variations of steps (a), (b) and (c) comprise conducting a first dosing regimen of steps (a), (b) and (c) once, twice or three times, followed by one or more second dosing regimens of steps (a'), (b') and (c') wherein one or more of the (a'), (b') and (c') steps in the second dosing regimen is longer than the corresponding step in the first dosing regimen.

65B. The method of embodiment 8B wherein the variations of steps (a), (b) and (c) comprise conducting a first dosing regimen of steps (a), (b) and (c) once, twice or three times, followed by one or more second dosing regimens of steps (a'), (b') and (c') wherein one or more of the (a'), (b') and (c') steps in the second dosing regimen is shorter than the corresponding step in the first dosing regimen.

66B. The method of any of embodiments 1B-67B wherein the one or more formula 1 compounds is or are administered orally, intramuscularly, intravenously, subcutaneously, topically, vaginally, rectally, intracranially, intrathecally, intradermally, as an aerosol or by a buccal route.

67B. The method of embodiment 66B wherein the one or more formula 1 compounds is or are present in a solid formulation predominantly as a solid or the one or more formula 1 compounds is or are present in a liquid formulation predominantly as a solvate, colloid or a suspension or the one or more formula 1 compounds is or are present in a gel, cream or paste.

68B. The method of any of embodiments 2B-67B wherein the subject's viral infection, intracellular bacterial infection, extracellular bacterial infection, fungal infection, yeast infection, extracellular parasite infection, intracellular parasite infection, protozoan parasite, multicellular parasite, autoimmune disease, cancer, precancer, chemotherapy, radiation therapy, immunosuppressive therapy, anti-infective agent therapy, a wound, a burn, or the presence of an immunosuppressive molecule, gastrointestinal irritation or any combination of the foregoing is (a) a DNA virus infection or an RNA virus infection (HSV, CMV, HBV, HCV, HIV, SHIV, SIV); (b) a mycoplasma infection, a *Listeria* infection or a *Mycobacterium* infection; (c) extracellular bacteria infection; (d) fungal infection; (e) a yeast infection (Candida, *Cryptococcus*); (d) protozoa (malaria, *leishmania*, cryptosporidium, toxoplasmosis, *pneumocystis*); (e) a multicellular parasite; (f) autoimmune diseases (SLE, RA, diabetes); (g) cancers (solid cancers selected from, e.g., ovarian, breast, prostate, glioma; disseminated cancers selected from lymphoma, leukemia, colon cancer, sarcoma); (h) precancers; (i) chemotherapies (adriamycin, cisplatin, mitomycin C); (j) radiation therapies; (k) immunosuppressive therapies; (l) anti-infective agent therapies; (m) wounds (surgical or otherwise); (n) $1^{st}$ degree, $2^{nd}$ degree or $3^{rd}$ degree burns; (o) immunosuppressive molecules; (p) gastrointestinal irritation (irritable bowel, Crohn's disease, chronic diarrhea); or (q) any combination of (a) through (p).

69B. The method of embodiment 68B wherein the RNA virus infection is a retroviral infection or a hepatitis virus infection.

70B. The method of embodiment 68B or 69B wherein the one or more formula 1 compounds is one formula 1 compound.

71B. The method of embodiment 70B wherein the one or more formula 1 compounds is or are in a composition that comprises, (a) one or more nonaqueous liquid excipients, wherein the composition comprises less than about 3% v/v water; (b) a solid that comprises a pharmaceutically acceptable excipient; or (c) one or more liquid excipients, wherein the composition comprises more than about 3% v/v water.

72B. The method of embodiment 68B or 71B wherein the formula 1 compound is 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β, 17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one or 16β-bromo-3β,7β,-dihydroxy-5α-androsten-17-one.

73B. The method of embodiment 72B wherein the formula 1 compound is 16α-bromo-3β-hydroxy-5α-androstan-17-one.

74B. The method of embodiments 1B-73B wherein the formula 1 compound excludes one or more of any formula 1 compounds.

75B. A method to treat involuntary weight loss, oral lesions, skin lesions, opportunistic infections, diarrhea or fatigue in an subject comprising intermittently administering one or more compounds of formula 1 to the subject (e.g., involuntary weight loss from viral infection, gastrointestinal infection, chemotherapy, anorexia).

76B. The method of embodiment 75B wherein the subject has an immunosuppression condition.

77B. The method of embodiment 76B wherein the subject is a human.

78B. The method of embodiment 77B wherein the subject is a human 1 day to 18 years old (e.g., 1 month to 6 years old).

79B. The method of any of embodiments 75B-78B wherein the subject's specific immunity remains impaired compared to a typical comparable control subject who does not have the subject's pathological condition.

80B. The method of embodiment 79B wherein the subject's CD4 cell count does not increase significantly during one or more courses of dosing (e.g., dosing for 1 week to about 2 weeks or more).

81B. The method of clam 80B wherein the subject's CD4 cell count is about 20 to about 100 $CD4^+$ cells/$mm^3$ or about 20 to about 75 $CD4^+$ cells/$mm^3$.

82B. The method of any of embodiments 1B-81B wherein the subject has a pathogen(s) infection or a malignancy and the pathogen(s) or malignancy does not become resistant to the formula 1 compound over a time normally associated with the development of measurable resistance in at least about 50% of subjects who are treated with a therapeutic treatment(s) other than a formula 1 compound(s).

83B. The method of embodiment 82B wherein the pathogen infection is an HIV, SIV, SHIV or HCV infection.

84B. The method of embodiments 82B or 83B wherein the formula 1 compound is one or more of 16α-bromo-3β-hydroxy-5α-androstan-17-one, 16α-bromo-3β,7β-dihydroxy-5α-androstan-17-one, 16α-bromo-3β,7β,17β-trihydroxy-5α-androstene, 16α-bromo-3β,7β-dihydroxy-5α-androstane, 16α-bromo-3β,7β-dihydroxy-5α-androstene, 16α-bromo-3β,7β, 17β-trihydroxy-5α-androstane, 16β-bromo-3β,17β-dihydroxy-5α-androstane, 16β-bromo-3β,17β-dihydroxy-5α-androstene, 16β-bromo-3β,7β,17β-trihydroxy-5α-androstane, 16β-bromo-3β-hydroxy-5α-androstan-17-one, 16β-bromo-3β-hydroxy-5α-androsten-17-one, 16β-bromo-3β,7β,-dihydroxy-5α-androstan-17-one, 16β-bromo-3β,7β,-dihydroxy-5α-androsten-17-one or a physiologically acceptable ester, carbonate, carbamate, amino acid conjugate or peptide conjugate thereof.

85B. The method of embodiment 84B wherein the formula 1 compound is 16α-bromo-30-hydroxy-5α-androstan-17-one or a physiologically acceptable ester, carbonate, carbamate, amino acid conjugate or peptide conjugate thereof.

86B. The method of any of embodiments 1B-85B, wherein the formula 1 compound is a compound named in any of compound groups 1 through 42-25-10-6, or the formula 1 compound is a species in any genus described in any of compound groups 1 through 42-25-10-6.

In other embodiments, the invention provides methods to modulate immune cells or immune responses in a subject. The following numbered embodiments describe some of these methods.

1C. A method to modulate a subject's innate immunity or to enhance a subject's Th1 immune response or to reduce a subject's Th2 immune responses comprising administering to the subject a compound(s) of formula 1, including any formula 1 compound that is described or disclosed herein, including the compounds described in embodiments 1-64 and 1A-11A above.

2C. The method of embodiment 1C wherein the subject's innate immunity is enhanced.

3C. The method of embodiment 1C or 2C wherein the subject suffers from an innate immunity suppression condition, a suppressed Th1 immune response or an unwanted Th2 immune response.

4C. The method of embodiment 3C wherein the innate immunity suppression condition, the suppressed Th1 immune response or the unwanted Th2 response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule or any combination of the foregoing.

5C. The method of any of embodiments 1C-3C wherein the subject's Th1 immune response is enhanced.

6C. The method of embodiment 1C wherein the subject's Th2 immune response is reduced.

7C. The method of embodiment 6C wherein the subject has a condition comprising an unwanted immune response (e.g., autoimmune disease, SLE, diabetes).

9C. The method of embodiment 6C or 7C wherein the subject is a vertebrate, a mammal, a primate or a human.

10C. The method of embodiment 9 wherein the vertebrate's, the mammal's the primate's or the human's specific immunity modulation is (i) an enhanced CTL or Th1 response to a virus infection or to a malignant cell in vitro or in vivo, (ii) enhanced antigen presentation or biological activity by dendritic cells or dendritic cell precursors, or (iii) enhanced killing of virus-infected or of malignant cells.

11C. The method of 10C wherein the vertebrate is a human, the virus infection is an HIV infection and the CTL or Th1 response comprises an enhanced response to one or more of the HIV's gag protein or to the HIV's gp120.

12C. The method of embodiment 1C, 4C, 10C or 11C wherein the subject's Th1 cells, tumor-infiltrating lymphocytes (TIL cells), NK cells, peripheral blood lymphocytes, phagocytes, monocytes, macrophage, neutrophils, eosinophils, dendritic cells or fibrocytes are activated as measured by, e.g., enhanced $^3$H-thymidine uptake compared to untreated controls or by an increase in the number of the cell type in circulation or demonstrable movement of the cell type from one tissue or compartment (e.g., skin) to another tissue or compartment (e.g., blood, lymph node, spleen or thymus).

13C. The method of embodiment 1C, 4C, 10C, 11C or 12C, wherein the formula 1 compound(s) modulates transcription of one or more genes in the subject's NK cells, phagocytes, monocytes, macrophages, neutrophils, eosinophils, dendritic cells or fibrocytes are activated (e.g., as measured by increased protein kinase C activity or by modulation of a biological activity of a steroid receptor or an orphan nuclear hormone receptor).

14C. The method of embodiment 1C wherein the formula 1 compound(s) enhances lysosome movement in one or more of the subject's NK cells, phagocytes, monocytes, macrophages, neutrophils, eosinophils, dendritic cells or fibrocytes.

15C. The method of embodiment 1C wherein the formula 1 compound(s) enhances protein kinase C activity in one or more of the subject's NK cells, phagocytes, monocytes, macrophages, neutrophils, eosinophils, dendritic cells or fibrocytes (e.g., PKCα, PKCβ, PKCγ and PKCζ).

16C. A composition comprising a partially purified or a purified complex comprising a formula 1 compound and a steroid receptor, a serum steroid-binding protein (e.g., human serum albumin, α1-acid glycoprotein, sex hormone-binding globulin, testosterone-binding globulin, corticosteroid-binding globulin, androgen binding protein (rat)) or a binding partner (e.g., complexing agent, liposome, antibody).

17C. A product produced by the process of contacting the partially purified or the purified composition of embodiment 16C with one or more sterile containers, one or more syringes, one or more pharmaceutically acceptable excipients (e.g., excipient as defined in draft spec above and including sugars, lactose, sucrose, fillers, lubricants, binders, or any excipient named in any reference cited herein), one or more cells, one or more tissues, plasma or blood.

18C. The method of any of embodiments 1C-17C wherein the subject has an infection, a hyperproliferation disorder, a hypoproliferation condition, an immunosuppression condition, an unwanted immune response or wherein the subject has recently experienced or will shortly experience trauma, surgery or a therapeutic treatment wherein the therapeutic treatment is one other than the method of embodiment 1C.

19C. The method of embodiment 18C wherein the immunosuppression condition or the unwanted immune response is associated with a viral infection, an intracellular bacterial infection, an extracellular bacterial infection, a fungal infection, a yeast infection, an extracellular parasite infection, an intracellular parasite infection, a protozoan parasite, a multicellular parasite, an autoimmune disease, a cancer, a precancer, a chemotherapy, a radiation therapy, an immunosuppressive therapy, an anti-infective agent therapy, a wound, a burn, the presence of an immunosuppressive molecule, gastrointestinal irritation, or any combination of the foregoing.

20C. The method of embodiment 19C wherein the subject's immunosuppression condition is ameliorated or the unwanted immune response is reduced.

21C. The method of embodiment 19C wherein the subject's immunosuppression condition is associated with a viral infection.

22C. The method of embodiment 21C wherein the viral infection comprises a DNA virus or an RNA virus infection.

23C. The method of embodiment 22C wherein the RNA virus infection comprises a retroviral infection or a hepatitis virus infection.

24C. The method of any of embodiments 18C-23C wherein the subject suffers from one or more of chronic diarrhea, involuntary weight loss (usually at least about 5% or more), cachexia (usually at least about 5% or more), muscle wasting, one or more oral lesions (usually at least about 1 cm$^2$), one or more genital lesions (usually at least about 1 cm$^2$), skin lesions (usually at least about 1 cm$^2$) or an opportunistic infection associated with AIDS.

25C. A method (e.g., to determine a biological activity of a formula 1 compound or to modulate transcription of a gene in a cell or cell-free transcription system) comprising: (a) contacting the formula 1 compound(s) with a cell or cell population in vitro or in vivo; (b) measuring one or more of (i) a complex between a binding partner and the formula 1 compound, (ii) proliferation of the cell or cell population, (iii) differentiation of the cell or cell population (iv) an activity of a protein kinase C, (v) a level of phosphorylation of a protein kinase C substrate, (vi) transcription of one or more target genes, (vii) enhancement or inhibition of the cellular response to steroids, e.g., glucocorticoids, (viii) inhibition of steroid-induced transcription, e.g., glucocorticoids, sex steroids, (ix) inhibition of retrovirus (e.g., HIV, SIV, FIV or SHIV) LTR-driven transcription, or (x) modulation of the numbers of an immune cell population in circulation in vivo (e.g., circulating peripheral blood lymphocytes in a mammal such as a primate or a human); and (c) optionally comparing the result obtained in step (b) with an appropriate control.

26C. The method of embodiment 25C wherein the binding partner is a steroid receptor, a transcription factor or a steroid hormone superfamily orphan receptor.

27C. The method of embodiment 25C wherein the biological activity determined is a modulating activity of the formula 1 compound for replication or cytopathic effects associated with a retrovirus, a hepatitis virus or a protozoan parasite.

28C. The method of embodiment 25C wherein the biological activity determined is a modulating activity of the formula 1 compound for replication, cytopathic effects associated with the retrovirus, the hepatitis virus or the protozoan parasite or the biological activity determined is metabolism (assay by $^3$H-thymidine uptake) of a cell or cell population comprising NK cells, phagocytes, monocytes, macrophages, basophils, eosinophils, fibrocytes, transformed cells, virus-infected cells, bacteria-infected cells or parasite-infected cells.

29C. The method of embodiment 25C wherein the target gene is a virus gene, a bacterial gene, a parasite gene, a gene associated with cancer.

30C. The method of embodiment 29C wherein the virus gene is a polymerase gene, a reverse transcriptase gene, an envelope gene, a protease gene or a gene associated with viral nucleic acid replication or a viral structural gene.

31C. The method of embodiment 30C wherein the polymerase gene encodes a DNA polymerase or encodes an RNA polymerase.

32C. The method of embodiment 30C wherein the reverse transcriptase gene encodes a human, primate, avian or feline retrovirus reverse transcriptase.

33C. A method comprising administering a compound(s) of formula 1 to a human or primate who has a retroviral infection and a CD4 count of 550 or less.

34C. The method of embodiment 33C wherein the human has a CD4 count of about 20 to about 100 or about 20 to about 80.

35C. The method of embodiment 33C wherein the human has a CD4 count of about 30 to about 150.

36C. The method of embodiment 33C wherein the human has a CD4 count of about 500 or less, about 450 or less, about 400 or less, about 350 or less, about 300 or less, about 250 or less, about 200 or less, about 150 or less, about 100 or less, about 50 or less or about 25 or less or about 20 or less.

37C. The method of any of embodiments 33C-36C wherein the formula 1 compound(s) is present in a composition that comprises one or more nonaqueous liquid excipients and less than about 3% v/v water or any of the formulations as disclosed in the specification or any of the numbered embodiments above.

38C. The method of any of embodiments 33C-37C wherein the formula 1 compound(s) is administered according to an intermittent dosing protocol as disclosed in the specification or any of the numbered embodiments above.

39C. The method of any of embodiments 30C-45C wherein the human is coinfected with hepatitis C virus, hepatitis B virus, HSV-1, HSV-2, a malaria parasite, a *Pneumocystis* parasite, or a *Cryptosporidium* parasite.

40C. The method of embodiment 46C wherein level of the HCV is reduced in the human.

41C. A method comprising administering a formula 1 compound(s) to a subject, or to a nervous system cell(s) in tissue culture whereby the formula 1 compound(s) binds to a receptor associated with a cell(s) in the nervous system and (1) elicits a biological response in the cell(s) in the nervous system or in the cell(s) in tissue culture and/or (2) elicits a neuronal response that is transmitted to a distant site(s) or cell(s) where the method optionally is used to screen a formula 1 compound(s) for its biological activity, to treat a pathological condition (e.g., pathogen infection such as a virus (HIV), a malignancy or a neurological disorder, e.g., AIDS associated dementia, Alzheimer's, Parkinson's, Multiple Sclerosis) in the subject or to determine the bioavailability or metabolism of the formula 1 compound(s) to the subject or the cell(s) in the nervous system or in tissue culture, wherein metabolism is optionally determined by comparing the biological effect of a formula 1 compound(s) with a control compound, which can be a different formula 1 compound.

42C. The method of embodiment 41 wherein the receptor associated with the cell in the nervous system is a neurotransmitter receptor(s) (e.g., a γ-aminobutyric acid receptor such as type A, a NMDA receptor) and/or a steroid receptor (e.g., androgen receptor, estrogen receptor).

43C. The method of embodiment 41C or 42C wherein the cell(s) in the nervous system is a neuron(s), and astrocyte(s) and/or a glial cell(s).

44C. The method of embodiment 41C, 42C or 43C wherein the biological response in the cell(s) in the nervous system or in the cell(s) in tissue culture is increased or decreased transcription of a gene(s) (e.g., a neurotransmitter, vasopressin, a heat shock protein), increased or decreased secretion of a protein(s) (e.g., vasopressin), reduced damage from oxidative stress, enhanced nitric oxide release and/or enhanced neurite growth.

45C. The method of any of embodiments 1C-44C wherein the compound(s) of formula 1 is any one or more formula 1 compound selected from the compounds or one or more of the species of compounds within the genera named in compound groups 1 through 21-10-6.

46C. A method to (a) modulate the expression of at least one immune cell antigen by an immune cell in a subject, wherein the immune cell antigen is selected from CD3, CD11c, CD14, CD16, CD19, CD25, CD38, CD56, CD62L, CD69, CD45R$^{-4}$, CD45RO, CD123, HLA-DR, IL-1, IL-2, IL-4, IL-6, IL-8, IL-10, TNFα, IGF$_1$ and γIFN, or (b) activate CD8$^+$ T cells or CD8$^-$T cells in a subject, wherein the activation comprises at least transiently enhanced expression of CD25 or CD69 by the T cells, or (c) increase the proportion of CD8$^+$ or CD8$^-$lymphokine activated killer cells in a subject's CD16+ cells (e.g., CD8$^+$, CD16$^+$, CD38$^+$ or cells CD8$^-$, CD16$^+$, CD38$^+$), or (d) increase the proportion of (i) CD8$^-$, CD16$^+$ natural killer cells, (ii) CD8$^+$, CD16$^+$ natural killer cells or (iii) CD8$^-$, CD16$^+$ cells that mediate antibody-dependent cell-mediated cytotoxicity, or (iv) CD8$^+$, CD16$^+$ cells that mediate antibody-dependent cell-mediated cytotoxicity, or (e) increase the proportion of dendritic cell precursors in a subject's circulating white blood cells (e.g., Lin$^-$, HLA-DR$^+$, CD123$^+$ or Lin$^-$HLA-DR$^+$, CD11c$^+$ cells) or (f) increase the proportion of CD45RA$^+$ T cells or CD45$^+$, R$^+$ T cells in a subject's circulating white blood cells, or (g) change (increase or decrease) the proportion or relative numbers of CD62L+ T cells in a subject's circulating white blood cells, or (h) increase the proportion of CD8+ or CD4+ T cells that express CD62L in a subject's circulating CD8+ or CD4+ T cells, or (i) decrease the proportion of CD8+ or CD4+ T cells that express CD62L in a subject's circulating CD8+ or CD4+ T cells, or (j) increase the proportion of HLA-DR+, CD8+, CD38+ cells in a subject's circulating white blood cells, or (k) decrease the level of IL-4 or IL-10 that is expressed by or present in a subject's white blood cells or in a subject's plasma (or that is expressed after the subject's white cells are stimulated in vitro), (l) at least transiently increase the number of dendritic cell precursors or dendritic cells that are present in a subject's white blood cells or in a subject's plasma, or (m) enhance the capacity of CD4+ T cells to express IL-2, IL-12 or γIFN, the method comprising administering to the subject a formula 1 compound and a pharmaceutically acceptable excipient.

47C. The method of embodiment 46C wherein formula 1 has the structure

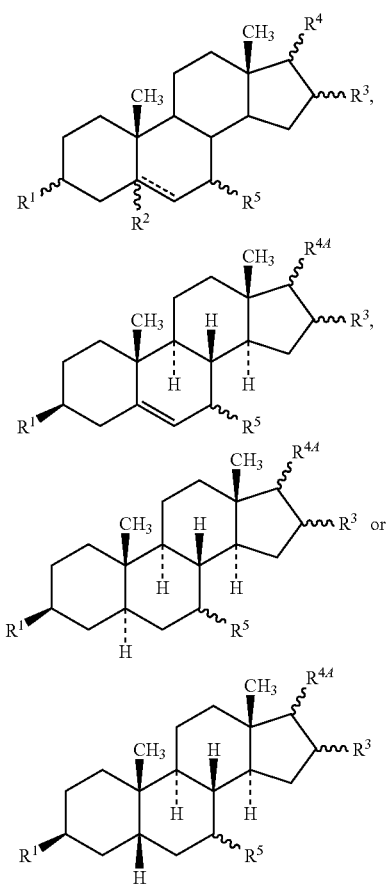

wherein $R^1$ is —OH or a group (e.g., a $C_{1-30}$ ester) that can hydrolytically convert under physiological conditions to —OH, either of which may be in the α- or β-configuration; $R^2$ is hydrogen in the α- or β-configuration, or $R^2$ is absent when there is a double bond at the 5-6 position; $R^3$ is —H or —Br, either of which may be in the α- or β-configuration; $R^4$ is —OH or a group (e.g., a C1-30 ester) that can hydrolytically convert under physiological conditions to —OH, either of which may be in the α- or β-configuration, or $R^4$ is =O and the hydrogen atom bonded to the same carbon is absent; $R^{4A}$ is $R^4$, —C(O)—$CH^3$ or —C(O)—$(CH_2)_{1-6}$—$CH^3$; $R^5$ is —H or —OH or a group (e.g., a $C_{1-30}$ ester) that can hydrolytically convert under physiological conditions to —OH, either of which may be in the α- or β-configuration, or $R^5$ is =O and the hydrogen atom bonded to the same carbon is absent; and the dotted line at the 5-6 position is an optional double bond, or wherein the formula 1 compound has the structure shown in any formula 1 compound named or described herein, including the compounds described in embodiments 1-64 and 1A-11A above.

48C. The method of embodiment 46C or 47C wherein the formula 1 compound is administered to the subject daily over a period from one to about 15 days, e.g., for 1, 2, 3, 4, 5, 6, 7, 8, 9, 10, 11, 12, 13, 14, 15 or more days.

49C. The method of embodiment 48C wherein the expression of the immune cell antigen is detectably modulated for at least about 4-7 days after the last administration of the formula 1 compound to the subject, e.g., for at least 4, 5, 6, 7 or more days.

50C. The method of embodiment 48C or 49C wherein the expression of the immune cell antigen is detectable at least about 8-90 days after the last administration of the formula 1 compound, e.g., for at least about 8, 10, 12, 15, 20, 25, 28, 30, 35, 40, 42, 45, 49, 50, 55, 56, 60, 63, 65, 70, 75, 77, 80, 84, 85, 90, 91 95, 98, 100 or more days.

51C. The method of any of embodiments 46C-51C wherein the subject has an immunosuppression condition, a pathogen infection or a conditions associated with a deficient Th1 immune response or an excessive Th2 immune response.

52C. The method of embodiment 51C wherein the pathogen infection is a viral infection, a bacterial infection, a yeast infection, a fungal infection or a viroid infection, e.g., wherein the pathogen infection is a viral infection such as a DNA virus infection or an RNA virus infection (e.g., an infection caused by a Hepadnavirus, a Parvovirus, a Papovavirus, an Adenovirus, a Herpesvirus, Retrovirus, a Flavivirus, a Togavirus, a Rhabdovirus, a Picornavirus, a Bunyavirus, a Reovirus, an Orthomyxovirus or a Paramyxovirus, such as a HIV1, HIV2, SIV, SHIV or another virus described herein or in the cited references).

53C. The method of embodiment 52C wherein the subject has an immunosuppression condition that is associated with or caused by a pathogen infection.

54C. The method of any of embodiments 46C-53C wherein the subject is a mammal, a human, a primate or a rodent.

55C. The method of any of embodiments 46C-54C wherein about 0.05 mg/kg/day to about 20 mg/kg/day is administered parenterally (e.g., by intravenous, subcutaneous, intramuscular, or intramedullary injection), topically, orally, sublingually or bucally to the subject, e.g., about 0.1 mg/kg/day, about 0.2 mg/kg/day, about 0.5 mg/kg/day, about 1.0 mg/kg/day, about 1.5 mg/kg/day, about 2 mg/kg/day, about 2.5 mg/kg/day, about 3.0 mg/kg/day, about 4 mg/kg/day or about 6 mg/kg/day, i.e., about 0.1-10 mg/kg/day, typically about 0.2-7 mg/kg/day.

56C. The method of embodiment 55C wherein the subject is concurrently taking one or more second therapeutic agents to treat a pathogen infection, e.g., a viral infection, such as a HIV-1 infection, a HIV-2 infection, a HAV infection, a HBV infection, a HCV infection, an Epstein Barr virus infection, a HSV-1 infection, a HSV-2 infection, human herpesvirus 6 infection, human herpesvirus 7 infection, human herpesvirus 8 infection, or a bacterial infection or a parasite infection, such as a malaria infection, leishmaniasis, cryptosporidiosis, toxoplasmosis, a mycoplasma infection, a *Trichomonas* infection, a *Chlamydia* infection, a *Pneumocystis* infection, a *Salmonella* infection, a *Listeria* infection, an *Escherichia coli* infection, a *Yersinia* infection, a *Vibrio* infection, a *Pseudomonas* infection, a *Mycobacterium* infection, a *Haemophilus* infection, a *Neisseria* infection, a *Staphylococcus* infection or a *Streptococcus* infection.

57C. The method of embodiment 56C wherein the one or more second therapeutic agents is a protease inhibitor, a reverse transcriptase inhibitor, a viral, bacterial or parasite DNA or RNA polymerase inhibitor, an antibacterial antibiotic or an antifungal agent, such as AZT, ddI, ddC, D4T, 3TC, a viral (e.g., HIV) fusion inhibitor, hydroxyurea, nelfinavir, saquinavir, ritonavir, indinavir, chloroquine, a chloroquine analog, amphotericin B, fluconazole, clotrimazole, isoniazid, dapsone, rifampin, cycloserine, erythromycin, a tetracycline antibiotic, vancomycin, ethambutol, pyrazinamide, a fluororquinolone (e.g., ciprofloxacin, norfloxacin), a cephalosporin antibiotic, a β-lactam antibiotic or an aminoglycoside antibiotic (e.g., streptomycin, kanamycin, tobramycin).

58C. The method of any of embodiments 46C-57C wherein the subject is a human, a primate, a canine, a feline or a rodent.

59C. A composition comprising an effective amount of an immune cell subset modulatory compound of formula 1 and a pharmaceutically acceptable carrier.

60C. The composition of embodiment 59C wherein the immune cell subset is (1) $CD8^+$ T cells, (2) $CD4^+$ T cells, (3) $CD8^-$ lymphokine activated killer cells, (4) $CD8^-$ lymphokine activated killer cells, (5) $CD8^-$, $CD16^+$ natural killer cells, (6) $CD8^+$, $CD16^+$ natural killer cells, (7) $CD8^-$, $CD16^+$ cells that mediate antibody-dependent cell-mediated cytotoxicity, (8) $CD8^+$, $CD16^+$ cells that mediate antibody-dependent cell-mediated cytotoxicity, (9) dendritic cells or dendritic cell precursors, (10) $CD45RA^+$ T cells, (11) $CD45RO^+$ T cells, (12) $CD45RA^+$, $CD45RO^+$ T cells, (13) $CD8^+$, $CD62L$ T cells, (11) $CD4^+$, $CD62L^+$ T cells or (14) $HLA-DR^+$, $CD8^+$, $CD38^+$ T cells.

61C. A method to detect a biological response associated with the administration of a compound of formula 1 to a subject comprising (1) obtaining a sample from the subject, (2) administering the compound of formula 1 to the subject to obtain a treated subject (3) obtaining a second sample from the treated subject, (4) within 24 hours of obtaining the sample, analyzing the sample to obtain control information for detecting the biological response, (5) within 24 hours of obtaining the second sample, analyzing the second sample for the presence or absence of a biological response to obtain experimental information and (6) optionally comparing the control information with the experimental information to detect the presence, absence, relative magnitude or absolute magnitude of the biological response 62C. The method of embodiment 61C wherein the compound of formula 1 further comprises a pharmaceutically acceptable carrier.

63C. The method of embodiment 61C or 62C wherein the biological response associated with the administration of the compound of formula 1 to the subject is modulation of the expression of a cell surface antigen, an increased absolute or relative number of cells in an immune cell subset, a decreased absolute or relative number of cells in an immune cell subset or an unchanged absolute or relative number of cells in an immune cell subset.

64C. The method of embodiment 63C wherein the immune cell subset is $CD8^+$ T cells, $CD4^+$ T cells, $CD8^+$ lymphokine activated killer cells, $CD8^-$, $CD16^+$ natural killer cells, circulating dendritic cell precursors, circulating dendritic cells, tissue dendritic cell precursors, tissue dendritic cells, $CD8^+$ lymphokine activated killer cells, $CD8^-$ lymphokine activated killer cells, $CD8^-$, $CD16^+$ natural killer cells, $CD8^+$, $CD16^+$ natural killer cells, $CD8^-$, $CD16^+$ cells that mediate antibody-dependent cell-mediated cytotoxicity, $CD8^+$, $CD16^+$ cells that mediate antibody-dependent cell-mediated cytotoxicity, $CD45RA^+$ T cells, $CD45RA^+$, $CD45RO^+$ T cells, $CD45RO^+$ T cells, $CD8^+$, $CD62L$ T cells, $CD4^+$, $CD62L^+$T cells or $HLA-DR^+$, $CD8^+$, $CD38^+$ T cells, monocytes or macrophages.

65C. The method of embodiment 64C wherein the biological response is at least transient modulation of an immune cell antigen or an immune accessory cell antigen (e.g., an adhesion molecule at the surface of endothelial cells or a cytokine receptor at the surface of T cells or B cells).

66C. The method of embodiment 65C wherein the immune cell antigen is a protein, glycoprotein or cell surface antigen usually or only expressed by lymphoid cells (lymphocytes or white blood cells or their precursors, e.g., T cells, B cells, monocytes, macrophage, LAK cells, NK cells, dendritic cells).

67C. The method of embodiment 65C wherein the immune cell antigen is a CD molecule, an interleukin or a cytokine, optionally selected from CD16, CD25, CD38, CD62L, CD69, CD45RA, CD45RO, IL-1, IL-2, IL-4, IL-6, IL-8, IL-10, $TNF\alpha$, $IGF_1$ and $\gamma IFN$.

68C. The method of any of embodiments 61C-67C wherein the subject is a human, a primate, a canine, a feline or a rodent.

69C. A method to alter the Th1-Th2 balance in a subject comprising administering an effective amount a compound of formula 1 to a subject whereby the subject's expression or secretion of IL-4 or IL-10 is detectably modulated.

70C. The method of embodiment 30 wherein the subject's expression or secretion of IL-4 or IL-10 is decreased and the Th1-Th2 balance in the subject's Th1 immune responses to an infection or immunosuppression condition is detectably enhanced.

71C. The method of any of embodiments 1C-70C, wherein the formula 1 compound is a compound named in any of compound groups 1 through 42-25-10-6, or the formula 1 compound is a species in any genus described in any of compound groups 1 through 42-25-10-6.

Variations and modifications of these embodiments, the claims and the remaining portions of this disclosure will be apparent to the skilled artisan after a reading thereof. Such variations and modifications are within the scope and spirit of this invention. All citations herein are incorporated herein by reference in their entirety. All citations herein are incorporated herein by reference with specificity.

EXAMPLES

The following examples further illustrate the invention and they are not intended to limit it in any way.

Example 1

BrEA Formulation

Two lots of a non-aqueous BrEA formulation were made at a BrEA concentration of 50 mg/mL in 25% polyethylene glycol 300, 12.5% dehydrated ethyl alcohol, 5% benzyl benzoate, and 57.5% propylene glycol as follows. BrEA was obtained from Procyte, Inc. The remaining excipients are shown below.

| Excipient | Specification | Supplier Lot No. | Final Product Concentration |
|---|---|---|---|
| Propylene glycol | USP | Arco Chemical HOC-61220-01104 | 57.5% (v:v) |
| Polyethylene glycol 300 | NF | Union Carbide 695752 | 25% (v:v) |
| Dehydrated alcohol | USP | McCormick Distilling 97K10 | 12.5% (v:v) |
| Benzyl benzoate | USP | Spectrum Pharmaceuticals MG025 | 5% (v:v) |

The formulation was prepared by suspending BrEA in polyethylene glycol 300, and sequentially adding propylene glycol, benzyl benzoate, and dehydrated ethyl alcohol to form a solution, which was diluted to the final desired volume with additional propylene glycol. The procedure is described below.

The calculated amount of polyethylene glycol 300 was added to a compounding vessel. Then, while mixing, the calculated amount of BrEA was added to the vessel, and mixed for at least 5 minutes to form a smooth, creamy liquid propylene glycol was added to the vessel, and mixed for a minimum of 5 minutes to form a uniform suspension. The calculated amount of benzyl benzoate is added to the vessel, and mixed for approximately 5 minutes to form a translucent liquid suspension. Dehydrated alcohol was added to the vessel, and mixed for approximately 5 minutes to form a clear, colorless solution. Propylene glycol was then added to achieve the desired final formulation, and mixed for approximately 5 minutes. The drug solution was transferred to a volume-dispensing device set to deliver 1.2 mL per vial. Under nitrogen pressure, the solution was filtered through two 0.2 μm polyvinylidene fluoride filters in series into 2 cc amber glass vials. The vials were capped with Teflon-coated, butyl-rubber stoppers and crimp sealed. Materials used in the product vials are listed below.

| Material | Source | Product Code | Description |
|---|---|---|---|
| Vial | Wheaton | 2702-B51BA | Tubing vial, 2 mL/13 mm, glass, type 1 amber |
| Stopper | Omniflex | V9239 FM257/2 | 13 mm, Teflon coated, butyl rubber stopper |
| Seal | West | 4107 | Flip seal, 13 mm, mist gray bridge |

Product specifications were examined by one or more of the following assays.

| Test | Specification | Method |
|---|---|---|
| Physical Examination | Clear colorless solution with slight alcoholic odor | |
| Volume recovery | NLT* 1.0 mL | USP23<1> |
| Specific gravity | TBD | USP23<841> |
| Assay for active component | 90-110% of label | HPLC |
| Sterility | sterile | USP23<71> |
| Endotoxin | <0.1 EU/mg | USP23<85> |
| Particulate matter | ≧10 μm NMT** 6000/cnt ≧25 μm NMT 600/cnt | USP23<788> |

*NLT—no less than
**NMT—no more than

| Lot Analysis | | | |
|---|---|---|---|
| Test | Specification | Lot 1 | Lot 2 |
| Physical Examination | Clear colorless solution with slight alcoholic odor | Positive | Positive |
| Volume recovery | NLT 1.0 mL | 1.15 mL | — |
| Specific gravity | TBD | 1.0411 | — |
| Assay for active component | 90-110% of label | 103.10% | 104.25% |
| Sterility | sterile | sterile | — |
| Endotoxin | <0.1 EU/mg | 0.024 EU/mg | — |
| Particulate matter | ≧10 μm NMT 6000/cnt ≧25 μm NMT 600/cnt | 26 15 | — |

Example 2

BrEA Drug Substance and BrEA Formulation Stability

An accelerated stability study of 6 months duration is conducted using BrEA and the formulations from example 1. Samples are taken at 1, 2, 3, 4, 5, and 6 month time points and compared with the specifications listed in example 1. Real time stability (25° C., 60% relative humidity) is conducted using BrEA formulation Lots 1 and 2, with sampling time points at 3, 6, 9, 12, 18, 24, and 36 months. After 3 months of storage at 40° C. and 75% relative humidity, the assay potency of BrEA is at least 95% of the label value. The results from the stability testing indicate that BrEA is stable for at least 3 months at elevated temperature and humidity in the Lot 1 and 2 formulations.

Example 3

Primate Intermittent Dosing Protocol

Pig-Tail Macaque Monkeys infected with the $SHIV_{229}$ retrovirus were treated with a BrEA formulation as described in example 1. $SHIV_{229}$ is a recombinant retrovirus containing HIV and SIV sequences. J. Thompson et al., abstract #75, 16$^{th}$ *Annual Symposium on Nonhuman Primate Models for AIDS*, Oct. 7-10, 1998, Atlanta, Ga., M. Agy et al., abstract #67, 16$^{th}$ *Annual Symposium on Nonhuman Primate Models for AIDS*, Oct. 7-10, 1998, Atlanta, Ga. In monkeys, it establishes an aggressive infection that leads to severe symptoms of end-stage disease in infected untreated animals at about 180-210 days after infection. Four pig-tail macaques (2/group) received subcutaneous injections of the formulation at 1 or 2 mg/kg body weight for 10 consecutive days (Protocol 1). On week 8, 3 of the 4 monkeys were retreated and 2 treatment naïve monkeys were treated with 5 mg/kg of the formulation on an every other day basis for a period of 20 days (Protocol 2). On week 19, all primates receiving treatment began a 3 course treatment regimen with 3 mg/kg the BrEA formulation once daily for 10 consecutive days, repeated every four weeks for a total of 3 treatment courses (Protocol 3).

The animals were infected with 1-100 $TCID_{50}$ units administered intravenously or intrarectally. Viral titers in the first group of animals ranged from $10^6$ to $10^8$ before dosing began. All animals demonstrated an initial rise in plasma viral SHIV RNA. After a period of 2 to 3 weeks, titers began to decline and 3 of the 4 animals showed a response to therapy with average viral titers of 0.76 log below baseline at weeks 4 to 5 after initiation of treatment. By week 8, titers in all animals had returned to baseline values. Blood glucose levels dropped significantly, alkaline phosphatase levels were elevated and SGOT/GGT values trended towards the high end of normal. No other significant changes were observed in any of the parameters monitored. The CD4 levels in all monkeys remained less than 100 cells/mm$^3$ at the end of the first protocol.

Three of the five monkeys on the second regimen (Protocol 2) responded to the BrEA therapy with a greater depth and duration of response than observed at the lower dose levels. In the responding animals, the average decline below baseline was 1.47 log. The non-responding animal from Protocol 1 responded when administered the BrEA formulation in Protocol 2. Two animals did not respond, one each from the treatment experienced and treatment naïve groups. The third regimen (Protocol 3) is ongoing and animals are being monitored.

The monkeys on this study were salvaged from an infectivity study and the first cohort of four monkeys on study (Protocol 1) were expected to live only a few weeks past the initiation of these experiments as they were beginning to deteriorate due to disease related causes. One animal died at day 356 from a toxic reaction to the anesthetic used during acquisition of a blood sample for analysis. At the time of this application, the remaining monkeys are receiving multiple rounds of therapy appear to be in good clinical health. Their survival was greater than 380 days from the time of infection. Treatment by intermittent dosing of the BrEA formulation was used. Three control monkeys were infected with 1-10,000 SHIV$_{229}$ TCID$_{50}$ units and did not receive treatment. These animals are considered the no treatment arm of a survival study. The mean time to death for pig-tailed macaques infected with SHIV$_{229}$ was 193 days. Monkeys receiving therapy remained in good clinical health for over 350 days with CD4 levels less than 20 cells/mm$^3$ and without opportunistic infections or disease-related symptoms, other than a mild anemia in one animal.

These results show completely unexpected therapeutic responses by the primates infected with the SHIV retrovirus, which is quite virulent. The results show that the majority of subjects in these treatment protocols not only had significantly prolonged survival compared to untreated controls, but also the clinical symptoms associated with retroviral infection improved dramatically, despite the fact that CD4 counts remained low, i.e., less than about 100 CD4 cells/mm$^3$ initially and less than about 20 CD4 cells/mm$^3$ later in the treatment protocols. To date, results such as this, i.e., (1) good clinical health in a majority of subjects having low CD4 levels (less than about 150 cells/mm$^3$, especially less than about 75 cells/mm$^3$) and (2) no clinical sign of viral resistance to treatment despite intermittent dosing over a prolonged time period, are unprecedented in primates, humans or any other animal. The SHIV$_{229}$ model is extremely pathogenic in pig-tailed macaques. Events that occur in this model over several weeks would typically take several years in humans infected with HIV. Treatment of monkeys infected with this virus and treated with commonly used antiretrovirals, e.g., AZT, 3TC or a protease inhibitor, are not expected to significantly affect the course of disease progression. The clinical condition of the animals continues to improve, e.g., weight gain is about 8-15% per animal. These results show that the treatment using the intermittent dosing protocol is highly effective despite the apparent impairment of the subject's specific immunity, as shown by the low CD4 counts. Increased CD4 counts may be attained using immune stimulators such as IL2 or they may increase spontaneously in some subjects such as humans, depending on the treatment protocol, the duration of dosing or the subject's initial medical condition. The antiviral effects shown here appear to function at least in part by enhancing the subject's immune responses, e.g., enhanced immune response by phagocytic cells (NK cells, monocytes and/or macrophages), and/or enhancing any residual specific immune responses, if any, that the subject may be able to muster.

Example 4

Human Treatment Protocol

A dose escalation clinical trial is performed using a non-aqueous formulation containing BrEA or another formula 1 compound(s) that is prepared essentially as described in example 1. The patients are treatment naïve or treatment experienced and about 3-10 patients are examined at each dose level. The initial dose is 25 mg of BrEA or another formula 1 compound(s) that is administered parenterally, e.g., s.c. or i.m. The dose is administered once or once or twice per day for 1-12 days, followed by no dosing for at least 7 days (e.g., 7 to 90 days). Subsequent doses are administered once or once per day for 1-12 days, followed by no dosing for at least 7 days (e.g., 7 to 90 days). Other dose levels tested are 20 mg, 50 mg, 75 mg, 100 mg, 150 mg, 200 mg, 250 mg and 300 mg with each dose administered once per day as a single dose or as two, three or more subdivided doses. An efficacy dosing trial is performed using the same dosing protocol as the dose escalation trial or it may alternatively comprise dosing once or twice every other day for 17 days, followed by no dosing for 7-90 days and then repeating the dosing once or twice every other day for 3-17 days. This protocol is repeated indefinitely (e.g., at least about 3-18 months) using the optimal dose(s) obtained from the dose escalation trial, e.g., about 10-200 mg/day of a formula 1 compound.

Example 5

Animal Pharmacological Studies

Nonclinical studies were conducted using an oral and a subcutaneous formulation of BrEA. Rats were orally administered $^{14}$C BrEA solubilized in different excipients to determine the levels of drug in blood and various tissues. The results of these preliminary pharmacokinetics studies indicated that the absorption of BrEA by oral administration is about 0.1 to 15%, with at least about 80% excreted in the feces.

The nonaqueous BrEA formulation of example 1 was administered as a single subcutaneous dose to rabbits. More than 90% of the drug left the injection site within 24 hours of administration, and reached a maximum concentration in the plasma of about 1.2% of the injected dose at eight to twelve hours post administration. The circulating half-life of the drug in the plasma was about twelve hours. The drug did not accumulate to a significant extent in any major organ and was primarily excreted in the urine.

BrEA was administered subcutaneously to rats using the formulation of example 1. Approximately 90% of the drug left the injection site within 24 hours of administration, and reached a maximum concentration in the plasma of about 0.2% of the injected dose at one hour post administration. Elimination from the plasma was biphasic, with half-lives of about 12 and 72 hours respectively. BrEA did not accumulate to a significant extent in any major organ, and was excreted primarily in the feces. A study is also performed in Rhesus Monkeys with the example 1 formulation to determine plasma pharmacokinetics.

A pharmacokinetic analysis of $^{14}$C BrEA in plasma was conducted in two female Rhesus Monkeys. Trace labeled compound (16α-bromo-3-beta-hydroxy-5α-[4-$^{14}$C]-androstan-17-one [50 mCi/mmole]) was used at a dose of 1 mg/kg as a subcutaneous injection in the scapular region using an injection volume of 1 mL/kg. The BrEA was formulated in 25% polyethylene glycol 300, 12.5% absolute ethanol, 5% benzyl benzoate, and qs with propylene glycol. 40 µCi were injected per animal. Blood samples were taken at 0, 0.5, 1, 2, 4, 8, and 24 hours for determination of $^{14}$C activity. The radioactivity in the plasma rose to near peak concentration in 8 hours and remained at approximately the same level through the end of the study at 24 hours.

A pharmacokinetic analysis of $^{14}$C BrEA was conducted in New Zealand White rabbits. Twenty µCi of $^{14}$C 16α-bromo-3-beta-hydroxy-5α-[4-$^{14}$C]-androstan-17-one (50 mCi/mmole) plus 1 mg/kg unlabeled BrEA was administered to each of three New Zealand White rabbits as a subcutaneous injection in the scapular region using an injection volume of 1 mL/kg. The drug was formulated in 25% polyethylene glycol 300, 12.5% absolute ethanol, 5% benzyl benzoate, and qs with propylene glycol. Blood samples were taken at 0.5, 1, 2, 4, 8, 12, 24 hours for all three animals, and at 48 hours for two of the animals. Twenty-four and 48 hours after administration, one and two animals respectively, were sacrificed, and the following organs/tissues were collected: brain, heart, kidneys, liver, lungs, skeletal muscle, spleen, and injection site muscle and skin. In addition to the organs and tissues, urine and feces were collected as well as the cage wash. BrEA did not accumulate to a significant degree in any of the organs listed above. Of the organs, the greatest mass of drug was observed in the liver, containing approximately 0.8% and 0.12% of the injected dose at 24 and 48 hours, respectively (average 0.13%).

| Percentage of Drug in Organs (Rabbits) | | | |
| --- | --- | --- | --- |
| Organ or Tissue | Animal 201 24 hours | Animal 301 48 hours | Animal 302 48 hours |
| Brain | 0.005 | 0.002 | 0 |
| Heart | 0.008 | 0.003 | 0.002 |
| Kidneys | 0.155 | 0.055 | 0.050 |
| Liver | 0.76 | 0.145 | 0.125 |
| Lungs | 0.029 | 0.019 | 0.011 |
| Spleen | 0.002 | 0 | 0 |
| Skeletal muscle | 0.002 | 0 | 0 |
| (sample wt. in grams) | (3.8 g) | (6 g) | (5 g) |
| Skin | 0.008 | 0.002 | 0.004 |
| (sample wt. in grams) | (8 g) | (6 g) | (9 g) |

The average percentages of the administered dose in whole blood was calculated by multiplying the concentration of drug in whole blood by the assumed volume of blood in the animals, 200 mL. The amount of drug in the blood reaches a maximum at around 8 hours, and a small amount was still evident at 48 hours. The amount of BrEA in whole blood was consistently lower than in plasma, suggesting the drug is not taken up to an appreciable extent by red blood cells.

In vivo experiments were conducted to determine the bioavailability of BrEA via oral administration using different formulations. BrEA was (1) solubilized in soya oil, vitamin E oil, a mixture of vitamin E and cremophore or (2) BrEA was micronized and combined with or without a surfactant. These formulations are described below. The formulations were administered orally to rats and BrEA levels were determined in the blood, liver, spleen, kidney, and the lymph nodes. In the studies using micronized BrEA, the brain was evaluated for drug uptake. Twenty-four hour urine and feces were collected when BrEA was solubilized in vitamin E and soya oils and vitamin E mixed with Cremophore. The data from these studies indicate that BrEA enters into the lymphatics but is eliminated rapidly from the other tissues. The amount of $^{14}$C radioactivity recovered in the feces 24 hours after administration was 78 to 83%. A brief summary of each experiment is provided below and the results are provided in Table 6.

BrEA (5 mg in 1.0 mL of soya oil or vitamin E oil) supplemented with $^{14}$C-labelled BrEA was administered intragastrically to rats. Solubilization of BrEA in the vitamin E or soya oil was facilitated with 50 µL ethanol. Animals (3/time point) were assayed at 1.5, 3, 5.5, and 24 hours after administration and the $^{14}$C-radioactivity was measured in the blood, liver, spleen, kidney, lymph nodes and 24 hour feces and urine. The results indicate that, on the basis of $^{14}$C-radioactivity, some of the BrEA is taken into the lymphatic system. The uptake is greater with soya oil than vitamin E oil in the blood, liver, and lymph nodes.

BrEA (5 mg in 1.0 mL of a vitamin E and cremophore) supplemented with $^{14}$C-labelled BrEA was administered intragastrically to rats. Solubilization of BrEA in the vitamin E-cremophore mixture was facilitated by the adding 60 µL ethanol. Animals (4/time point) were sacrificed at 2, 3, 5.5, and 24 hours and $^{14}$C-radioactivity was measured in the blood, liver, spleen, kidney, lymph nodes and 24 hour feces and urine. The results indicate that a small portion of the drug is taken up by the lymphatic system. Judging from the values in plasma, liver and lymph nodes, it appears that drug uptake is slower compared with soy oil or vitamin E and its presence in the tissues is more persistent.

Rats, in groups of three males, were orally administered 1.0 mL of 0.9% NaCl containing 10 or 32 mg BrEA micronized with a surfactant, Synperonic PE/F 127 (2.5% wt/wt). Rats were examined at 1.5, 5 and 24 hours after administration. Blood, liver, spleen, kidney, lymph nodes, and brain were assayed for $^{14}$C radioactivity. The levels of BrEA in the blood, in comparison to the experiments with BrEA in Vitamin E oil and soya, were higher, 0.3% at 1.5 hours, and increased after 5 hours to 0.8% and 0.9% of the 10 and 32 mg dose, respectively. Additionally, the values in the lymph nodes were similar to those measured at 1.5 hours and the levels were sustained at 5 hours (5.3 and 5.0%) and 24 hours (3.7 and 3.1%) for the 10 and 32 mg dose, respectively (refer to Table 6).

In a repeated dose experiment, rats were intragastrically administered 1.0 mL 0.9% NaCl containing 2 mg BrEA micronized with Synperonic PE/F 127 (2.5% wt/wt) every 6 to 16 hours. Rats (3/time point) were sacrificed at 40, 72, 84, 90 and 96 hours after the first administration. Blood, liver, spleen, kidney and lymph nodes were assayed for $^{14}$C radioactivity. Higher levels in the blood, liver, kidneys and lymph nodes were noted in this experiment over previous studies.

Rats, in groups of three males, were orally administered 1.0 mL of 0.9% NaCl containing 2, 4 or 10 mg BrEA micronized without a surfactant. Rats were sacrificed at 1.5, 5 and 24 hours after administration and blood, liver, spleen, kidney, lymph nodes and brain were assayed for $^{14}$C radioactivity. The concentration of BrEA micronized without a surfactant in the observed tissues was lower than BrEA plus a surfactant.

Example 6

Inhibition of Parasites In Vitro

For in vitro antimalarial testing, micro-titer plates were used. The concentration of drugs was prepared as pMol/well according to WHO standard procedures (WHO, 1990). The test compound was dissolved in 15% DMSO in sterile RPMI-1640. Both chloroquine sensitive (e.g., WS/97) and resistant (e.g., MN/97) isolates of *Plasmodium* species are used.

A schizont inhibition assay was performed as follows. The micro-titer plates were predosed with various concentrations of the test compound. 50 µL of parasitised erythrocyte suspension in RPMI-1640 (0.2 mL erythrocyte +0.3 mL serum +4-5 ml RPMI-1640) were dispensed in microtiter wells that contained various concentrations of drug. Triplicate readings were made for each concentration.

A $^3$H-hypoxanthine incorporation assay was performed as follows. The testing was carried out according to the procedure of Desjardins et al. 1979. After 30 hr culture at 37 degrees C., the same microtiter plates from schizont inhibition assays with another triplicate wells were pulsed with $^3$H-hypoxanthine for overnight. The cell suspensions were washed twice on millipore glass fiber filter with Millipore filter apparatus. The filter discs were counted for DPM by a Beckman LS6000 β-scintillation counter. The activity of the drug was measured by plotting DPM against concentration of drug.

Activity of compounds against Chloroquine sensitive
T996/86 *P. falciparum* in vitro

| Concentration (µM) | DHEA* | BrEA* | Etienic Acid Methyl Ester* | Etianic Acid Methyl Ester* |
|---|---|---|---|---|
| 30 | 65.6 | 98 | 60 | 61.5 |
| 15 | 44 | 60.1 | 45.7 | 47.4 |
| 7.5 | 38.3 | 50 | 40.9 | 45.3 |
| 3.25 | 37.2 | 43.7 | 46 | 41.4 |
| 1.875 | 23.2 | 40.9 | 41 | 43.4 |
| 0.938 | 37.2 | 31.8 | 43.3 | 47.1 |
| IC$_{50}$ | 19.0 µM | 7.5 µM | 19.5 µM | 17.5 µM |

| Concentration (nM) Chloroquine | % Inhibition Chloroquine |
|---|---|
| 200 | 95.9 |
| 100 | 94.6 |
| 50 | 97.3 |
| 25 | 94.5 |
| 12.5 | 86.8 |
| 6.25 | 27.2 |
| IC$_{50}$ | 9.0 nM |

*% inhibition

The activity of 16α-chloroepiandrosterone and 16α-bromodehydro-epiandrosterone against chloroquine sensitive T996.86 and chloroquine resistant KI *P. falciparum* in vitro is shown below.

|  |  | T996.86 | KI |
|---|---|---|---|
| 16-chloroepiandrosterone | IC$_{50}$ | ~9.25 pg/mL | ~9.25 µg/mL |
| DHEA-Br | IC$_{50}$ | ~25.0 pg/mL | ~25.0 µg/mL |

Other formula 1 compounds, e.g., any compound in compound group 1 through 25-6 are used in a similar manner to inhibit *Plasmodium* parasites.

Example 7

Four-Day In Vivo Protocol for Inhibition of *Plasmodium berghei*

The 4-day suppressive test has been widely used and it can be performed within a 1-week period. The test consists of the inoculation of parasitised erythrocytes on the first day of the experiment (D$_0$), followed by an injection of the test compound, which is also administered on the 2$^{nd}$, 3$^{rd}$ and 4$^{th}$ days of the protocol. On the 5$^{th}$ day, blood films are taken and antimalarial activity is assessed either by calculating parasitemia, or by scoring parasite numbers on a predetermined scale (i.e., 1-5). Peters (*Ann. Trop. Med. Parasitol.* 64: 25-40, 1970) described a basic procedure using this 4-day test.

The protocol is summarized as follows. Five female TO mice were used per test group. *P. berghei* HP15 ANKA parasites were collected by cardiac puncture using a heparinised syringe from a donor mouse having a 30+% parasitaemia. The blood was diluted with diluting agent (50% HIFCS+50% sterile PBS) to a final concentration of 1% parasitaemia or 1×10$^7$ infected erythrocytes per 0.2 mL of the infecting suspension. Each mouse was inoculated intravenously, which produced a more uniform infection rate than intraperitoneal administration of 0.2 mL of the infecting suspension. Test compounds were prepared at doses of 100 mg/kg in (16.7% DMSO+83.3% Celacol). The steroid formulations were administered intraperitoneally 2 hours after parasite inoculation. The compounds were administered once a day starting on D$_0$, and continued on the following three days. Blood films were made from tail blood on the day after the last dosing of compound and the blood was fixed with 100% methanol and stained with 10% Giemsa. Parasitaemias were scored on a scale of 0-5, where 5 is equal to the control.

An inoculum of 1% parasitaemia 1×10$^7$ erythrocytes/mL, 0.2 mL per mouse (female strain TO mice), was delivered by intravenous injection. Drug administration commenced 2 hours after inoculation on Day 1 and continued for 3 days. The results are shown below from blood films from all 20 mice on Day 5 when parasitaemias were assessed.

| Compound | Treatment | Parasitaemia Score (0-5) |
|---|---|---|
| BrEA | 100 mg/kg × 4 days i.p.* | 1 |
| Etienic Acid | 100 mg/kg × 4 days i.p. | 2 |
| DHEA | 100 mg/kg × 4 days i.p. | 1 |
| Chloroquine | 3 mg/kg × 4 days i.p. | 1 |
| control | N/A | 5 |

*i.p. = intraperitoneal injection

In a similar protocol, mice are inoculated with a solution containing 1×10$^7$ erythrocytes/mL by I.V. injection. Two hours later give drug is delivered by I.V. injection. BrEA or another formula 1 compound is given (0.2 mL I.V. or S.C.) once a day for 4 days. Tail snips are used to obtain blood after the study. Mice infected with *P. berghei* were used to obtain infected cells. Parasites are harvested from cardiac mouse blood, and uninfected mice are infected using 0.2 ml of blood with 14% parasitaemia per mouse I.V. Two hours later, the first dose of BrEA (100 mg/kg I.V. or S.C.) is delivered to the infected animals. The BrEA formulation was a sterile solution containing 15 mg/mL of BrEA in 45% hydroxypropyl- β-cyclodextrin and 0.9% saline. At 1, 2, 3 and 4 days after the infection of the animals, BrEA (100 mg/kg I.V. or S.C.) is delivered to the infected animals. No deaths occurred in the group receiving I.V. BrEA at day 30, but all control animals were dead by day 10. All animals treated with BrEA by S.C. delivery were dead by Day 11.

Example 8

Rat In Vitro and In Vivo Study

In the in vitro protocol the parasite (*Plasmodium falciparum*, chloroquine sensitive strain WT and chloroquine resistant strain Dd2) level is adjusted to 1% and the hemocrit is adjusted to 7% with medium. Using a 96 well plate, 50 μL of parasite and 100 μL of drug mixed with media are added to each well and the procedure is done in triplicate. The plate is placed in a chamber containing a physiological gas mixture and incubated at 37° C. The media/drug mixture is changed at 24, 48 and 72 hours. On day 5 (96 hours) slides of each well are made, stained with Gemsia and 500 red blood cells are counted for each slide. The triplicates are averaged and data are reported in percent inhibition.

In the in vivo protocol, Lewis rats weighing 80-85 grams were given a standardized IP injection of parasite (*Plasmodium berghei*). Rats were then intravenously injected 2 hours later with one of the treatments described in the table below, returned to their housing, fed standard lab chow and allowed free access to water. Animals were weighed and treated again 24, 48, and 72 hours after the first treatment and again returned to their housing and they were allowed free access to food and water. The animals were weighed again and then bled using a 26-gauge needle on day 5, 11 and 28 post inoculation. Hemocrits were measured and blood smears are prepared for each rat. The blood smears were then stained using Gemsia and the level of parasitemia (defined as the percent of red cells with parasites) were determined. Animals were again returned to their housing and observed twice daily for evidence of progressive disease, defined as listlessness and or adverse drug reaction, which is defined as a loss of 20% of original body weight, for a total of 28 days. If either progressive disease or drug reaction is noted, the animals are euthanized.

The BrEA formulation was a sterile solution containing 15 mg/mL of BrEA in 45% hydroxypropyl-β-cyclodextrin and 0.9% saline.

| Group 1 | Group 2 | Group 3 | Group 4 |
|---|---|---|---|
| Control 0.9% saline | Chloroquine Control 40 mg/kg | BrEA Low Dose 30 mg/kg | BrEA High Dose 60 mg/kg |

The intravenous injections were given on days 0, 1, 2 and 3 and the results are shown below. The results showed that treatment in vivo with a formulation comprising BrEA reduced parasitemia to a level comparable to that seen with the chloroquine ("Clq") control. The results are summarized below.

| | % RBC parasitemia |
|---|---|
| Day 4 | |
| saline control | 16% |
| chloroquine control | 10% |
| low dose BrEA | 9% |
| high dose BrEA | 7% |
| Day 11 | |
| saline control | 36% |
| chloroquine control | 16% |
| low dose BrEA | 12% |
| high dose BrEA | 11% |

Example 9

Human Clinical Study

Parasite Infection

Response to drug treatment was graded as per World Health Organization criteria (WHO 1973) in infected patients. Evaluation of therapeutic response was determined using the parasitic and fever clearance times. Parasite clearance was expressed as three indices; the time for the parasite count to fall by 50% of the pre-treatment (baseline) value ($PC_{50}$), (ii) the time for the parasite count to fall by 90% of the baseline value ($PC_{90}$) and (iii) the time for the parasite count to fall below the level of microscopic detection (parasite clearance time PCT) (N. J. White and S. Krishna *Trans. R. Soc. Trop. Med. Hyg.* 83: 767-777, 1989; White et al., *J. Infect. Dis.* 165: 599-600, 1992; White et al., *J. Infect. Dis.* 166: 1195-1196, 1992). The fever clearance time was defined as the time from drug administration till the oral or rectal temperature fell to or below 37.2° C. and remained so for at least 48 h.

Venous blood (5 mL) was obtained from two patients before treatment and at 4, 6, 8, 12, 18, 20, 24, 30 and 36 h after treatment or at 4 or 6-hourly intervals after treatment until there was complete clearance of peripheral parasitemia. Blood was collected aseptically and transferred to 10 mL syringes containing 2 mL of acid citrate dextrose (ACD) for in vitro culture. Prior to incubation, the plasma was separated from the red blood cells and the red blood cells were washed twice. Parasites were cultured by modification of standard in vitro culture techniques (W. Trager and J. B. Jensen, *Science* 193:673-675, 1976; A. M. Oduola et al., *J. Protozool.* 39: 605-608, 1992). Samples were dispensed into sterile centrifuge cubes within 10 min of collection and spun down. The supernatant plasma was stored while the packed cells were washed twice with culture medium (washing medium, RPMI-1640 medium, containing 25 mM HEPES buffer and 25 mmol/L NaOH). The buffy coat was removed by vacuum aspiration. A 1:10 fold dilution was done for each blood sample with complete washing medium [CMP (washing medium supplemented with 10% human plasma)]. One milliliter each of the sample was transferred into 2 wells of a 24 well micro culture plate. Cultures were incubated at 37 degrees C. in an atmosphere of 5% $CO_2$, 5% $O_2$ and 90% $N_2$ premixed gas. The culture medium was changed daily and thin blood smears were prepared for microscopy at 24 and 48 h after the culture has been set up. The culture samples were diluted with unparasitized washed type A Rh-positive red blood cells if the proportion of parasitized red blood cells was more than 2%.

Microscopy. During the in vivo study, thin and thick blood films were fixed with dehydrated methanol (100%) and heat, respectively, were stained with 10% Giemsa for 20 min. Parasitemia was quantified in thin films by counting 2000 red blood cells in clear contiguous fields and finding the proportion that was parasitized. In thick films, parasitemia was quantified by counting parasites against leukocytes. A film was declared negative if no parasites were found after examination of 200 microscope fields of a thick smear. During in vitro and ex vivo study, pretreatment thin and thick smears were, graded for ring stages by the method of Jiang as modified by Li et al. (J. B. Jiang et al, *Lancet* 2(8293): 285-288, 1982; K. Silamut and N. J. White *Trans. R. Soc. Trop. Med. Hyg.* 87: 436-443, 1993; X. L. Li et al, *Chi. J. Parasitol. Dis.* 12: 296, 1994). Approximately 5000 erythrocytes were counted in clear contiguous fields 24 and 48 h after incubation of blood obtained at each time point and graded for maturity into tiny rings, small rings, large rings, pigmented trophozoites and schizonts. Functional viability was estimated as the percentage of asexual ring forms capable of maturing to pigmented trophozoites or schizonts after 24-48 h of in vitro culture (W. M. Watkins et al., *Trans. R. Soc. Trop. Med. Hyg.* 87: 75-78, 1993).

Calculation of parameters. The patients presented with acute symptomatic severe non-cerebral pure *P. falciparum* malaria. They had oral fluid intolerance, body temperatures greater than 39° C., greater than 5000 parasites per micro liter of blood, asexual parasitemia and they had a negative urine test for antimalarial drugs. They were administered 25 mL intravenously every four hours with BrEA suspended in sterile 45% β-cyclodextrin in saline at a concentration of 25 mg/mL. This regimen was continued for four days. Parasitemia quantification and clinical examination were done once every 6 hours for the first 72 hours, followed by daily assessment of the parameters up to day 7 (168 hrs) and thereafter on day 14.

Blood films were Giemsa-stained and parasitemia quantification was done in thick films by counting 2000 parasites against leukocytes, and the thin films by finding the proportion of infected red blood cells. Response to drug treatment was graded according to WHO criteria. Evaluation of therapeutic response was done using the parasitic and fever clearance times. Parasite clearance was expressed as three indices: The time for the parasite count to fall by 50% of the pretreatment (baseline) value ($PC_{60}$); to fall by 90% of the baseline value ($PC_{90}$); and to fall below the level of microscopic detection (parasite clearance time) PCT.

The fever clearance time was defined as the time from drug administration until the oral/rectal temperature fell to below 37.2 degrees C. and remained so for greater than 48 hours. The parasite clearance rate at day 14 was 100%. The clinical response thus included an effect on parasitemia in both patients and amelioration of one or more symptoms of infection.

| Intravenous BrEA Malaria Patient Trial | | |
|---|---|---|
| | Patient A | Patient B |
| Fever clearance time | 12 hrs | 18 hrs |
| Parasite clearance times | | |
| Time to 50% clearance | 18 hrs | 24 hrs |
| Time to 90% clearance | 24 hrs | 48 hrs |
| Time to 100% clearance | 48 hrs | 64 hrs |

Example 10

Cellular Studies In Vitro

The effect of BrEA on pentosephosphate shunt (PPS) activity in normal human RBC was examined using whole cells. Since glucose-6-phosphate dehydrogenase ("G6PD") is the limiting enzyme of the PPS, PPS flux measurement is considered to better reflect G6PD activity in the whole cell compared to G6PD activity measurement in a cell lysate. G6PD activity measured in a cell lysate is typically about 1100-fold higher than the PPS flux in whole resting unstimulated RBC (G6PD activity in cell lysate: 165; PPS flux 0.142 micromoles/hour/ml RBC). PPS flux and G6PD activity in the whole RBC depends on a number of factors (the concentration of NADPH, NAD, and ATP, and intracellular pH), which are kept constant if the measurement is performed in the lysate and may vary in the whole RBC. Levels of G6PD activity in cells is considerably above normal basal needs and inhibition of overall G6PD activity might have no or minor consequence on PPS flux in the whole cell. For example, RBC with the Mediterranean G6PD mutant with about 1-3 percent residual activity compared with normal individuals have no impairment in basal PPS flux, but show impaired flux when flux through PPS is stimulated by methylene blue addition. A series of experiments were performed using varying amounts of BrEA and PPS flux was measured in unstimulated basal RBC and in methylene-blue (MB)-stimulated RBC.

The data below shows PPS flux (micromoles/hour/ml RBC) in basal unstimulated, and MB-stimulated normal RBC. Different concentrations of BrEA (0.3, 3.5 and 7 micromolar, final) were supplemented to suspensions of washed RBC suspended in RPMI, pH 7.4 at 10% hematocrit, whereby PPS flux was immediately measured without further incubation and without further washings. A minor inhibition of MB-stimulated PPS flux was observed with BrEA at 7 μM.

| | PPS flux |
|---|---|
| control, unstimulated RBC | 230 |
| DMSO control, unstimulated RBC | 270 |
| DMSO control, MB stimulated RBC | 5090 |
| 0.3 μM BrEA, unstimulated | 250 |
| 0.3 μM BrEA, MB stimulated | 5000 |
| 3.5 μM BrEA, unstimulated | 270 |
| 3.5 μM BrEA, MB stimulated | 4950 |
| 7 μM BrEA, unstimulated | 295 |
| 7 μM BrEA, MB stimulated | 4660 |

The data below shows average values of 3 experiments, where basal, unstimulated, and MB-stimulated PPS flux (micromoles/hour/ml RBC) was measured in normal RBC. In these experiments, different concentrations of BrEA ~0.8, 8 and 80 micromolar, final) were supplemented to suspensions of washed RBC suspended in RPMI, pH 7.4 at 10% hematocrit. After a 90-min incubation at 37° C. with and without BrEA, PPS flux was measured. The results showed a dose-dependent inhibition of MB-stimulated PPS flux. Inhibition was 10% at 8 micromolar (p=0.006 vs control+DMSO) and 25% at 80 micromolar (p=0.002 vs control+DMSO).

| | PPS flux |
|---|---|
| control, unstimulated RBC | 430 |
| control, MB stimulated RBC | 5410 |

-continued

|  | PPS flux |
| --- | --- |
| DMSO control, unstimulated RBC | 480 |
| DMSO control, MB stimulated RBC | 4890 |
| 0.8 µM BrEA, unstimulated | 410 |
| 0.8 µM BrEA, MB stimulated | 4930 |
| 8 µM BrEA, unstimulated | 450 |
| 8 µM BrEA, MB stimulated | 4430 |
| 80 µM BrEA, unstimulated | 450 |
| 80 µM BrEA, MB stimulated | 3660 |

Example 11

Inhibition of Parasite Growth

The effect of Epi (16α-bromo-epiandrosterone) on parasite (*Plasmodium falciparum*) growth was shown. EPI was active at a concentration of 1 µM.

| Parasitemia after treatment | | | | |
| --- | --- | --- | --- | --- |
|  | Time 0 | 24 hrs | 48 hrs | 72 hrs |
| control + DMSO | 5% | 5.40% | 3.10% | 5.20% |
| Epi 1 µM | 5% | 5.70% | 5.50% | 1.60% |
| Epi 10 µM | 5% | 5.60% | 0.90% | 0 |
| Epi 100 µM | 5% | 0 | 0 | 0 |
| Epi 500 µM | 5% | 0 | 0 | 0 |
| control + DMSO | 2% | 8.80% | 11% | 8% |
| Epi 50 nM | 2% | 9.90% | 9.20% | 8.30% |
| Epi 1 µM | 2% | 5.80% | 6.10% | 2.10% |
| Epi 2.5 µM | 2% | 7.30% | 5.80% | 3.20% |
| Epi 5 µM | 2% | 5.40% | 6% | 1.80% |
| Epi 10 µM | 2% | 4.20% | 3% | 0 |
| Epi 50 µM | 2% | 0 | 0 | 0 |

Parasitemias were determined by standard methods (microscopic inspection of at least 500 cells, stained with Diff-Quick™ (Baxter). Parasites were cultured under standard conditions in RPMI-1640 supplemented with Hepes/Glucose (10 mM), glutamine (0.3 g/liter) and 10% human plasma. The hematocrit was 1%.

Example 12

Stimulation of Phagocytosis

The capacity of BrEA to influence phagocytosis of *Plasmodium* parasite-infected RBC is examined using adherent human monocytes. The parasitemia level is about 8-10% and human monocytes are obtained from buffy coats from blood as follows. Peripheral blood mononuclear cells are separated from freshly collected platelet-poor buffy coats discarded from blood samples of healthy adult donors of both sexes. Separated cells are washed once with luke-warm PBS supplemented with 10 mM glucose (PBS-G) and resuspended at $5\times10^6$ cells/mL in ice-cold RPMI 1640 medium supplemented with 23 mM $NaHCO_3$ and 25 mM Hepes, pH 7.4 (RMBH). Dynabeads M450 Pan B and Pan T (Dynal) are added to cells in a 4:1 ratio for 20 min at 4° C. B-lymphocytes and T-lymphocytes are removed as specified by the manufacturer. The remaining monocytes are washed 2 times in RMBH, resuspended in AIM V cell culture medium (Gibco) at $1\times10^6$ cell/mL. The monocyte layer is collected, washed with PBS-G at 37° C. and resuspended in AIM V medium at $1\times10^6$ cells/mL. Purified cells are >90% monocytes as assessed by CD14 expression.

Phagocytosis of opsonized parasitized RBC (PE) is determined as follows. Phagocytosis of fresh-serum opsonized PE is initiated by mixing 10 PE/monocyte. Suspensions are briefly centrifuged (150×g for 5 sec at room temperature) to improve contact between PE and monocytes. To avoid attachment of monocytes after centrifugation and during the whole incubation period, cells are kept in suspension at $5\times10^6$ cells/5 mL AIM V medium in 6 cm diameter teflon bottom dishes (Heraeus) in a humidified incubator (95% air, 5% $CO_2$) at 37° C. On average, at least 90% of the monocytes phagocytose PE, as assessed by microscopic inspection. Control cells are kept under similar conditions without phagocytosis. Quantitative assessment of phagocytosis is performed by a previously described bioluminescence method (E. Schwarzer, et al., *Br. J. Haematol.* 1994 88: 740-745).

Erythrocyte treatments and parasite cultures are as follows. Fresh blood (Rh+) is used to isolate erythrocytes (RBC). Washed RBC are infected with schizont/trophozoite parasite stages (Palo Alto strain, mycoplasma-free). Stage specific parasites are isolated by the Percoll-mannitol method. Briefly, normal schizont-stage parasitized RBC (SPE) separated on Percoll-mannitol gradient (parasitemia >95% SPE) are mixed with RBC suspended in growth medium (RPMI 1640 medium containing 25 mmol/L Hepes, 20 mmol/L glucose, 2 mmol/L glutamine, 24 mmol/L $NaHCO_3$, 32 mg/L gentamicin and 10% AB or A human serum, pH 7.30) to start synchronous cultures at selected hematocrit values. The inoculum parasitemia is adjusted to 20% normal SPE for isolation of ring parasitized RBC (RPE) and to 5% normal SPE for isolation of trophozoite-stage parasitized RBC (TPE). At 14-18 hours after inoculum parasites are at ring-stage in the first cycle; at 34-33 hours, parasites are at trophozoite-stage in the first cycle; and at 40-44 hours after inoculum parasites are at schizont-stage in the first cycle. RPE, TPE and SPE are separated on Percoll-mannitol gradients. The parasitemia is usually 8-10% RPE, and >95% TPE. Nonparasitized and parasitized RBC are counted electronically. To assess total parasitemia and relative contribution of RPE, TPE and SPE, slides are prepared from cultures at indicated times, stained with Diff-Quik™ parasite stain and about 400-1000 cells are examined microscopically.

The effect of a formula 1 compound such as BrEA in parasitized RBC is examined using various concentrations of the compound, e.g., BrEA, e.g., 0.5 µM, 1 µM, 10 µM, 25 µM and 50 µM. Trophozoite-parasitized RBC, schizont-parasitized RBC or ring-parasitized RBC are examined as described.

Example 13

Human Malaria Clinical Trial

The clinical trial protocol that incorporates about 15-20 patients is established. For a phase 1, 1 µl or 11 trial, the patients are mildly infected with one or more *Plasmodium* parasites and they are mildly symptomatic (less than about 8-10% parasitemia of RBC). Before treatment, the patients are optionally tested for infection with HIV, HCV, TB, and *Cryptosporidium*. Patients with one or more co-infections are given standard care for the coinfection. The patients are hospitalized for treatment for one week. Two or more dose groups, e.g., 25, 50 or 100 mg/day of BrEA administered parenterally, e.g., by intramuscular, subcutaneous or intravenous injection, on 3, 4 or 5 days of the week when patients are dosed. Dosing is on consecutive days or on an intermittent schedule, e.g., 2, 3 or 4 doses with one dose administered every other day.

The formulation containing BrEA is as described herein, e.g., the formulation of example 1 or a formulation that comprises 100 mg/mL BrEA, PEG300 ~30% v/v, propylene glycol 30% v/v, benzyl benzoate 30% v/v and benzyl alcohol 2% v/v. At day 5-7, if less than about 50% reduction in parasitemia is observed, the patients are given standard care for malaria (mefloquine). During the week of treatment and for 1, 2 3, or more weeks there after, blood samples are taken periodically for evaluation of parasitemia, pharmacokinetics, plasma cytokines (e.g., IL-2, IL-4, IL-10, IGF1, γIFN, GM-CSF), and intracellular cytokines (e.g., IL-2, IL-4, IL-10, IGF1, γIFN, GM-CSF). The patients are optionally treated again at about 2 to 12 weeks after the initial dosing, using the same or a similar protocol as that used in the initial dosing protocol.

An exemplary open-label study of a BrEA formulation administered intramuscularly to semi-immune patients with uncomplicated malaria is conducted. The formulation comprises 100 mg/mL BrEA, PEG300 ~30% v/v, propylene glycol 30% v/v, benzyl benzoate 30% v/v and benzyl alcohol 2%. Patients will remain at the hospital as in-patients for the first 7 days of the study. Patients will receive one daily intramuscular administration of 50 mg or 100 mg of BrEA for 5 consecutive days. Daily evaluation for the first 7 days, and up to study day 14, may include parasitemia evaluation (twice daily), chemistry, hematology and drug levels (pharmacokinetic evaluation). If, after study day 7, the parasitemia levels decrease from the screening value and the patient is clinically stable, the patient may be followed on a daily basis for parasitemia (twice daily) for up to an additional 7 days as hospital in-patients. If a patient becomes clinically unstable at any time during the study, the patient will be discontinued and may be offered the standard treatment for malaria. Patients deficient in glucose-6-phosphate dehydrogenase enzyme may be excluded, since BrEA inhibits the enzyme. Other considerations that may lead to exclusion of patients from the trial include patients diagnosed with any of the following: severe anemia (hematocrit <21% or hemoglobin <7 g/dL); renal or liver failure by history and/or laboratory results respiratory distress as evidenced by dyspnea or respiratory rate $\geq$30 per minute; hypotension (systolic blood pressure <90 mm Hg); tachycardia (heart rate >130 beats/minute); pregnant or breast-feeding women; significant active co-morbid illness (acute medical diagnosis requiring specific therapy; patients with parasitemia >10% on peripheral smear.

Blood samples may be collected from each patient for future clinical evaluation such as the determination of activation markers or immunological analyses (e.g., assay for intracellular or extracellular interleukins IL-1β, IL-2, IL-4, IL-6, IL-10 and IL-12, γIFN and TNFα).

Example 14

Liposome Formulation

Liposomes suitable for parenteral administration are prepared as follows. 400 mg of phosphatidyl choline and 80 mg of BrEA are dissolved in chloroform and methanol (2:1 v/v) and the solution is dried by rotary evaporation under reduced pressure. The resulting film is rehydrated by adding 8.0 mL of a 0.9% w/v NaCl solution and agitating the solution. The sizes of the liposomes are optionally measured, e.g., by photon correlation spectroscopy (Malvern Zetasizer 3000 or equivalent). The liposomes are optionally sized by, e.g., sonication to reduce the average size below 400 nm, or by filtration using suitable filters. Similar procedures are used to prepare liposome preparations that contain a formula 1 compound at about 15-100 mg/mL. The formulation is used to deliver the compound orally or parenterally (I.M., S.C., I.V.).

Example 15

Cyclodextrin Formulation

A cyclodextrin formulation containing BrEA is prepared as follows. 45 g of hydroxypropyl-β-cyclodextrin is added to 1 L of sterile physiological saline and the mixture is stirred for about 4-24 hours, until a clear solution is obtained. Non-micronized BrEA is added to give a concentration of 20 mg/mL and the mixture is stirred until a clear solution is obtained. The solution is sterilized by filtration using a 0.2 μm pore size filter and dispensed into sterile containers. Similar procedures are used to prepare cyclodextrin formulations that contain a formula 1 compound at about 15-100 mg/mL. The formulation is used to deliver the compound orally, parenterally (I.M., S.C., I.V.) or by a buccal or sublingual route.

Example 16

Suppository Formulation

A suppository formulation containing a formula 1 compound such as BrEA is prepared as follows. Sufficient non-micronized BrEA is measured to obtain a desired number of units that comprise 500 mg each of BrEA. The BrEA is blended with a suppository base, e.g., triglyceride from edible vegetable oil, to provide desired characteristics, e.g., a free fatty acid content of about 0.1% w/w, a saponification value of about 242, an iodine value of about 3, moisture at about 0.1% w/w and a closed capillary melting point of about 35° C.

Example 17

Human HCV Clinical Trial

A female patient infected with HIV and HCV was dosed I.V. with BrEA for 3 consecutive days using a formulation that contained 20 mg/mL BrEA in 45% w/v hydroxypropyl-β-cyclodextrin and saline. Four mL of the formulation (80 mg BrEA) was administered to the patient every 4 hours during the 3 day treatment period. The patient's predosing HCV level was 6.5 $Log_{10}$ as measured by PCR and the HCV level was 6.2 $Log_{10}$ on the first day of dosing, 5.5 $Log_{10}$ on the $3^{rd}$ day of dosing and 4.9 $Log_{10}$ three days after the last dose was administered. HIV RNA levels as measured by PCR was 5.2 $Log_{10}$ (predosing), 5.8 $Log_{10}$ (first day), 5.9 $Log_{10}$ (third day) and 5.4 $Log_{10}$ (day 6). The NK cell counts (cells/mm$^3$) were 28, 41 and 38 at predosing, day 0 and day 3.

Example 18

Formulation

A formulation comprising 100 mg/mL BrEA, 30% v/v PEG300, 30% v/v propylene glycol, 30% v/v benzyl benzoate and 2% v/v benzyl alcohol was prepared by suspending BrEA in polyethylene glycol 300, and sequentially adding propylene glycol and benzyl benzoate, to form a solution, which was diluted to the final desired volume with additional propylene glycol. The procedure is described below.

The calculated amount of polyethylene glycol 300 was added to a compounding vessel. Then, while mixing, the calculated amount of BrEA was added to the vessel, and mixed for at least 5 minutes to form a smooth, creamy liquid propylene glycol was added to the vessel, and mixed for a minimum of 5 minutes to form a uniform suspension. The calculated amount of benzyl benzoate is added to the vessel, and mixed for approximately 5 minutes to form a translucent liquid suspension. Propylene glycol was then added to achieve the desired final formulation, and mixed for approximately 5 minutes. The drug solution was transferred to a volume dispensing device set to deliver 1.2 mL per vial. Under nitrogen pressure, the solution was filtered through two 0.2 µm polyvinylidene fluoride filters in series into 2 cc amber glass vials. The vials were capped with Teflon-coated, butyl-rubber stoppers and crimp sealed.

Example 19

Opportunistic Infection Clinical Protocol

A double blind, randomized, placebo controlled study of 100 mg of BrEA administered intramuscularly to late stage HIV-infected patients at risk for opportunistic infections (OIs). HIV-1 seropositive patients with a CD4 cell count $\leq 100$ cells/mm$^3$, HIV RNA at $1 \times 10^6$ copies/mL and a Karnofsky score of at least 60 are identified for potential inclusion into the protocol. Patients in all clinical protocols must understand and sign a written informed consent form prior to screening evaluations.

BrEA in the formulation of example 16 is used. Administration of drug or vehicle will be for 3 to 5 consecutive days followed by about 35-90 days of observation, e.g., 37 days of observation. An exemplary treatment regimen comprises 5 days of treatment followed by 37 days of observation, which is repeated for a total of 7 courses over 42 weeks. The incidence rate of OIs as well as the time to resolution or control of the OIs will be monitored and compared to a placebo control group. The patients may be monitored monthly for 2 or 3 months after completion of the study for follow-up. The incidence of OIs or conditions associated with AIDS are monitored, e.g., as tuberculosis (TB), candadiasis, *Pneumocystis* pneumonia (PCP), diarrhea, or Kaposi's sarcoma, may be evaluated as protocol endpoints. If a patient is diagnosed with one or more of the protocol specified opportunistic infections, the protocol regimen a treatment for the OI will be initiated, e.g., Fluconazole for Candidiasis or for PCP, trimethoprim and sulfamethoxazole or Dapsone. A similar protocol is used with other formula 1 compounds.

Example 20

Human HIV Clinical Protocol

Patients infected with HIV are dosed with an i.m. injection of 25-200 mg of BrEA using a formulation containing 100 mg/mL BrEA, PEG300 ~30% v/v, propylene glycol 30% v/v, benzyl benzoate 30% v/v and benzyl alcohol 2% v/v. The patients are dosed once per day for 5 consecutive days followed by a period of about 28 days or longer with no BrEA treatment. The patients were them provided with one more course of 5 consecutive days of dosing with BrEA, followed by a non-dosing period of at least about 28 days. Up to 5 rounds of 5-day treatments, followed by at least 28 days of no dosing were provided. Immunological responses were then assayed using blood or plasma samples from the patients by flow cytometry and other known analytical methods. Immune cell subsets or other measured markers were assayed within 24 hours of obtaining the sample from each patient. Labeled antibodies, e.g., anti-CD antigen antibodies conjugated with fluorescent dyes (FITC, phycoerythrin, allophycocyanin or PerCP), were prepared and used essentially according to standard protocols using commercially available reagents, see, e.g., PharMingen, 1998 Research Products Catalog, technical protocols at pages 732-774, human cell surface molecules at pages 182-295 and mouse, rat and hamster cell surface molecules at pages 2-173 and cytokine and chemokine reagents at pages 344-489.

The clinical protocol is a phase I/II, open-label, randomized study of 3 dose levels of BrEA administered intramuscularly to HIV-infected patients who are treatment naïve. There will be 3 treatment groups and each group will consist of 2 parts (Parts A and B). Patients will receive the same dosage of BrEA throughout Parts A and B of the study. If a patient experiences an antiviral response (an HIV RNA titer at least 0.5 log below the average of the screening and baseline values) or benefits (any decrease in HIV RNA titers below the average of the screening and baseline values) from the treatment received during Parts A and B of the study, the patient may continue receiving 5-day treatment courses of the BrEA formulation of example 2 at the dose initially received. This treatment course may be repeated up to six times.

All patients may be monitored for levels of HIV RNA (Chiron Quantiplex™ branched chain DNA assay), T-cell subsets [CD4/CD8], proviral HIV DNA (PBMC), interleukins [IL-2, 4, 6, 8, 10, and 12] (serum), γIFN (serum), insulin-like growth factor [IGF-1] (serum) and tumor necrosis factor [TNF] (serum) throughout the study. PBMC quantitative co-culture (cells) may be conducted on a subset of patient samples. Assays for additional activation markers may be conducted. Analysis of chemistry and hematology panels and urinalysis is planned. Additionally, patients co-infected with hepatitis B and/or C viruses, malaria or tuberculosis may be monitored regularly for viral titers or microbiological cultures. Serial blood and urine samples will be collected from a subset of patients for pharmacokinetic determination after the first dose on Part A and the last dose on Part B.

Treatment may consist of more than one intramuscular injection. Intramuscular injections may be administered in different locations (i.e., left or right upper arms or thighs or buttocks) and a single 100 mg or 200 mg dose of BrEA may be delivered to patients in two or more subdoses of less than 100 mg (e.g., 50 mg).

There are two segments of this study, Segment 1 and 2. Both segments consist of two parts, Part A and Part B. The first 12 patients enrolled on the study will be assigned to the design described in Segment 1. The remaining 24 patients will be assigned to Segment 2 of the study. The design of each segment is provided below.

Part A will consist of a single intramuscular injection of a BrEA formulation. The day the patient receives the injection will be study day 1. Patients participating in the pharmacokinetic subgroup will have serial blood and urine samples collected, beginning on study day 1. Part B of the study begins on study day 8 (Segment 1) or study day 15 (Segment 2).

Segment 1 Part B consists of 5 consecutive daily intramuscular injections of the formulation of example 1 at the same dose as received in Part A of the study. The day the patient receives the first dose will be on about study day 8-12. The 5-day treatment course is followed by an approximate 28-day observation period (or approximately 32 days from a first dose on day 8 to the initiation of a second treatment course on day 40). During the observation period, patients will be asked to return to the clinic on a weekly basis for various tests.

Patients participating in the pharmacokinetic subgroup will have serial blood and urine samples collected, beginning approximately on study day 12-17.

Segment 2 Part B consists of 5 consecutive daily intramuscular injections of the formulation of example 2 at the same dose the patient received during Part A of the study. The day the patient receives the first dose will be about at study day 15. The 5-day treatment course is followed by an approximate 45 day observation period (or approximately 49 days from the first dose on study day 15 to the initiation of the next treatment course on study day 64). During the observation period, patients will be asked to return to the clinic on a weekly basis for various tests. Patients participating in the pharmacokinetic subgroup will have serial blood and urine samples collected, beginning approximately on study day 19.

Randomization in this dose escalation study is as follows. When 4 of the 12 patients per treatment group have completed 5 days of daily dosing on Part B and have not experienced a serious drug-related adverse event, enrollment into the next higher dose level will occur, after consultation between the sponsor and investigators.

The first four patients enrolled will be assigned to the 50 mg dose group. If no serious drug-related adverse events are experienced, the next 8 subjects will be randomized to either the 50 mg or 100 mg dose level in a 1:1 fashion. If no serious drug-related adverse events occur in patients receiving 100 mg, then the next 24 patients will be randomized to either the 50, 100, or 200 mg dose group in a 1:2:3 fashion.

If 4 of the 12 patients in a dose group experience a serious drug-related event (Grade III or IV), 2 additional patients will be enrolled at the same dose level. Additionally, patient enrollment on to the next dose level, if enrolling, will be temporarily on hold until safety is assessed. If one of the 2 additional patients experiences a serious drug-related event, dosing in this dose level will discontinue. Upon consultation with the sponsor and investigators, additional patients may be enrolled at a dose between the dose-limiting group and the next lower dose group to determine the maximum tolerated dose (MTD). Enrollment of additional patients at a specific dose level will be determined in a protocol amendment.

The results indicated that a single 50 mg or 100 mg dose of BrEA increased the numbers of activated CD8$^+$ and CD4$^+$ T cells (e.g., CD8$^+$, CD69$^+$, CD25$^-$ cells) that were circulating in the patient's blood. Also, the circulating numbers of dendritic precursor cells, NK cells, LAK cells and cells that mediate ADCC (antibody-dependent cell-mediated cytotoxicity mediated by the CD8$^+$, CD16$^-$ immune cell subset) functions were increased. Further increases were usually observed on dosing for 5 consecutive days.

Some of the results are summarized below. Course 1, 2 and 3 refer to each 5 consecutive day treatment regimen of one daily injection with BrEA (50 or 100 mg BrEA per injection). In the diagrams below, HE2000 refers to the formulation containing 100 mg/mL BrEA, PEG300 ~30% v/v, propylene glycol 30% v/v, benzyl benzoate 30% v/v and benzyl alcohol 2% v/v. The data shown below was obtained from patient blood samples at baseline (on the day dosing was initiated) and at various times after the patients received at least one dose of BrEA. The results showed significant increases in immune cell populations and cytokine expression profiles associated with Th1 responses. The patients in this protocol initially had CD4 counts of at least 200 per mm$^3$ and a serum HIV RNA load of 5,000 to 1×10$^6$ RNA copies/mL. After dosing with one course of BrEA (5 consecutive daily i.m. injections), all patients showed increases in levels of immune cells including activated CD8 T cells (e.g., CD8$^+$, CD69$^+$, CD25$^-$), LAK cells (e.g., CD8$^+$, CD16$^+$, CD38$^+$), NK cells (e.g., CD8$^-$, CD16$^+$), ADCC cells (e.g., CD8$^-$, CD16$^+$) and dendritic cells (Lin$^-$, HLA-DR$^+$, CD11c$^+$ or Lin$^-$, HLA-DR$^+$, CD123$^+$). Average CD4 IL-10 production dropped from a median of 66% to 4% of the cells, while CD4 IFNγ went from a median of 8% to 63%, leading to a Th2 to a Th1 shift in cytokine production.

In the diagrams below baseline data is indicated by "BL" or by "pre".

| Increased immunophenotypes after BrEA therapy | | | | |
|---|---|---|---|---|
| Phenotype | Baseline[a] | Course 1 | Course 2 | Course 3 |
| CD8+CD69+CD25− | 18 | 54 | 56 | 75 |
| n = | (13) | (13) | (9) | (4) |
| [b]p = | | <0.001 | <0.001 | 0.04 |
| CD8+CD16+CD38+ | 8 | 27 | 28 | 25 |
| n = | (10) | (10) | (4) | (4) |
| p = | | <0.001 | 0.047 | 0.02 |
| CD8−CD16+ | 53 | 253 | 288 | 249 |
| n = | (12) | (12) | (4) | (2) |
| p = | | <0.001 | 0.02 | 0.04 |
| Lin− HLA-DR+ CD11c+/CD123+ | 3.2 | 17.7 | 11.4[c] | 14.7[c] |
| n = | (10) | (10) | (5) | (4) |
| p = | | <0.001 | 0.02 | 0.04 |
| IL2+CD4[d] | 3.14[e] | 29.25 | 31.42 | 13.59 |
| n = | 13 | 13 | 3 | 4 |
| p = | | <0.001 | 0.09 | 0.04 |
| IL10+CD4[d] | 66 | 20.9 | 8.9 | 15.3 |
| n = | 13 | 13 | 5 | 3 |
| p = | | 0.005 | 0.005 | 0.03 |
| Th1 Response[d] | 17 | 66 | 64 | 53 |
| n = | (13) | (13) | (5) | (5) |
| p = | | 0.001 | 0.033 | 0.025 |

[a]Median values of cells/μL
[b]paired value t test
[c]Test not available at baseline for patients receiving second and third courses, baseline value from initiation of 2$^{nd}$ course = 6.4
[d]% of CD4
[e]Baseline values from day 8 (preceding the first five-day treatment)

| Median activated T cells (CD8$^+$CD69$^+$CD25$^-$) vs. baseline by course | |
|---|---|
| Course 1 baseline | 19 cells/μL |
| Course 1 | 53 cells/μL n = 13, p < 0.001 |
| Course 2 baseline | 19 cells/μL |
| Course 2 | 54 cells/μL n = 9, p < 0.001 |
| Course 3 baseline | 19 cells/μL |
| Course 3 | 74 cells/μL n = 4, p = 0.04 |

| Median LAK response (CD8$^+$CD16$^+$CD38$^+$) vs. baseline, responders, by course | |
|---|---|
| Course 1 baseline | 8 cells/μL |
| Course 1 | 26 cells/μL n = 10, p < 0.001 |
| Course 2 baseline | 12 cells/μL |
| Course 2 | 27 cells/μL n = 4, p = 0.04 |
| Course 3 baseline | 12 cells/μL |
| Course 3 | 25 cells/μL n = 4, p = 0.02 |

| Median NK, ADCC (CD8$^-$CD16$^+$) responders vs. baseline by course | |
|---|---|
| Course 1 baseline | 52 cells/μL |
| Course 1 | 255 cells/μL n = 12, p < 0.001 |

-continued

Median NK, ADCC (CD8⁻CD16⁺) responders vs. baseline by course

| | |
|---|---|
| Course 2 baseline | 59 cells/µL |
| Course 2 | 291 cells/µL n = 4, p = 0.02 |
| Course 3 baseline | 56 cells/µL |
| Course 3 | 249 cells/µL n = 2, p = 0.04 |

Median dendritic cell response (Lin⁻HLA-DR + CD123⁺/CD11c⁺) by course

| | |
|---|---|
| Course 1 baseline | 3.2 cells/µL |
| Course 1 | 17.7 cells/µL n = 10, p = 0.001 |
| Course 2 baseline | 6.6 cells/µL |
| Course 2 | 11.6 cells/µL n = 5, p = 0.02 |
| Course 3 baseline | 6.3 cells/µL |
| Course 3 | 14.7 cells/µL n = 4, p = 0.04 |

16α-Bromoepiandrosterone normalizes IL-10⁺ cells in HIV-infected patients

| | % of CD4⁺ cells that are IL10⁺ |
|---|---|
| Normals (HIV⁻) | 8% n = 6 |
| HIV⁺ patients | 64% n = 13, p < 0.001 |
| treated HIV⁺ patients | 4% n = 13, p < 0.001 |

16α-Bromoepiandrosterone increases Th1 cell proportion in HIV-infected patients

| | median % of CD4⁺ cells that are IFNγ⁺ and IL10⁻ |
|---|---|
| Normals (HIV⁻) | 43% |
| HIV⁺ patients | 8% p < 0.05 |
| treated HIV⁺ patients | 63% p < 0.001 |

Median Th1 (IFNγ dominance) vs. baseline

| | median % of IFNγ⁺ T cells |
|---|---|
| Course 1 baseline | 17% |
| Course 1 | 66% n = 13, p = 0.00 |
| Course 2 baseline | 5% |
| Course 2 | 64% n = 4, p = 0.0 |
| Course 3 baseline | 5% |
| Course 3 | 53% n = 4, p = 0.0 |

Example 21

Treatment of Symptoms of HIV Infection

Two HIV infected patients with chronic diarrhea were dosed with BrEA as follows. A BrEA formulation (40 mg/mL BrEA in 25% v/v PEG 300, 12.5% v/v ethanol, 5% v/v benzyl benzoate, ~57.5% v/v propylene glycol) was delivered subcutaneously. The patients received 60 mg of BrEA in 1.5 mL daily for 10 days. During the period of dosing, the diarrhea ceased. After the 10-day dosing period ended, diarrhea resumed. In other patients receiving oral BrEA, diarrhea also went into remission.

Example 22

Subcutaneous Formulation

A BrEA formulation was prepared essentially as described herein. The formulation contained 50 mg/mL BrEA, 40% v/v PEG 200, 2% v/v benzyl alcohol, 2% v/v benzyl benzoate and ~66% v/v propylene glycol (qs). The formulation is particularly suitable for subcutaneous administration of the compound.

Example 23

Preparation of BrEA Hemihydrate

Procedure 1

Crude BrEA was prepared by bromination of epiandrosterone, followed by crystallization from methanol. The hemihydrate was prepared by dissolving 25 g of crude BrEA in 75 mL of refluxing ethanol with moderate agitation. To the BrEA solution 12.5 mL of water was slowly added while maintaining the solution at reflux with agitation. Agitation of the solution was maintained and the solution was then allowed to cool to about 20-25° C. and kept at about 20-25° C. for about 15 minutes to obtain a suspension of BrEA hemihydrate crystals. The crystals were recovered by filtration, washed with a solution of 25 mL of water:ethanol (5:1 v/v) at about 20-25° C. and then vacuum dried for about 13 hours at 50-60° C. until the product weight was constant. The crystals were primarily rod and needle shaped, with smaller amounts of other shapes such as tablets.

The procedure gave 22.5 g of BrEA hemihydrate (yield 90%) with a water content of 2.6% w/w by KF analysis, a purity of 100% by HPLC area analysis, an FTIR spectrum with carbonyl peaks at 1741 cm$^{-1}$ and 1752 cm$^{-1}$. The FTIR scan of anhydrous BrEA shows a single carbonyl peak at 1749 cm$^{-1}$. The DSC scan showed three endotherms. One had a broad shallow peak with an onset at about 109-110° C. and ending at about 150° C. This broad DSC peak is consistent with the loss of water from the hemihydrate crystals as the temperature of the sample increased. The second endotherm at about 83-100° C. is consistent with the loss of the small amount of residual ethanol from the sample. A DSC scan of anhydrous BrEA does not have the broad endotherm that is observed with the hemihydrate. Also consistent with the loss of water from the hemihydrate over the 100-150° C. range is a sharp third endotherm peak in the hemihydrate DSC scan at about 163-164° C., which is the melting point of anhydrous BrEA. The FTIR was obtained using USP method <197>, where the BrEA hemihydrate sample was prepared in KBr. The DSC thermogram was obtained by scanning from 25° C. to 250° C. with a heating rate of 10° C./minute.

Example 24

Preparation of BrEA Hemihydrate

Procedure 2

The hemihydrate was prepared by dissolving 10 g of crude BrEA in 40 mL of refluxing acetone with moderate agitation. To the BrEA solution 4.0 mL of water was slowly added while maintaining the solution at reflux with agitation. Agitation of the solution was maintained and the solution was then allowed to cool to about 20-25° C. and kept at about 20-25° C. for about 15 minutes to obtain a suspension of BrEA hemihydrate crystals. The crystals were recovered by filtration, washed with a solution of 6.0 mL of water:acetone (10:1 v/v) at about 20-25° C. and then vacuum dried overnight (about 13-15 hours) at 50-60° C. until the product weight was constant. The procedure gave 7.0 g of BrEA hemihydrate (yield 70%) with a water content of 2.6% w/w by KF analysis and an FTIR spectrum with carbonyl peaks at 1741 cm$^{-1}$ and 1752 cm$^{-1}$.

Example 25

Analysis of BrEA Hemihydrate Particle Size

BrEA hemihydrate crystals were prepared essentially as described herein and sized using a particle sizing apparatus (Malvern Instruments). The analysis model used was for a polydisperse sample and a volume distribution type. The analysis showed a range of crystal diameter sizes from about 0.5 μm to about 880 μm. About 90% of the crystals had a diameter of about 20 μm to about 220 μm and the majority of the crystals had a diameter of about 30-200 μm. The mean crystal diameter was about 93 μm. The specific surface area of the crystals was about 0.25 m$^2$/g.

To the extent not already indicated, it will be understood by those of ordinary skill in the art that any of the various specific embodiments, compounds or compositions described herein may be further modified to incorporate other appropriate features, e.g., as shown in any other of the specific embodiments disclosed herein or in the cited references.

$R^2$ is —OH or an ether;
$R^3$ is —H, —OH, —F, —Br or an ester;
$R^4$ is —OH or an ester; and
$R^5$ is —CH$_3$ or —CH$_2$OH.

2. The compound of claim 1 having the structure

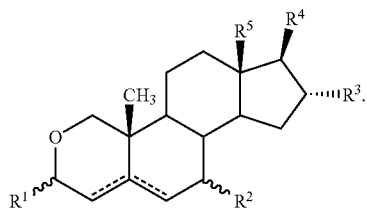

3. The compound of claim 2 wherein $R^1$ is —OH or —OCH$_3$.

4. The compound of claim 3 wherein $R^4$ is —OH or —O—C(O)—CH$_3$.

5. The compound of claim 1 having the structure

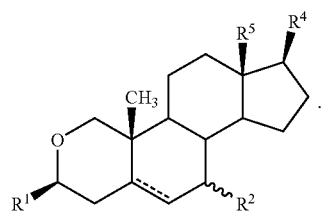

What is claimed is:

1. A compound having the structure

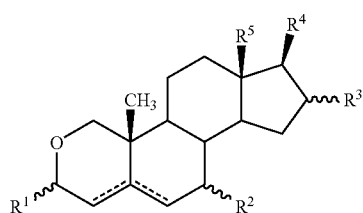

wherein,
$R^1$ is —OH, an ester or an ether;

6. The compound of claim 5 having the structure

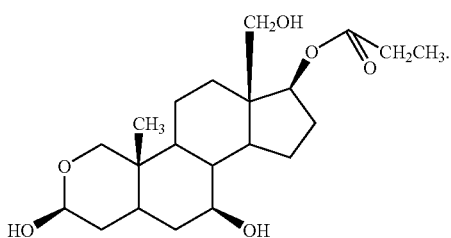

7. A pharmaceutical formulation comprising one or more excipients and a compound having the structure

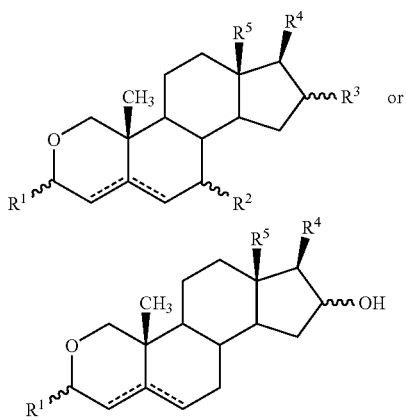

wherein,
R$^1$, R$^2$ and R$^4$ independently are —OH, an ester or an ether;
R$^3$ is —H, —OH, a halogen, an ester or an ether; and
R$^5$ is —CH$_3$ or —CH$_2$OH.

8. The pharmaceutical formulation of claim 7 wherein the compound has the structure

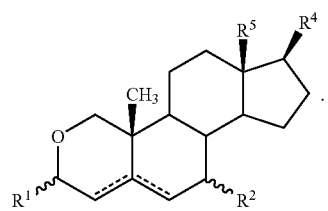

9. The pharmaceutical formulation of claim 7 wherein the compound has the structure

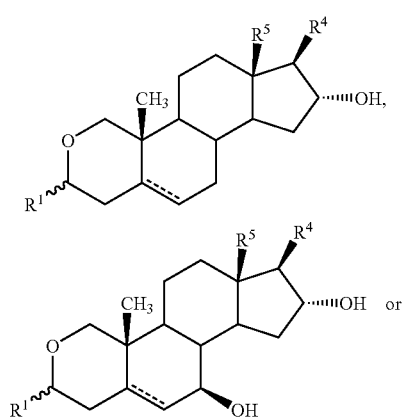

-continued

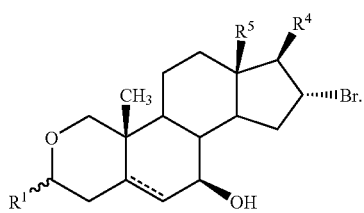

10. The pharmaceutical formulation of claim 7 wherein R$^3$ is —OH or an ester.

11. The pharmaceutical formulation of claim 8 wherein the compound has the structure

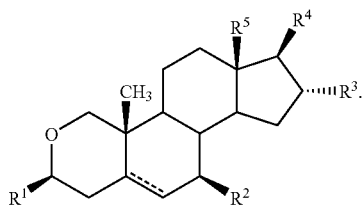

12. The pharmaceutical formulation of claim 11 wherein R$^1$ and R$^2$ independently are —OH or an ether.

13. The pharmaceutical formulation of claim 12 wherein R$^4$ is —OH or an ester and R$^5$ is —CH$_3$.

14. The pharmaceutical formulation of claim 9 wherein the compound has the structure

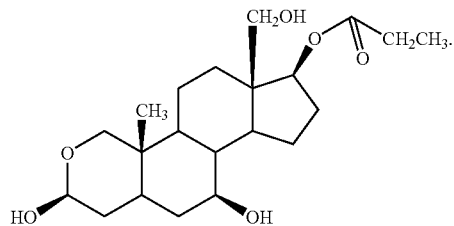

15. The pharmaceutical formulation of claim 9 wherein R$^1$ is —OH or —OCH$_3$, R$^4$ is —OH and R$^5$ is —CH$_3$.

* * * * *

UNITED STATES PATENT AND TRADEMARK OFFICE
CERTIFICATE OF CORRECTION

PATENT NO. : 7,723,532 B2  Page 1 of 1
APPLICATION NO. : 11/552095
DATED : May 25, 2010
INVENTOR(S) : Frincke et al.

It is certified that error appears in the above-identified patent and that said Letters Patent is hereby corrected as shown below:

On the Title Page,

Item "(*) "Notice:    Subject to any disclaimer, the term of this patent is extended or adjusted under 35 U.S.C. 154(b) by 477 days."

should read as

Item (*) Notice:    Subject to any disclaimer, the term of this patent is extended or adjusted under 35 U.S.C. 154(b) by 36 days.

Signed and Sealed this

Twenty-ninth Day of June, 2010

David J. Kappos
*Director of the United States Patent and Trademark Office*